US012807955B2

(12) United States Patent
Bovijn et al.

(10) Patent No.: US 12,807,955 B2
(45) Date of Patent: Nov. 24, 2026

(54) METHODS OF TREATING DECREASED BONE MINERAL DENSITY WITH KRINGLE CONTAINING TRANSMEMBRANE PROTEIN 1 (KREMEN1) INHIBITORS

(71) Applicant: Regeneron Pharmaceuticals, Inc., Tarrytown, NY (US)

(72) Inventors: Jonas Bovijn, Tarrytown, NY (US); Olukayode Sosina, Tarrytown, NY (US); Luca Andrea Lotta, Tarrytown, NY (US); Aris Baras, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 944 days.

(21) Appl. No.: 17/855,053

(22) Filed: Jun. 30, 2022

(65) Prior Publication Data

US 2023/0021584 A1 Jan. 26, 2023

Related U.S. Application Data

(60) Provisional application No. 63/218,212, filed on Jul. 2, 2021.

(51) Int. Cl.
*C12N 15/113* (2010.01)
*A61P 19/10* (2006.01)

(52) U.S. Cl.
CPC .......... *C12N 15/1138* (2013.01); *A61P 19/10* (2018.01); *C12N 2310/14* (2013.01); *C12N 2310/531* (2013.01)

(58) Field of Classification Search
CPC .................................................. C12N 15/1138
See application file for complete search history.

(56) References Cited

PUBLICATIONS

Li et al , Roles of Dickkopf-1 and its receptor Kremen1 during embryonic implantation in mice, Fertility and Sterility, 2008, vol. 90, suppl.2, pp. 1470-1479 (Year: 2008).*

Zhong et al , Osteoblast Targeted Disruption of Kremen Increases Bone Accrual in Mouse, Journal of Bone and Mineral Research, 2010, vol. 25, Supp. SUPPL. 1, pp. S175. Abstract No. SA0210 (Year: 2010).*

Ke et al., "Sclerostin and Dickkopf-1 as Therapeutic Targets in Bone Diseases", Endocrine Reviews, 2012, 33(5), pp. 747-783.

Stuss et al., "Assessment of Wnt pathway selected gene expression levels in peripheral blood mononuclear cells (PBMCs) of postmenopausal patients with low bone mass", Bosnian Journal of Basic Medical Science, 2020, 21(4), pp. 461-470.

Ellwanger et al., "Targeted Disruption of the Wnt Regulator Kremen Induces Limb Defects and High Bone Density", Molecular and Cellular Biology, 2008, 28(15), pp. 4875-4882.

Schulze et al., "Negative Regulation of Bone Formation by the Transmembrane Wnt Antagonist Kremen-2", PLOS One, 2010, 5(4), pp. e10309.

Rochefort, "The osteocyte as a therapeutic target in the treatment of osteoporosis", Ther Adv Musculoskel Dis, 2014, 6(3), pp. 79-91.

Lara-Castillo et al., "LRP receptor family member associated bone disease", Reviews in Endocrine & Metabolic Disorders, 2015, 16(2), pp. 141-148.

Zhang et al., "Prioritization of Osteoporosis-Associated Genome-wide Association Study (GWAS) Single-Nucleotide Polymorphisms (SNPs) Using Epigenomics and Transcriptomics", JBMR Plus, 2021, 5(5), pp. 2473-4039.

Zhu et al., "Twelve years of GWAS discoveries for osteoporosis and related traits: advances, challenges, and applications", Bone Research, 2021, 9(23), pp. 1-19.

Swerdlow et al., "Selecting instruments for Mendelian randomization in the wake of genome-wide association studies", Int J Epidemiol, 2016, 45, pp. 1600-1616.

Emilsson et al., "Co-regulatory networks of human serum proteins link genetics to disease", Science, 2018, 361 (6404), pp. 769-773.

* cited by examiner

*Primary Examiner* — Ekaterina Poliakova-Georgantas
(74) *Attorney, Agent, or Firm* — Armstrong Teasdale LLP

(57) ABSTRACT

The present disclosure provides methods of treating a subject having decreased bone mineral density or at risk of developing decreased bone mineral density, and methods of identifying subjects having an increased risk of developing decreased bone mineral density.

10 Claims, 39 Drawing Sheets

Specification includes a Sequence Listing.

| Beta, per allele, SD units of eBMD (95% CI) | Beta, per allele, g/cm$^2$ units of eBMD (95% CI) | P-value | Genotype counts, RR\|RA\|AA genotypes | AAF |
|---|---|---|---|---|
| 0.13 (0.08, 0.17) | 0.015 (0.009, 0.021) | $2.1x10^{-7}$ | 418366\|1371\|0 | 0.0016 |

Figure 1

| Genetic exposure | Beta, per allele, SD units of eBMD (95% CI) | Beta, per allele, g/cm$^2$ units of eBMD (95% CI) | P-value | Genotype counts, RR\|RA\|AA genotypes | AAF |
|---|---|---|---|---|---|
| pLoF variants, AAF < 1% | 0.18 (0.08, 0.29) | 0.022 (0.009, 0.035) | 0.00065 | 419465\|272\|0 | $3.0x10^{-4}$ |

Figure 2

| Genomic coordinates and alleles for genetic variant | Transcript(s) | Coding DNA change | Protein change | Variant classified as pLOF | AAF, fraction of 1 |
|---|---|---|---|---|---|
| 22:29137557:C:T | ENST00000400335; ENST00000407188; ENST00000327813 | c.847C>T; c.841C>T; c.847C>T | p.Arg283Cys; p.Arg281Cys; p.Arg283Cys | FALSE | 8.46E-06 |
| 22:29137557:C:T | ENST00000400335; ENST00000407188; ENST00000327813 | c.847C>T; c.841C>T; c.847C>T | p.Arg283Cys; p.Arg281Cys; p.Arg283Cys | FALSE | 6.87E-05 |
| 22:29137557:C:T | ENST00000400335; ENST00000407188; ENST00000327813 | c.847C>T; c.841C>T; c.847C>T | p.Arg283Cys; p.Arg281Cys; p.Arg283Cys | FALSE | 4.64E-06 |
| 22:29137557:C:T | ENST00000400335; ENST00000407188; ENST00000327813 | c.847C>T; c.841C>T; c.847C>T | p.Arg283Cys; p.Arg281Cys; p.Arg283Cys | FALSE | 1.72E-05 |
| 22:29073216:GC:G | ENST00000400335; ENST00000407188; ENST00000327813 | c.90delC; c.90delC; c.90delC | p.Gly31fs; p.Glu31fs; p.Gly31fs | TRUE | 6.48E-06 |
| 22:29094283:T:G | ENST00000400335; ENST00000407188; ENST00000327813 | c.123T>G; c.117T>G; c.123T>G | p.Asp41Glu; p.Asp39Glu; p.Asp41Glu | FALSE | 1.16E-06 |
| 22:29140320:A:G | ENST00000400335; ENST00000407188; ENST00000327813 | c.1162A>G; c.1207A>G; c.1213A>G | p.Thr388Ala; p.Thr403Ala; p.Thr405Ala | FALSE | 8.46E-06 |
| 22:29125344:G:T | ENST00000400335; ENST00000407188; ENST00000327813 | c.559G>T; c.553G>T; c.559G>T | p.Glu187*; p.Glu185*; p.Glu187* | TRUE | 6.48E-06 |
| 22:29125365:G:A | ENST00000400335; ENST00000407188; ENST00000327813 | c.580G>A; c.574G>A; c.580G>A | p.Gly194Arg; p.Gly192Arg; p.Gly194Arg | FALSE | 3.89E-05 |

Figure 3

| Genomic coordinates and alleles for genetic variant | Transcript(s) | Coding DNA change | Protein change | Variant classified as pLOF | AAF, fraction of 1 |
|---|---|---|---|---|---|
| 22:29125365:G:A | ENST00000400335; ENST00000407188; ENST00000327813 | c.580G>A; c.574G>A; c.580G>A | p.Gly194Arg; p.Gly192Arg; p.Gly194Arg | FALSE | 6.03E-05 |
| 22:29125365:G:A | ENST00000400335; ENST00000407188; ENST00000327813 | c.580G>A; c.574G>A; c.580G>A | p.Gly194Arg; p.Gly192Arg; p.Gly194Arg | FALSE | 5.92E-05 |
| 22:29125365:G:A | ENST00000400335; ENST00000407188; ENST00000327813 | c.580G>A; c.574G>A; c.580G>A | p.Gly194Arg; p.Gly192Arg; p.Gly194Arg | FALSE | 0.000137438 |
| 22:29137644:C:A | ENST00000400335; ENST00000407188; ENST00000327813 | c.934C>A; c.928C>A; c.934C>A | p.Gln312Lys; p.Gln310Lys; p.Gln312Lys | FALSE | 1.16E-06 |
| 22:29094396:G:T | ENST00000400335; ENST00000407188; ENST00000327813 | c.236G>T; c.230G>T; c.236G>T | p.Gly79Val; p.Gly77Val; p.Gly79Val | FALSE | 3.48E-06 |
| 22:29098872:G:A | ENST00000400335; ENST00000407188; ENST00000327813 | c.271G>A; c.265G>A; c.271G>A | p.Gly91Arg; p.Gly89Arg; p.Gly91Arg | FALSE | 1.72E-05 |
| 22:29137405:TC:T | ENST00000400335; ENST00000407188; ENST00000327813 | c.699delC; c.693delC; c.699delC | p.Asp234fs; p.Asp232fs; p.Asp234fs | TRUE | 2.32E-06 |
| 22:29073155:GC:G | ENST00000400335; ENST00000407188; ENST00000327813 | c.28delC; c.28delC; c.28delC | p.Leu10fs; p.Leu10fs; p.Leu10fs | TRUE | 6.48E-06 |
| 22:29137575:C:T | ENST00000400335; ENST00000407188; ENST00000327813 | c.865C>T; c.859C>T; c.865C>T | p.Arg289Cys; p.Arg287Cys; p.Arg289Cys | FALSE | 4.64E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29137575:C:T | ENST00000400335; ENST00000407188; ENST00000327813 | c.865C>T; c.859C>T; c.865C>T | p.Arg289Cys; p.Arg287Cys; p.Arg289Cys | FALSE | 1.16E-06 |
| 22:29137575:C:T | ENST00000400335; ENST00000407188; ENST00000327813 | c.865C>T; c.859C>T; c.865C>T | p.Arg289Cys; p.Arg287Cys; p.Arg289Cys | FALSE | 6.48E-06 |
| 22:29142018:T:G | ENST00000400335; ENST00000407188; ENST00000327813 | c.1283T>G; c.1328T>G; c.1334T>G | p.Ile428Ser; p.Ile443Ser; p.Ile445Ser | FALSE | 1.94E-05 |
| 22:29142018:T:G | ENST00000400335; ENST00000407188; ENST00000327813 | c.1283T>G; c.1328T>G; c.1334T>G | p.Ile428Ser; p.Ile443Ser; p.Ile445Ser | FALSE | 1.27E-05 |
| 22:29094298:G:C | ENST00000400335; ENST00000407188; ENST00000327813 | c.138G>C; c.132G>C; c.138G>C | p.Gln46His; p.Gln44His; p.Gln46His | FALSE | 6.48E-06 |
| 22:29125319:G:A | ENST00000400335; ENST00000407188; ENST00000327813 | c.534G>A; c.528G>A; c.534G>A | p.Trp178*; p.Trp176*; p.Trp178* | TRUE | 1.16E-06 |
| 22:29140320:A:C | ENST00000400335; ENST00000407188; ENST00000327813 | c.1162A>C; c.1207A>C; c.1213A>C | p.Thr388Pro; p.Thr403Pro; p.Thr405Pro | FALSE | 1.16E-06 |
| 22:29121374:T:C | ENST00000400335; ENST00000407188; ENST00000327813 | c.370T>C; c.364T>C; c.370T>C | p.Cys124Arg; p.Cys122Arg; p.Cys124Arg | FALSE | 1.16E-06 |
| 22:29138623:G:A | ENST00000400335; ENST00000407188; ENST00000327813 | c.965-1G>A; c.959-1G>A; c.965-1G>A | | TRUE | 3.48E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29138623:G:A | ENST00000400335; ENST00000407188; ENST00000327813 | c.965-1G>A; c.959-1G>A; c.965-1G>A | | TRUE | 6.48E-06 |
| 22:29121482:G:C | ENST00000400335; ENST00000407188; ENST00000327813 | c.477+1G>C; c.471+1G>C; c.477+1G>C | | TRUE | 1.16E-06 |
| 22:29137353:G:A | ENST00000400335; ENST00000407188; ENST00000327813 | c.643G>A; c.637G>A; c.643G>A | p.Ala215Thr; p.Ala213Thr; p.Ala215Thr | FALSE | 1.30E-05 |
| 22:29137353:G:A | ENST00000400335; ENST00000407188; ENST00000327813 | c.643G>A; c.637G>A; c.643G>A | p.Ala215Thr; p.Ala213Thr; p.Ala215Thr | FALSE | 8.11E-06 |
| 22:29140353:CA:C | ENST00000400335; ENST00000407188; ENST00000327813 | c.1196delA; c.1241delA; c.1247delA | p.His399fs; p.His414fs; p.His416fs | TRUE | 1.16E-06 |
| 22:29121438:C:T | ENST00000400335; ENST00000407188; ENST00000327813 | c.434C>T; c.428C>T; c.434C>T | p.Thr145Ile; p.Thr143Ile; p.Thr145Ile | FALSE | 6.48E-06 |
| 22:29138834:G:A | ENST00000407188; ENST00000327813 | c.1168+1G>A; c.1174+1G>A | | TRUE | 1.16E-06 |
| 22:29125366:G:T | ENST00000400335; ENST00000407188; ENST00000327813 | c.581G>T; c.575G>T; c.581G>T | p.Gly194Val; p.Gly192Val; p.Gly194Val | FALSE | 8.46E-06 |
| 22:29137600:C:T | ENST00000400335; ENST00000407188; ENST00000327813 | c.890C>T; c.884C>T; c.890C>T | p.Ser297Phe; p.Ser295Phe; p.Ser297Phe | FALSE | 6.95E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29138738:A:G | ENST00000400335; ENST00000407188; ENST00000327813 | c.1079A>G; c.1073A>G; c.1079A>G | p.Tyr360Cys; p.Tyr358Cys; p.Tyr360Cys | FALSE | 2.32E-06 |
| 22:29138738:A:G | ENST00000400335; ENST00000407188; ENST00000327813 | c.1079A>G; c.1073A>G; c.1079A>G | p.Tyr360Cys; p.Tyr358Cys; p.Tyr360Cys | FALSE | 6.48E-06 |
| 22:29098925:G:A | ENST00000400335; ENST00000407188; ENST00000327813 | c.324G>A; c.318G>A; c.324G>A | p.Trp108*; p.Trp106*; p.Trp108* | TRUE | 1.16E-06 |
| 22:29137447:T:TCC | ENST00000400335; ENST00000407188; ENST00000327813 | c.738_739dupCC; c.732_733dupCC; c.738_739dupCC | p.Arg247fs; p.Arg245fs; p.Arg247fs | TRUE | 2.32E-06 |
| 22:29142017:A:AT | ENST00000400335; ENST00000407188; ENST00000327813 | c.1288dupT; c.1333dupT; c.1339dupT | p.Tyr430fs; p.Tyr445fs; p.Tyr447fs | TRUE | 3.48E-06 |
| 22:29094255:TA:T | ENST00000400335; ENST00000407188; ENST00000327813 | c.98-2delA; c.92-2delA; c.98-2delA | | TRUE | 6.48E-06 |
| 22:29094338:AT:A | ENST00000400335; ENST00000407188; ENST00000327813 | c.169delT; c.163delT; c.169delT | p.Cys57fs; p.Cys55fs; p.Cys57fs | TRUE | 1.16E-06 |
| 22:29121477:TC:T | ENST00000400335; ENST00000407188; ENST00000327813 | c.474delC; c.468delC; c.474delC | p.Phe158fs; p.Phe156fs; p.Phe158fs | TRUE | 1.16E-06 |
| 22:29140297:GTCTGGCA:G | ENST00000400335; ENST00000407188; ENST00000327813 | c.1140_1146delTCTGGCA; c.1185_1191delTCTGGCA; c.1191_1197delTCTGGCA | p.Ala382fs; p.Ala397fs; p.Ala399fs | TRUE | 4.64E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29094403:TG:T | ENST00000400335; ENST00000407188; ENST00000327813 | c.244delG; c.238delG; c.244delG | p.Glu82fs; p.Glu80fs; p.Glu82fs | TRUE | 6.48E-06 |
| 22:29138783:G:A | ENST00000400335 | c.1123+1G>A | | TRUE | 1.16E-06 |
| 22:29138753:GC:G | ENST00000400335; ENST00000407188; ENST00000327813 | c.1098delC; c.1092delC; c.1098delC | p.Ser367fs; p.Ser365fs; p.Ser367fs | TRUE | 6.14E-05 |
| 22:29138753:GC:G | ENST00000400335; ENST00000407188; ENST00000327813 | c.1098delC; c.1092delC; c.1098delC | p.Ser367fs; p.Ser365fs; p.Ser367fs | TRUE | 1.94E-05 |
| 22:29138753:GC:G | ENST00000400335; ENST00000407188; ENST00000327813 | c.1098delC; c.1092delC; c.1098delC | p.Ser367fs; p.Ser365fs; p.Ser367fs | TRUE | 0.000113071 |
| 22:29138753:GC:G | ENST00000400335; ENST00000407188; ENST00000327813 | c.1098delC; c.1092delC; c.1098delC | p.Ser367fs; p.Ser365fs; p.Ser367fs | TRUE | 4.64E-05 |
| 22:29138753:GC:G | ENST00000400335; ENST00000407188; ENST00000327813 | c.1098delC; c.1092delC; c.1098delC | p.Ser367fs; p.Ser365fs; p.Ser367fs | TRUE | 6.87E-05 |
| 22:29138753:GC:G | ENST00000400335; ENST00000407188; ENST00000327813 | c.1098delC; c.1092delC; c.1098delC | p.Ser367fs; p.Ser365fs; p.Ser367fs | TRUE | 4.23E-05 |
| 22:29125269:G:A | ENST00000400335; ENST00000407188; ENST00000327813 | c.484G>A; c.478G>A; c.484G>A | p.Gly162Arg; p.Gly160Arg; p.Gly162Arg | FALSE | 1.16E-06 |
| 22:29094387:G:C | ENST00000400335; ENST00000407188; ENST00000327813 | c.227G>C; c.221G>C; c.227G>C | p.Gly76Ala; p.Gly74Ala; p.Gly76Ala | FALSE | 0.000113071 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29137495:A:C | ENST00000400335; ENST00000407188; ENST00000327813 | c.785A>C; c.779A>C; c.785A>C | p.Asp262Ala; p.Asp260Ala; p.Asp262Ala | FALSE | 2.32E-06 |
| 22:29140285:G:A | ENST00000400335; ENST00000407188; ENST00000327813 | c.1127G>A; c.1172G>A; c.1178G>A | p.Trp376*; p.Trp391*; p.Trp393* | TRUE | 1.16E-06 |
| 22:29142101:G:A | ENST00000327813 | c.1416+1G>A | | TRUE | 1.16E-06 |
| 22:29094273:A:G | ENST00000400335; ENST00000407188; ENST00000327813 | c.113A>G; c.107A>G; c.113A>G | p.Asn38Ser; p.Asn36Ser; p.Asn38Ser | FALSE | 2.90E-05 |
| 22:29094273:A:G | ENST00000400335; ENST00000407188; ENST00000327813 | c.113A>G; c.107A>G; c.113A>G | p.Asn38Ser; p.Asn36Ser; p.Asn38Ser | FALSE | 1.30E-05 |
| 22:29094273:A:G | ENST00000400335; ENST00000407188; ENST00000327813 | c.113A>G; c.107A>G; c.113A>G | p.Asn38Ser; p.Asn36Ser; p.Asn38Ser | FALSE | 8.46E-05 |
| 22:29125282:G:A | ENST00000400335; ENST00000407188; ENST00000327813 | c.497G>A; c.491G>A; c.497G>A | p.Gly166Asp; p.Gly164Asp; p.Gly166Asp | FALSE | 4.53E-05 |
| 22:29125282:G:A | ENST00000400335; ENST00000407188; ENST00000327813 | c.497G>A; c.491G>A; c.497G>A | p.Gly166Asp; p.Gly164Asp; p.Gly166Asp | FALSE | 3.44E-05 |
| 22:29125282:G:A | ENST00000400335; ENST00000407188; ENST00000327813 | c.497G>A; c.491G>A; c.497G>A | p.Gly166Asp; p.Gly164Asp; p.Gly166Asp | FALSE | 1.69E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29094267:C:T | ENST00000400335; ENST00000407188; ENST00000327813 | c.107C>T; c.101C>T; c.107C>T | p.Thr36Ile; p.Thr34Ile; p.Thr36Ile | FALSE | 5.80E-06 |
| 22:29094267:C:T | ENST00000400335; ENST00000407188; ENST00000327813 | c.107C>T; c.101C>T; c.107C>T | p.Thr36Ile; p.Thr34Ile; p.Thr36Ile | FALSE | 1.30E-05 |
| 22:29094267:C:T | ENST00000400335; ENST00000407188; ENST00000327813 | c.107C>T; c.101C>T; c.107C>T | p.Thr36Ile; p.Thr34Ile; p.Thr36Ile | FALSE | 1.69E-05 |
| 22:29137674:G:C | ENST00000400335; ENST00000407188; ENST00000327813 | c.964G>C; c.958G>C; c.964G>C | p.Ala322Pro; p.Ala320Pro; p.Ala322Pro | FALSE | 1.16E-06 |
| 22:29125329:G:T | ENST00000400335; ENST00000407188; ENST00000327813 | c.544G>T; c.538G>T; c.544G>T | p.Glu182*; p.Glu180*; p.Glu182* | TRUE | 6.48E-06 |
| 22:29137417:A:G | ENST00000400335; ENST00000407188; ENST00000327813 | c.707A>G; c.701A>G; c.707A>G | p.Tyr236Cys; p.Tyr234Cys; p.Tyr236Cys | FALSE | 6.48E-06 |
| 22:29137417:A:G | ENST00000400335; ENST00000407188; ENST00000327813 | c.707A>G; c.701A>G; c.707A>G | p.Tyr236Cys; p.Tyr234Cys; p.Tyr236Cys | FALSE | 4.64E-05 |
| 22:29137417:A:G | ENST00000400335; ENST00000407188; ENST00000327813 | c.707A>G; c.701A>G; c.707A>G | p.Tyr236Cys; p.Tyr234Cys; p.Tyr236Cys | FALSE | 6.87E-05 |
| 22:29137417:A:G | ENST00000400335; ENST00000407188; ENST00000327813 | c.707A>G; c.701A>G; c.707A>G | p.Tyr236Cys; p.Tyr234Cys; p.Tyr236Cys | FALSE | 2.32E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29125392:G:A | ENST00000400335; ENST00000407188; ENST00000327813 | c.607G>A; c.601G>A; c.607G>A | p.Asp203Asn; p.Asp201Asn; p.Asp203Asn | FALSE | 9.27E-05 |
| 22:29125392:G:A | ENST00000400335; ENST00000407188; ENST00000327813 | c.607G>A; c.601G>A; c.607G>A | p.Asp203Asn; p.Asp201Asn; p.Asp203Asn | FALSE | 1.51E-05 |
| 22:29125392:G:A | ENST00000400335; ENST00000407188; ENST00000327813 | c.607G>A; c.601G>A; c.607G>A | p.Asp203Asn; p.Asp201Asn; p.Asp203Asn | FALSE | 1.72E-05 |
| 22:29137657:T:C | ENST00000400335; ENST00000407188; ENST00000327813 | c.947T>C; c.941T>C; c.947T>C | p.Phe316Ser; p.Phe314Ser; p.Phe316Ser | FALSE | 6.48E-06 |
| 22:29137657:T:C | ENST00000400335; ENST00000407188; ENST00000327813 | c.947T>C; c.941T>C; c.947T>C | p.Phe316Ser; p.Phe314Ser; p.Phe316Ser | FALSE | 1.74E-05 |
| 22:29140312:T:C | ENST00000400335; ENST00000407188; ENST00000327813 | c.1154T>C; c.1199T>C; c.1205T>C | p.Leu385Pro; p.Leu400Pro; p.Leu402Pro | FALSE | 8.46E-06 |
| 22:29140312:T:C | ENST00000400335; ENST00000407188; ENST00000327813 | c.1154T>C; c.1199T>C; c.1205T>C | p.Leu385Pro; p.Leu400Pro; p.Leu402Pro | FALSE | 6.87E-05 |
| 22:29098866:C:G | ENST00000400335; ENST00000407188; ENST00000327813 | c.265C>G; c.259C>G; c.265C>G | p.Pro89Ala; p.Pro87Ala; p.Pro89Ala | FALSE | 1.16E-06 |
| 22:29125325:C:G | ENST00000400335; ENST00000407188; ENST00000327813 | c.540C>G; c.534C>G; c.540C>G | p.Tyr180*; p.Tyr178*; p.Tyr180* | TRUE | 1.16E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29125325:C:G | ENST00000400335; ENST00000407188; ENST00000327813 | c.540C>G; c.534C>G; c.540C>G | p.Tyr180*; p.Tyr178*; p.Tyr180* | TRUE | 1.16E-06 |
| 22:29138723:C:T | ENST00000400335; ENST00000407188; ENST00000327813 | c.1064C>T; c.1058C>T; c.1064C>T | p.Ser355Phe; p.Ser353Phe; p.Ser355Phe | FALSE | 5.80E-06 |
| 22:29140353:C:T | ENST00000400335; ENST00000407188; ENST00000327813 | c.1195C>T; c.1240C>T; c.1246C>T | p.His399Tyr; p.His414Tyr; p.His416Tyr | FALSE | 8.46E-06 |
| 22:29137341:G:A | ENST00000400335; ENST00000407188; ENST00000327813 | c.632-1G>A; c.626-1G>A; c.632-1G>A | | TRUE | 6.48E-06 |
| 22:29073204:GC:G | ENST00000400335; ENST00000407188; ENST00000327813 | c.78delC; c.78delC; c.78delC | p.Gly27fs; p.Gly27fs; p.Gly27fs | TRUE | 6.48E-06 |
| 22:29125288:C:T | ENST00000400335; ENST00000407188; ENST00000327813 | c.503C>T; c.497C>T; c.503C>T | p.Ala168Val; p.Ala166Val; p.Ala168Val | FALSE | 1.16E-06 |
| 22:29125297:G:T | ENST00000400335; ENST00000407188; ENST00000327813 | c.512G>T; c.506G>T; c.512G>T | p.Cys171Phe; p.Cys169Phe; p.Cys171Phe | FALSE | 1.16E-05 |
| 22:29137492:T:G | ENST00000400335; ENST00000407188; ENST00000327813 | c.782T>G; c.776T>G; c.782T>G | p.Phe261Cys; p.Phe259Cys; p.Phe261Cys | FALSE | 1.16E-06 |
| 22:29167105:G:C | ENST00000327813 | c.1478G>C | p.Ter493Serext*? | TRUE | 2.59E-05 |
| 22:29167105:G:C | ENST00000327813 | c.1478G>C | p.Ter493Serext*? | TRUE | 8.46E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29073228:G:T | ENST00000400335; ENST00000327813 | c.97+1G>T; c.97+1G>T | | TRUE | 2.32E-06 |
| 22:29094320:G:A | ENST00000400335; ENST00000407188; ENST00000327813 | c.160G>A; c.154G>A; c.160G>A | p.Gly54Arg; p.Gly52Arg; p.Gly54Arg | FALSE | 1.30E-05 |
| 22:29094320:G:A | ENST00000400335; ENST00000407188; ENST00000327813 | c.160G>A; c.154G>A; c.160G>A | p.Gly54Arg; p.Gly52Arg; p.Gly54Arg | FALSE | 4.64E-06 |
| 22:29094320:G:A | ENST00000400335; ENST00000407188; ENST00000327813 | c.160G>A; c.154G>A; c.160G>A | p.Gly54Arg; p.Gly52Arg; p.Gly54Arg | FALSE | 2.54E-05 |
| 22:29094320:G:A | ENST00000400335; ENST00000407188; ENST00000327813 | c.160G>A; c.154G>A; c.160G>A | p.Gly54Arg; p.Gly52Arg; p.Gly54Arg | FALSE | 6.87E-05 |
| 22:29137579:C:T | ENST00000400335; ENST00000407188; ENST00000327813 | c.869C>T; c.863C>T; c.869C>T | p.Pro290Leu; p.Pro288Leu; p.Pro290Leu | FALSE | 8.46E-06 |
| 22:29094321:G:A | ENST00000400335; ENST00000407188; ENST00000327813 | c.161G>A; c.155G>A; c.161G>A | p.Gly54Glu; p.Gly52Glu; p.Gly54Glu | FALSE | 1.16E-06 |
| 22:29137340:A:G | ENST00000400335; ENST00000407188; ENST00000327813 | c.632-2A>G; c.626-2A>G; c.632-2A>G | | TRUE | 1.16E-06 |
| 22:29137521:G:A | ENST00000400335; ENST00000407188; ENST00000327813 | c.811G>A; c.805G>A; c.811G>A | p.Glu271Lys; p.Glu269Lys; p.Glu271Lys | FALSE | 2.32E-06 |
| 22:29073213:T:TCGGCCC | ENST00000407188 | c.87_91+1dupCCCCGG | | TRUE | 1.16E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29137654:G:A | ENST00000400335; ENST00000407188; ENST00000327813 | c.944G>A; c.938G>A; c.944G>A | p.Gly315Glu; p.Gly313Glu; p.Gly315Glu | FALSE | 2.32E-06 |
| 22:29138746:A:G | ENST00000400335; ENST00000407188; ENST00000327813 | c.1087A>G; c.1081A>G; c.1087A>G | p.Thr363Ala; p.Thr361Ala; p.Thr363Ala | FALSE | 8.46E-06 |
| 22:29137340:A:C | ENST00000400335; ENST00000407188; ENST00000327813 | c.632-2A>C; c.626-2A>C; c.632-2A>C | | TRUE | 0.00010305 |
| 22:29094324:A:T | ENST00000400335; ENST00000407188; ENST00000327813 | c.164A>T; c.158A>T; c.164A>T | p.Lys55Met; p.Lys53Met; p.Lys55Met | FALSE | 1.16E-06 |
| 22:29137647:G:A | ENST00000400335; ENST00000407188; ENST00000327813 | c.937G>A; c.931G>A; c.937G>A | p.Ala313Thr; p.Ala311Thr; p.Ala313Thr | FALSE | 6.48E-06 |
| 22:29137647:G:A | ENST00000400335; ENST00000407188; ENST00000327813 | c.937G>A; c.931G>A; c.937G>A | p.Ala313Thr; p.Ala311Thr; p.Ala313Thr | FALSE | 6.87E-05 |
| 22:29137360:G:T | ENST00000400335; ENST00000407188; ENST00000327813 | c.650G>T; c.644G>T; c.650G>T | p.Gly217Val; p.Gly215Val; p.Gly217Val | FALSE | 6.87E-05 |
| 22:29094390:A:G | ENST00000400335; ENST00000407188; ENST00000327813 | c.230A>G; c.224A>G; c.230A>G | p.Glu77Gly; p.Glu75Gly; p.Glu77Gly | FALSE | 1.16E-06 |
| 22:29167083:CAG:C | ENST00000327813 | c.1457_1458delAG | p.Gln486fs | TRUE | 3.44E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29138812:GC:G | ENST00000407188; ENST00000327813 | c.1148delC; c.1154delC | p.Ala383fs; p.Ala385fs | TRUE | 3.89E-05 |
| 22:29138812:GC:G | ENST00000407188; ENST00000327813 | c.1148delC; c.1154delC | p.Ala383fs; p.Ala385fs | TRUE | 6.95E-05 |
| 22:29138812:GC:G | ENST00000407188; ENST00000327813 | c.1148delC; c.1154delC | p.Ala383fs; p.Ala385fs | TRUE | 0.000113071 |
| 22:29138812:GC:G | ENST00000407188; ENST00000327813 | c.1148delC; c.1154delC | p.Ala383fs; p.Ala385fs | TRUE | 4.64E-05 |
| 22:29094363:A:G | ENST00000400335; ENST00000407188; ENST00000327813 | c.203A>G; c.197A>G; c.203A>G | p.Tyr68Cys; p.Tyr66Cys; p.Tyr68Cys | FALSE | 6.77E-05 |
| 22:29094363:A:G | ENST00000400335; ENST00000407188; ENST00000327813 | c.203A>G; c.197A>G; c.203A>G | p.Tyr68Cys; p.Tyr66Cys; p.Tyr68Cys | FALSE | 1.16E-06 |
| 22:29094363:A:G | ENST00000400335; ENST00000407188; ENST00000327813 | c.203A>G; c.197A>G; c.203A>G | p.Tyr68Cys; p.Tyr66Cys; p.Tyr68Cys | FALSE | 5.83E-05 |
| 22:29140318:T:A | ENST00000400335; ENST00000407188; ENST00000327813 | c.1160T>A; c.1205T>A; c.1211T>A | p.Leu387His; p.Leu402His; p.Leu404His | FALSE | 1.16E-06 |
| 22:29098926:A:G | ENST00000400335; ENST00000407188; ENST00000327813 | c.325A>G; c.319A>G; c.325A>G | p.Lys109Glu; p.Lys107Glu; p.Lys109Glu | FALSE | 8.46E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29098926:A:G | ENST00000400335; ENST00000407188; ENST00000327813 | c.325A>G; c.319A>G; c.325A>G | p.Lys109Glu; p.Lys107Glu; p.Lys109Glu | FALSE | 1.04E-05 |
| 22:29125372:A:T | ENST00000400335; ENST00000407188; ENST00000327813 | c.587A>T; c.581A>T; c.587A>T | p.His196Leu; p.His194Leu; p.His196Leu | FALSE | 6.48E-06 |
| 22:29125372:A:T | ENST00000400335; ENST00000407188; ENST00000327813 | c.587A>T; c.581A>T; c.587A>T | p.His196Leu; p.His194Leu; p.His196Leu | FALSE | 3.39E-05 |
| 22:29125372:A:T | ENST00000400335; ENST00000407188; ENST00000327813 | c.587A>T; c.581A>T; c.587A>T | p.His196Leu; p.His194Leu; p.His196Leu | FALSE | 2.09E-05 |
| 22:29125372:A:T | ENST00000400335; ENST00000407188; ENST00000327813 | c.587A>T; c.581A>T; c.587A>T | p.His196Leu; p.His194Leu; p.His196Leu | FALSE | 1.72E-05 |
| 22:29140318:TCA:T | ENST00000400335; ENST00000407188; ENST00000327813 | c.1163_1164delCA; c.1208_1209delCA; c.1214_1215delCA | p.Thr388fs; p.Thr403fs; p.Thr405fs | TRUE | 2.32E-06 |
| 22:29094354:A:G | ENST00000400335; ENST00000407188; ENST00000327813 | c.194A>G; c.188A>G; c.194A>G | p.Gln65Arg; p.Gln63Arg; p.Gln65Arg | FALSE | 2.32E-06 |
| 22:29141946:C:T | ENST00000400335; ENST00000407188; ENST00000327813 | c.1211C>T; c.1256C>T; c.1262C>T | p.Ser404Phe; p.Ser419Phe; p.Ser421Phe | FALSE | 6.48E-06 |
| 22:29094256:A:G | ENST00000400335; ENST00000407188; ENST00000327813 | c.98-2A>G; c.92-2A>G; c.98-2A>G | | TRUE | 8.46E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29094256:A:G | ENST00000400335; ENST00000407188; ENST00000327813 | c.98-2A>G; c.92-2A>G; c.98-2A>G | | TRUE | 3.48E-06 |
| 22:29094391:G:C | ENST00000400335; ENST00000407188; ENST00000327813 | c.231G>C; c.225G>C; c.231G>C | p.Glu77Asp; p.Glu75Asp; p.Glu77Asp | FALSE | 1.16E-06 |
| 22:29125384:G:C | ENST00000400335; ENST00000407188; ENST00000327813 | c.599G>C; c.593G>C; c.599G>C | p.Cys200Ser; p.Cys198Ser; p.Cys200Ser | FALSE | 6.87E-05 |
| 22:29125384:G:C | ENST00000400335; ENST00000407188; ENST00000327813 | c.599G>C; c.593G>C; c.599G>C | p.Cys200Ser; p.Cys198Ser; p.Cys200Ser | FALSE | 8.59E-05 |
| 22:29125384:G:C | ENST00000400335; ENST00000407188; ENST00000327813 | c.599G>C; c.593G>C; c.599G>C | p.Cys200Ser; p.Cys198Ser; p.Cys200Ser | FALSE | 1.16E-06 |
| 22:29138687:C:T | ENST00000400335; ENST00000407188; ENST00000327813 | c.1028C>T; c.1022C>T; c.1028C>T | p.Thr343Met; p.Thr341Met; p.Thr343Met | FALSE | 2.32E-06 |
| 22:29138687:C:T | ENST00000400335; ENST00000407188; ENST00000327813 | c.1028C>T; c.1022C>T; c.1028C>T | p.Thr343Met; p.Thr341Met; p.Thr343Met | FALSE | 6.48E-06 |
| 22:29138687:C:T | ENST00000400335; ENST00000407188; ENST00000327813 | c.1028C>T; c.1022C>T; c.1028C>T | p.Thr343Met; p.Thr341Met; p.Thr343Met | FALSE | 8.46E-06 |
| 22:29138737:T:G | ENST00000400335; ENST00000407188; ENST00000327813 | c.1078T>G; c.1072T>G; c.1078T>G | p.Tyr360Asp; p.Tyr358Asp; p.Tyr360Asp | FALSE | 6.48E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29121450:G:A | ENST00000400335; ENST00000407188; ENST00000327813 | c.446G>A; c.440G>A; c.446G>A | p.Cys149Tyr; p.Cys147Tyr; p.Cys149Tyr | FALSE | 2.32E-06 |
| 22:29167083:CA:C | ENST00000327813 | c.1457delA | p.Gln486fs | TRUE | 2.32E-06 |
| 22:29073212:CT:C | ENST00000400335; ENST00000407188; ENST00000327813 | c.83delT; c.83delT; c.83delT | p.Leu28fs; p.Leu28fs; p.Leu28fs | TRUE | 1.16E-06 |
| 22:29121416:A:G | ENST00000400335; ENST00000407188; ENST00000327813 | c.412A>G; c.406A>G; c.412A>G | p.Ser138Gly; p.Ser136Gly; p.Ser138Gly | FALSE | 3.24E-05 |
| 22:29121416:A:G | ENST00000400335; ENST00000407188; ENST00000327813 | c.412A>G; c.406A>G; c.412A>G | p.Ser138Gly; p.Ser136Gly; p.Ser138Gly | FALSE | 3.48E-06 |
| 22:29121416:A:G | ENST00000400335; ENST00000407188; ENST00000327813 | c.412A>G; c.406A>G; c.412A>G | p.Ser138Gly; p.Ser136Gly; p.Ser138Gly | FALSE | 1.69E-05 |
| 22:29121416:A:G | ENST00000400335; ENST00000407188; ENST00000327813 | c.412A>G; c.406A>G; c.412A>G | p.Ser138Gly; p.Ser136Gly; p.Ser138Gly | FALSE | 6.87E-05 |
| 22:29098873:G:T | ENST00000400335; ENST00000407188; ENST00000327813 | c.272G>T; c.266G>T; c.272G>T | p.Gly91Val; p.Gly89Val; p.Gly91Val | FALSE | 6.48E-06 |
| 22:29094257:G:A | ENST00000400335; ENST00000407188; ENST00000327813 | c.98-1G>A; c.92-1G>A; c.98-1G>A | | TRUE | 1.16E-06 |
| 22:29098911:G:C | ENST00000400335; ENST00000407188; ENST00000327813 | c.310G>C; c.304G>C; c.310G>C | p.Asp104His; p.Asp102His; p.Asp104His | FALSE | 1.16E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29142057:A:T | ENST00000400335; ENST00000407188; ENST00000327813 | c.1322A>T; c.1367A>T; c.1373A>T | p.Lys441Met; p.Lys456Met; p.Lys458Met | FALSE | 1.16E-06 |
| 22:29094270:C:A | ENST00000400335; ENST00000407188; ENST00000327813 | c.110C>A; c.104C>A; c.110C>A | p.Ala37Asp; p.Ala35Asp; p.Ala37Asp | FALSE | 2.32E-06 |
| 22:29094344:G:A | ENST00000400335; ENST00000407188; ENST00000327813 | c.184G>A; c.178G>A; c.184G>A | p.Glu62Lys; p.Glu60Lys; p.Glu62Lys | FALSE | 1.16E-06 |
| 22:29121372:G:A | ENST00000400335; ENST00000407188; ENST00000327813 | c.368G>A; c.362G>A; c.368G>A | p.Gly123Asp; p.Gly121Asp; p.Gly123Asp | FALSE | 4.64E-06 |
| 22:29142110:T:G | ENST00000400335; ENST00000407188 | c.1375T>G; c.1420T>G | p.Ter459Gluext*?; p.Ter474Gluext*? | TRUE | 8.46E-06 |
| 22:29137559:CT:C | ENST00000400335; ENST00000407188; ENST00000327813 | c.851delT; c.845delT; c.851delT | p.Phe284fs; p.Phe282fs; p.Phe284fs | TRUE | 2.32E-06 |
| 22:29098953:A:C | ENST00000400335; ENST00000407188; ENST00000327813 | c.352A>C; c.346A>C; c.352A>C | p.Met118Leu; p.Met116Leu; p.Met118Leu | FALSE | 2.32E-06 |
| 22:29137407:C:T | ENST00000400335; ENST00000407188; ENST00000327813 | c.697C>T; c.691C>T; c.697C>T | p.Pro233Ser; p.Pro231Ser; p.Pro233Ser | FALSE | 1.16E-06 |
| 22:29094395:G:A | ENST00000400335; ENST00000407188; ENST00000327813 | c.235G>A; c.229G>A; c.235G>A | p.Gly79Ser; p.Gly77Ser; p.Gly79Ser | FALSE | 6.48E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29121359:C:T | ENST00000400335; ENST00000407188; ENST00000327813 | c.355C>T; c.349C>T; c.355C>T | p.Pro119Ser; p.Pro117Ser; p.Pro119Ser | FALSE | 2.32E-06 |
| 22:29098893:T:C | ENST00000400335; ENST00000407188; ENST00000327813 | c.292T>C; c.286T>C; c.292T>C | p.Tyr98His; p.Tyr96His; p.Tyr98His | FALSE | 2.32E-06 |
| 22:29142029:C:A | ENST00000400335; ENST00000407188; ENST00000327813 | c.1294C>A; c.1339C>A; c.1345C>A | p.Pro432Thr; p.Pro447Thr; p.Pro449Thr | FALSE | 1.16E-06 |
| 22:29121379:C:G | ENST00000400335; ENST00000407188; ENST00000327813 | c.375C>G; c.369C>G; c.375C>G | p.Tyr125*; p.Tyr123*; p.Tyr125* | TRUE | 1.16E-06 |
| 22:29121359:C:A | ENST00000400335; ENST00000407188; ENST00000327813 | c.355C>A; c.349C>A; c.355C>A | p.Pro119Thr; p.Pro117Thr; p.Pro119Thr | FALSE | 7.12E-05 |
| 22:29121359:C:A | ENST00000400335; ENST00000407188; ENST00000327813 | c.355C>A; c.349C>A; c.355C>A | p.Pro119Thr; p.Pro117Thr; p.Pro119Thr | FALSE | 2.43E-05 |
| 22:29121359:C:A | ENST00000400335; ENST00000407188; ENST00000327813 | c.355C>A; c.349C>A; c.355C>A | p.Pro119Thr; p.Pro117Thr; p.Pro119Thr | FALSE | 0.000135428 |
| 22:29094342:A:G | ENST00000400335; ENST00000407188; ENST00000327813 | c.182A>G; c.176A>G; c.182A>G | p.Asn61Ser; p.Asn59Ser; p.Asn61Ser | FALSE | 4.64E-06 |
| 22:29138806:ATGGGGGCT:A | ENST00000407188; ENST00000327813 | c.1142_1149delTGGGGGCT; c.1148_1155delTGGGGGCT | p.Met381fs; p.Met383fs | TRUE | 5.80E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29137558:G:A | ENST00000400335; ENST00000407188; ENST00000327813 | c.848G>A; c.842G>A; c.848G>A | p.Arg283His; p.Arg281His; p.Arg283His | FALSE | 1.16E-06 |
| 22:29137558:G:A | ENST00000400335; ENST00000407188; ENST00000327813 | c.848G>A; c.842G>A; c.848G>A | p.Arg283His; p.Arg281His; p.Arg283His | FALSE | 1.94E-05 |
| 22:29137558:G:A | ENST00000400335; ENST00000407188; ENST00000327813 | c.848G>A; c.842G>A; c.848G>A | p.Arg283His; p.Arg281His; p.Arg283His | FALSE | 0.000113071 |
| 22:29098878:G:A | ENST00000400335; ENST00000407188; ENST00000327813 | c.277G>A; c.271G>A; c.277G>A | p.Val93Met; p.Val91Met; p.Val93Met | FALSE | 8.46E-06 |
| 22:29098878:G:A | ENST00000400335; ENST00000407188; ENST00000327813 | c.277G>A; c.271G>A; c.277G>A | p.Val93Met; p.Val91Met; p.Val93Met | FALSE | 5.80E-06 |
| 22:29098878:G:A | ENST00000400335; ENST00000407188; ENST00000327813 | c.277G>A; c.271G>A; c.277G>A | p.Val93Met; p.Val91Met; p.Val93Met | FALSE | 1.30E-05 |
| 22:29094276:G:A | ENST00000400335; ENST00000407188; ENST00000327813 | c.116G>A; c.110G>A; c.116G>A | p.Gly39Asp; p.Gly37Asp; p.Gly39Asp | FALSE | 9.27E-06 |
| 22:29094276:G:A | ENST00000400335; ENST00000407188; ENST00000327813 | c.116G>A; c.110G>A; c.116G>A | p.Gly39Asp; p.Gly37Asp; p.Gly39Asp | FALSE | 6.48E-06 |
| 22:29125415:TAGTG:T | ENST00000400335; ENST00000407188; ENST00000327813 | c.631_631+3delAGTG; c.625_625+3delAGTG; c.631_631+3delAGTG | p.Thr211fs; p.Thr209fs; p.Thr211fs | TRUE | 6.48E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29137654:G:T | ENST00000400335; ENST00000407188; ENST00000327813 | c.944G>T; c.938G>T; c.944G>T | p.Gly315Val; p.Gly313Val; p.Gly315Val | FALSE | 1.16E-06 |
| 22:29137650:C:T | ENST00000400335; ENST00000407188; ENST00000327813 | c.940C>T; c.934C>T; c.940C>T | p.Gln314*; p.Gln312*; p.Gln314* | TRUE | 1.16E-06 |
| 22:29137650:C:T | ENST00000400335; ENST00000407188; ENST00000327813 | c.940C>T; c.934C>T; c.940C>T | p.Gln314*; p.Gln312*; p.Gln314* | TRUE | 9.27E-05 |
| 22:29137539:ACC:A | ENST00000400335; ENST00000407188; ENST00000327813 | c.831_832delCC; c.825_826delCC; c.831_832delCC | p.His278fs; p.His276fs; p.His278fs | TRUE | 1.69E-05 |
| 22:29137539:ACC:A | ENST00000400335; ENST00000407188; ENST00000327813 | c.831_832delCC; c.825_826delCC; c.831_832delCC | p.His278fs; p.His276fs; p.His278fs | TRUE | 6.48E-06 |
| 22:29137539:ACC:A | ENST00000400335; ENST00000407188; ENST00000327813 | c.831_832delCC; c.825_826delCC; c.831_832delCC | p.His278fs; p.His276fs; p.His278fs | TRUE | 6.95E-06 |
| 22:29140311:C:T | ENST00000400335; ENST00000407188; ENST00000327813 | c.1153C>T; c.1198C>T; c.1204C>T | p.Leu385Phe; p.Leu400Phe; p.Leu402Phe | FALSE | 1.04E-05 |
| 22:29140311:C:T | ENST00000400335; ENST00000407188; ENST00000327813 | c.1153C>T; c.1198C>T; c.1204C>T | p.Leu385Phe; p.Leu400Phe; p.Leu402Phe | FALSE | 2.59E-05 |
| 22:29140311:C:T | ENST00000400335; ENST00000407188; ENST00000327813 | c.1153C>T; c.1198C>T; c.1204C>T | p.Leu385Phe; p.Leu400Phe; p.Leu402Phe | FALSE | 4.23E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29140311:C:T | ENST00000400335; ENST00000407188; ENST00000327813 | c.1153C>T; c.1198C>T; c.1204C>T | p.Leu385Phe; p.Leu400Phe; p.Leu402Phe | FALSE | 6.87E-05 |
| 22:29121371:G:C | ENST00000400335; ENST00000407188; ENST00000327813 | c.367G>C; c.361G>C; c.367G>C | p.Gly123Arg; p.Gly121Arg; p.Gly123Arg | FALSE | 1.16E-06 |
| 22:29125368:G:T | ENST00000400335; ENST00000407188; ENST00000327813 | c.583G>T; c.577G>T; c.583G>T | p.Asp195Tyr; p.Asp193Tyr; p.Asp195Tyr | FALSE | 7.53E-05 |
| 22:29125368:G:T | ENST00000400335; ENST00000407188; ENST00000327813 | c.583G>T; c.577G>T; c.583G>T | p.Asp195Tyr; p.Asp193Tyr; p.Asp195Tyr | FALSE | 1.69E-05 |
| 22:29138740:G:C | ENST00000400335; ENST00000407188; ENST00000327813 | c.1081G>C; c.1075G>C; c.1081G>C | p.Val361Leu; p.Val359Leu; p.Val361Leu | FALSE | 1.62E-05 |
| 22:29073228:G:A | ENST00000400335; ENST00000327813 | c.97+1G>A; c.97+1G>A | | TRUE | 1.16E-06 |
| 22:29121465:G:A | ENST00000400335; ENST00000407188; ENST00000327813 | c.461G>A; c.455G>A; c.461G>A | p.Arg154Gln; p.Arg152Gln; p.Arg154Gln | FALSE | 0.000110035 |
| 22:29121465:G:A | ENST00000400335; ENST00000407188; ENST00000327813 | c.461G>A; c.455G>A; c.461G>A | p.Arg154Gln; p.Arg152Gln; p.Arg154Gln | FALSE | 4.64E-05 |
| 22:29121465:G:A | ENST00000400335; ENST00000407188; ENST00000327813 | c.461G>A; c.455G>A; c.461G>A | p.Arg154Gln; p.Arg152Gln; p.Arg154Gln | FALSE | 6.87E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29121465:G:A | ENST00000400335; ENST00000407188; ENST00000327813 | c.461G>A; c.455G>A; c.461G>A | p.Arg154Gln; p.Arg152Gln; p.Arg154Gln | FALSE | 0.00010363 |
| 22:29121465:G:A | ENST00000400335; ENST00000407188; ENST00000327813 | c.461G>A; c.455G>A; c.461G>A | p.Arg154Gln; p.Arg152Gln; p.Arg154Gln | FALSE | 0.00020979 |
| 22:29121465:G:A | ENST00000400335; ENST00000407188; ENST00000327813 | c.461G>A; c.455G>A; c.461G>A | p.Arg154Gln; p.Arg152Gln; p.Arg154Gln | FALSE | 0.000565355 |
| 22:29098885:C:T | ENST00000400335; ENST00000407188; ENST00000327813 | c.284C>T; c.278C>T; c.284C>T | p.Pro95Leu; p.Pro93Leu; p.Pro95Leu | FALSE | 8.46E-06 |
| 22:29098885:C:T | ENST00000400335; ENST00000407188; ENST00000327813 | c.284C>T; c.278C>T; c.284C>T | p.Pro95Leu; p.Pro93Leu; p.Pro95Leu | FALSE | 6.48E-06 |
| 22:29098885:C:T | ENST00000400335; ENST00000407188; ENST00000327813 | c.284C>T; c.278C>T; c.284C>T | p.Pro95Leu; p.Pro93Leu; p.Pro95Leu | FALSE | 1.16E-05 |
| 22:29121464:C:T | ENST00000400335; ENST00000407188; ENST00000327813 | c.460C>T; c.454C>T; c.460C>T | p.Arg154Trp; p.Arg152Trp; p.Arg154Trp | FALSE | 7.62E-05 |
| 22:29121464:C:T | ENST00000400335; ENST00000407188; ENST00000327813 | c.460C>T; c.454C>T; c.460C>T | p.Arg154Trp; p.Arg152Trp; p.Arg154Trp | FALSE | 4.64E-05 |
| 22:29121464:C:T | ENST00000400335; ENST00000407188; ENST00000327813 | c.460C>T; c.454C>T; c.460C>T | p.Arg154Trp; p.Arg152Trp; p.Arg154Trp | FALSE | 6.87E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29121464:C:T | ENST00000400335; ENST00000407188; ENST00000327813 | c.460C>T; c.454C>T; c.460C>T | p.Arg154Trp; p.Arg152Trp; p.Arg154Trp | FALSE | 4.75E-05 |
| 22:29121464:C:T | ENST00000400335; ENST00000407188; ENST00000327813 | c.460C>T; c.454C>T; c.460C>T | p.Arg154Trp; p.Arg152Trp; p.Arg154Trp | FALSE | 9.07E-05 |
| 22:29121464:C:T | ENST00000400335; ENST00000407188; ENST00000327813 | c.460C>T; c.454C>T; c.460C>T | p.Arg154Trp; p.Arg152Trp; p.Arg154Trp | FALSE | 0.000113071 |
| 22:29142025:C:G | ENST00000400335; ENST00000407188; ENST00000327813 | c.1294C>G; c.1339C>G; c.1345C>G | p.Pro432Ala; p.Pro447Ala; p.Pro449Ala | FALSE | 1.16E-06 |
| 22:29098908:G:A | ENST00000400335; ENST00000407188; ENST00000327813 | c.307G>A; c.301G>A; c.307G>A | p.Glu103Lys; p.Glu101Lys; p.Glu103Lys | FALSE | 4.64E-05 |
| 22:29098908:G:A | ENST00000400335; ENST00000407188; ENST00000327813 | c.307G>A; c.301G>A; c.307G>A | p.Glu103Lys; p.Glu101Lys; p.Glu103Lys | FALSE | 6.87E-05 |
| 22:29098908:G:A | ENST00000400335; ENST00000407188; ENST00000327813 | c.307G>A; c.301G>A; c.307G>A | p.Glu103Lys; p.Glu101Lys; p.Glu103Lys | FALSE | 8.46E-06 |
| 22:29098908:G:A | ENST00000400335; ENST00000407188; ENST00000327813 | c.307G>A; c.301G>A; c.307G>A | p.Glu103Lys; p.Glu101Lys; p.Glu103Lys | FALSE | 3.89E-05 |
| 22:29098908:G:A | ENST00000400335; ENST00000407188; ENST00000327813 | c.307G>A; c.301G>A; c.307G>A | p.Glu103Lys; p.Glu101Lys; p.Glu103Lys | FALSE | 2.55E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29142005:GA:G | ENST00000400335; ENST00000407188; ENST00000327813 | c.1273delA; c.1318delA; c.1324delA | p.Ile425fs; p.Ile440fs; p.Ile442fs | TRUE | 1.16E-06 |
| 22:29138713:G:A | ENST00000400335; ENST00000407188; ENST00000327813 | c.1054G>A; c.1048G>A; c.1054G>A | p.Ala352Thr; p.Ala350Thr; p.Ala352Thr | FALSE | 0.000110106 |
| 22:29138713:G:A | ENST00000400335; ENST00000407188; ENST00000327813 | c.1054G>A; c.1048G>A; c.1054G>A | p.Ala352Thr; p.Ala350Thr; p.Ala352Thr | FALSE | 8.35E-05 |
| 22:29138713:G:A | ENST00000400335; ENST00000407188; ENST00000327813 | c.1054G>A; c.1048G>A; c.1054G>A | p.Ala352Thr; p.Ala350Thr; p.Ala352Thr | FALSE | 0.000226142 |
| 22:29138713:G:A | ENST00000400335; ENST00000407188; ENST00000327813 | c.1054G>A; c.1048G>A; c.1054G>A | p.Ala352Thr; p.Ala350Thr; p.Ala352Thr | FALSE | 0.000152356 |
| 22:29138713:G:A | ENST00000400335; ENST00000407188; ENST00000327813 | c.1054G>A; c.1048G>A; c.1054G>A | p.Ala352Thr; p.Ala350Thr; p.Ala352Thr | FALSE | 0.000185443 |
| 22:29138713:G:A | ENST00000400335; ENST00000407188; ENST00000327813 | c.1054G>A; c.1048G>A; c.1054G>A | p.Ala352Thr; p.Ala350Thr; p.Ala352Thr | FALSE | 6.87E-05 |
| 22:29138713:G:A | ENST00000400335; ENST00000407188; ENST00000327813 | c.1054G>A; c.1048G>A; c.1054G>A | p.Ala352Thr; p.Ala350Thr; p.Ala352Thr | FALSE | 0.000395026 |
| 22:29138818:A:AT | ENST00000407188; ENST00000327813 | c.1153_1154insT; c.1159_1160insT | p.Ser385fs; p.Ser387fs | TRUE | 5.80E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29138756:C:G | ENST00000400335; ENST00000407188; ENST00000327813 | c.1097C>G; c.1091C>G; c.1097C>G | p.Pro366Arg; p.Pro364Arg; p.Pro366Arg | FALSE | 6.48E-06 |
| 22:29167104:T:A | ENST00000327813 | c.1477T>A | p.Ter493Argext*? | TRUE | 1.16E-06 |
| 22:29094282:A:T | ENST00000400335; ENST00000407188; ENST00000327813 | c.122A>T; c.116A>T; c.122A>T | p.Asp41Val; p.Asp39Val; p.Asp41Val | FALSE | 1.16E-06 |
| 22:29121443:C:T | ENST00000400335; ENST00000407188; ENST00000327813 | c.439C>T; c.433C>T; c.439C>T | p.Gln147*; p.Gln145*; p.Gln147* | TRUE | 1.16E-06 |
| 22:29138759:G:T | ENST00000400335; ENST00000407188; ENST00000327813 | c.1100G>T; c.1094G>T; c.1100G>T | p.Ser367Ile; p.Ser365Ile; p.Ser367Ile | FALSE | 8.46E-06 |
| 22:29138765:C:T | ENST00000400335; ENST00000407188; ENST00000327813 | c.1106C>T; c.1100C>T; c.1106C>T | p.Pro369Leu; p.Pro367Leu; p.Pro369Leu | FALSE | 6.48E-06 |
| 22:29138765:C:T | ENST00000400335; ENST00000407188; ENST00000327813 | c.1106C>T; c.1100C>T; c.1106C>T | p.Pro369Leu; p.Pro367Leu; p.Pro369Leu | FALSE | 1.16E-06 |
| 22:29140308:C:G | ENST00000400335; ENST00000407188; ENST00000327813 | c.1150C>G; c.1195C>G; c.1201C>G | p.Leu384Val; p.Leu399Val; p.Leu401Val | FALSE | 8.46E-06 |
| 22:29140308:C:G | ENST00000400335; ENST00000407188; ENST00000327813 | c.1150C>G; c.1195C>G; c.1201C>G | p.Leu384Val; p.Leu399Val; p.Leu401Val | FALSE | 1.16E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29094257:G:T | ENST00000400335; ENST00000407188; ENST00000327813 | c.98-1G>T; c.92-1G>T; c.98-1G>T | | TRUE | 3.48E-06 |
| 22:29137524:C:T | ENST00000400335; ENST00000407188; ENST00000327813 | c.814C>T; c.808C>T; c.814C>T | p.Leu272Phe; p.Leu270Phe; p.Leu272Phe | FALSE | 4.29E-05 |
| 22:29094387:G:T | ENST00000400335; ENST00000407188; ENST00000327813 | c.227G>T; c.221G>T; c.227G>T | p.Gly76Val; p.Gly74Val; p.Gly76Val | FALSE | 6.48E-06 |
| 22:29125342:C:T | ENST00000400335; ENST00000407188; ENST00000327813 | c.557C>T; c.551C>T; c.557C>T | p.Thr186Ile; p.Thr184Ile; p.Thr186Ile | FALSE | 1.16E-06 |
| 22:29138717:C:T | ENST00000400335; ENST00000407188; ENST00000327813 | c.1058C>T; c.1052C>T; c.1058C>T | p.Ala353Val; p.Ala351Val; p.Ala353Val | FALSE | 1.16E-06 |
| 22:29098926:A:T | ENST00000400335; ENST00000407188; ENST00000327813 | c.325A>T; c.319A>T; c.325A>T | p.Lys109*; p.Lys107*; p.Lys109* | TRUE | 1.16E-06 |
| 22:29121405:T:A | ENST00000400335; ENST00000407188; ENST00000327813 | c.401T>A; c.395T>A; c.401T>A | p.Leu134Gln; p.Leu132Gln; p.Leu134Gln | FALSE | 1.16E-06 |
| 22:29098934:T:G | ENST00000400335; ENST00000407188; ENST00000327813 | c.333T>G; c.327T>G; c.333T>G | p.Cys111Trp; p.Cys109Trp; p.Cys111Trp | FALSE | 9.16E-05 |
| 22:29098934:T:G | ENST00000400335; ENST00000407188; ENST00000327813 | c.333T>G; c.327T>G; c.333T>G | p.Cys111Trp; p.Cys109Trp; p.Cys111Trp | FALSE | 9.72E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29098934:T:G | ENST00000400335; ENST00000407188; ENST00000327813 | c.333T>G; c.327T>G; c.333T>G | p.Cys111Trp; p.Cys109Trp; p.Cys111Trp | FALSE | 0.000206157 |
| 22:29098934:T:G | ENST00000400335; ENST00000407188; ENST00000327813 | c.333T>G; c.327T>G; c.333T>G | p.Cys111Trp; p.Cys109Trp; p.Cys111Trp | FALSE | 8.59E-05 |
| 22:29125267:C:T | ENST00000400335; ENST00000407188; ENST00000327813 | c.482C>T; c.476C>T; c.482C>T | p.Ala161Val; p.Ala159Val; p.Ala161Val | FALSE | 3.89E-05 |
| 22:29137351:G:A | ENST00000400335; ENST00000407188; ENST00000327813 | c.641G>A; c.635G>A; c.641G>A | p.Gly214Asp; p.Gly212Asp; p.Gly214Asp | FALSE | 1.16E-06 |
| 22:29137353:G:C | ENST00000400335; ENST00000407188; ENST00000327813 | c.643G>C; c.637G>C; c.643G>C | p.Ala215Pro; p.Ala213Pro; p.Ala215Pro | FALSE | 1.16E-06 |
| 22:29098924:G:C | ENST00000400335; ENST00000407188; ENST00000327813 | c.323G>C; c.317G>C; c.323G>C | p.Trp108Ser; p.Trp106Ser; p.Trp108Ser | FALSE | 4.64E-06 |
| 22:29140329:G:A | ENST00000400335; ENST00000407188; ENST00000327813 | c.1171G>A; c.1216G>A; c.1222G>A | p.Ala391Thr; p.Ala406Thr; p.Ala408Thr | FALSE | 1.16E-06 |
| 22:29098866:C:A | ENST00000400335; ENST00000407188; ENST00000327813 | c.265C>A; c.259C>A; c.265C>A | p.Pro89Thr; p.Pro87Thr; p.Pro89Thr | FALSE | 1.16E-06 |
| 22:29094296:CAG:C | ENST00000400335; ENST00000407188; ENST00000327813 | c.138_139delGA; c.132_133delGA; c.138_139delGA | p.Asn47fs; p.Asn45fs; p.Asn47fs | TRUE | 1.16E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29137359:G:A | ENST00000400335; ENST00000407188; ENST00000327813 | c.649G>A; c.643G>A; c.649G>A | p.Gly217Ser; p.Gly215Ser; p.Gly217Ser | FALSE | 4.64E-06 |
| 22:29137359:G:A | ENST00000400335; ENST00000407188; ENST00000327813 | c.649G>A; c.643G>A; c.649G>A | p.Gly217Ser; p.Gly215Ser; p.Gly217Ser | FALSE | 6.48E-06 |
| 22:29137359:G:A | ENST00000400335; ENST00000407188; ENST00000327813 | c.649G>A; c.643G>A; c.649G>A | p.Gly217Ser; p.Gly215Ser; p.Gly217Ser | FALSE | 1.72E-05 |
| 22:29142019:T:G | ENST00000400335; ENST00000407188; ENST00000327813 | c.1284T>G; c.1329T>G; c.1335T>G | p.Ile428Met; p.Ile443Met; p.Ile445Met | FALSE | 3.48E-06 |
| 22:29125417:G:T | ENST00000400335; ENST00000407188; ENST00000327813 | c.631+1G>T; c.625+1G>T; c.631+1G>T | | TRUE | 1.30E-05 |
| 22:29125417:G:T | ENST00000400335; ENST00000407188; ENST00000327813 | c.631+1G>T; c.625+1G>T; c.631+1G>T | | TRUE | 0.000113071 |
| 22:29125417:G:T | ENST00000400335; ENST00000407188; ENST00000327813 | c.631+1G>T; c.625+1G>T; c.631+1G>T | | TRUE | 8.46E-06 |
| 22:29125417:G:T | ENST00000400335; ENST00000407188; ENST00000327813 | c.631+1G>T; c.625+1G>T; c.631+1G>T | | TRUE | 4.64E-05 |
| 22:29125417:G:T | ENST00000400335; ENST00000407188; ENST00000327813 | c.631+1G>T; c.625+1G>T; c.631+1G>T | | TRUE | 9.74E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29121423:C:T | ENST00000400335; ENST00000407188; ENST00000327813 | c.419C>T; c.413C>T; c.419C>T | p.Thr140Met; p.Thr138Met; p.Thr140Met | FALSE | 3.48E-05 |
| 22:29098869:G:C | ENST00000400335; ENST00000407188; ENST00000327813 | c.268G>C; c.262G>C; c.268G>C | p.Asp90His; p.Asp88His; p.Asp90His | FALSE | 4.64E-05 |
| 22:29098869:G:C | ENST00000400335; ENST00000407188; ENST00000327813 | c.268G>C; c.262G>C; c.268G>C | p.Asp90His; p.Asp88His; p.Asp90His | FALSE | 2.32E-06 |
| 22:29121444:A:T | ENST00000400335; ENST00000407188; ENST00000327813 | c.440A>T; c.434A>T; c.440A>T | p.Gln147Leu; p.Gln145Leu; p.Gln147Leu | FALSE | 2.32E-05 |
| 22:29137633:A:T | ENST00000400335; ENST00000407188; ENST00000327813 | c.923A>T; c.917A>T; c.923A>T | p.Asp308Val; p.Asp306Val; p.Asp308Val | FALSE | 7.62E-05 |
| 22:29137633:A:T | ENST00000400335; ENST00000407188; ENST00000327813 | c.923A>T; c.917A>T; c.923A>T | p.Asp308Val; p.Asp306Val; p.Asp308Val | FALSE | 0.000185443 |
| 22:29137633:A:T | ENST00000400335; ENST00000407188; ENST00000327813 | c.923A>T; c.917A>T; c.923A>T | p.Asp308Val; p.Asp306Val; p.Asp308Val | FALSE | 3.44E-05 |
| 22:29137633:A:T | ENST00000400335; ENST00000407188; ENST00000327813 | c.923A>T; c.917A>T; c.923A>T | p.Asp308Val; p.Asp306Val; p.Asp308Val | FALSE | 7.77E-05 |
| 22:29137633:A:T | ENST00000400335; ENST00000407188; ENST00000327813 | c.923A>T; c.917A>T; c.923A>T | p.Asp308Val; p.Asp306Val; p.Asp308Val | FALSE | 5.22E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29137633:A:T | ENST00000400335; ENST00000407188; ENST00000327813 | c.923A>T; c.917A>T; c.923A>T | p.Asp308Val; p.Asp306Val; p.Asp308Val | FALSE | 0.000113071 |
| 22:29094282:A:G | ENST00000400335; ENST00000407188; ENST00000327813 | c.122A>G; c.116A>G; c.122A>G | p.Asp41Gly; p.Asp39Gly; p.Asp41Gly | FALSE | 8.46E-06 |
| 22:29094282:A:G | ENST00000400335; ENST00000407188; ENST00000327813 | c.122A>G; c.116A>G; c.122A>G | p.Asp41Gly; p.Asp39Gly; p.Asp41Gly | FALSE | 6.87E-05 |
| 22:29094282:A:G | ENST00000400335; ENST00000407188; ENST00000327813 | c.122A>G; c.116A>G; c.122A>G | p.Asp41Gly; p.Asp39Gly; p.Asp41Gly | FALSE | 4.64E-06 |
| 22:29094282:A:G | ENST00000400335; ENST00000407188; ENST00000327813 | c.122A>G; c.116A>G; c.122A>G | p.Asp41Gly; p.Asp39Gly; p.Asp41Gly | FALSE | 6.48E-06 |
| 22:29138716:G:T | ENST00000400335; ENST00000407188; ENST00000327813 | c.1057G>T; c.1051G>T; c.1057G>T | p.Ala353Ser; p.Ala351Ser; p.Ala353Ser | FALSE | 1.30E-05 |
| 22:29138716:G:T | ENST00000400335; ENST00000407188; ENST00000327813 | c.1057G>T; c.1051G>T; c.1057G>T | p.Ala353Ser; p.Ala351Ser; p.Ala353Ser | FALSE | 4.64E-06 |
| 22:29140294:A:G | ENST00000400335; ENST00000407188; ENST00000327813 | c.1136A>G; c.1181A>G; c.1187A>G | p.Tyr379Cys; p.Tyr394Cys; p.Tyr396Cys | FALSE | 6.87E-05 |
| 22:29140294:A:G | ENST00000400335; ENST00000407188; ENST00000327813 | c.1136A>G; c.1181A>G; c.1187A>G | p.Tyr379Cys; p.Tyr394Cys; p.Tyr396Cys | FALSE | 9.27E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29140294:A:G | ENST00000400335; ENST00000407188; ENST00000327813 | c.1136A>G; c.1181A>G; c.1187A>G | p.Tyr379Cys; p.Tyr394Cys; p.Tyr396Cys | FALSE | 1.30E-05 |
| 22:29094269:GC:G | ENST00000400335; ENST00000407188; ENST00000327813 | c.111delC; c.105delC; c.111delC | p.Asn38fs; p.Asn36fs; p.Asn38fs | TRUE | 6.48E-06 |
| 22:29125389:G:A | ENST00000400335; ENST00000407188; ENST00000327813 | c.604G>A; c.598G>A; c.604G>A | p.Gly202Ser; p.Gly200Ser; p.Gly202Ser | FALSE | 1.16E-06 |
| 22:29137540:C:T | ENST00000400335; ENST00000407188; ENST00000327813 | c.830C>T; c.824C>T; c.830C>T | p.Thr277Ile; p.Thr275Ile; p.Thr277Ile | FALSE | 2.20E-05 |
| 22:29137540:C:T | ENST00000400335; ENST00000407188; ENST00000327813 | c.830C>T; c.824C>T; c.830C>T | p.Thr277Ile; p.Thr275Ile; p.Thr277Ile | FALSE | 6.48E-06 |
| 22:29094389:G:C | ENST00000400335; ENST00000407188; ENST00000327813 | c.229G>C; c.223G>C; c.229G>C | p.Glu77Gln; p.Glu75Gln; p.Glu77Gln | FALSE | 3.44E-05 |
| 22:29098940:A:G | ENST00000400335; ENST00000407188; ENST00000327813 | c.339A>G; c.333A>G; c.339A>G | p.Ile113Met; p.Ile111Met; p.Ile113Met | FALSE | 1.27E-05 |
| 22:29098939:T:C | ENST00000400335; ENST00000407188; ENST00000327813 | c.338T>C; c.332T>C; c.338T>C | p.Ile113Thr; p.Ile111Thr; p.Ile113Thr | FALSE | 1.16E-06 |
| 22:29121428:A:C | ENST00000400335; ENST00000407188; ENST00000327813 | c.424A>C; c.418A>C; c.424A>C | p.Asn142His; p.Asn140His; p.Asn142His | FALSE | 1.16E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29121428:A:C | ENST00000400335; ENST00000407188; ENST00000327813 | c.424A>C; c.418A>C; c.424A>C | p.Asn142His; p.Asn140His; p.Asn142His | FALSE | 8.46E-06 |
| 22:29137350:G:T | ENST00000400335; ENST00000407188; ENST00000327813 | c.640G>T; c.634G>T; c.640G>T | p.Gly214Cys; p.Gly212Cys; p.Gly214Cys | FALSE | 6.48E-06 |
| 22:29137350:G:T | ENST00000400335; ENST00000407188; ENST00000327813 | c.640G>T; c.634G>T; c.640G>T | p.Gly214Cys; p.Gly212Cys; p.Gly214Cys | FALSE | 8.46E-06 |
| 22:29138770:C:T | ENST00000400335; ENST00000407188; ENST00000327813 | c.1111C>T; c.1105C>T; c.1111C>T | p.Gln371*; p.Gln369*; p.Gln371* | TRUE | 1.16E-06 |
| 22:29073134:G:GCGCCGCC | ENST00000400335; ENST00000407188; ENST00000327813 | c.5_11dupCGCCGCC; c.5_11dupCGCCGCC; c.5_11dupCGCCGCC | p.Arg7fs; p.Arg7fs; p.Arg7fs | TRUE | 2.32E-06 |
| 22:29140284:T:C | ENST00000400335; ENST00000407188; ENST00000327813 | c.1126T>C; c.1171T>C; c.1177T>C | p.Trp376Arg; p.Trp391Arg; p.Trp393Arg | FALSE | 1.16E-06 |
| 22:29137404:T:C | ENST00000400335; ENST00000407188; ENST00000327813 | c.694T>C; c.688T>C; c.694T>C | p.Phe232Leu; p.Phe230Leu; p.Phe232Leu | FALSE | 5.80E-06 |
| 22:29137552:T:C | ENST00000400335; ENST00000407188; ENST00000327813 | c.842T>C; c.836T>C; c.842T>C | p.Leu281Pro; p.Leu279Pro; p.Leu281Pro | FALSE | 0.0001374 |
| 22:29094362:T:C | ENST00000400335; ENST00000407188; ENST00000327813 | c.202T>C; c.196T>C; c.202T>C | p.Tyr68His; p.Tyr66His; p.Tyr68His | FALSE | 1.04E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29094362:T:C | ENST00000400335; ENST00000407188; ENST00000327813 | c.202T>C; c.196T>C; c.202T>C | p.Tyr68His; p.Tyr66His; p.Tyr68His | FALSE | 3.89E-05 |
| 22:29094362:T:C | ENST00000400335; ENST00000407188; ENST00000327813 | c.202T>C; c.196T>C; c.202T>C | p.Tyr68His; p.Tyr66His; p.Tyr68His | FALSE | 8.46E-06 |
| 22:29094362:T:C | ENST00000400335; ENST00000407188; ENST00000327813 | c.202T>C; c.196T>C; c.202T>C | p.Tyr68His; p.Tyr66His; p.Tyr68His | FALSE | 4.64E-05 |
| 22:29094362:T:C | ENST00000400335; ENST00000407188; ENST00000327813 | c.202T>C; c.196T>C; c.202T>C | p.Tyr68His; p.Tyr66His; p.Tyr68His | FALSE | 1.72E-05 |
| 22:29125385:T:G | ENST00000400335; ENST00000407188; ENST00000327813 | c.600T>G; c.594T>G; c.600T>G | p.Cys200Trp; p.Cys198Trp; p.Cys200Trp | FALSE | 6.48E-06 |
| 22:29094333:T:G | ENST00000400335; ENST00000407188; ENST00000327813 | c.173T>G; c.167T>G; c.173T>G | p.Leu58Arg; p.Leu56Arg; p.Leu58Arg | FALSE | 1.16E-06 |
| 22:29121443:C:A | ENST00000400335; ENST00000407188; ENST00000327813 | c.439C>A; c.433C>A; c.439C>A | p.Gln147Lys; p.Gln145Lys; p.Gln147Lys | FALSE | 1.72E-05 |
| 22:29137498:T:C | ENST00000400335; ENST00000407188; ENST00000327813 | c.788T>C; c.782T>C; c.788T>C | p.Ile263Thr; p.Ile261Thr; p.Ile263Thr | FALSE | 8.46E-06 |
| 22:29137498:T:C | ENST00000400335; ENST00000407188; ENST00000327813 | c.788T>C; c.782T>C; c.788T>C | p.Ile263Thr; p.Ile261Thr; p.Ile263Thr | FALSE | 6.48E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29137498:T:C | ENST00000400335; ENST00000407188; ENST00000327813 | c.788T>C; c.782T>C; c.788T>C | p.Ile263Thr; p.Ile261Thr; p.Ile263Thr | FALSE | 1.16E-06 |
| 22:29073133:G:T | ENST00000400335; ENST00000407188; ENST00000327813 | c.3G>T; c.3G>T; c.3G>T | p.Met1?; p.Met1?; p.Met1? | TRUE | 1.16E-06 |
| 22:29098922:C:A | ENST00000400335; ENST00000407188; ENST00000327813 | c.321C>A; c.315C>A; c.321C>A | p.Tyr107*; p.Tyr105*; p.Tyr107* | TRUE | 1.16E-06 |
| 22:29137530:G:T | ENST00000400335; ENST00000407188; ENST00000327813 | c.820G>T; c.814G>T; c.820G>T | p.Asp274Tyr; p.Asp272Tyr; p.Asp274Tyr | FALSE | 6.48E-06 |
| 22:29125270:G:A | ENST00000400335; ENST00000407188; ENST00000327813 | c.485G>A; c.479G>A; c.485G>A | p.Gly162Glu; p.Gly160Glu; p.Gly162Glu | FALSE | 2.43E-05 |
| 22:29125270:G:A | ENST00000400335; ENST00000407188; ENST00000327813 | c.485G>A; c.479G>A; c.485G>A | p.Gly162Glu; p.Gly160Glu; p.Gly162Glu | FALSE | 6.48E-06 |
| 22:29125282:G:T | ENST00000400335; ENST00000407188; ENST00000327813 | c.497G>T; c.491G>T; c.497G>T | p.Gly166Val; p.Gly164Val; p.Gly166Val | FALSE | 1.16E-06 |
| 22:29125282:G:T | ENST00000400335; ENST00000407188; ENST00000327813 | c.497G>T; c.491G>T; c.497G>T | p.Gly166Val; p.Gly164Val; p.Gly166Val | FALSE | 3.44E-05 |
| 22:29138676:CG:C | ENST00000400335; ENST00000407188; ENST00000327813 | c.1018delG; c.1012delG; c.1018delG | p.Glu340fs; p.Glu338fs; p.Glu340fs | TRUE | 2.54E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29121383:G:A | ENST00000400335; ENST00000407188; ENST00000327813 | c.379G>A; c.373G>A; c.379G>A | p.Asp127Asn; p.Asp125Asn; p.Asp127Asn | FALSE | 1.16E-06 |
| 22:29125344:G:A | ENST00000400335; ENST00000407188; ENST00000327813 | c.559G>A; c.553G>A; c.559G>A | p.Glu187Lys; p.Glu185Lys; p.Glu187Lys | FALSE | 0.000211606 |
| 22:29125344:G:A | ENST00000400335; ENST00000407188; ENST00000327813 | c.559G>A; c.553G>A; c.559G>A | p.Glu187Lys; p.Glu185Lys; p.Glu187Lys | FALSE | 4.64E-05 |
| 22:29125344:G:A | ENST00000400335; ENST00000407188; ENST00000327813 | c.559G>A; c.553G>A; c.559G>A | p.Glu187Lys; p.Glu185Lys; p.Glu187Lys | FALSE | 0.000206157 |
| 22:29125344:G:A | ENST00000400335; ENST00000407188; ENST00000327813 | c.559G>A; c.553G>A; c.559G>A | p.Glu187Lys; p.Glu185Lys; p.Glu187Lys | FALSE | 0.000480901 |
| 22:29125344:G:A | ENST00000400335; ENST00000407188; ENST00000327813 | c.559G>A; c.553G>A; c.559G>A | p.Glu187Lys; p.Glu185Lys; p.Glu187Lys | FALSE | 0.000226693 |
| 22:29125344:G:A | ENST00000400335; ENST00000407188; ENST00000327813 | c.559G>A; c.553G>A; c.559G>A | p.Glu187Lys; p.Glu185Lys; p.Glu187Lys | FALSE | 0.00011127 |
| 22:29125344:G:A | ENST00000400335; ENST00000407188; ENST00000327813 | c.559G>A; c.553G>A; c.559G>A | p.Glu187Lys; p.Glu185Lys; p.Glu187Lys | FALSE | 0.000339213 |
| 22:29094281:G:C | ENST00000400335; ENST00000407188; ENST00000327813 | c.121G>C; c.115G>C; c.121G>C | p.Asp41His; p.Asp39His; p.Asp41His | FALSE | 2.32E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29138677:G:A | ENST00000400335; ENST00000407188; ENST00000327813 | c.1018G>A; c.1012G>A; c.1018G>A | p.Glu340Lys; p.Glu338Lys; p.Glu340Lys | FALSE | 1.30E-05 |
| 22:29138677:G:A | ENST00000400335; ENST00000407188; ENST00000327813 | c.1018G>A; c.1012G>A; c.1018G>A | p.Glu340Lys; p.Glu338Lys; p.Glu340Lys | FALSE | 4.64E-05 |
| 22:29138677:G:A | ENST00000400335; ENST00000407188; ENST00000327813 | c.1018G>A; c.1012G>A; c.1018G>A | p.Glu340Lys; p.Glu338Lys; p.Glu340Lys | FALSE | 6.87E-05 |
| 22:29138677:G:A | ENST00000400335; ENST00000407188; ENST00000327813 | c.1018G>A; c.1012G>A; c.1018G>A | p.Glu340Lys; p.Glu338Lys; p.Glu340Lys | FALSE | 1.04E-05 |
| 22:29138677:G:A | ENST00000400335; ENST00000407188; ENST00000327813 | c.1018G>A; c.1012G>A; c.1018G>A | p.Glu340Lys; p.Glu338Lys; p.Glu340Lys | FALSE | 8.47E-06 |
| 22:29073186:CG:C | ENST00000400335; ENST00000407188; ENST00000327813 | c.58delG; c.58delG; c.58delG | p.Ala20fs; p.Ala20fs; p.Ala20fs | TRUE | 1.30E-05 |
| 22:29141987:C:T | ENST00000400335; ENST00000407188; ENST00000327813 | c.1252C>T; c.1297C>T; c.1303C>T | p.Gln418*; p.Gln433*; p.Gln435* | TRUE | 2.32E-06 |
| 22:29098920:T:C | ENST00000400335; ENST00000407188; ENST00000327813 | c.319T>C; c.313T>C; c.319T>C | p.Tyr107His; p.Tyr105His; p.Tyr107His | FALSE | 1.94E-05 |
| 22:29137671:C:T | ENST00000400335; ENST00000407188; ENST00000327813 | c.961C>T; c.955C>T; c.961C>T | p.Gln321*; p.Gln319*; p.Gln321* | TRUE | 4.64E-06 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29167043:G:A | ENST00000327813 | c.1417-1G>A | | TRUE | 9.27E-06 |
| 22:29098884:C:T | ENST00000400335; ENST00000407188; ENST00000327813 | c.283C>T; c.277C>T; c.283C>T | p.Pro95Ser; p.Pro93Ser; p.Pro95Ser | FALSE | 1.51E-05 |
| 22:29121372:G:T | ENST00000400335; ENST00000407188; ENST00000327813 | c.368G>T; c.362G>T; c.368G>T | p.Gly123Val; p.Gly121Val; p.Gly123Val | FALSE | 1.85E-05 |
| 22:29125396:G:A | ENST00000400335; ENST00000407188; ENST00000327813 | c.611G>A; c.605G>A; c.611G>A | p.Gly204Asp; p.Gly202Asp; p.Gly204Asp | FALSE | 2.32E-06 |
| 22:29094291:G:C | ENST00000400335; ENST00000407188; ENST00000327813 | c.131G>C; c.125G>C; c.131G>C | p.Gly44Ala; p.Gly42Ala; p.Gly44Ala | FALSE | 1.69E-05 |
| 22:29094291:G:C | ENST00000400335; ENST00000407188; ENST00000327813 | c.131G>C; c.125G>C; c.131G>C | p.Gly44Ala; p.Gly42Ala; p.Gly44Ala | FALSE | 1.30E-05 |
| 22:29098870:A:G | ENST00000400335; ENST00000407188; ENST00000327813 | c.269A>G; c.263A>G; c.269A>G | p.Asp90Gly; p.Asp88Gly; p.Asp90Gly | FALSE | 1.72E-05 |
| 22:29138755:C:G | ENST00000400335; ENST00000407188; ENST00000327813 | c.1096C>G; c.1090C>G; c.1096C>G | p.Pro366Ala; p.Pro364Ala; p.Pro366Ala | FALSE | 1.16E-06 |
| 22:29094348:CTT:C | ENST00000400335; ENST00000407188; ENST00000327813 | c.190_191delTT; c.184_185delTT; c.190_191delTT | p.Phe64fs; p.Phe62fs; p.Phe64fs | TRUE | 1.16E-06 |
| 22:29094390:A:AG | ENST00000400335; ENST00000407188; ENST00000327813 | c.236dupG; c.230dupG; c.236dupG | p.Leu80fs; p.Leu78fs; p.Leu80fs | TRUE | 4.64E-05 |

Figure 3 (cont.)

| Genomic coordinates and alleles for genetic variant | Transcript(s) | Coding DNA change | Protein change | Variant classified as pLOF | AAF, fraction of 1 |
|---|---|---|---|---|---|
| 22:29125383:T:C | ENST00000400335; ENST00000407188; ENST00000327813 | c.598T>C; c.592T>C; c.598T>C | p.Cys200Arg; p.Cys198Arg; p.Cys200Arg | FALSE | 1.16E-06 |
| 22:29138753:G:T | ENST00000400335; ENST00000407188; ENST00000327813 | c.1094G>T; c.1088G>T; c.1094G>T | p.Ser365Ile; p.Ser363Ile; p.Ser365Ile | FALSE | 1.16E-06 |
| 22:29125296:T:C | ENST00000400335; ENST00000407188; ENST00000327813 | c.511T>C; c.505T>C; c.511T>C | p.Cys171Arg; p.Cys169Arg; p.Cys171Arg | FALSE | 2.32E-06 |
| 22:29142029:C:T | ENST00000400335; ENST00000407188; ENST00000327813 | c.1294C>T; c.1339C>T; c.1345C>T | p.Pro432Ser; p.Pro447Ser; p.Pro449Ser | FALSE | 8.46E-06 |
| 22:29142029:C:T | ENST00000400335; ENST00000407188; ENST00000327813 | c.1294C>T; c.1339C>T; c.1345C>T | p.Pro432Ser; p.Pro447Ser; p.Pro449Ser | FALSE | 4.64E-05 |
| 22:29142077:C:T | ENST00000400335; ENST00000407188; ENST00000327813 | c.1342C>T; c.1387C>T; c.1393C>T | p.Gln448*; p.Gln463*; p.Gln465* | TRUE | 1.16E-06 |
| 22:29137668:T:C | ENST00000400335; ENST00000407188; ENST00000327813 | c.958T>C; c.952T>C; c.958T>C | p.Tyr320His; p.Tyr318His; p.Tyr320His | FALSE | 1.16E-06 |

Figure 3 (cont.)

SEQUENCE LISTING

<160> NUMBER OF SEQ ID NOS: 36

<210> SEQ ID NO 1
<211> LENGTH: 95216
<212> TYPE: DNA
<213> ORGANISM: homo sapien

<400> SEQUENCE: 1

```
gcactgacgg cccatggcgc cgccagccgc ccgcctcgcc ctgctctccg ccgcggcgct     60
cacgctggcg gcccggcccg cgcctagccc cggcctcggc cccggacccg gtgagtgtga    120
gcgacccccc gccgcccgcc ctgagcggag cccactcgag gggcgacaag ggccggccgg    180
cctgagagcc ccctccctcc cgcttcagga ccttccgggc cccttcccct cgcccctagg    240
cgacgcccct caggccggga tggtcccttc ctgggacccg ggctaccccc aggcccgtca    300
tcgacgcccc cgggcccggt actgtccccc ggctgcagga cccggtgctc ctcagcgacg    360
cccctcagcc caggaggccc tctccgcctt gagtcttcca agaccctctg cgacgccccc    420
cgggctggga catcttctct gtctcgggat ctgggacccg ctgcccgagt ccctcagcga    480
ccccaaccag gccgggacgc cccctctccc cggtacctcc tgggatcccg tcccaagtcc    540
ccagcgactt cccccgggcc gggacgtcct ctgctccccg gtacctccta ggatcccgtc    600
ccaaaatccc cagcgactcc ccacgggcca ggaggccccc tgctccccgg tacctcctgg    660
gatcccgtcc ccaagtcccc agcgacccct cccgggccgg gacgacccct gctccccagt    720
acctcctggg atcccgcccc aagtccttca tcgacgcacc ttgcaccggg acgactcccc    780
cgctacaaga ggctatacgc ccctctccga gacctccagc gacatccctc ccctgggcca    840
aggtcccctc cctgagcctc actgcgacgc ccccgcgtcc cccagtcctc tcctcccgcc    900
tacaccggtg gaacccggcg cctccccgcg cagagcagag cggaggcggg aggagccggc    960
gctcagcccc ttttcccgag tcctcggctg cacccgcttg gcggacatta taacttctgc   1020
ctcgcgagga acgggatgga cttgttcgcc ctgctagagg caggttaggg tcctgggacg   1080
accttgtacc cagacggacg ggacgtgccc tctctctccg ctgggccgct ttgaacttcc   1140
ctatgactca ggtgatggcg cagaaggggg agagaaaaaa ggaagcagtg atgggaaact   1200
tctccccaac tgagtttagg gtgctcttcc tgagggtgca acgccgagct ccgtgttttg   1260
ggtcagccca caccttagac aggtcactca ctacccaggc caaggccaag gccaggtctt   1320
cccgaggtga ggccctggac caggatgaag cttggctttt gcttaacttc cacacgcaac   1380
cttgtagccg aatcctttct aagtggaaga gaaggcaaga gggcgttgca tttctctgca   1440
ggctgtttgg gtgttgagca taggccattt gtgaaaggga tgggaagagt ttattaccag   1500
tctgcaggag taggaaaacc cgcctctggg ttctccaccc aaagtcacag actgatgttg   1560
gaaaggatgg gattttgctg gtgtaagaaa actcagagtt gctttgttta ctcattggct   1620
tggattagcg aaaaagctag gacttggtgt tgtcacttac tgggtgactt tgggccatgc   1680
cttcagctct ctgagcctca gtttcctcat ctgtaaagac aggataactt ctttgcagag   1740
tgttgtgaag attaaatgat atactgtagg taacataccc gcatatagga gggagtcaat   1800
aaacatattt taataatact tttatagggc ctcacagttc atcgagtgct agacacctca   1860
tttaccctgg gaatgctaag agctttcggt ctgattcatt tctgtaaaag gctaagcttg   1920
gctttaaatt agtagaactg gggtctccaa gtgttgtaaa cctgaggctc agtaagtggt   1980
ttctgagtga tcaccgtctt ttatgggact tctacagtat gatcacttct actgttgtga   2040
ggagtgaggg acattccgag agccaggata tgtcaacatg actgtaacct ggtaacccct   2100
```

```
tagctccact ttgctatctg tgtggtcagg gtttaatgtc ccctacaaag agagaggtat   2160
gggtggaaat agactggttc cccttctgga aagggcagag cagcagctct gatttgcatc   2220
aagtgagcca actctcctta agctcgttgg aagctagtct cttcccagat atctttgctt   2280
ttttaaggtc aaatgcagca tctcttatca agtttgcacc ccaaattttg gtgtactttt   2340
atttaggagt ctggggtagg ggcaaataat cgttgtgaaa taatttgtga taagtggccc   2400
aagttcccaa ctcactgagc cttgccagct tggtgcctta ccgtcctgat aactcagtgc   2460
tttgcttttt tgacttttcc tgtctagttg cagaagcaat tttagggaga taccccatgg   2520
tcttcaccaa cacatcctgt ctagatccta ctcactagct tttaaaatcc ttcccaataa   2580
aacacacaca catacacaca cacacataca cacacacact ttactctgag gatatgccaa   2640
acttgccatt ttatattttt tgatactgta attttctcta aaattttgtg gatggaaaaa   2700
attatttcaa tatttatatt ctgcacaatt ttgtaatatt taaattactg gtggtttgca   2760
tttttgaatg ctgactttat aaaaacagtt agctcattcc ccatcaatcc tacttctaat   2820
tacaatgtgt agccaacccc aaatgatctc ccttcttttc attcttcctc taagattctc   2880
ttccttcctt cacaactcat aagaaggaaa gtagaaggta atggaatcta gactttcctt   2940
caaggaggag tgcaaccagg gccatgtggt cgagaggttc tctgtagtag gtcccatctg   3000
gaatttatgg aatttatggt ctactcactt gagtatttta ctacctttag ggtctattag   3060
gtgcacatca acagagcttc tccactcagg ttatgtttgc tgtgaatacc ttttataagt   3120
ttatagactg atgctcattc tcctctacct cctcatctgg aatttgcccc actagccagt   3180
agtgtgtttg ccctaaaacc tatgagttca gttaacagct agagcttcat actgtctacc   3240
aattcttggt tctcttgggg acttcattaa tgctaataga attacctgta agcgacatgg   3300
gggctgaagc agtgaaggag tgaagggtgc ataccagtta cttgcatact ctgagtattt   3360
taagaaacac catttcgacc tgctatcaaa gacctctgat atttttgtga aaatatactt   3420
tagtccctag acaaaccatt taaatctttg aggccgggcg cggtggctca cacctgtaat   3480
cccagcattt tgggaggtca aggcagacgg atcacctgag gtcaggagtt caaggccagc   3540
ctggccaaca tggtgaaacc ccatctctac taaaaataca aaaaattagc cgggcatggt   3600
ggcacgtgcc tgtaatccca gctacttggg aggctaaggc aggagaatcg ctggaaccca   3660
ggaggcagag gtagcggtga gttgagatca caccattgca ctccagcctg ggcaataaga   3720
gcaaaactct gtttcaaaat aaacaaataa ataaaaagta tttgagatag gcaatgagtc   3780
cctttataaa tcttaaagca agaaagcatt ccttttaggc tcactactca taaacagaaa   3840
gttgatgcac ttcttgtata tcaatacaga tattattgat aaactcatgg tttagcatag   3900
ttagaccaaa agcaataaat gagtaagata aaatatattg ctttaaatag cttcacaata   3960
tacagattag ggatttttgg tgatggggaa tataccatcc ttagtttaga atttttgagt   4020
ctggaaatgt caactgataa tctaggtcag gtgtgggcaa gcattttttg tagaggaaga   4080
cagtaaataa tatgagattc atgggcctta tactatctgt gttgcaatta ttcaactctg   4140
tagggcaaaa gcagcacaga caaaagacaa atgaatgggt gtgacagtgt ttcagtaagg   4200
ctttatggac actgaaattt gaatttccta tttttattta tttttttaaa gagacggagt   4260
ctcactctgt cacccaagct gaagtgcagt ggcgcaatct cggctcactg caacctccgc   4320
ttcccgggtt ctagcagttc tcctgcctca gcctctcaag tagctgggat aacaggcatg   4380
catcaccatg cctggctagt attttatttt tagtagagac ggggtttcac catgttgccc   4440
```

```
aggctgggaa tttcctataa tttttatgtt aacaaaatat tgttcatttg atttttcaaa   4500
actaaaatat ttttaaaatt atagattttt taagtcttag cttgtgggcc atacagaaac   4560
aggcagtgag ccagatctgg gccacaggct gtgctttgct gagttctgtt caaggtccat   4620
gtcttctgat ttttttcagt gttcactggt ctagaaaagg tgagaaggag gcttgatttt   4680
ggtgaatgaa tgaaactttt accatttact gttaactaac tttaagatac atatgggaga   4740
aatggttaaa atggtacatt ttatgttaat attttactac aatttttttt taaaaagata   4800
cgtatgggga aaagtttgtg cacgtacatt tgggtcttta ataggacttt tagaccaggt   4860
gcagtggctc aagcctgtaa tcccagcagt ttggaaggct caggtgaatg gatcccttga   4920
gcccaggagt ttgagaccag cctaggcaac atagtgagac cctgtctctg taaaaccctg   4980
tctctacaaa aaataaacca aaattagaca gatgtcgtgt agtcctagct actcaagagg   5040
ctgaggtggg aggatcactt gagctgggag gtcagggttg cagtgagctg agattgtgcc   5100
actgcactcc agtctgggca acagagcaag accctgtctc aaaaacaaac aaacaaacaa   5160
acaaaaacac cttgaaaatg tcctaaagag aaattcagca tggttcagtg tacactacat   5220
aaatagtgcc tgccttggaa ctggcctatg gtttgttcaa ctatgcctgc agatgttgct   5280
tagaacaaac cgttgagaga tctatttctc agaggaaagc ccaggcagca ggtggcacca   5340
gccctgacac agaaaaacag ccaggaaaaa aaaaaaaaag aagaagaaga agaaaacaaa   5400
cttctatgac tttcctaacc agttaatttt tatgtccatg gttctgttgt catatttaaa   5460
gtcgttttaa aaaataacaa tgtgcttagc atagctgatt attttgtttt aattaaaaca   5520
tttctgaaaa aacaaaatga aacattcaaa cataccaagt tgattgtgct tgtactgtgg   5580
aacagttaat gcaaaacact tgagagaggc cggaagtttg gatctgtagt tttgccttga   5640
gtgtctgccg cctgaataag gacaacatag gaggaagtga atgtgtccct tagaaaacta   5700
cctgtatagg tttgaagtga gatccagcac ccccaacgcc acttggcagg ttaccttctg   5760
gccggctcac tgggcagcct tgtcattggt gagaatgatg actgacattc cttctatatt   5820
cagtttgacc ttgagaatcc agctggaacc cgtaagtatt agtctaggag gagcagtctg   5880
aggtcactct atttttcctc cctgtcttat cttcatagtt gtcctcccaa gatggcggtg   5940
cttccctcaa cccttacctc accttctgag actttgtctg tattcagact gatgagggaa   6000
aggaaagagg ccatcgcaaa aaaatgtcag attggcgtcc atacacctca caaataacta   6060
ctccacagaa acgtgacttc tcttctaagg gaattccttc ccctcctttt aaattctctt   6120
tctaggtaaa caccttccta gcctgcactt gtaccagttt aaagaggaat gaatgaattg   6180
gggtgctagg gagcaccttg gcagacaaaa tgttttaggc cacctcacac gcaaagttgc   6240
ctctctccct gcatttatac aacagggccc tctcagagct acccctctgc cgggcccagc   6300
ttctagcttc ccttgccacg gatttaatct ctggcaagta gccaaagcat taaactttta   6360
ttgttcaatt tgccacaagg gcggggccct gcttctagtg ggctgaggag gctgcagctg   6420
cttccaaacc caagtgtcac accacattag caactgcaga ctttgagggc tggatttctt   6480
tcagtttggt tagattcttg gttagaacca gaacggtata ctcacacaca aaattttaaa   6540
gctaggaaat agtaaaaaca gtgtaggcaa cttttaaagg tgattcagag cggctgtagc   6600
tatcagcgtg tatgattgac tctgcgtggt ttcttcacac cttccaaaca gacatattag   6660
atggctgtac atgtgcctta gtgtcctaaa gttggaggaa aacatggcaa ccaagtagtt   6720
ctcttctaga ctagtaggga ttgctaacca atcccatcac agtatgtaaa ttacttgctg   6780
ttgttcaatc tataaaaatt catcttcaaa gaaaattatt gggctggtaa aaatattttt   6840
```

aataatgacc acagaagcca tatttgtttt tctttgatgt tcttccgaag acccttctgg 6900
ttctaatcag attgttccca cataaaatac agtggaaatc tacaataata aaatccctat 6960
tcctatgtct atggggaaat aaacaggatg ggactgtcc ttttaagggg ctttcccctt 7020
ccctttcccc agactcaaag cctctattac tggtgggtgt tttggcatca gttaagggcc 7080
ttcaatcctt ccctccctcc atgttttgct ctttcattaa agtgtttctg ttgtctaatt 7140
atatcctttc aatcaaatta gagactgtag catctggtga gggctgtaac tgctgccatc 7200
tgcacctcgt ctatacaggc cttttcagct gagaatcact caacttccaa atggcaggaa 7260
gagatttgga aaaagtttag ttggagggga gattaactta aaaggagtgt cttcaaaggc 7320
tgggtgcgat gccctgcttg ctgtgatgtg tgcatggcca atgcagagct tcactggcct 7380
ggctcaccaa agattcttcc ctagcgcttc tggcagatga agggtttttg gttgtcttag 7440
ctgaaatgac taggccttct ttgttagggg cttggagggg gccaggggct gagctgagaa 7500
agtctccctt gagaacaatc tttagttata tgaccactgg ttaatgggtg tgacactttc 7560
tgtttatttg accatttctt ctaactcagt gatttcaact ggaggagatt ttgcccccag 7620
gggacatttt gcaatacttg gagacatttt ggctgtcaca actaaagagg tactactggc 7680
atctagccgg tagaggccag ggatgctgct gctaaacatc ctagaatgca caggagagcc 7740
cccacgccaa agagttatac agcccaaaat gtcagtagca ctgaggttga gaaaccccgt 7800
cctgattgta ttattttttt gtcctttttt tttttttttt tttttagcgt caagctttcc 7860
tgttaccagc aatgaatttt ttttttttata ctttaagttt tagggtacat gtgcacaacg 7920
tgcaggttag ttacatatgt atacatgtgc catgttggtg tgctgcaccc attaacttgt 7980
catttaacat taggtatatc tcctaatgct atccctcccc actcccccg tccttctttt 8040
tactgttagt tgcctgccta ggaacagttg attctgatca gcatcttttt tcactcttaa 8100
gcagattctt cattatccac atctaacctc tttaagcatt tctgtggaca gtgtttcaga 8160
aaccttaatt cagtaagggg gtctgtgatt cactgtgtct ttttattctc tctagagtac 8220
aattgtcaga tacattacag gatgcccaat taagtttgag attcagacaa acaccaaata 8280
atttttaatt aaagtctgtt tcatgcaatg tttaggaata cttgtcttaa aaaattcttt 8340
gatgtttatc tgaaattcaa atttaactga gaattctgtt tttatttgtc aaatctggca 8400
accctaatcg agcttcatgg aacactccat gaaactttaa agctttgaca atcagaatta 8460
atctgttggc cactatttgc tcttattctt attgctccaa gtgaccagag atgatggttc 8520
catctactta taaatgagtg ttacactgag cctttccttc tgccctaaac tgtctccctg 8580
gccagaactt atgaaaccca tctcttgagt catattttta tgttgggacc aattaacaag 8640
tacttatcaa attcctcctg tgtgcccagc atctctgatt aggacttatc cctgtgccaa 8700
ttgacagaag gctacaactt tgttgcttcg agttttactt tgaaatgtgc tctagagata 8760
tatggtctac ctggtatcag ctccccactc aggagctctt atattatttg tctatcccat 8820
atcagccaag ggaaactgaa aagcccagag tctggcttcc atggagtatt ggctgccctc 8880
caggactcta ttattgggga attttcttgc catctgacat taaaaatagg tcacaggcat 8940
tactaacaaa acttgtctag aagctggatt atatccagtt gaccttcaga caacatggaa 9000
aaaggttgct caagtgatag tgaggcaagg cgtagatttg agctgggtgc ctcctgctta 9060
aagcaaacta agaatataaa attcatattt ttattttatt ttattttatt ttattttta 9120
gatggagtct cgctctgttg cccaggctgg ggggcagtgg cactcctggc ctcaagtaat 9180

```
cctcccacct tggcctccca aagtactggg attacaaggg tgagccactg cacccagccc   9240
ccatccattt cctttaaata gcagagtccc tggtttaaat agcaaatatt tgatttcctt   9300
gatttacata aacttgtact tgatttacat gaactttcct agaacttctc ataggtattg   9360
ctaggtaagt cttgaggctg gcctaggagg aatacattgg tgaggaaact aatgcaccct   9420
gaatgtatct gtaatggagc tttcccctag cccctcattc accagcttcc ctctttcaac   9480
agacacttag ccaggcacct tctatgtggt ctgtagttgc tgagaataca aaggtgagta   9540
agatgctcac aggctattgg aaacagggct atgtgcttcc tgagcagtta cacttcaagg   9600
taatcaagtc ctttaagagc tgtggcagca ggcactgtga cttgtttcaa aacctctggt   9660
ttctatagaa gttagtgcta cctattctag accctgagcc ttcaaatagt tcgccttttg   9720
tttttgtgtt ttctttagag ctggcttata atgagctgag gtattgtcca tcagcaagct   9780
gaagtttcag ctttaaaata tctcacgttt cctgtatcct tatgtgaaaa cttttttttga   9840
gacaaggtct cactctgtca cccaggcatg attacagctc actgcagact caagacagac   9900
ccttgcccca gcctcccgag tagctgggag gtacctgccg ccacgcctgg ctaattttta   9960
aaaaatattt tttgtagaga cagcttttcg ctatgttgcc aagtctatga aaactttata  10020
gtatgaaatt ttatttcaag attcaggaag atatttatga ataaatatct aaggtagatt  10080
tatttgtgct cacatattac attgagagat agatgcttta catcagcaaa gtataataga  10140
atatattcta ttggtattgg aagtaaaatc catcaaggtg ctttggttaa taaatgaaat  10200
atttttctta gagttctgct gagtcagtga cttttgacta tttgaatgag tccattcttt  10260
aactgaagtt taatctctac atattataga cctgaatgct gataggttaa tggacatttt  10320
tttctcaaaa agtgtctttt ggacttcaat ttgatggttg tgatacgaga aaggggtcct  10380
gatctagacc ccaaaagggg gttcttggat cttgcataag aaagaattca ggggtccggc  10440
acagtggctc acgcctgtaa tcccaacact ttgggaggct gaggccggcg gatcacttga  10500
ggtcaggagt ttgagaccag cctggcgaac atggggaaac cctgtctcta ctaaaaatac  10560
aaaagttagc cagccatggt ggtgggtgcc tgtaatccca gctactaggg aggctgaggc  10620
aggaaaacca cttgaaccta ggaggcggat gttgcagtga gctgagattg cgccaccgca  10680
ctccagcttg ggcgacagag tgagactcat ctcaaaaaaa aaaagaaaga attcaggaca  10740
agtccacaga gtaaagtgaa aaggagttta ttagagaagt aaatcaacaa aagaatggct  10800
actccatagg cagagcagcc ccgagggcag ctggttggct atttttatgg ttatttcttg  10860
accatatgct aaacaagggg tagattactc atgagatttc cgggaagggg gtgaggaggt  10920
cccggaactg agggatcctc tttttttag gtcatatagg gtaacttctg gatgttgctg  10980
tggcatttgt aaactgtcat ggtgcttgta ggagtgtctt ttggcatgct aatatattat  11040
aattagtgtg taatgagctg tgaggatgac cagaggtcac tttcatcact atcttggttt  11100
tggggggttt tggctggctt ctttaccaca tcctgtttta tcagcgaaat cttcgtgacc  11160
tgtgtcttgt gctggcctcc tatcttatcc tgtgactaag aatgcctaaa ctgggatgta  11220
tcccagcagg tcccagcctc attttaccca tctgctgttc aagatggagt ggctctgact  11280
caaatacctc tattttatgg gtttataata tggtaaatga taaataaaaa ttcctgaaca  11340
ctaatgcata ttcaggatga ctattcctgg cagaaacaca catgcttcac agtgacaagc  11400
atggcatgtt ttccaggggg ccctgcctgg gtaggagtgg agcatatgca agatgagagc  11460
cagatgggaa aagagtggta cccaagccac tgcattctgg accttctctg ccttgataat  11520
tatttgtttt ttgaattttt atttaacaaa taaggccttc tctccgaagc gttttcatgg  11580
```

ttcttctgaa ttcaaacatc tggtcttatg cttaccctgt aagttcagtt tttcttataa 11640
tggtctttta agtaattaaa tatttcatct cttagtagag atagataaac tggagattca 11700
aatagaagac ctcatgtccc cttccaaaag tataaattct ttagttaaag tatctttgag 11760
aggcatggcc tttccttccg tactgttttt aagggcacca tctccttaaa tggaaaagaa 11820
gatctaaaag gtattttaat aaaaaagcta ctagtacata aaacattaca gtgatttttg 11880
ttgtggtaat tccactttgg gcaaaagggc agctcgttct atggtcattt ggcactgtta 11940
acacataatc caagaacgtg atatatgagt atcaattttg attttagatg gctaacttta 12000
tggccgaatt tgtttatagt tcttgaaaaa aggctaaggt agattaattt caaaataaca 12060
tgttggtaac tattttcaag atgttctttg aaaaattttt tattatggga aatttaggac 12120
acaaatagag aagagagtat aaggaagtcc catgtatcta tctcccgact cccacaatta 12180
ttaaccatgg ctaatgttat ttcatctata ccctcttcat tccccttact acattatttt 12240
gtaaccaatt tcagatatgt cacctcatct gtaaacattt tagtatgtat ctctaaatgc 12300
taaggattcc tttcaaaaac atagtaatag taccattatt acacgtagaa aaaaaaacaa 12360
taattcctta atgccatcaa atatccagtc aatgttcaga tgttcctgat tgtcttatta 12420
gtatttttta cacttcagtc aggatctaaa caaggtgtat ttaggtaatg tgagtcctaa 12480
atctctatta agccttagat ttcccctttt tttcttttct tgcaatttac ttgttgaaga 12540
tgtagtttct tttaagcaag aagaatgcct aagtaggccg ggcacaatag ctcttgcctg 12600
taatcctagc actttgggag gcagaggcag gtggatagct tgagcccagg agtttgagtt 12660
tggcctagac aatgtagacc ccatatctac aaaaaattaa aaaattagcc aggtgtggtt 12720
acacatgcct atagtcccag ctatgtggga ggctgagatg ggaggatcac ttgagcccag 12780
gaggtagagg ccgcagtgag ccatgattgc tccactgaac tccagcctgt gtgacagagc 12840
aataccctgt ctcaaaaaaa aaaagtgcct aagtgcctct cagagggaag gcccacatgg 12900
gaggtgaggt tttttttttt tttaaccata taattcttac ttccattaga gaaacgtaga 12960
attagagaat tttaagcctg gaagagattt ttagccatga gtactttcca gtcatatcac 13020
cccagacttt tggacctgat tttcatttat ttagatcttg aacttgaaat tgcagacatt 13080
tacagtgaag ggacgttgag ataatctggc tcgactctcc taatttcaca gatgaggaaa 13140
ccaaggaaga aactgaggcc caatgatgtc tgagtggttt gttcaaacca cagtgttagc 13200
tgcttctctg atatcatttc ccctttattg cactgattct ccatatgtac tatgtgtgta 13260
cagggttgtt gtttttttccc taaactgtcc tctctctatt ctagatctga tgacattcct 13320
ctatgtaatt gtagaaatca ctgctcttgg agagccattt ttgaagatgg gagtgtgtcc 13380
tatcacagcc tcagtggtgt tgggttggaa aaggctggga acccctgcct tcccagggcc 13440
acatgcccct ttactacagg gtttcacata actgaaatca gctttcccat agtgcttttg 13500
agtgtctgag ggcaaagggt agtctgccca ggggcttcaa agtggtgcaa gttcccaccg 13560
ggcaccagtc cgtatttgaa acccaacagg gcgataggtg tgctatgtga atatttgacg 13620
gcactgtcat gttgccctct ctctatatat atcttttttg agatagggtc tcactccatc 13680
gcccaggctg gagtgcagtg gcatgaccat ggctcactgc agctttgact tcctgggctc 13740
cacctcagcc tcccaaataa ctaggattac aagcacacac caccacaccc agcaaatttt 13800
taattttaat tttaatttta attttgtaga gatggaggtc tccctatgtt gcccaggctg 13860
gtcttgaact cctgggctca agtgatcctc ttgtcttagc ctcccaaagt tctgggatta 13920

```
caggcatgag ccataccctc taaatattaa aaaaagcatt tatacctaaa ccttagattt  13980
ctataatcta tctacctacc aagtttcata gactttttta aagaacgaag gatattctca  14040
ttggaatatg ttctctgctg tcttgcttta agatgctgta attgaattta atgtgaattg  14100
attcatgttg atttcaagcc aggctaaaac cagacagatt cttccaacat aagatcagta  14160
gaagtgctaa gcggtcccac agagaacaga gacttaactt tggtggatta aaaaaaaaca  14220
atgactctca taagcatcat atgtagagat ctaactagta attctaccag aaaaccaaga  14280
atatagagaa aaatgttgta tttctcaata gtgtgttttt ggacaaatta agaattacct  14340
agttatagag ttttatagag agcatattct tcagctttat taaatcttac caaagattag  14400
gatgtctttt agattaacta ctgttttcct accactatct tatacatgtc aagttttttt  14460
tttttgacg gaattttact ctttgttgcc caggccagag tgcaatggtg cgatcttggc  14520
tcactgcaac ctccgcctcc cgggtttaag tgattctcct gcctcaacct cccaagtagc  14580
tgggattaca ggaatgcacc aacatgctcg gctaattttg tatttttagt agagatgggg  14640
tttctccata ttgatcaggc tggtctcaaa ctcccgacct caggtgatcc gcacaccttg  14700
gcctcccaaa gtgctgggat tacaggcatg agccaccacg cccagccaag ttttaattat  14760
tttaaaagaa taccttgtta tagtttaaac atgaacttta aaactgcaga gcaggtatta  14820
tacaacctgg cagaattttt cctgggactc tattaacttg tgttttcctc acttatgatt  14880
agtataaata ttgaattatg tggttttagt agcataaata aatgaagatg tgtttcatca  14940
tatttatagc tgaaatttg attaagaaaa acctatttgc tcctctgtat ctttttccct  15000
taccgcttat ccattgaacg ctaggattca acacaggatt caaaccatat atatgttcca  15060
tcttgatggt agcctaactt taaacagaat tgtagtagga tgatgtgccc acatactcat  15120
gttatcttac cttttatagc taattatttt atggaccaga ataacgtgcg cacgcgtgca  15180
cgcgtgcata cacacacaca cacacacaca cacgcacaca catattttga gatggggttc  15240
ccgctctgtc acccagggta tagtgccttg gtgcgatctt ggctcactgc aacctctgcc  15300
tcccaggctc aagcgatccg cctacctcag tctcctgagt agctgtgacc acaagcacac  15360
accaccacgc ttggctaatt ttttgtattt ttggtagaga tggggtttcg ccatgttgcc  15420
caggctggtc tcgaactctt gatatcaagt gatctgccca tctcagcctc ccaaagtgct  15480
gggattacag gcgtgggcca ccgcacctgg cctcagaata acctcagtta tcatgatgct  15540
tataatattt ctaagcttat ataaagtttg attattttta tacctttatg attatacaat  15600
aataattttt gaatacctac tatgtaccga gtactttact tgcacacgtt ccaattcttc  15660
caactgccct gagctgtaga taatcaaatc tctcattttg caagtcaaga aactgaggct  15720
caaggaggtt aggcaagtgc ttgtagcttg taaactgaaa agctgaggtc tggctctaga  15780
gcccctaaca tacgctttcc atactctacc acattgttgc tagaagttgt gtgataaaga  15840
aaaaaaaatt actgaaaaag ttttcctagc ttttctccta ccccacaggc tgtactttct  15900
cagtcatcat tgccaagtgt ggtatgttgg agggccccag ggctcagccc cagatgttgg  15960
ggctgataca cacagtatcc tattctctct acacgtaagt gctggggacc atatttctag  16020
ctttagcctc agccttttc ctcaactcca gactcatgta gccatttgcg tactctacat  16080
ctccactcag ttttctgaag atgtcaagtt taacctatcc aaaaccaaac tcttaattct  16140
accccaaaac actctgacct tcctgagccc tccctattac agtaaatggt atcactactc  16200
agctggttgc tcaggcccct ttggtgtgct gtgtgaccca tctgtctctc agaccctgta  16260
tccaaacccc cagcaaatac ttttgccact accttcaaaa tatatctgga atcggtccac  16320
```

ttctcaccac cccacagctg ccagcctagt ccaggccatc cttgtttctc gcccatcctt 16380
ctacagtaac tacctacttt tctccctgcc taggtcctgc ctgtcagttg tttttcctcc 16440
acccaacagc tagacaattc tattaaaaga taagtcacaa aaatgaataa ataaagataa 16500
gtcacattat gtcattcccc tgctctaaac cctccagtgg cttcccctta cacttagaac 16560
aaaagccaaa atctcattta tctaaccctc aagaccttac acgtcctgac cttgcctgcc 16620
cttccctgct cattctcctg ctccagtcag attagaggag cagctttgta gctccccaaa 16680
tctgccaagc atattgccat ttgcaggggc tttgcatttg ctggaccctc tgccagttac 16740
acacctgccg cctcgttcac tgggtttgct tcctcccttc atccacatct ctgctcacta 16800
ggctttccct gacccaccct aggagagaac cctcaccatt ccatcgtact ccctttactc 16860
tgcttcattc cttctaatag cacttatcac tatctgatgt tcattttgat cagtttatta 16920
taaacatgta agctccatga atacaggata tttgttcatc tctgtagccc cagtgctgtg 16980
aacagtgcca ggcacatagt attgaataaa tatttgctga actaattaat gaataatttc 17040
ctagacatta gatctcttgc tttcactcat tctcttttca ctgaatacgt aaataaacag 17100
ttggctctgt gtgtgtgtgt ttcttactgg tttaagccgc tccttgctta tttagccaaa 17160
gcttacatca gtttcgtagc agtagaaaat aagggaggct gggagctaca tgatagacct 17220
tatgaacaca aagaaggaaa cagcagacac tggggtctac ttgagggtgg agggtgggag 17280
gagggagatc agcaggaaga taactgttgg gtacctgggt gatgaaataa tctgtacaac 17340
acacccctgt gacatgagtt tacctgtgta acaaaccttc acatgtaccc ctgaacccaa 17400
aataaaagtt aaaaaactta acatgatcac gatagaaaac agtgtggagg ttcctcaaat 17460
gattcaaaat agaatgacca tattctagca atctcagttc taggtatata ttcaaaggaa 17520
ataaaatcac tgttttgaag aaaaaaaata agggaggtag ggtcctattt acctaacata 17580
caccctagta ctctgatgaa atcaagatgc gctagatgac tttaaatgca gagcattcga 17640
gttggtttcc cttgcttttc tctgtaattg atatgtactg ggcaagtctg gtcaaaaaac 17700
aatcacagaa tctgatacac tgcctcagtt tcaccagtgt aactgagaac aagattgggt 17760
ctgagaggaa cagacccaag caaagaagcc tgcactttcc catttccact ctcagatgcc 17820
atctcgtctc catgaggact gtcatgtgtg tgcattttat ttatttattt attgagacag 17880
agtttcactc ttgttgcccc agctggagtg caaaggcacg atctcggctc accacaacct 17940
ccgcctcctg ggttcaagcg attctcctgc ctcagcttcc caagtagctg ggattacagg 18000
catgcactac cacccccggc taattttgta tttttagtag agacggcgtt tctccatgtt 18060
ggccaggctg gtctcgaact cctgacctca ggtgatccgc tcgcctcggc ctcccaaagt 18120
gctgggatta caggcttgag ccactgtgcc cggccatgga ttctttttat tacacattct 18180
gctacattct tttgtattac aaaccaagtc atccgagtct caggaacccc acctgtcctg 18240
cagtttgcta tgtatagcta agaccttcca ttgatctatt gagctgcatc tctgatttct 18300
ggcccctgga tcacccttca cactttaaaa aaaattttat ttttatccta tatatttaag 18360
gggtacagta tgatgttttg atgtacaaat tctgatagga gaaaaacatg tattaacaca 18420
cagcaattaa aattctagca attggcaagg gttggctgat gttcttagaa tcatctagtc 18480
tagtggttct caaacctgat tgcttaacag aaccacctgg gctgcctttc agaaatacag 18540
gtttcaggtc ctgctctagc tctgggattg ggatagagct ctggtgtgtc tggtgtggta 18600
cataccacac acattgtctc tctctctctc tttctctcag atcacatata tttcttgtga 18660
tagtaagtgt tgtgaagcaa acaaagggca gaaaaatagg agtaaagatg atgagaaggg 18720
ctttctgaga aggtagtgtt cagtctgtga tgggaagtat taggggaaga acattttggg 18780
caggaaatag catagtgtgt tcacagaatt aaaagcagac cagtgtggcc gaagcacagc 18840
gagtgagtaa gggaagagct ctgcttcatg ggaggaaggg gctgaggctg catcacagag 18900
gccttgcaga caccgaggaa gagtctgagt tttgttttga gtgccatcat tcttttaaga 18960
actatggaga atggattgtg agagaacaga agtggaagct gtgagaccca aactgttctc 19020
tgatgataaa ggggactata ctggtggcat caaagatgga gagaaggcag tttcagggtg 19080
tatgttttag ggaagtcaac aggacttgct gacgaatcgg aagtggagtg agggagagaa 19140
tgggagaagc aagaatgatg ctgaggaggg tccattagag gcagtatagg gtgtggtcga 19200
gtgcccagct cccttatctg taaaatgggg tactaaggta cctctctggg ttggtggcaa 19260
gttgacattt gtgaagcact tagacagagt ttggcacatg gtaaaacact gtgtaaatat 19320
tagaagtgat ttggatgatg tttattcatc caaggtcgca cagctggtca gcagcaggtc 19380
caggacaaga agccaaggct tagtctcttg gtttagtgca ttttatgcga cactgaactg 19440
cctccttcaa tttatgcctc ctttgaactt atttgtgcag actcttggta gaggggtttg 19500
gtccttatgg tacacgaaga gttgcactta tcataacaca tgagcattgc accaaacatg 19560
ataaattgtt agggttggtg gggtgtggtg gctgacacct ataatcccag cactctggga 19620
ggcccaggtg ggtggatcac ttgaggttgg gagtttgaga ccagcctggc caacatggtg 19680
aaaccctgta tctactaaaa atacaaaatt agctgggcat ggtggtgggt gcctgtaatc 19740
ccagttacta gggaggccga ggcaggagaa tcgcttgaac ctgggaggcg gaggttgtgg 19800
tgagccaaga ttgcaacact gcactccagc ctgggcaaca gagtgagact ccattcaaaa 19860
aataaaaata ataaaaaata aattcctagg gtttcttgca taggtggaca ttcagattat 19920
tttggctatc cataaaatgg tgccattcca gacaaaacac agggcctgga tggtcagagg 19980
aaggaggtgc tggaagagag atgttctgtg gatagtttga agtattaaaa gaaatatctg 20040
ccagaatgtg ttcatgttgt tcacacgctt agactggagt aggcacatgg atgacaacag 20100
gagatggcat taagagtcct taatactgga agttataggt cagtgcatgc caggagaagg 20160
aaagaaatgc agctaagaat gctagtgtaa ctcccccagg ttgtcagttt tctaatgata 20220
tatcttaaag aagtgtttga agtgcttctg tcagtttcaa ctaagctaat tttaaaaaat 20280
tgttctttgt actgtgcctg tctcatgaac ctcttcgagt ttaatgcatg caatatgtgg 20340
gtgaaaatcc tatcagcctc agtccccatc ccccaaagtc tgagaagcag attttagaaa 20400
cacattgttg cacctgtgag gatttgtcat tttattaaat tggacctgag accattttca 20460
atgtgcctca tcaaaagaat ttcagaaaga ggtgagagaa aatgccagcc cggcccttcc 20520
tccctcatgt tgactgtctg ttttgttcca cctctatctc aaacagcatg gggaggactg 20580
ttcttcatta ccagggaatg tgagtcattc ccagatttgt gtgattggga ttccaaagca 20640
ttgctgtatc cgatgatctt attaaatcca agtgtcagtg cagcctttca gactgtaggg 20700
aagagctcag ttacagctgg tgacctggtt ccagttacca cacagagcca ctggcgagag 20760
cagtgacccc ctcagagtat ccagaattcc acatggatgg ctgttaccaa ctgttcccag 20820
atttaggggt ttcctggttc acttcatggg cttcagtaca cttcagctcc ctgtttattt 20880
cctagttggg atctgtatac tttaggggaa aatgttctag tgtctgtaga caagctagtg 20940
ccaagattag cctagctttt tgagggtacc ttgtttcaga tttattcagc cccagaagtg 21000
ttaactgcac tgtgtccagg atctagcaag acactatcca tttccagctt ggtccaaaca 21060
aaacaaaaca tcaaccaaag agggaggaaa ccatgaatgt tgccagaaaa ttagtttgct 21120
ctgtcttttt tttcttctag agtgtttcac agccaatggt gcggattata ggggaacaca 21180
gaactggaca gcactacaag gcgggaagcc atgtctgttt tggaacgaga ctttccagca 21240
tccatacaac actctgaaat accccaacgg ggaggggggc ctgggtgagc acaactattg 21300
caggtaagat ggggccactc agtactttaa aaagatagat atatatctag tctcttcttc 21360
caaccccttt catcccagct cacaactagg ggaagtcttt tgaccaactc aagagactta 21420
tcttgtcagt tttaaaaata tttctttcac accttacaca cacacacaca cacacacaca 21480
cacacacaca cacacacaat ttaccactct tttttttttt ttttgagacg gcgtctcgct 21540
ctgtcgccca ggctggagtg cagtggcgcg atctcggctc actgcaagct ccgcctcccg 21600
ggttcacgcc attctcctgc ctcagcctcc cgagtagctg ggactacagg cgcccgccaa 21660
cacgcccggc taatttttcg tgtttttagt agagacaggg tttcaaccgt gttagccagg 21720
atggtctcga tctcctgacc ttgtgatccg cccgcctcag cctcccaaag tgctggggtt 21780
acaggcgtga gccaccgcgc ccggccaatt taccactctt ttcaacatgg gttgttttaa 21840
tgctggcttt gaaagctctg cttttctgtc tgatcacttc cttgtctctt tgggagggtt 21900
ttcttagtta gccctaccac cagtggacaa tacacagtta gcagagcagc ctacactacc 21960
gagaatgtcg tggtcagaca gcaccatgtg tgacccaaat ctccctctgc ttctgagcaa 22020
aggaagctgc ctacattgtt gtgcctccgg ccagcccagg ataaccttgc tctgggaaca 22080
gctgtatcca tcagatgtgt gccatttact tccttttagt cgactaaggt gtttctttgc 22140
ttttcacctc ccgtctgact ctagcagggg atcttaacct gacatctatg gtgcttcaaa 22200
agtgattcac aatttcctgg ggatgatcca tagctttgat cagcttctca aagttatctg 22260
tgattgaaaa caagttcagg atcactggta tgtagggtcc agaacaaaga ctgtaagcac 22320
ttttggttat acatttgtgc tgcttatgcc caagatcctg gtaatgagac ttatggttca 22380
gcaatgcatt gaatttaatt attattagta caggtgcaaa ggcagcctct tgagctactg 22440
ggacagggaa aaatgattgt tgaactatat accctgtccc tggttctaca tacattggaa 22500
tctcaaccat ggcactgttg acgcagctga gccaacatat attttcctgt attgtatggg 22560
ccacactgtt taccttctgc cctctacata cctttgctaa cgctctaggg cccttgtagt 22620
tgtctcaaag tcaccaggcc tttagtctat gttttcttta tccctatacc tttctctatc 22680
ttgtatcaac tgaccattcc ctcctagttg ctattgactt attttgtttg ttataaaagt 22740
gttaaaagct tattcttaaa aaaaaaaact tctccaacac cacaaatata tgtggtttaa 22800
atagttaaaa ttccccattt tacctatttt ccctgaaacc ctccccacca agtcccaagt 22860
cccagagaca accaatttgg gtatttgcca cttcacattt tgctatctgt tgtattttat 22920
tgttcaagtt acacatgctt attaaatagt tcttttatat tttattttcc aagttataca 22980
tgttaattta ttttttgcat aaattaaaaa attagtccca ccccattttt tattaccttc 23040
ccctaggttt tctattcata ggaatagttg gttgggttgg gaagagtgtt taggaagaga 23100
gacaagtatt tggtttttgt ttttccatag ttgcttatct tcttgttcca aaatatctct 23160
tggtagtagg ctgttggttt attctattgc tctgttgctt cctatcaagc aagtcttctc 23220
agaagagctc atgtttttaa gtctgacttt aaggtaaatt ttaagtttcc agtgaggcct 23280
aatttatgtg aaaaattttt ctttcttgtg gattagcacc cacttctact cacaggcttc 23340
tagaaatgta cccataaaca tccattaaga gagcagtgag agccaggagg gaccaccttt 23400
ctccttagcc ctgatcagcc atcacatcaa accctctcgt ttgatttgat ggaatgcagg 23460
agacctgaac tatttaatac cagtttatac tttggaaaag ggaggctgaa attgttgatt 23520
atcacatcaa agagcccagg ccttttgttt tagcactgca gcaaagtcaa ggatgaattt 23580
gcttgttctt tattaagcta ttctgatgct tttcaatatg gttttgacat tgataataaa 23640
cagttttcta agggctttac caaataaata catcaaagct gaacaccgaa tagagggagg 23700
aaaatgacaa tgaaatactg tttaaagaag ggctttgtac aagttctcct actttgattt 23760
ctcaactgac acccgacacc atgtttgtct tgtgtgactt tttcagaccc atcacattag 23820
agatgtctga gagttggtga gtgatgggaa tgcacttttc tgggctcaaa gtaactggct 23880
tagaagggaa ggcagagact ggggaagagc agagttggtg ctggcacctg cctttgggca 23940
caagaaacaa aaggacgctt tgtactttgg gaaagcttat cttctacgcc acatgacagg 24000
cttagcccac tctggcctga taggggttgc tcccagctcc tgctgcagga tctttatgcc 24060
catttccggc ctaaccggag tgtcagcttt ccagtgttct gagtctaaat aaaaggggct 24120
tggaaagcgg tgaagagagg cgagcctttt ctgtgtgtcc agtagcccct gccattttat 24180
ttatctgctt cagtagtgtt gcttgttatt gttatgccac ctatgagttg aaaagacctt 24240
aaagcatgta tttattccag gccattctca tttagaaatg tgaaatagag ctttaaaaaa 24300
tattatctcc atatcagaag ttgatacctc atgacaggat cacaagttct agctgagact 24360
ctgacgcagt tttcttcagt attctctgag gagtcagcat tttgaggaag gaatagcacc 24420
catttctagc aaatgtgagc ctcgtcctgg tgaaagtttg tcagtggagt ctgtatttta 24480
tttttatttt atttttttat ttttgagacg gagtttcgct cttgttacgc ctggcccagt 24540
ggagtcttta ttaagtgaat tttgttttac tgtttaaaaa ttacaccatt ggagtattca 24600
ctatagagga aataaaataa aaccagaaaa gaaaaaaagc tgaaatcacc agtagttcca 24660
gtgtctagag atactttata agagtttggt gtacattctt tcctaaataa gtcttttcaa 24720
aacatggaat tatgtcatct attgggtttt ataactgcct ctttaaaaaa aaaatctaat 24780
aaggctgggc acggtggctc acgcctgtag tctcagcact ttgcggggcc gagatgggca 24840
gatcacttga ggtcaggagt tggagaccag actggccaat atggtgaaac cccacctcta 24900
ctaaaaacaa aaattagtca ggcatggcgg cgggcacttg tagtcccagc tactcgggag 24960
gcttgaggca ggagaatcgc ttgagcctgg gagtcggagg ttgcagtgag ccgagatcat 25020
gccactgcac tccagctcag cctgggtgac agattgagag tttgtctcaa aaaaaaaaaa 25080
gcctcataag acattgtgaa tatatttgca aattaataag actggtctct ataccacata 25140
ttcccttcta tggatataca atttatttaa ccaaaccttt attgttggat atttgctgtt 25200
tccacctgtt ttttatatta taaaaatgtt ttgttgaaca tctttatagg taagatttcc 25260
ttagaataaa ttcctaaaga ggaaattgcc aagtggaggg tttgcatatt tctagggcct 25320
ttggctctaa ttcccaaatt gccgctctga ccatttgtgt cagtttgcat attcatcagc 25380
ggcattgaga gcccctgtgc ttactcagcc ttggaatctc catgctcaca ttcaaggtgc 25440
cagtgctatt tggcatgatg tgtgcagtgg ccatttgtcc tagttatgct atagtgaatt 25500
tgcccaaaca tatattacct ttactcactt ccccccaaac tctgaagtat atgtcagaat 25560
agatatgttt gttcttgtaa tattaccatt ttttcccttt tgatgagaga tggcactgag 25620
atacagacca actattagaa ataatacaga agctaaagca tttccttttc tgtaaaactg 25680
aaaagcaatg aaccagttga attaaaacat cagaagtcat caattgtgtc cttttcccca 25740
acagaaatcc agatggagac gtgagcccct ggtgctatgt ggcagagcac gaggatggtg 25800

```
tctactggaa gtactgtgag atacctgctt gccagagtaa gactgtaata cccaatgtga  25860
tggtttacag gactgtgaac actaagagtg cgtagaggga ggcccctgcc agaggtcagg  25920
tagttaggct ggtggatttc atggagcatg tgaaaggaga agccatcctg ggcgaggatt  25980
ttcacttctc ttgttgaggc ttttcaggaa taggaatgct gatttcctta gcacctcatt  26040
ctaaaggtat tcccttgatg ggtaagcccc atgagaattc ctacttttgg ttaatttctg  26100
attctttcag gtatagagag ggcaaccgct cagaagcagc ctaggggaga aaaatatctt  26160
gtacttttg gaatgaacat ctttatacat agtgaaactc agttatggca ctacttatta  26220
cttggatttg aatgggtccc cagaagtaat atttgataaa tgccttgcta aataccatac  26280
aaagctcatg tggtagttct tttacccaca ttagcctaac atgttctact gtttataata  26340
ataactcaca acccaatttc ttcagccttt tactaaaatg cctgttttct aactgtttca  26400
ttcatttatt cccgtattca cttttttcc ttttttttt ttttttttt ttgtgacaga  26460
gtctggctct gtcaccaggc tggagtgcag tggcgtgatc tcagttcact gcaacctcca  26520
cctcccaggt tcaagtgatt ctcctgcctc agctttcgca gtagctggga ctgcaggcgt  26580
gcaccaccac gcccagctaa tttttgtgtt ttagtagaaa tggggcttca ccatgttggc  26640
caggatggtc tcgatctctt gacctcgtga tccgcccgcc taggcctccc aaagtgttgg  26700
gattacaggc gtgagccacc acacccggca cctgtattca ctgtttatta tatgcaaact  26760
acaaagacaa taggataccc tgaccctcag gagtgtatgg tataggatga atcttaaaaa  26820
gatacagtca tgcaccacac aaaacagacc acatatacaa tggtggtccc atatggagta  26880
tctcaactga ttgttcagtc agttacagat cacacttctt tttctactct tctttcttcc  26940
ttctttcttc ccttctcact actacacttg actagtcttt ttttttttt ttgagacaga  27000
gtctcactct gtctcccagg ctggagtgca gtggtgccat ctcaactcac tgcaacggcg  27060
ccatctcggc tcactgcaac ctccgcctcc tggattcaag tgattctcct gcctcagcct  27120
cccgagtagc tgggattaca ggcatgtgcc accacgcccg gctaattttg tatttttagt  27180
agagacgggg tttctccatg tggtcaggct ggtcttgaac tcctgacctc aggtgatccg  27240
cccgccttgg cctcccaaag tgctgggatt acaggcgtgg actagtcttt atatatgtat  27300
ataaagatta taatggagct gaaaaatttc tgttgcctac tgatgttgta gctgtcatga  27360
tgctgtagtg caacacatta ctcatgtgtt tgtggtgatg ctggtataaa taaacacact  27420
gcacttccag tcacacagaa gtataacata tacaattatg tacagtacat aatacttgat  27480
aatgatagta aacaactatg ttactggttt atgtatttac tatactatac tttttactgt  27540
tattttagac tatattcctt ctacttatta aaaaagcagt taacagtgaa acagcctcag  27600
gcagctcctt catgaggtat tctagaagaa ggcattgttt tcacagatga cagctccatg  27660
tgggttattg tctccttcca gtgggacaaa atgtggaggt ggaagacagt gatattgatg  27720
atcctgacct tgtgtggcct aggttattgt gtgtgtttgt gtcttagttt ttttaaaaaa  27780
gtttaaaaag taaatgaaag taaaacattt aaaaaatata atagaaaaaa ccttatagaa  27840
gaaagatata aaggctgggc acgttggctc acgcctgtaa tcccaggact ttgggaggct  27900
gaagcgggca gatcacttga ggccaggagt tccaggccag cttggccaac atggcaaaac  27960
cccatctcta ctaaaaatac aaaaattagc caggtttggt ggcatgcacc tgtaatccca  28020
ggtacttggg aggctgaaca gcaagaatca cttgaacctg ggaggcagag attgcactga  28080
gctgagatca tgccactgca ctccaatctg ggaaacacaa caagagtctg tctccaaaaa  28140
```

aaaaaaaaaa aaaaaaaagg atgtaaggga agaacatatt tttgtacagc tatacaatgt 28200
gtttgtgttg taagctaagt gttattatga aatagtcaaa aagctaaagt aattaaaaag 28260
tttataaagt aaaaaagtta tagtaagcta aggttaattt attattcaag aaaaattatt 28320
tttaatgaat ttagtgtagc ctaaatgttc agtgtttata aagtctacag taatgtatgg 28380
taatgtccta ggccttcaca ttcactcacc actcactcac tgactcaccc agagcaactt 28440
gcagtcctgt aagcttcatt cgtggcaagt gccatgaaat aggtaaacca atttttatct 28500
tgtatacagt atttgtactg taccttttct atgtttagat atgtttagat acagaagtac 28560
ttaccattat gttacagttg cctacagtat tcagtacagt aacatgctgc tcaggtttgt 28620
agcctaggag tgacaggcta tcccattata gactaggtgt gtagtagact atcacatctc 28680
agtttgtgca agtgcactct atgatggtca cacaacaaca aaattatatg acaatgcagt 28740
tctcagagcg aaaccttgcc taagagatac atgactatac ttttaaacaa ggtaaagaaa 28800
atactgtgtg tagaaaggtc ttgcagaagg tttgaaccac agaaactaaa gcaagatctg 28860
cttctataag gagtctatta atgtagtata tataatgtat tttaaaatat gccagaagag 28920
ctcagtgcct agagctgagg aaaaagacag tgaattcgta acatcctatc tgggttattt 28980
ttttcttatt atttaaacct gctctttgca ttgccctctt tctcacctct caggtcagga 29040
gtcttgtgta tgggatctgg caaccctttc actgatacct ggaatagcat ctgaatgctg 29100
aggcctccag ggggaaaggc agcccctgac cagtgctgca gacctagtac tcaccttttg 29160
cttagcttca ctatccttcc aacctgagtg tgccttcatc cagtccccaa acttagaaaa 29220
cagtaaagac cagaagaatg ggcttttgct cagtctgctt aatcaaattt ttaaaatgaa 29280
aaacatctca tttgcctcta gttatgtaaa gaagaaagaa gcagagggag aggaaagcag 29340
attttcctcg gtccatttgt tcaacacaaa gatagtcttt tagtaccagc ctgtgtcatt 29400
ctcttgggag tggtaaagag ggggtttcaa tctgggcact tttatttgga aagataatct 29460
ttgacttgca tttctaaaat acagtctggg ccaataggga ctgattcatg tggtcattga 29520
aaccaggttc cagaagaaag aattataaca aaatgctata aaccgcttag tatgcctcta 29580
atttgtaata tttaccggat atgctttcct gttccaaaaa aggaaaatta aatattattt 29640
cagtttttct gtggcccctt gataaccctc taaaatctct aaagctagcc ttgagatggt 29700
ctgggcagag agatttgtag aagttgggaa tgagagctct atagtacctg gtttctgggg 29760
atagagggtg ggtggtgtct ggctttggtt ctttggaaaa cccttcagtt taccctgtgg 29820
ggaccagggc tccccatcaa gccggacctc agacattgag tctggcagca tattgtactt 29880
ctagtgtgtc tgattaacat agttgagcaa aacctgtttt acagtttgta gcaagagatg 29940
tttgtaattg cctggtggat ttaacagaga tacagccatc ctattttagg ccacttttgc 30000
cctatttctg gatgtggagt cacaattttc atgaataata ctaaacctct gcatgaagcc 30060
tgctattcat gattagtatt gaacttgtca tacagaaaaa gtcctgtgac atgatcagat 30120
tcctggaaag ttcatatctg aatataacag acccagcagg agccaggggg aatgaatgtt 30180
tagggacaaa gcagaatctg gctgaatggt gggccattgt gtggaaacca gatctctgcc 30240
ccttggtgtg ttatgtgtag agctacaaca agcaggaggc agacctgaag tacaactcaa 30300
atgggagcag agggaaatct gaactgctct tgacctgcag agcatggatc agaacttact 30360
gttaaaagaa caactcggag gtaattggat ttgcccctga aactgctttt gccagaatgt 30420
ttctcagaaa ccctaagttc ttattgcagc caggagaaat gcagacttca aaagcaaatt 30480
ccaacgtctt cgggtttaac atgtctctag atcccacgct ttagatctct aaggcctgtt 30540

```
ggtttgacta ttgagagcta ttttttgttt gctgaaaaac attcccccaa tttctacaaa  30600
cccagctata aaaattcatc tttgaaatag ggacatttga atacagactg agtattagat  30660
tatattaagg aattactgtc aattttatta gctacaataa tggcgtggtg gtgaagtcct  30720
ttaaaattac agatactgaa atatttgtgg ttgaaatgac ataatatttg ggatttgttt  30780
taaaacaatc cagcccccca aacagtgact aggtaggggt aagggaaata gatgaaacaa  30840
gaatggttta aaaaaaagtg gattatttgt tgatgctggg tgatgggttc attattcttt  30900
cccacttttg tgtatgtttg caactttgaa taataaaaat ttaaaattat ttttataata  30960
ttttaaatat aaagagtaaa taaacacagc attctgagta tctagattca aatatgtaac  31020
atgattaacc taaattgtaa tttttttttt ttttttttga gacagagtct tgccctgtca  31080
cacatgttgg agtgcagtgg cgaaattttg gctcattgca gcctctacct ctaggctcaa  31140
acagtcttcc cacctcagcc tcctgagtag ctgggcctac aggcacatgc catcacacct  31200
ggatgatttt tgtatttttt gtagagacag ggttttgcca tgttccccta gccggtctca  31260
tactcctggg ctcagcaatc ctcctgcctt ggcctcccaa attgctggga ttgcaggcat  31320
aagccaccac acccagccaa ttgtaataat tttacacata gcccacaggt atctgatgtc  31380
attgttaaag ttagttatta aagttttagt tattaaactt gctaaaacta ttagttattt  31440
aaagttatta gaactattag ttattgaggt taaagttagt aaataaagtt taaaatcaca  31500
agaacttggc tgggcgcagt ggctcacgcc tgtaatccca gcactttggg aggccaaggt  31560
gggcggatca cctgaggtca ggagttcaag accagcctgg ccaacatctc tactaaaaat  31620
acaaaaaataa actgggcgtg gtggtgcaca tctgtagtcc cacctattcg ggaggctgag  31680
gtaggagaat cacttgaacc tgggaagcag cggttgcagt gagctgagat ggcgccattg  31740
cactgcagcc tgggcgacag agcaagactc catttcaaaa aaataaataa aataaaatca  31800
caataactta gacatattta gaagttatta gttgtgtcaa atgacatttc ttaagctctg  31860
accatctgtc agaccttgta caaaacgggg gacacaagga tagtatgttc tgcagcctgt  31920
ggggaatcct cagtctggga cagaagacag acaaatgaac agataagcat atgcgagata  31980
ctctataata agtgaggtga gcaaaaggtt cggagcaccc aggagggcca tctgtctggc  32040
atggtaggga ggcaggggct actgtctgtt gaagagggct tctggaaaga gtggggtctt  32100
gtttagggct tctctacttt aaagtacatc cagtcacctg ggatcttatt aaaatacaga  32160
ttcttatcag tatgtctaga acagacccgt tacattttta acaaggttct gggatgccag  32220
agctgcagga ctacacttta agtagcaagg ttctagatgt tagggctggg tgggttgggg  32280
tagtaagggc attggaggca aagggaacag tttgtgcccc tgcatgtgca tgagcgtgcg  32340
tgtgcgcaca cacacacaca tacacacaca cacacacaca cacacacaca cacactctga  32400
tgaattccaa gcaagttggt gttgctgaaa cataaatttt aagaagaaag gggcaggaga  32460
tgaggtctga gaagtacaca gggctagatg atgtcaggtc ttatggtctg ggtatgaagc  32520
ctggacctga tccaggaaga tgatgatgaa gctgaggtga gggctgagtg tctgagggag  32580
gcatttctcc atagttcgtt gagcctctgt attagggatt tgggtcaaga tttcccactt  32640
ttaacctatg agaagttctc tagtgattgt atcattcaca cacatcagcc ctaagaggat  32700
gccagcagtt gcacttctgc aatacgtgtg gaaccttagg tccatctcag ctggtgacct  32760
caccagctca ggtttctttt aactaaataa tacctggact tgttaaaaat agatttaaaa  32820
tagatttcag atgttagtat ttgccttaca aaagtcagcc caaaaaatag gatgtgaaag  32880
```

```
gttcccatta tccctgataa gggtttttaa aactgtgttt agagtatgtg taaaaagcca  32940
agggcactgt ggcagtggtg gtcaaggcag tttctcaatt atagaaaatg ttttgtttct  33000
gtcagcactt tctgtgtttt aatgtcagca ctgctttcta gtatgtttca gctattgctg  33060
agtacctact atgtacaaaa agcacttata ttcacattat cttttttttt tttttctttt  33120
tgagacagag tctcactctg tcacccaggc tggagtgcag tggtgtgatc ttggctgact  33180
gcaagctccg cctcccgggt tcacgccatt ctcctgcctc agccttctga gtagctggga  33240
ctccaggcgc ccgccatcac gcccagctaa tttttttttt tttttgtatt tttaatagag  33300
acggggtttc accttgttag ccaggatggt ctcaatctcc tgacctcgtg atccgcccgc  33360
ctcggcctcc caacacatta tcttatttaa cgttttcaac aatcctatga agcaggtggc  33420
atgtctactc tcccgcctcc atttctcaga taagaaaatt gagcccagat agttaagtga  33480
tttgatgagg attacagtct gagtcaaaca ggatttttga ccaggactcc tgatagctag  33540
accagtgcct tttccttcta gcacttgaga acagtcccat ttcctttatt tccttgaaaa  33600
caggggctct gggatggatt ccggctactg ttgaggtcat tcttcagaat tttctttgtg  33660
aattgtttgg gaattaaagt ttgaaattct gatagtatgg tgaattatta agattgcttt  33720
tgtgacattg tggaaaccaa agggttaact cagtggcgac agagggtctg cagttcatgc  33780
tgttagctct aagtcatttt attttcttct ttggctttgg gaaatcctaa gccccaggag  33840
taaagcaggc tgagatggga tctgggaagc atttgctgcc caacagagcc actctgcagt  33900
atgctgggct atctctgtgg gtgtccccag accagctgtt ctcagcgagg aaagggctcc  33960
cctggggttg gacccactgc acaaaacagt tcgtcagcag ctttgtctgg gccttaggtt  34020
ctcccccaat accatgtctt cactgctgtg ggctgaaatt caccttctct gaaatgacac  34080
atccccgtgt accatttata cttttttttt tttttttttt tttgagacag agttttgctc  34140
ttgttgccca ggctggagtg cagtggtgtg atctcagctc actgcaacct ctgccttctg  34200
gtttcaagag attctcctgc ctcagcctcc caagtagctg gattacaggt gcccacaacc  34260
gtgcccagct aatttttgta tttttagtag agacggggtt caccatgttg gccaggctgg  34320
tctcaaactc ctgaccttgt gattcgcctg cctcggcttc ccaaagtgct gggattacag  34380
gcatgagcca ccacacttgg ctgtgtacca tttatacttt acagctaaag tgaaaattcc  34440
aacttttgtt gatagccaaa gcaatattga aatgaacatt aataggccag gtgaggtggc  34500
tcatgcttat aatcccagca ctttgggaga ccaaggtggg aggatcgcta gagccaagga  34560
gttcaagact agcctgggca acatagggag accctgtctt tacagaaaac ttaaaaattc  34620
accaggtatg gtagcatgtg cctatggtcc cagctactca ggaggattgc ttgagctcag  34680
gaggttgagg ctgagctcgc atcacaggca cccttgtttt acttgattgt acttttattt  34740
gtggaagagt gctgatggaa tttatggagg ctttacctct ttaagcctct ccttggtagc  34800
cactgaaaaa agccatatat ttcaacaatc ttccccacac ctagcacagt ggagagtgta  34860
aaagtgcttg ctaagtattc tttcttggct gggtgtggtg gctcatgcct gtaatcccaa  34920
cactttggga ggccaagatg ggcagatcgc ttgagcccac gagttcaacg ccagcctggg  34980
caatgtggtg aaaccctgtc tctaccaaaa atacaaaaat tagccaggtg tgatgggcat  35040
gtagcctgta gtccagctac ttgggaggct aaggcaggag aatcgcttga acccaggagg  35100
cggaggttgc ggtaagccta gattgcgcca ttgcacttta gtctgggcga tgagagtgaa  35160
accctgtctc aaaagacaaa attctttctt gatgccatga agtcttatct cttcctctct  35220
tcccataaga gacaacacaa gctggtggaa agatggaaag aatgtggaca tctgagtcac  35280
```

acccagttag gtttgaatca ttatctgctt aatagcttta ggcacaatga ctctcagttg 35340
tgcctgggtt tcctcattgg tgccttccag agtttttttt gaagattaaa tgaataaaat 35400
gcatgctgcc ctaagtccta gcacatatca ggtagacatg aaagtaccaa caggtattgt 35460
gatggtatgc tctccccagg gaatggacta ccgttagtat gtccctgtca tctaattcct 35520
agaatatgtt attcataacc tgcattttat ttctgcccat ctctttttta tctaactgac 35580
catgggtctt aggagcaggc atcagctgct gcagtggctg ctccctgtgg cctgttgcag 35640
cactgaactc ggtgaacaca agaggcccca cgtttgtttg ttgtttgttt gtgacagggt 35700
cttgctctgt tgcccaggct ggagtgcagt ggcacgatca tggatcactg cagccttgac 35760
ctcccagact caagtgatcc tcccacctca gtgtcccaag tagctgggac aacaggcgca 35820
cactactatg cctggcaaat atttttactt tttgtagaga tggagtcttg ctatgttgcc 35880
caggctggtc tcaaactcct gggctcaagc aatcctccca cctcggcctc ccaaagtact 35940
aggattccag gtgtgagcca ctctgcctgg ctcccatgtt tgttcctaca atgaggtttt 36000
atgtactcaa ttatttttttg gtttttgcca gtgggtatta tttaattttc cattaaaaaa 36060
atacagactt tctgaaccaa atggatatca gttcagtcac agatacaaat gttctaaagc 36120
acagttgtgt aaagcacact agggacttaa aaaggaaaac tcattcaaat tgatagggat 36180
gactttactg aaaatcttta taccagcact tgcctataag gaagaaatag cccctcaatc 36240
ttatgatgta attgggaatc tgagttataa acctaagaga aaattgcaga ccagcacacc 36300
aatcatataa ataagtgttg aattatgagg tagagtgttg tgagtttctg aagacaagag 36360
gactcagtaa agattgtgga aattggaaga aaggtggctg gtggctgaat gggtcaggga 36420
acagcaggac agaggcttgg aggaagcaca gaattgatga gtgtgtgggt tgggatccag 36480
gcttcctgag tagaggagtg gacaaaaagg aaccaggtca gacctggaaa gcaagagtta 36540
attagatggg actgatatgc tgaaagccct agtttaggaa gagaagcaag tccagtgtca 36600
tttacaggac ggatcaaagg aagaaagttt ggggaagaga ggatgcgtgt agatttctaa 36660
actcaaggga taagggcctg ggctatcatg gcagcagtga gacaagacag gaaggattaa 36720
gtccaagatg cacttaggaa gaagacagaa cttgttgaca agtggaatat gtaagggata 36780
aaacagcagg aagaggttcc ttgcctggga tatttgtggt gtccctgaaa aaaaaagtcc 36840
aagtcaacaa acgagctttt cttcccaggg acacagcagt tatcattcct cttgaacttg 36900
gactgacctt ttaccaagta atgtgtacta gttgtttatt gctgtgtaat gagccatccc 36960
cagccgcagt gacttaagcg ccaacagttt atcatttctc ccagttctct gggtcgactg 37020
agtttcagct gagtggttct tctgctgctg tcacctgggc ttagtgaggt gcctgcattc 37080
aactgggagc tctgctggca ttcaaggtgg cttcagacct ctatccagtg acttctctca 37140
acagcagggt attcagactt cttatacggt ggctggcttc caagagagaa gcagcagaag 37200
ctgccattcc tcttaaggca tgaactcaga agaagtccac cacattctat ggatcaaagc 37260
aagtggcaag gcccgattta agaagtgggg aaatctatta aagtgggagc aacacacatg 37320
tacagggagg ggagaaatta ctagagcctc ttttgactct ttatcacatt aactcaccag 37380
aaactaagtt tcagagaagg aactcccacc aggagggaac tactgctgtg atagatcctg 37440
gccttatggg atcaggattt ttaggaactc ttactacctc cccctaaggg cagaattcca 37500
cagaggaaga aaaagctgtg cttacttatt tatttggggg tgttgctgta agactcgggg 37560
gcacaattaa gactgttgga agaatcagag tgactgaaaa ggaagtttat gtttagaaat 37620
aaagttacag aggtagtgtg gggccatatc atgagaaggg gttggaccaa gatggcagct 37680
gtcagatttg gaacggaagt tgcagatgaa cagcacaggg tgcagtgagc ttacggtcac 37740
gggtctgagg gtgtggatga atccacactt aacctgttga tgctctgaaa gaagtaggat 37800
accagctgca gcgtctcaga tgtacatagt ttttctttcc atggagggga gaaatcagct 37860
actgaggcac cagtgtgggg tccttgaggc agaagatagt attgacacag agttaaatga 37920
catttaaaat cagcagagaa gcactttggg aggctgaggc aggaggatca ctggaggcca 37980
caagtttgag acaagcctgg gcaacatagt gagaccccat ctctacaaga tacacaaata 38040
attagccagc catggtagta cacactggta gtcccagcta ctcgggaggc tgagatggga 38100
agatcacttg agctcaggag ttcaagactg cagtgagtat gattgtatca ctgcactcca 38160
gcctgggcaa cagagtgaga ccctgtctct attaaaaaaa aaaaaaaaaa ttaggccggg 38220
tgcggtggct cacgcctgta atcccagcac tttgggaggc cgaggcgggc ggatcatgag 38280
gtcaggagat cgagaccatc ctggctaaca cagtgaaacc ccgtctctac taaaaaaata 38340
caaaaaatta gccgggcgtg gtggcgggcg cctgtagtcc cagctacgcg ggaggctgag 38400
gcaggagaat ggcgtgaacc cgggaggcag agcttgcagt gagctgagat cgcgccactg 38460
cactccagcc tgggcgacag agcgagactc cgtctcaaaa aaaaaaaaaa aaaaaaaaaa 38520
ttagcagagg agttacatca tttctgaaga agcagatttt acttaggaaa aaaaaaaaag 38580
gagctctgca gagccttgga aagagttttt tagtttttta agacatagga caagaactta 38640
gcatctggtt tcttaaagca aatatcccag atctggtgag agcagtggaa tagaaaacat 38700
aataatagtc agggctgctt cttagtgaat taccagctga agatttagat tcaaactgag 38760
cctttactat gatggccgtg ccttctgtct tcgataatga tttggttacc aggactagaa 38820
ctcattcaag ctaacttgag caaaagaaat caatttgaag accattggga tgtatcacag 38880
aacccaaacc ctgtatccca agaaactaga aagaaagcag ggactttcac tatctgtctc 38940
tgtggccact tcatctccct tctctgcctc tctctcagct tgttatccat ccttcttcct 39000
cttcgtggac cagcagaatt ggctcattca tccactcacg tggctcaaac ttgagtttgg 39060
ttgcctcaac tcctacttga caaatcccta caatttcagt gcttgcattc actgagcgga 39120
tcccaattcc agcttcctaa gaaagagaat ctggtggccc cagtgtgagg cagctgtggc 39180
cagaggatgg agccctttgt cttgtcccca gccagcagta gttatgggag cagatgctct 39240
gagaaggtgc tgtgggtaat aggtggttct caaagaacag ctgtcagcca tggaggcccc 39300
catggaggtg tgtgcagtac cttcacaatg aagccacagt tatattcaaa tgtaacaatg 39360
tttagtgggc ctgcctgatt gcttcccagt tgtttcttat gatagtaaaa gaacaatagt 39420
tcctgggtta atgtgaatgg aggaccttct ctctttaact cctccaaaat ttttatcttc 39480
aacatctgaa tatttgtaat taattttcac aagttttgaa gcctcagcta agataaacaa 39540
ggggtccatt tgtatgttaa gataattttt taaaaattga aagtgatgaa gcctctttgg 39600
taagaggaaa aatgcatgac caagccacaa ggatttcaaa gtaagcttga aatgaaaaag 39660
gaatttgaag acaaatatcc tttttcaaat tggcttttcc tccctgcttc tgggaagcgc 39720
taagggtggg acacgatcta gaaatccact cagttgagta gtaatgcttt tgaagcaaca 39780
tgacgtgtct tctccgacta gacttcgagc cacactttcc aggacaagtc agaggcagtg 39840
gccccctcag aggctgactg ggaccgcaga ggcttccctc gtggtgaaca gagtgttgag 39900
ggactaatgt gtttgagaat tcagtcttga atctcaggtc tcagggagtc actttcattt 39960
agttgcccag actggtccta taagaaaagg ggtcagagac atgaaaaaca aaaacaaaaa 40020

```
cccatggaat gggagtcggc aatcctggag cttaccctgg ctctccattc tgccttatgt  40080
gtgcccacac aaggccttta accttgttag actggtttct tctttgtcca gtaggaataa  40140
tatcatctgt cctgcctccc tgaaggggct agagcttcct gtgagctgac ttatgtgaaa  40200
atgtgctgta tgctatacag atgtaagaga ttaatatttt aatatccgga atcaaaccgt  40260
tttctgaggt ggctgccttt gatttttgtc ttttaaatca gcctatttta tttttctgtt  40320
attcagcaag ttgttcttgt ttgtgtggtg aatgatgaaa gccttattgt atataatgat  40380
gacaaacact atttattcag cacattctat tctgctaggc cttgtggtat ttactttatt  40440
tacattatct cattttattt ctcacaagaa ccctttgagg tccgtattga ttctcattcc  40500
gctgttgatg aaactgagct gagaagggct gtgatggaga ggccagaatt taccctaggg  40560
tttgtctcac tgtaaaaggc cacctgctcc tggacacatg gtggtggcac cagtgccctt  40620
cagaacatta tcaagtccta ggaagggagc aagcaaaacc cactcctgag ccacagtgtg  40680
gatggcagaa agtgaggagc ataatggccc tccctcttat agaagctgca tgttctgttt  40740
ttcatacggt tcttataagc tccacacttt tgttctaagc ctaggaagca gcaaattaag  40800
aagaggttaa gcaaagactg caggcattga cagtaataag aagtagatgc ccacaaagac  40860
ccctttcagt tctaatgttc tgaggttgca gcagccttga cagcaactgt tttagactga  40920
atgtttgtcc cccacccacc cccaccattc ttatgttgaa gccctaaccc tgcaatgtga  40980
tggtatttgg agatgaggcc cttggggagg taattaggct tagatgaggt catgagagtg  41040
ggactcccag gatgggatta gtgtccccat aaggagagga agagggctgg gtgcagtggc  41100
tcatgcctgt aatcccagta ctttgggagg ctgaggcagg tggatcacct gaggtcagga  41160
gttcgagacc agcctggcca acatggtgaa accccatctc tactaaaaat acaaaaaaat  41220
tagctaggca tggtggcggg cacctgtaac cccagctact cgggaggctg aggcaggaga  41280
atcacttgaa cccagtgggt ggaggttgca gtgaaccaag atcacaccat tgtactccag  41340
cctgtgcaac aagagtgaaa ctccgtgtca aaaaaaaaaa aaaaaaaaag gagcggaaga  41400
gaaatcagag ctacatctcc ctctgccatg tgcggacaca gcaagaaggt tttggtctga  41460
aagccaggaa gagggccctc atcaggaact gaaactgcca gtaccttgac cttagacttc  41520
ttagcctcca gaaccatgtc cattgtttaa gccaccagcc tatggtattt tgttatagca  41580
gtctgcgtgg actgagacag caaccaaaag acaaattaac tattaaagtc agatactaga  41640
acataaaaaa gcacaccagt ctggggccat tttgaagtat atttgatgac ctcaagttac  41700
caagaaatat ttaaagagta ggctaaattt gttaaatttg tttaagaaag atctaatgca  41760
tgttagaaag gtttcatcca aaatgattaa gataaaatgt taagttttaa agttaagctt  41820
tatggaaaac tcaattatct agaatgatgt tcctacatag ccaaagaaga cagtgagaag  41880
aaaggagtca aaaccaactg ttcctagctt taagtggatg tcgttaagtg gttgagtctg  41940
ctttccactt tcactctacc ttattcattc actctgccca agaagtacct ttatccactc  42000
taatggcatt cgcagcaacc tggatgggat tggagattat attccaagtg tgaaggaact  42060
caggaatgga aaaccaaaca ttgtatgttc tcactcataa gtgggagcta agctatgaag  42120
atgcaaaggc gtaagaatga cacagtggac tttgaggact caggggggaaa aggtgggaac  42180
ggggtgaggg ataaaagact acaaattgag tgcagtgtat actgctcagg tgatgggtgc  42240
accaaaatct cacaaatcaa actaaagaac ttactcatgt aaccaaacac cacctgttcc  42300
ccaagaacct atggaaataa aaaaaaaaaa aaccagaagt accattatcc actcattcca  42360
```

```
tgatttcagt gggtgacaca ggaagtgctt gttcattcag catatagtcc tagagcacct  42420
gctttgtgac cgggaccact ccaggccctg ggaatacagg ggtgtgtgga agatatagtc  42480
ctgcccttta gttgctcata gttaatcagg tagagagaca agtaaacagg tgttcagaat  42540
caaactcagc atagactgct gtaggactac acagcaggga cacataaccc tctttcttgt  42600
gggggatagg gtggggagga tgggagggcc atggggcttc ccaggggaaa tgatgttcag  42660
gctgaaatct taagaaggga ataatattct aagcacaggg aatagcatgt gcaaaaaccc  42720
ggaggccaga gagcaaagtc cagttgggaa acttgcaaat acactacaat ttggtctctg  42780
tatagaatgt gagctgaagg gtagacaggt catggtggtg ggagagggga agggggagca  42840
gcacaggagc agcagcagtg taccatgtga gaaagtttgg actttatcct ggggggcaac  42900
cagagagctt tgagggtttg gggaagggct ccatttacct caccagctgc tgctgctttt  42960
ccctttctct gctaccagtc acgctcactt cttgtagttc ctgccaaggc cacaatcttt  43020
cttgcttcag gcctttgcac ttctgtctgg aatgtactgc aaagattatt ctggttgcag  43080
tttgctaact agattagagt agggtaagcc tagaaatgga gatagaatag gaggctgatg  43140
cagtggtcta agtgaaagga gatggtgacc aaaactgggg aagtggcagc gtggacagag  43200
aggcaagggc agatgtatgt gatattgtag gaggtagaat tgacagtgtc acaattggca  43260
agtgattgcc tttgggggca agtttgatac cttaggccac tgatgttcaa atgggttaga  43320
agggcagcag gctgtggtct gattcccagt gatctacctc atggtgtgtt tcaagacctc  43380
actgtcctat tgaaacatga accacctgga tttgctcaac aaattaataa agcttagagg  43440
ttccagctgt gttaatgcaa gccatggcca tgtttatgtc taaccttaac atttatgatt  43500
atatgcctta ggctttctgt aaactaatac ataataacat gcttacttgt aagcataatg  43560
gaataaatga gagaaaaatc agagtaaatg accaagatga tcatcatcaa gtagctctta  43620
ttaacaacca ttaaatgcct ggctcaggtt tccacgcaca aggtccttta acaaactcag  43680
tttatatcat atgctcttga ccagagaagc ttgactcact gcagttgttt aaaccctaaa  43740
acccagacat ttccaagcca ggcccctcca cccccaacac tggactccta ctgcatagag  43800
cttttctgtt tacatttgct actatagaga tttagtttgt ttccgaagga tgcattttaa  43860
cttttgtgtg gtgagccaca tttgttatat ttgaaccatg tgtgacgcaa gggagaaagg  43920
taaccacttg gcttagaggg ggaagggtga gtctttgggt taacagaggt acttcctgcc  43980
aatttaaaat gagctggtta gatggtggaa tacattaaaa cgtgtgtgtg tctgtgtgtg  44040
tgtgtgtaca tgcgcacata cacatgaata tatttttata tgcccaaaag actaatgtgg  44100
atataaagct tattaaactg gaccatgctg ttttccagtc tgaaacataa aggaaaaaaa  44160
tgctattgga ccgggcgcag tagctcacgc ctgtaatccc agcactttgg gaggccaagg  44220
tgggcggatc gcaaggtcag gagatcgaga ccatcctggc taacatggtg aaaccctgtc  44280
tgtactaaaa atacaaaaaa ttagccgggc gtggtggcgg gcgcctatag tcccagctac  44340
ttgggaggct gaggcaggag aatggcgtga acccgggagg cggagcttgc agtgagccaa  44400
gatggcacca ctgcactcca gcctgggcaa cagagcaaga ctccgtctcc aaaaaaaaaa  44460
aaaatgctat ctaagagtct atatgcctgt cactttggaa ttgtataata cataactctc  44520
agctgaccta gaagtgcttc tgagaccagg cctcatttgt gttttgttat atcttcagtt  44580
atataaacca tgaggaacaa atggagaaag ggaaaggact tcagctgata gtggagtgat  44640
tcataaatcg ataacataga tggaaaacta aggtccacag agattcatcg tccatgaccc  44700
atgatgaatt aatttcttta ttcaataaag ctatatttag tattataagg tatattatct  44760
```

```
attgctgcct aacaaattac ctcaaaactt ggtggcttaa aacaacacac attcattatc  44820
tcatgcattc tgcgggtcag gaaatgtggg gtatgacttc gcaatatcct gcttcaaggc  44880
gtctcacaaa gctgcaagcc aggtgtctac cagagctgga gtctcatctg aaggctcaac  44940
tgaggaaaga tctactttca acctcacgta gttgttggta ggatttagtt aattgtggac  45000
cattgggtga aattcttttt cttgtgggat gttggctgaa gtccaccctc agttccttac  45060
cacacagcct ctgacatggc atattgcttc attattgctt cacagaaata tgcaaagcga  45120
gaaaacaata gagagtctgc aagcaagatg aagtcataat cttttgtaac ctaatcccag  45180
aagtgacatc ccatcaagtt tgccacattc tacttgtcaa aagcatgtca gcagtccagc  45240
tcacactcag gggaggaga ttatacaagg gcatgaatac caggaagggg ggatctgtct  45300
taggcagttt gggctgctgt aacaaaatac catagagtgg gtggcttaaa caacagacat  45360
ttatttctca tagttcaagg ggctaggaag tccagggtca aggtgctggt gactcagtgc  45420
ctggtgaggc ctctcttcct agtttgctga gggctacctt cttgctgcag agagagaggg  45480
ggctctggtc tcttcctcat ataagggcag tgattccatc atgggggctc agccatcata  45540
atctcatcta aacctaatta cctcccaaag gcctcacctc cagatacctt catattggga  45600
attcaggctt caatatatta attttaggga gtaatagggg gaaaaaacct tttcccatac  45660
attcatacac ttctcttcta acaccagata tagggatttg tctcaaacca gccaattctc  45720
caagtttcca gacaccacct gggggtccta caattaagtt atggcactac ctaactcagt  45780
cccacaagac tgccccccac ttcagatgcc aattacaagg agtgggtccc aacttggcta  45840
caaattgggg tttcccacaa ccctctcctc tggtttgcta atttgctata acagctcaca  45900
gaactcaggg aaacacactt accagtttat tataaaggat ataggtgtgg ctaagcatgg  45960
tggctcacac ctgtaatccc agcactttgg gaggctgagg caggaggatc gcttgagcct  46020
aggagttcaa aaccagcctg agcaacatag tgagacccca tctcaattca atagttaaaa  46080
aaataaaatt aaaaggctat aggtgaactg cagatgaaga gatatatagg gtgaggtcag  46140
gaaggatcct gtacacagga gcttctgttc ttgtggagtt tgccatacct ggcacagata  46200
tttattcacc aacccagaag ctctccaaat ggcatctttt aggaatttta acgatggctt  46260
cattacatag gcatgattga ttattaactc aatttctaga ctctctcctc tccctggagg  46320
atgtgggggt gtgggactga aagttccaag cttttaatca tggcttcatc tttcttgtga  46380
ccaccctcca tcctgaagct atccaggagc ctaccaagag ttgcctcatt agaacaaaag  46440
atgctctggt cacccagaaa attcccggag agttgctctg tgccagggca gagaccaagt  46500
gtcacggggg tatgcaaaca ttgagtgcat agcagaatca ttgaggtaca tctttgaaag  46560
ctgtctacca gagttggtac atatatttag ctttctttgt tctcagctac agctttttct  46620
actagaccaa accatctgat gtgtggctgt gaaacactaa tatgctcagt gtggtgggct  46680
gaagaatggc cctccaaaga tgttcatgat ataatcccta gaatctgtga atacgttacc  46740
ttagatggca taggagattt tgcagatatg atgaaagatt ttgtgataga ttatccaggt  46800
gagaccaatg taatcacagg gtccttagag aggcaggagg atctgagtca gagaagacag  46860
atgtgacaat ggaaacagag ggaggaagaa gaggtgatga aggaaacaga gggaggaagg  46920
agaggtgatg atggaaacag ggaggaggga gaggtgatga aggaaatgga ggagggagag  46980
gtgatgaagg aaatggagga gggagaggtg atgatggaaa cagggaggag ggagaggtga  47040
tgaaggaaat ggaggaggga gaggtgatga aggaaacagg gaggagggag aggtgatgaa  47100
```

ggaaatggag gagggagagg tgatgaagga aacagggagg agggagaggt gatgaaggaa 47160
atggaggagg gagaggtgat gatggaaaca gggaggaggg agaggtgatg atggaaacag 47220
ggaggaggga gaggtgatga aggaaatgga ggagggagag gtgataatgg aaacagggag 47280
gagggagagg tgatgaagga aacagggagg agggagaggt gatgatggaa acagggagga 47340
gggagacgtg atgatggaaa cagggaggaa ggagaggtga taaaggaaac ggaggaggga 47400
gaggtgatga tggaaacgga ggagggagag gtgacgatgg aaacagggag gagggagagt 47460
tgatgatgga aacagggaga aaggagaagt gatgaaggaa acggaggaag gagaggtgct 47520
gacggaaaca gagggtgaaa tggtgcggct gcaagccaag gcatatgggc agctgctagg 47580
aggttgaaaa ggcaaggaat ggattctccc cttgagcctc taggaggaac ttggctccac 47640
taacaccttg agtttagacc cataagcccc acttagtact cctgacctcc agaactgaaa 47700
gataataaat ttatgttatt taaagccact aggtttgtgg taatttgtcc cagcagcaat 47760
aaggaactaa tatattcacc aaaagtcctt gaggaaaccc acttgtggaa tctttgaagg 47820
aattaggagc ttaaatagaa ggtataggat aatgggcttc tgagagggct tttcctgccc 47880
tctggtaact ctgaaacata atttacatta ttggagtctt tctgttttta ggaaattgtt 47940
cctagttttc ttcaatacta aatcctatca atattaaaca gttttttttt tttttaaata 48000
cgtattcggt tagttaaatg tagacctagt ctcacatact cttcaaaata aaacaaaaac 48060
atggttttta gcagaggaca ctaaagcttc cattttcaaa gctggttgct tgttgtttat 48120
ttgtacctca ggagtggaaa tactggctga gatgaaagta cctggcacaa atcgcttttc 48180
cttcttggtg tttcacagcc agatgttgcg aaattctttt gtttttcttt tttctttagt 48240
gcctggaaac cttggctgct acaaggatca tggaaaccca cctcctctaa ctggcaccag 48300
taaaacgtcc aacaaactca ccatacaaac ttgcatcagt ttttgtcgga gtcagaggtt 48360
caaggtgatg actctgtggc tgtgtaacta tagaaaaata taaagatgta aatgcatttt 48420
gctgagataa cttaaaaata agtgctaagt aaaataagcc agacacaaaa ggccacatat 48480
tgtatgattc cacttacatg aattgtctag aataggcaaa tccataggga tagaaagcag 48540
gttagtggtt gccagagggt gggaagcggg aggaattggt actaactgct aatcaacaca 48600
gaatttcttt tctgggttat gaatgttctg gaattagatg gcagtgactg cacaacacag 48660
tgactatacc aataaccact gaaatataca ctgaaacagt gaatgttatg ttatgtgaat 48720
tacatttcag tttttaaaaa acctaaaata actaaacttc tagaaaaata aacagaaaat 48780
cctaaaatat tgggttagac aaagatttat aaattggaca caaaaacaaa tcattttaaa 48840
aagttggtaa attgaactta tcaatattaa aatattatct tcaaaaaata gagttaagaa 48900
tatgaaaggc agaccacaga ctaggagaaa gtagttgtta aatatatatc tgataaagga 48960
cttgtataca gaatatataa agaacactta cagctcaaca atatgacaac ttgattttaa 49020
aaatcagcaa aaaatttgaa gagacatttt atcccccaaa aatacataga tggccaataa 49080
acacatgaaa agatgctcag catcaccagt tgtcagggaa atacaaatta aaaccacaat 49140
gagataccac tgcacaccac ttcaggatgt ctgaagttaa tactgaaaat actaagaatt 49200
gataaggatg tggagcaact gaactctcat agactgctag taggaatgta aaatgctaca 49260
gcttctttga agaaagatct taaagtttct ttcaaagtta aatatgcaca taccttaaaa 49320
ctcagcaata tcacgcctgg atagttaccc aagataaatg aaaacctgtg ttcacatcaa 49380
gacttatata tgaatgttca tagcagcatt attcataata gctccaaact gtaaataatc 49440
taaacgtcca ttaactgatg aatggagaaa taaagtacag tatatccata ctgtggaata 49500

```
ccactcagca ataaaacgaa gagacatatt aagacctact ggctgggcac ggtggctcat  49560
gcctataatc ccagcacttt gggaggccaa ggtgggtgga tcacgaggtc aggagttgga  49620
gaccagcctg accaacatgg tgaaaccccg tctgtactaa aaatacaaaa attagccggg  49680
catggtggtg tgtgcctgta atcccagcta ctcaggaggc tgaggcggga gaattgcttg  49740
aacacaggag gcggaggttg ctgtagtgag ccgagatcgc accactgcac tccagcctgg  49800
gcaacagggc gagactctgt ctcaaaaaaa aaaaaaaaaa aaaaaaaaag acatactgtt  49860
atatacaacg tggatgaatc tccaaaacag taggctaatt gaaagaactt aaacacaaga  49920
ctacatactg aactcaaaat gtatcccaaa tctaactgta aaatgtaaaa ttataaaact  49980
tctagaagac gatataagag aaaatcttca tgacttgagt ttaggcaaaa agttctcaca  50040
tgaggcacca aaagcacgac ccatcatgag aaaaaattgg tacattttaa tttggacttc  50100
ataaaaatgt aaagatcttg ctctgtgaaa gatattttta acaggatgaa aagacaagct  50160
atagcctggg agaaaatatt tgcaaatcac atatgtgaca aaggacttgt atccataatg  50220
tgtaaaatta aaaaaaaaaa aagccaaaca actcaatagt taaaaaaact gaacaaagca  50280
atttaaaaat gggcaaaaga cctgaacaga agatatacag atggcaaata agcatatgaa  50340
aagaagccaa agaagatata cagatgacaa ataagcacat gaaaagatag tcatctgggc  50400
gtggtggctc aagcctgtaa tcccagcact ttgggaggcc aaggcaggag gatcacttga  50460
ggtcaggagt ttgagaccag cctggccaac atggcaaaac cctgtctcta ctaaaaatac  50520
aaaaattagc tgggcgtggt agcacacctg tagtcccagt tactcgggaa gctgagacag  50580
gacaattgct tgcacctggg aggtggaggt tgcggtgagc caacatcata ccactgtact  50640
ccaacctgga tgacagagtg agactctatc tgaaaaacaa aagaaaacaa agaaagaaaa  50700
agaagatata gtcgacatca ttagccatta aggtaatgcc aattaaaact aaaatgagat  50760
atcactacat acctattaaa atggctaaaa taaaatatac tgaaaataac aagtgctgac  50820
aaggatacag agcaactggg actttcatat attgttggtg cagatctaga atggtagtca  50880
ttctggaaaa agtttggcac ttttttataa agttaaatat acatctacca tatgacctag  50940
taattccatt cctagttatt accctagaga catgaaaact tatattcaca taaaaatcag  51000
tacacaaatg cttatagcag ttctattcat aattatgaat aactagaaac agcccaacag  51060
ataaacaagc tgtgatacat ccatacaatg aactctgctc agcaataaga aggagtaaac  51120
tattgataca aacaccaatt tggatgactc tcaaagacat tatgctgact gaaagaagcc  51180
agtctcaaaa agattacata ctatatgatt ctatttatgt gacattttcg aaaagacaaa  51240
actacagtaa aggaaaatgc gtcagtggtt gccagggttt ctgggggagg gggcctataa  51300
agcaatagtg caaagaaaat tattggggta atggagctgt tctgaatcct gattgtactg  51360
gtggttgcac aaatcttttt tttttttttc tttgagacag agtctcactg tgttgcccag  51420
gctgcagtgc agtgatgcag tctcggctca ctgcaacatc cacctccagg gttcaagcaa  51480
atctcctgcc tcagcctccc aagcagttgg gattacaggt gcccacgacc acacctggct  51540
aatatttgta tttttagtag agacggggtt tcactttgtt ggccagactg gtctctaact  51600
cctgatctca agtgatccac ctgcctcggc ctcccaaagt gctgggatta cagacgtaag  51660
ccaccatgcc cggctgtggt tacacaaatc tatacaagtg ttaaaattta tagaactata  51720
tgccaaaata ctatatagca atgtaaaaac aaaattgtaa aatggggcct ataatgtgtt  51780
tgctttgagg gttagctata aagcactcac tgcctggctc atagtaaaca gtcaataaaa  51840
```

```
tgtttagctg ttactcacat ttgaagttta tgagattttc tcccccttaa aacttactga  51900
agtgcagtag aaacacaaac attaaaaagt gatgctcgcc gacagggaaa cacattggtg  51960
gttgcgtact tattgttcag cttgaaatta agtgttgcaa gagtggaaga agggggaggt  52020
cccaggggaa gggaccctgg gaagttgagg ctgattgctt gctggaagcc caccctgcca  52080
ggctccttca ggccatctga catccctgat gatgcttacc gtgtgctgct tctctgttgt  52140
ggcagtttgc tgggatggag tcaggctatg cttgcttctg tggaaacaat cctgattact  52200
ggaagtacgg ggaggcagcc agtaccgaat gcaacagcgt ctgcttcggg gatcacaccc  52260
aaccctgtgg tggcgatggc aggatcatcc tctttgatag tgagtatgcc ctgtgcccat  52320
cactgcccaa ggcacaggaa cccttggacc agagcaacaa gcctgcccac cctccctccc  52380
ttctatgtat tcattcattc acttggcaat agacaatact tgtgactaga ccctgggaat  52440
acagcacagt gcatgaagac tcagcccctg ccttctggaa gagagaacag acacttaaaa  52500
agggattagc tacagtcatg ccaaacggtt tgaagcaacg tggcctattc tgtgatgctt  52560
agacaaccca gaaatgataa cctttccaat tttacataga cactaatata acaatccagt  52620
atcagcttta ttatactctt gctttaatat aatttccaaa cccttttgac tgtttttttt  52680
ttaggcattt gggatttata tattattgtg atagacctga ggagacagcg tagctctaag  52740
ttgtttttc aggcctggca ttgggtttgc cctgacccac ctcctctcta aactgccgca  52800
tttgtgagat actggccagg ggcagagtgt gttcagaatg ggagtggatc cagggccttg  52860
acctcaccaa catcatgttc taaccactga gccagctgat tcctcatcat aatccaccag  52920
catcctctca gtggcagtga aactttatga taattacagc gctgtgcagc accagattta  52980
aagatagtgg aggcagacaa aaaaaaaaaa aggctcgaga ttaccaagaa atattgtagt  53040
gtctgtggtg tctttggcct ttaggctaga ggaggtgcgc tactggcatc tcaaccaggc  53100
agcatggcta gttttgagca aaaatgacat atggtttatt agtttcctag gactgccata  53160
acagattatc accaactggg tggcttaaaa caacaaacat tcattctctg acagttctgg  53220
aggctagaaa tccaaaatcg aggtgtcagc agggctgtgc tctctccaaa gtctccaggg  53280
aagccctcct cacttctggt ggttgtcggc gatccttggc atttgttggc tgcaccactc  53340
cagtctctgc cttctctttc acatggccat cttccctctg tgtgtgtctg tgtgtctatg  53400
tctctgtgtg tctccttaaa aggaaccaat cattggattt agggcccacc ttaatttagt  53460
atagcctcat cttaactcgg ttacataaca ttcacaggta ccaggtgtta ggactcgaac  53520
ttatctttct aggggacaca attcagccac tatatatatg gtgactataa aacccagcca  53580
aggtttataa ctgagccttt tacatgttat agcttagata ttatctaaag tgtgtttgta  53640
tttggggtgg gaagacagga ttagtgaaca gaacttacag tcaattggtt tttttagcta  53700
agtgtgccca ttggagactg ccagttgatt cctatacatc ctgttatgtc cagaccaatg  53760
cttagtttga tacctttgtt ttggctaaag actgaacttt ggctaatgat taacgaatct  53820
tgctaatgct tagttggcaa ataactaccc actgcacatc tatttaacct tttattctag  53880
agttcattat tataagattc tctgccttaa cactgtaact caggagagta agttttctga  53940
acttgcagaa tgcctggtat actcttaagt gaaaaaacaa aggaaatgtt tcttgagtac  54000
ctagtatgca tgaaggcctt atctaaatta tcacattcgg ttctcttggc acccttctga  54060
agtaggggtt attgtgatta ctctcatttc acagaagaca gccacatgac atggacagga  54120
taaataactt gctgggattc atactgctaa gaaaccacta gagaggtgct agagaggaaa  54180
gaggagtagt gtgagggttt actacctgtt ttttgacttt aaatagaatg cagtgtcaat  54240
```

taaaaaatgg aaaatgagtg tccacagata tatggagaaa ttggaaccct catacattgc 54300
tggtgggaat gtaaaatggt gcagctgctt tggaaaacag tctggccagc ctggccaaca 54360
tggtgaaacc ccatctctac taaaaataca aaaattagct ggttgtggtg gcacacgtgc 54420
ctgtaatccc agctactcgg gaggctgagg cacaagaatc acttgaaccc aggaggtgga 54480
ggttgcagtg agctgagata gcgctctgcc tggcgacaga gcgagactcc atctcaaaaa 54540
aaaaaagtaa acagtctggc atttcctcaa aacgtgaaca gagagtaact gtatgaccca 54600
gcaattccat tcttaggtat atacctgaga gaactgaaaa catgtttcca caaaaaacat 54660
acataccaat gttcctagca acattattca taatagccaa aaagcggcag caaaccaaat 54720
gtctatcagc tgatgaatgg ataaacaaag tggatatcca tatgatggaa tattattcaa 54780
ccataaaaat aaataaagta ctgaggcatg ctacaacatg gatgaacctt gaaaccatta 54840
ttctaaatga aagaaccaga tgcaaagggc tacatatttt atgatctcat ttatatgaaa 54900
tgtccagaat aggcaaagcc acacaaatgg aagccagatt ccgggttgcc aagggctggg 54960
ggaaggggaa gaatatggag tgactgctta ataggtacgg attttctttt tagggtgata 55020
aaaatgttct ggaattaggg atgatgattg tataacattg tggatatact gaataccact 55080
gattcatata tagatagtcc ccaacttagg acagtcaact tatgattttt caactttgca 55140
gtaggtttat cagggtatta aatgcatatt tcactttgat attttcaatt tacaatgagt 55200
ttatcaggac ataaccccat tataagtcaa ggaacatctg tactttaaaa tggttaaaat 55260
ggtggatttt agatcaagaa gaaatagaat gtagtttttta taagacagtc tttgaattag 55320
tacattttta ttgggcatct gctgtgtggt agataaaagt atgttttcttt tagtatagtg 55380
cctttactgg aggtgtcaag cagaaataat ctggattaaa ttgtaaatgc agcactatgg 55440
aaatagtctc taaagtgcac accaagtagc atctttggta ctactaggaa agagtactgg 55500
ccctcacata aaggtgcact gaagtgaatt aattataaca acaattattg ctatttactg 55560
agtgcttgtc atgtgctaga cttgatgcca agtgcttttg tgaattttat gttatttaat 55620
ccttgtagca atcctgttga taagaaaact gtggatcaaa agatgaagta atttgtctat 55680
gctagtaagt gccagagcca ggattcaaac cctggtttgc cacatttgaa atttttctat 55740
tttcagcagc tagaatccct tttattaaca atagtaaaaa tagatcataa taacggatcc 55800
agttttatgc tttaaagtta tatgaacaaa gtatgcccag ttctgattat tcccacattg 55860
gccccttgtg cagctctcca gaagctgccc ttcctggctt gcatttgctc aaggactaag 55920
aaggctggca ttctgagagg ctgctcacgc catcctccag aggcccagat gcctgtggtc 55980
tacaggaccc ctgacagcag ccagttctgt aactcacacc ccattgctct gctgagaaag 56040
gtacaaaatg cagcactgta taaataatct ctaaaggtgc atctagaggc cggcacaggg 56100
gtgcacacct gtaattctag gctggaggct gaggcaggag aatcgcttca acccgggagg 56160
tggaggttgc agtgagccga gatcacacca ctgtactcca gcctgggcga cagagtgaga 56220
ctccatctaa aaaaaaaaag gtccatctag tagagagtaa aatagtttga acagctcaag 56280
taccgcctca tggaaatcct tatgactcat tgaacaaggc tgagcacttt ggaaatggtg 56340
accacagact gtcccatgat ttaggagggt gaagatgtct ccctaaagat attggagaag 56400
ttagatggtg agaaacgacc aggttacagt ctgtctccca gaacatgagg ccctgctacc 56460
agtgtggctc gcatgtgggt ctcagtcaga gtgtcagcga catcttcctg tcctctgctg 56520
attagaggaa cacccaggct cctctgcagt agaagtactc aggctgtgtt tgctctttgg 56580

-continued

```
cagacagacg acggggctag tgggggtgga gggtgagggg cagctggcag aagctgtctg  56640
ctcagtcatc actgccacat caagtaattt gtcacagact ctctggctga tttttcagca  56700
agctcatgga cttggagagg tcacagaggt gagctgtgta ctgtgggcaa gcacaacact  56760
gacgggggct tcatagcctc tgctacccct agggattata atttattgaa ttaacataac  56820
caaacagaag aacatgtagg ccagagtcaa cagtgggtta caggaactac ccaggctagc  56880
ctgttgggac tcccttggct tctaggccct gaagggaggg gtcagtcatc tggattggac  56940
cttattttgt agcattagtt gaacatttat cattgacagg agcctgtgct attcacttta  57000
catgcgttgt ctcccttaat tctcacagta ctgtgaagca ggtactgtta tgcttatttt  57060
acagatgaga aaactgaggc tcataaaagt tcagtaatct gcccaaggtc ccacagataa  57120
agatcctgcc ttcatggaac ctttatttta gtgggaaggg aagagattaa ttgtgaaagt  57180
gattggtcta aggatgggta ggatctggct cctgggactg tgttagcaat tgcatttcat  57240
agactctaag atgcctcaat tctgaggtgc aacattattt tatacaccat taagggaaaa  57300
agtatttcca gtttaacaat gacatgcatt gactaaaaga tacatcccag tttaaaagat  57360
taaagtgtat cccttagagt tgatgaaata tggtaccagc cttctttctt gggtgccaag  57420
aaagagtaga atctttccat cctgagtgga atctgattca tggctgggac ccatttggct  57480
aaggtttgtt tcctgagaca tgcccattat cattcctgtc tagaagtgga gcactcagct  57540
ggggttccgg gaagctgcct gtcatgacta gtgcctgagg cttcttccca aagaaatgga  57600
ctcagctagt atcgagaagg agcaggaaga ttgaagagaa tcacagaagg caggaggaca  57660
ccggcccccct gccatggagg gcttgcccag gtctatcctg ggccctccac tcacccagat  57720
tgtatatgtc gggctaatct ctccttcaaa aaataaggtc ttgactacta tatttcaagt  57780
ttcctgttgg attatcactg aattttaata atccatcata aagatcatct gttctcaaaa  57840
ctgctgaatt aaatatgctg tcagcatgga atccaaagtt ttaggtttaa ggtctgccct  57900
tgctattgaa aaataccagt ttcagttgga tactttattc ttttcaaata atggtaaaaa  57960
tagaataccc aacacttact gagcttatac tgtgtgtcac atcttacaca gaacacttca  58020
taagcattgc tcctgctaat tctcatgacc ccacgagaga gaaactatta ccattttcat  58080
tttatagatg aataaactga gatatacaga ggtttagtaa cctgctcaaa ttcatagtta  58140
gtacatggtg aagtcaggat tagaacccag gaagtctttc tccaaagctt gatttttctt  58200
taaattaggt tctaatttta ggtataatgt acatacagta aaaatcaccc tttcagttgt  58260
atacttcagt gggatttgac aaatatataa gcaatcgaga ttaggacttt tttttttat  58320
cacctcacaa gttcctttct gctcctttgt ggtcagttcc cttccccaac ccaactcctc  58380
agcaacaact gatctgtatt ctgttcatat atatatatat atatatatat atatatatat  58440
atatgtgtgt gtgtgtgtgt gtgtgtgtgt gtgtgtgtat atgtatatat gtgtgtatat  58500
atatgtatat atgtatatat atgtgtgtat atatatgtat atatatacat gtatatatat  58560
gcatatatac atgtatatat gtgtatatat atgtatatat gtatatatat gtatatatgt  58620
gtatatatat gtatatatgt atatatatat gtatatatat atatagtttt gtgttttgca  58680
gaatattata taaatggaat cacagtattt agccatttgt ctctggcttc tttcacttag  58740
aataatgctt ttttttttt ttttttttt ttgagatgga gtttcactct tgttgcccag  58800
tctagagtgc aatggcgcga tcttggctca cagcaacctc cgcctccctg gttcaagcca  58860
ttctcctgcc tcagcctccg gagtagctgg gattacaggc atgcaccacc acacatggct  58920
aattttgtat ttctagtaga gatggggttt ctccgggttg gtcaggctgg tctcaaactc  58980
```

```
cggacctcag gtgatccacc cgccttttcc tcccaaagtg ctgggattac aggtgtgagc  59040
caccacgacc ggccagaata atgctttatg attcacctat gttgttgcct gtatcagtag  59100
tttttttcct ttttattgct aagaagcgtt cctttgtaca gatgtatcgc aatctgttca  59160
tctattcacc aattgacaaa cattggtctg tctatgataa agctgttgta aacatccaag  59220
tacaggtgct tatgtggaca tatgttgtca tttctcttgg gtacctacct aggagtggga  59280
ttgctgggtc atgtgctaag tgcatattta gcattataag tcactgccaa ctgttttcca  59340
aagtggatgt gccattttgc attctgacca ccaatatgta tgattttcat ttgctccact  59400
ttctctccag ctacagatac ttttgtatga tctgtttttt aaatgtgatc cattctagta  59460
ggtatgtagt agtatctcat tgtggtttta atttgcattt ctctaattac caatgatatt  59520
gaacatcttt ttgtattctt atttgccatc tggtatattc ctttccccta aagaaattcc  59580
tttagcattt tgtctagtac aggttgactg tcaatagctt ctttcagcta ttgttcgaaa  59640
aagctttatt tcacctgcat ttttttgagt aatttttgct gggtattgat ttctgtgctg  59700
acagcttttt tctttcagta cttcaaagat attggtccat attcttgtga cttgtatggt  59760
ttttagagat gtctgctcta tctttattcc cctgtatgta atcttttcct cttccttgcc  59820
tgccttcaag attttatctt tggttttgag gccggatgtg gtggctcatg cctgtaatcc  59880
cagcactttg ggaggccgag gcgggtggat cacgaggtca ggagatcgag accatcctgg  59940
cgaacacggt gaaaccccgt ctctactaaa aatacaaaaa attagccagg cgaggtggcg  60000
catgcctgta gtcccagcta cttgggaggc tgaggcagga gaatggcgtg aacccaggag  60060
gtgaagcttg cagtgagcag agatcgcgtc attgcactcc agcctgggca acagagcgag  60120
actccatctc aaaaaaaaaa aaaagaaaaa agaaaaaaga ttttatcttt ggttttggtt  60180
ttcaactttt tttttttttt gagacagggt cttactctgt cacccaggct agagtgcagt  60240
agtgcagtca tggcccactg cagcctcgac ccccctgggc tcaagcaatc ctcctgcctt  60300
agcctcctga gtagctggga ttatgggcat gtgccaccat acccagctaa gtttttaatt  60360
ttgtatagag atagggtctc actatgttac ccagactgat cttgaactcc tgggctcaag  60420
cagtcctcct gccttaacct cccaaagtgc tgggattaca ggcatgagcc accatgccca  60480
gactggtttt caacatttaa ctatgatgtg tctaggtgtg tcttctttgt ctgttttttt  60540
ttgtttgttt tttttgcttt tgtttttgtt tttaattttt ttgtttgctt gggtttgctg  60600
aaattcttgg atctgtagtt tgtcaccttt tactgatttt ggaacatttt tcaccattat  60660
ctcttcaaac atttcttctg ttccattctt tttttcttct tttggcactg caattacacg  60720
tatgttagac tatttgatat tgtcctacag ctgttgggag ctctgttctc tttgtttcac  60780
tttgttttcc cctttgtttc atttggggat aatttctatt gacctgtctt catgtttatt  60840
gattctttcc tcagctgtgt ctagtatcct gataagccca tcaaaggaat tcttcagtgc  60900
ttgcttcagc agcacatata ctaaaattgg aacaaaacag agtatattag catggcccct  60960
gtgcaaggat gacatgcgaa ttcatgaagc attctataat taaaaaaaaa ttcatctcca  61020
atattgtttg atttccagta gatttttttt ttttttaaga gacaaggtct cactctgcca  61080
cctaggctgg agtgcaatgg tgcaatcata gctctctgca gccttgacct gctgggctca  61140
agtgatcctc ctgcgtcaga accctgagta gctgggactg caggcacaca ccaccatgcc  61200
tggctaattt taaaattttt gtagagatgg ggtctcactg tgttcctcag gctggttttg  61260
aactcctagc cttgagagat cctcctcccg tggcccctca aagtgttggg attacaggca  61320
```

-continued

```
tgagccacca tgccttgcct ccagtagatt atttaccgta ttcatcatgt agtctctgtc  61380
tgatcgttct agcatctggg tcatcattga gtctagttct gtagattgtt ttaacaatgt  61440
ctttcccccc tcccaccctt gcttttatat gtgtgttgta attttttatt gaatgccata  61500
tgctatgtat agaagaacac taggggctga gatagtgttt acacctgggc agatctgcat  61560
agtgtaggga ctgagccagt ctatcagaag ttgagctagg ttgtttctat cactaccctc  61620
aatgcacatc aggctttaaa ttcctccagt gacgggctgc tatcagcttg tgcttagtgt  61680
ggagcctaga gtacccgtga gttttcctca gtagccctgt tccatcctca gctttgagga  61740
gttcccacat gcctgtgcca cagaggggct ccttctccac cctctttccc tccctcagtg  61800
gtaggctatg gctgtttgtt acctggctgt actcatggtg aggtcatgga ggtggttctt  61860
ggttctcctg ccctgtcctc agtcttagac aggatgtgta aaggccacca gcctgaggtc  61920
ttttcagcat tcccacaccc ttcttctctc cctggcagcc aaacactgcc ttgcgtctgt  61980
ggtggatctt gggaaggaga atttcttgcc ctccctccag gagtagtaga gctctgcttt  62040
gcatcggctg cagtatcctg gactcaagag ggctcaaggc aatcagggac caatggcttt  62100
tgcttctgtt cttcccctag aagcagtgaa tcttcacctg gttactttga taggaagggg  62160
aatttcaagg aggctgaaat ttgggtttgt gaaatggtgt ttggtataga cttttctagt  62220
caaatcaggt ctactccctc ccccagaggc aaacagattt tgcttctgtc tgttttcagt  62280
ggccctggga gtaacaggat ttgcttcccc tctcccagct gccgaaggct tttactttct  62340
tagagaggag agtcccttcc tgcaagtgtg aagagaagga agtgggcagt attccattcc  62400
tgtccgccag tggcagcctg tcacctcctg cacactcatg ccactcaggg ggactgtggt  62460
ctgctggcca acccgagtca cttgtgaaag cactgagtgg aggtctgtgc agaaaagctc  62520
acaagtgagt gcaaaatgcc cgttgtgtct gggactccca gttgccctaa gctgagacac  62580
tagcccactc tcagccttta agagtttgtt aaaattttag tgctttcttg ttacttctct  62640
ggcggtcacc tcttcctcct gtgttctctc aaagatgaaa ctgtttgtgt ggcctgactc  62700
tccttgatgg ggctttgatt ttgtagaatt aagttcccct ggttgtcatg agacctcagc  62760
tgagttttaa gctttttctc attgttagga tagaagcagc attcacttgt tgttgttgtt  62820
ttgagacaga gcctcactct gttgcccagg ctggagtgca gtagcgtgat ctcggctcac  62880
tgcaacctcc agctcccggg ttcaagaaat tctcccgtct cagcctccct agtagctggg  62940
actatagtca cacgccacca cgcccagcta atttttgtat ttttagtaga gacggggttt  63000
caccatattg atcaggctgg tctttaactc ttgacctcag gtgatccacc tgccttggcc  63060
tcccaaagtg ctgggattac aggcgtgagc caccgcgccc ggactgcttg ttgttttcta  63120
catcctaaag ggaaccagaa ctcccccaaa gcctgctttt taaatcctag ccctggccgg  63180
gtgcggtggc acatgcctat aatcccagca ctttgggagg ccgggacggg tggatcacga  63240
ggtcaggaga tcgagaccat cctggctaac acggtgaaac cccatctcta ctaaaaatac  63300
aaaaaaagtt agccagcctg gtggtggaca cctgtagtcc cagctactcg gaaggctgag  63360
acaggagaat tggtgtgaac ccaggagaag gaggttgcag tgagccgaga tcacaccact  63420
gcactccagc ctgggagaca gacggagact ccttctcaaa aaaaaaaaaa aatagaatcc  63480
tagccctaca ttccctccca aggagtttca gttctaagat cttgtttaca tttcaccatg  63540
taagacagga aatcactgca tccccttttct agaacatgcc tatcaaaaac aggagtccag  63600
agaaagcaaa tgtgcccagt acagagtgct cagaatctag catgtttcct cactgcagaa  63660
agtcatttct tgtgctgcag tttccctgct tgaaaacgtg gtccctcatg ggagcgttgc  63720
```

atgggtactg gggacacaca agcagctgta aagcccttct cttttgacag ctttacctca 63780
tcgggtggct tccctgcaga gtggcctgag tggttcgtgt gctttgtctc atgtgccatc 63840
acacattccc gtgatacagg agcagatggt gctctctcca gccttgaaac tgagagaagc 63900
aagaggcccg cgagtgaagt gcggcccctg ccatcacttg gccctgccag tcccaagtcc 63960
agactctctg actccagccc tgccccaacc taggccacac cactgtgctg tgtgctaatt 64020
ctaaggtctc tggggggaaa aacatctcca cagtcatttt tcgagagtct cagcgattcg 64080
ttttgtgact gtcaggtttt acagatagaa acaatgtcct aaatgggatc ctgctcgtta 64140
ggaaggcttt agtgccttgg tgttggaagc gcgcctgtgg caaaggccca gactgagggc 64200
gtggtgtctt tttctctcct acagctctcg tgggcgcctg cggtgggaac tactcagcca 64260
tgtcttctgt ggtctattcc cctgacttcc ccgacaccta tgccacgggg agggtctgct 64320
actggaccat ccgggttccg gggcctccc acatccactt cagcttcccc ctatttgaca 64380
tcagggactc ggcggacatg gtggagcttc tggatggcta cacccaccgt gtcctagccc 64440
gcttccacgg gaggagccgc ccacctctgt ccttcaacgt ctctctggac ttcgtcatct 64500
tgtatttctt ctctgatcgc atcaatcagg cccagggatt tgctgtttta taccaaggta 64560
agacatcttt gcctccttgg gggttcttca gggcccacgt gccttgggct tctcttcttc 64620
acccttgtga cttgggcagt tcttgcgggg cagattgggc ctcaggaact actgactcaa 64680
cttgcagatc accccgaggc tgtggctcct tccctacccc catttcataa ctcatttatg 64740
tttcatgaga cagaaaagag gtgaaaacct gtcaatttgg ctattttagt aggtctaatg 64800
acagttttca tgggagggtt aaaagaattt aaaaaaacag aataactaaa aggaacagct 64860
gagactggga cagttggaag gttatcaaaa ggtcatctgg tccgtcctcc ttcctctaaa 64920
catcctagct aattccaaaa gactggcttg ccatcttcaa accctgctat gatggagcca 64980
cactctctgc ctctgtaatg tgagcacatg tgtgccgggc acatctcttt gccaggacac 65040
aagaaacaca gaaggtgttt gagacattgt ctttgtcctg gatagcaaac ctcaagaaga 65100
gttcaggtag tgtgtgctcc aggagaccca tgggaagagg ccctctctcc aggtgggaca 65160
gtcttgagga acaggtagca tttggatcaa taggaaaaaa gcgaaccttc caggcatagg 65220
gagccatagc tgccaagtac aggggcagag aagctgtaaa ccatgcccag gtgtctgaga 65280
tgagactagc cacattctgt gaagttgaca ggttcatcct tctgccttct aaagggtgac 65340
agcctgacag gttctgtttt ggggctggtg ggacccacct atggaaggaa ttgcacccag 65400
aattgaatca gagaagaact cttcttcata actcgtgctc tcctcccgca caactctttg 65460
ttgtctccat agccctgtcc ccagttaatt gctttttctc ttccagccgt caaggaagaa 65520
ctgccacagg agaggcccgc tgtcaaccag acggtggccg aggtgatcac ggagcaggcc 65580
aacctcagtg tcagcgctgc ccggtcctcc aaagtcctct atgtcatcac caccagcccc 65640
agccacccac ctcagactgt cccaggtagc aattcctggg cgccacccat gggggctgga 65700
agccacagag ttgaaggtag cgctcttgac agttataaag acaaaagcac ttgggtgttt 65760
cttattcaga ggcaggttgg gatactggct ctgtgaccta tagtctgtcc tggcttttga 65820
gggaaatttt cttattagct tggttcctta gtcctgaggg aaaagtgctc acctccaaaa 65880
attaggcaag cgtgcctttt gtacattgtg actaatcagc taatcccgta ttttcccaca 65940
ttgagattat ctttctagag ccccacatgg aaactcccta aatccactgg catttgcaag 66000
aactccattc attcactcac tgactcattc attcaaaaga tatataagtg cttcagtggt 66060
gccaggcact gttctaggta ctggattata gagtgaacca aacacaaccc ctgcccttct 66120
gtggcgtata aatgagagga gaaagataga aagcaaaata aaaatcagat aatgataaga 66180
gctatgaaga aaagtcatgc agggccaggt gcagtggctc atgcctgtaa ccccagcact 66240
ttgggaggcc gaggcaggaa gattgcttga ggccaggagt tcgagactag cctgagcaac 66300
atagggagac cctttctcta caaaaaataa aaaaaattat ctgggtgtgg tggtgcacgc 66360
ttgtggtccc agctacttag gaggttgagg tgggaggatc gcttgagccc aggagttcaa 66420
gaatgcagtg agctatgatt gcaccattac actccaacct gggtgacaga atgagacctt 66480
gtctcaaaaa gaaaagagta gaaaaattag ctgggcgtag tggcacatgc ctatagtctc 66540
agctactcgg gaggctgagg caggaggatt gcttgagccc aggagcttga ggatgcagtg 66600
agccaaggaa gtgatgcctt tatgagctgg tagaactgga aagtatcctc agtggtgacc 66660
tagcctggag gctttcaaat tgccctgggc ccctgcagga cccaccatag aaggtcaggg 66720
agaagggcct gtccagcact tcctgtgcgt cattaggctg tggttctcat aggtagcatc 66780
tcataggtca catatctcat tcctcggatg aggaaactga ggcccaaaga gtttacataa 66840
ctccatctgt ggttacacag tggtcccagt ggcagagaca aaatgcatgt catcccttta 66900
gattctgagt ccaatagact ttggatcatc ctgtctgcct ctccctgaga gtgacttgta 66960
gaacaaaggg aaatattcag aacacctggg gccccatgct tagcctgggt cagctgctcc 67020
tgaggctagg tttgctagct gccctcccac accggcctgc agggagcccc tcagccagac 67080
ttactcactt gggtattcca gccgacctcc tttcgaaaac caaccataaa caagtctggt 67140
aagctctgtc ttttgcactt gcaggatgga cagtctatgg tctggcaact ctcctcatcc 67200
tcacagtcac agccattgta gcaaagatac ttctgcacgt cacattcaag tgagtacaag 67260
agggagctgc ccaattccag gaaagggaag gctcagagtt cattttctat gatgcttcat 67320
ttgtctggtt acaactgtag aataagcaca tgattccaaa gccctcagtc ctagggaacg 67380
gaaggcagca gacattcccc cttctttgta gagtgaaatg tacaactgga caaatctcat 67440
taaggtttca gggattttgt ttgctctgtg tccaaggcat acaatttcaa ggaggattgc 67500
aacattcctg gcttaaaaag caaatgtgct agtcccttac ggagatcttt atgcaagact 67560
gaagatagct aggacgatgc cgtgcatact tcctgatgcc ttctagaaat tgagaaacat 67620
ccttaggaag agaattctca cattttatta actattgctc agtagttatt ttaaaacagt 67680
tattgaaaaa acttatggaa gctttatcat tcaattctga ccaatttggg ttaaaatata 67740
tttccttccc ttattttgct attcaagtct aacagttcca ccttccagga aaggggcaat 67800
tgttcatgct actaatgttt gtgtacttag aggggagctc gttctaattt ttcctagacc 67860
cctactctgt ctttccggtg ctttctactc caggttcttc tcatttcaca gcctccctga 67920
aaatgtatgt atgtccacta aaagctgtct ttttcctgac cgtctcactt gccctctgct 67980
acagacttct tatacattaa atgcgagctc ttccattgcg ttgtgaatgc tgcctttggc 68040
cacattggaa ccccttaca tagacacctc caccctacac ttgaaatttt tagtggaaat 68100
aatgtcctcg tgtgtgtgtg tgtgtgtgtg tgtctgcatg tgcatgtgtg tgtgtgtgtg 68160
tctgtgtctg tgtgtgtgtg tctgtgtgtg tgtgtatgtg tgttttaaag tcacaattca 68220
catgctctgg ggaagcctct caggctcagt cctgaccaca tcccctgtgg cagcaagaga 68280
gcccaatgct tcctatagcg tccagcatct gatagcatgg ctgaggccct aaagtgcatg 68340
cctaactctc ctctgacatc ggctgcagct tccctgccag gcagccgtgg gggctgaaca 68400
gagtccgggc cagcaccgga ggctagacgg gtctctgctt gaagcagaga agttttgtgt 68460
ttatcttgtt ttagctaggt gggcttccag gtaaatggca tttgaagaca gttcttttat 68520
ttaaaataaa agaatttgaa aatccataat ctctcaggct gggcttttcc agatttgaag 68580
aattctgcta gttagaaagt tctttgttat tctgatgcag acgctgccct gctgcacttg 68640
gcctcagccc ctgctgccca caggccacat ttcagttgca cgctagtcct tcagatcttt 68700
agaggtggct gtgaggtcct tcccaagacc ttgccccacc ccatttcata gatacagtat 68760
ctcgtgagat ggtaggttgt ttgcgttgtt ctaatctatt ggaaaaaata tttatctgct 68820
tgacagatcc catcgtgttc ctgcttcagg ggaccttagg gattgtcatc aaccagggac 68880
ttcgggggaa atctggagca ttttttacaa gccttccact tcaatttcca tctttaagaa 68940
gaaactcaag ggtcagagtc aacaagatga ccgcaatccc cttgtgagtg actaaaaacc 69000
ccactgtgcc taggacttga ggtccctctt tgagctcaag gctgccgtgg tcaacctctc 69060
ctgtggttct tctctgacag actcttcccc tcctctccct ctgcctcggc ctcttcgggg 69120
aaaccctcct cctacagact aggaagaggc accctgctgc cagggcaggc agagcctgga 69180
ttcctcctgc ttcatcgatt gcacttagga gagagactca aagccctggg gcccggccct 69240
ctctgcatct ctctctgatc tagctagcag tgggggtgtc aggacagtga ggctgagatg 69300
acagaggtgg tcatggctgg cacagggctc aggtacattc tagatggctg tcaggtggtg 69360
ggtagcttta gttacattga atttttcttg cttctctatt tttgtccaca cacaaatcag 69420
tttctcctga tctttatgtc ttggaacagg gccagacagg gagaactctc aggtactctt 69480
gggagttggt cccatacaag tgcggactcc tggacattag cgaggtgtaa agagggcagt 69540
gtctgtgctg ccccggcagc tttgctctcc agatgctgga ctagggtggg cctccttcag 69600
cctgggaggg tctgagaata agatctagtg acccccattt atatcaaacc tgatacctta 69660
cacatgggct tctttctaga ttcttctttc catagctcat ggagctgcag ggaaagcttt 69720
aagagctttg gtcatataaa acatccattc agctgggcgc gatggctcat gcctgtaatc 69780
ccagcactgt gggaggctga ggcgggcaga tcacctgagg tcaggagttc gagaccagcc 69840
tggccaacat ggtgaaaccc cgtctctact aaaaatataa aaattagtca ggcgtggtgg 69900
caggcgcctg taatcccagc tactcagaag gctgagacag aagaacagct tgaacccagg 69960
aggctgagat tgcagtgagc cgagatcgca ccactgcact ccagcctggg tgacaagagt 70020
gagactctgt ctcaaaaaaa caaaacacaa ataaacaaaa aaaatccatt catttactca 70080
tgcaataaat tctcctgcaa gcttttatgg gcactcagta agtactcagg attggcttta 70140
tcagccttgc cactgagcag ctcatggtcc tatggaacct gagccaggcc tcagtctctc 70200
catgattggc tcagctaact ctcagttcag agtggagagt atcaatcttg tgtttttgcc 70260
cttaggcagc actatatgag acatggggcc tgtggtcctt ccttctggtg tccccgtgt 70320
taaaagataa aaaacacccc aagggccggg cgcggtggct catgcctgta atcccagcac 70380
tttgggaggc tgaggcgggt ggatcacgag gtcaggtgat cgaaaccatc ctggctaaga 70440
tggtgaaacc ccgtctctac taaaaataca aaaaattagc tgggtgtggt ggtgggcgcc 70500
tgtagtccca gctgctcggg aggctgaggc aggagaatgg cgtgaacccg ggaggcggag 70560
cttgcagtga gcagagatca cgccactgca ctccagcctg ggtgacagtg caagactctg 70620
tctcaaaaaa aaaaaaaaca ctccaagggc catccgtgct ctctgcccct cctgtgggga 70680
ccaagtgggg ttaggaatgg ctcagtgggg aaggagagca ctcttgtccc cagtcccttg 70740
ccaccctgtc ccttagatag ggaggtgggc tgcagagatt ggtgccagaa gagggtgggt 70800

```
ttgggaattg gagctcctcc aaggagctcc tcctaagatt gagtgctgca gctgtagtgg  70860
ctgctggttg ggagagtaag tgccatcact aatttaaaag tccttgccat ctggaatcag  70920
gctttgtcaa cagcagctga gaaaagcagc ctgtgcctct gctggccagg cctaggccct  70980
cgtcagagcg tgcctctcca caaggcactt gggcctgggt gattgttgcg cctctggctt  71040
tggcgtttcc tctttgcagc actttgccta cctcccccaa gccctgagcc actgcctgct  71100
ggggctccta ctgaggttct ggaaacacct ctgcacctgc cgcccctggg aggaaagagg  71160
gccacacagg aagtgtctgc agggagaggt ggcactcggc agcctgagtt caggagaggt  71220
gcttggagct tcaggcagag gggccttcag aggagggaaa cggagcaatg tgtcacaggc  71280
aggcaggggc aggactgcca ccccaggccc cgtgggaggc ctgctgaggg cacagagctg  71340
ctcggtgcag ccttcatgct ttgatctgga aagagcagct gtccgcaggc ctctgtctcc  71400
aagaggcctg tcacacagga ggaccgctgg aaacatacca acacgtgcag tctcccctcc  71460
aagctattca tgctgtttgt ggaatctctc tcaaacataa gtgtcaggtg tgtgtcgtcc  71520
caacgggtcc tgtgctgtga atagatccat gtgcagcaca aagggaatgt ggcacgtggc  71580
cccaggaaga gttcacccgg ccagggggca gttgttcagt tgcctggggc tgacactgac  71640
cactggcctc tggggtgtcc tgcagcccaa atgcccacct tgccctcctc acatctcagt  71700
caggggaggc catgcccaag ccaatgtgct gtcacagcct gcagcggggg cagcacttcc  71760
tcggagggcc tgggaggtgc tggggatgcc ccagcgcttc tcttcctgcc tcgccctggc  71820
atggcccagc gcctctagga tcaacttacg atccgtggag cagccccggg aaacccaaat  71880
ctggctcagg acagcgtacg ggcaggaggg ctgtaaatca tcccaggcta agcctccgtg  71940
ggcactggct cctgccgcag cctggctatg gactcagtta gaaccaggta gaaagtcagc  72000
gacaccccac agaaggccac tgcggctagg taaacacctg agaaagaaac tgctccagaa  72060
gagatgacgt gggcttccag gagcatggag gaggtggcac ttgaactttt aggaaactcc  72120
ttagatgaga taaagtgggg gttggaggtg gcgaaaagag ggtaaccctg ggaaagtcag  72180
tcagaaccca tggcagaaga ctgcaggaga ggcaggggag gggcttcggg gaccactgtg  72240
gacagagctc tgaaagcacc ctggccaaag cccctcctga ggtgacagag cgtgggagga  72300
ggctgcactg ggcctgcgtg ccatcctcac ccctgttccc cgctggcgcc aggccctgcc  72360
ttcttggtac ctgtgccaac aggagagccc tcaccagccg atcttgtcac tctccgtggt  72420
gacagtgtct tggccagctg tggcccctag tttctagcag cgtttctcag tgtccttggc  72480
ccttctgaga aggcaggcgg gaggcacacg gtgccctgtt cttccccgtt tgtccagttg  72540
cttgcaaagc agagaatgag taggagtgaa cccgagtgac ttcacccgcc ctgtccccca  72600
cgtcaggaca ggcttgaggc ctctctgggc gtgagcgagg aaaccaggct gctctaactt  72660
ctgaagagtg ggctctggct caagactcca atcggccaga agcccacaga gatcaaagca  72720
ctagcaagtt cagctgtcct ggccctcggg tagaacccac gggcgtgcct gggtgcggct  72780
ccacccacat gccccactgt cagcccaggc aggagccttc ctggccgggc tcaggatctg  72840
cctgcagccc agccaggcca tcacccagcc ccgatgcatc ctggcactgc acgcttactc  72900
ttcacaagca cttatacgcg gatggcctcc gagaccctgc ctccctggtc tgctgaggtc  72960
aggccaggtc tcccacggag ccgggcagct ccacacccca ccacctggca ccgttaggtt  73020
tcagatctcc cgtgtggtgt ttgatgtcgg cttttgttcc taccttggga gtttggattg  73080
tttcctctgg tgtctttgtt taccttcctc actgttctac ctcctggcca ggtctcagct  73140
tagcttccct ggtgtggggt gtttttcaag ccttccagcc acagctgtct cccctcaggc  73200
```

```
tggacggctc cggggtgaca gggcttcacc ctctgcctgc agacccctgg tgggcacatc  73260
tcacaggctt ccgtcttgct gagttgggta cggaggcaga agtggggtgt ggaggaaagt  73320
cagagggaaa tctgcttcag aaaggaaggg tctttagaca caaagactgg aggcccttcc  73380
ccgcccgcac gggagctgcc atcgtgggtc tcatgcacgt caagaccttc ccacatccaa  73440
actcagcttc cagcagggat tttgactttg gatgacaagg ctttatttgt aaatatgctc  73500
ttaatatgca actttgagaa taaaatagaa acatcatgta ttttaaaata taagatgaag  73560
tgtgacgcac tgtatacaat ttaatatata tttttagggt tttgttattt aagaaaatgg  73620
aatgtaatgg tacttttaca aacgagaaaa aatgttattt ttactttctg gaaaaaataa  73680
atattctcat tgttgtagaa agagtgatgg gccctatgct gtcatttcta tgggagttcc  73740
ccagagagcg tgggacaagc ggagggtgtc tgtggtggga ttcctgcctc cccttgggtg  73800
ccagtcctcg ccttttgctt gctgtttcct agtagtgcct ccaaatttct tccagtcttg  73860
tgacagcttc gacccacagc cgaccttcag ctggtacgat ctgaaagatt aggtactcca  73920
aaaccattgc attgcagccc acatccaagg agggtcaggg cagagcacaa ggctctgcag  73980
cagagagatc tgggctcgag ccggcctaga tccagtccct cgactactca gcctcagctt  74040
ccccatctga aaagggtaat ggaatctatt cctcaggagg ctatggaggc tatgttttga  74100
caaaatgcct ctaaagtgct tatgtaatta ttatcccagg tggaactgac cttgcctctc  74160
agagcaacca gttcttcctc tccaccccct tcttgcccca cactttcctt cttaggaagg  74220
aaagaagcta atagaagctc cacgtatgag ctgcccactc tgcgccaggc actctgctgg  74280
cagacactgt gcatatccta caactcttcg ccatgggtac cactttccct ctttggcaga  74340
tgagacagct caggcatgga gaggctgtgg gggacagtag ctgggagcac agccctggag  74400
tcagccctcc aggattcagt ttcctccatt cattctctgt gaggccagtg agggtaaaac  74460
agggagcctt tgaagggttt cagcggagga gtgacatcag attcccagtt tagaaagcat  74520
tcctccttgc atctgggaaa acagatctga gcggggtaag accgagggca aggaaaccag  74580
tcgggagact ctacaggccc agccaggaga tgctgagggc atgcctgggc ccccaagcca  74640
gtgctgtgga gagagatgct gactgcactc ccagggcagg ggcacgtgca tggggctggg  74700
tagctcaggc tcacatccca gttccactgt tcaccatgtg acctggggtg agtaacacgg  74760
ccctgtgtgc ctgttttctc acctgtcaaa tggagacagt tatagtacct gcctttgtga  74820
ggcattgggc tgtatgaatt attattacct gcagtatgtt ttccatcaaa ggtagatgtt  74880
cctttcattc tagaatagag gtgggggtta agaatgagga ggtgtctggg atggtgctcc  74940
ggtacctgac atgggtgcct gagcggagag aggggccact cttcgacata aggaatgtaa  75000
aaggagccag gtgtgagagg aaacctgatg agttcttttg ggctaagtcc actgcagtcg  75060
ctgtgggaca ctgaggcaga gctgtccggc aggcattgga cagacagcct gagcccccca  75120
caaggagcac agggctctgc acaacccaag gaaacatggg caaaggtggc atcctcaggg  75180
tgagtgttgg ggccacccct cagaaggcta tgggggacag cgtcctggga tgcactgagg  75240
cagtgaggga gtgcctggca ggaccaaggt gggcaggagt aggacaggag acaaggactc  75300
ccctggaagc caaagaacct attggcaaaa ttgttttttt tgtttttttt ttttggagac  75360
ggagttttgc tcatcaccca ggatggagta tggtggtgca atctctgctc actgcaacct  75420
ccgcctcccg ggttcaagcg attctcctgc ctcagcctcc cggagtagct ggaattacag  75480
gcgcccgcca ccacgcccag ctaatttttg tatttttagt agagatgggg tttcaccatg  75540
```

ttggccaggc tggtctcaaa ctcctaacct caggtgatcc gcccgcctcg gcctcccaaa 75600
gtgctgggat tacaggtgtg agccaccgcg cctggtgagc aaagcttcta acctgactgg 75660
cacacacaga ctgctcgtgc tttgagtccc agttccagat tctcaggaga cagcttggcc 75720
aggtgaaatc tccctcatcc agccagtttt tgctaggata gtgttctctg agaaaagagg 75780
gcacaggcca gtccagctaa agaatattac caccgcagac gtggctctcg gtgggatgca 75840
tttgaccact tgcctgggaa tccctatgtg ctctgttaaa cttcaggttc ccgggcccca 75900
ccccagacct accacatcag aatccctgga agcattgcct cgacatggag tccgtgccct 75960
tcacttcacc actgtcccct ccctggctaa cttctgcctc caccctgcag ccagccccca 76020
tgctgccgca gatgttgcaa cataatggca cctttttttt ttttgagacg gagtctcgct 76080
ctgtctccag gctggagtgc agtggcgcta tttcagctca ctgcaacctc cgcctcctgg 76140
gttcaagcga ttctcctgcc tcagcctccc gagtagctgg gactacaggc acgtgccacc 76200
atgcccagct aatttttgtg tttttagtag agacggggtt tcaccatgtt ggccaggatg 76260
gtctcgatct cttgacctga tgatccgccc accttgccct cccaaagtgc tggtattaca 76320
ggcgtgagcc accgcgtccg acccatgatg gcccctttaa aggtcagctt cacttgactg 76380
tttatcttca ctgggctttc cttctctctc ctagaggctc tttccttcca tgaaggaaaa 76440
tatttttaat ggcaggaaat ggctggtgga aaacaaacag ggcggccttg ctggtgaatt 76500
tcttagggac aaattacgct gcaatagaaa aataaaataa atgcagccag aatgtgcaac 76560
tgtcccacct gaagaacccc tttgggatta tgggacaatg aggccaggat gagaccctca 76620
aacccatctg agtggactct ggggaccact gaccttgccc tgtgttctcc tgaacctgac 76680
agatgcagat attggagaat ccaccacccg ggagccagca ccagggcagc accagcccca 76740
tcctttgtca ggcagtcaaa ggctcttctt cctgtgaagg ggaacggggc tggacaaggg 76800
tgaccttgtc tccaggcttg gaagtcacat gaccatcttc tttcccctct gggccatgcg 76860
tgcctgaaac tgcagacagt ctctagaact cagagaactg ggaagctttt gttcctctgt 76920
ggcgaggtcg ggtcccgatg ggggattgtt ttcgctcagc tcaaagggac actttagaga 76980
tagaatactt caaccttaag aagcagcaac atttgcttgt agctggaagt cttcatttct 77040
ggtctccagc tgttgtctgg agccaccagg cctcccctga atgggcctat gcccagcaac 77100
tggtgggggg gggggcagtg cctgccggac tgaacatgaa ccagtctgtg caggacgccc 77160
atctccagga cagcttggct gcaaggacac cctgtcccct cccggtggtg gttgctgggc 77220
tttggaataa acccgttagc tctgggtgac tgagcgggga aaaggggctc cacaagaagc 77280
gttttagggg gaaagtagac ccaagcttga gctccagagt aacccctccg ggagaaacac 77340
caaacactcg gaaacagcca gggctttcgc aacagtgaag ctgcagatcc catttatttc 77400
cgtcttagta gcattgtctc tgttcaaatg aggtcactga acttttaaaa acttcactga 77460
gggtcgtgct tctttgcata ttgatcatgt gaatgtttag tggacttgcc ttagttgctg 77520
gtacctaaga tagagattaa gggccctcaa ggggtattca gacctcaaat tcagccaaac 77580
acaggcgcag cttttcctgg gtctgagtga gctgaggaaa gcacttttga atgtgcaagg 77640
acaataagat taataaccac taccatctct gcagtacgta ctgtgtacca gacgctgtgc 77700
caagtgacca acagacatta ccgaattcat ctttgccgca acccaacaag ggaactgagg 77760
gtcagagaag gggtccagcc aggggccgcc aaggttcgga ctcagcctgg gaccactggc 77820
tccaaagctg gggtccttta ctcctgttga gctgcaggcc cctccaacac aggcagtggg 77880
tgggccccca aatagctcat cttcaaggat atggcctccg gaaagcccag ggaaagtgtg 77940

```
gatcgatttt cctgggtcaa ggaagaatca aacctacact tctttaccta tttgatgaca  78000
caaacccctt tgagaaccag gggttggatg gagcctctcc ctgcaaaaaa gaccccatct  78060
gccaaactgc aggggtccag agaccccctg ccccctgaaa cccttccatg gacctcaggt  78120
ttagaatctc tccattaagc catgagcatg attatttgaa agttaaaatg aggccagaag  78180
ggataatagt aacagtcata ataatacgaa taacaggata cattttactg atcacctgtt  78240
gtcaggcatt tatgccaggg gtcggcaaac attttctgta aaaggctaaa tactaaacat  78300
tttagacttt gcaggctata cagtctcaga tccattgacc agaaccacag gccagccact  78360
gggaccctgg atgactccaa caagccctgg agccatctac gcaactccat gaggagtcgg  78420
gggatggggg ccaccaagct ccccttgtta ttagccacag acaatatgta aacaaatggt  78480
cacgcttgtg ttcccataaa acttcacgga caccaaaacc tgaagtttat ataatgttca  78540
tgtgtcacga aatgctacaa aatgctattc ttttgatttt ttccccccaa aattaaaaag  78600
tgtaaaaacc ggccaggcat gatgtctcat gcctgtaatc tcagcacttt gggaggctga  78660
ggtgggtgga tcacttgagg tcaggagttt gagactagcc tggccaacat ggtgaaaccc  78720
tgtctctact aaaaatataa aaattagcca ggtgtggtag cacatgcctg taatcccagc  78780
tactcaggag tctgaggcag gagaattgct tgaaccgggg aggtggaggt tgccgtgagc  78840
cgagattgtg ccattgcact ccagcctggg agacagagca agactctgtc ttaaaaaaaa  78900
aaaaaaaaag cacaggagtc aggatttgag cccactccca agcctgtttg ctttcctaag  78960
agacaagatg ggtacattta aattgtggag gaagaaaagg tgacagtgaa gcaggaagga  79020
agacccagga gcaagggcag tcccctgggc cctgggaata tcaggcagag aggctccatc  79080
ctcctgcagt ctttgctgaa tggtctgcac tgcaggggag ggcggctggt ttcctgagcc  79140
atccctctaa ccccctacaa gcggctccaa ggacagagtc tccagatcca ggacagctgg  79200
tggccttcac attgttttgc gtctcccagg ttctcttaat tataaccaat ttgccaccct  79260
cagcaattcc ttgttcccct ctgctaatac ccatgagttg gaaccatcag ccgaactccc  79320
agccaaacag gctaaaatca cttccctttc ccatgtaggg agtcctccag tctcttagaa  79380
actcgccttt cttctcagtc ctgtgagacg ggcgaggcct gcccttctgt gcgctgactt  79440
actgggctgg gatctgccct agcgggagac agaatctgct caactttctc cagctcctcc  79500
ccgccccttg caccccctcca ctctcccccc aacccctcct gctgactctt ggggctctgg  79560
cacactgcct gccaagcaca acctttcctt tttttcctct ctctaaagac agggtctcac  79620
tctgtcgccc aggctggaga gcagtggcac cgtcacaggg taaactccaa aactgggatt  79680
cagcctgggg gtgccccatg ggttcctggc ttgaagcagg aaggaactca agagtgagct  79740
gacagtaaag tgaaagcaag tctattaaga aagtaaagga ataaaggagg gctactccat  79800
agggagagca gcggcatggg ctgcttgact gagtagactt acggttattt cttgatgata  79860
tactaaacaa gggatggatt attcatgagt tttctggaaa aggggtgggg agttcccgga  79920
actgagggtt ccttcccttt ttagaccata tagggtaact tccagatatt gccatggcat  79980
tcataaactg tcatggccct ggtgggagtg tcttttcaca tgctaatgaa ttataattag  80040
catataatga ccagtgagga caaccagcca tgttggtttt ggcgggtttt gtccggcttc  80100
ttcactgcat ctcattttat cagcggggtc tttgtgacct gtatcttgtg aagccagtcc  80160
tgccgacctc ctatctcatc ctgtgactaa gaatgcccag cctccttaga atgcagccca  80220
gctggtctca gcctcatttt attcagcccc tattcaagat ggagtcgctc tgtttccatt  80280
```

gcctctgaca gcacaatcat agctcattgc agcctcactc tcctgggttt gaacaatcct 80340
tccatctcag cttcctgagt agctgggacc acaggcgtgg gctgctacgt ccagctgatt 80400
ttttcttttt tttttaatta ttgtagagac agcgtctcac tatgttgccc aggttagtct 80460
tgaactcctg ggctcaagtg atcctctcgt cttggcctcc cgaagtgctg agattacagg 80520
caccagccac catgcctggc tcctttataa cctccattta ttcatctaga aaataggtac 80580
aggctgggca tggtggctca tgcctataat cccagcactt tgggaggccg aggcgggcgg 80640
atcacctgag gtcaggaatt tgagaccagc ctggccaaca tgttgaaacc ccgtctctac 80700
taaagataca aaaaaatcag cctggcgtgc tactccctag ctactccggg aggctgaggc 80760
aggagaatcg cttgaacctg ggaggcggag gttgcagtga gccgagatct agtcactgca 80820
ctccagcctg ggtaacggca agacttcctc tcaaaaaaaa aaaaaagaaa gaaaagagat 80880
acagcagtag tttctcatag ggttgttgtg aagattaaat gaaataagaa aggtacaata 80940
tttagctcag tgactggcct gtgagtcctc aatacatttt aacaattttt atcagtaaac 81000
tcaggggacc accaggagca gggggcacct cagatttgcc ctgcctttca gattgagaac 81060
cctatttatc aaactccaag tttacaatgc acaaagtagg ggcagttccc tccttagaga 81120
ataattcctg acttggttcc ttcaagtagc tggtttcccc caggaccttc aatatgtgac 81180
cccatttaat aaaggtatct attgaccttt actttcttag ggacctagct gttgggtgaa 81240
aataccettt tctgccgact ccctgcctgc agtggatttc cttatctgtt gcttcaggta 81300
agggaacaaa tgcagaattt gaatgtcctc atagttcccc caatgctgca ggtggacaaa 81360
taggctaagg cccctggccc agctggcaga ggtaaggagc tgcccgcccg cccagctccc 81420
gctgcggcag agcccccagc cgccgcctcc tgccgccctc gcctttcctg caggagccgt 81480
cccagcgcag gcttgctcac cagcgccgcc ccgtggtaag actgcagatc tgcggaagaa 81540
ggccagccct gaaccgcaac tgctctcaag cccttccatt acagttacac ggattttttg 81600
cccagcgcgg tgatgcgtgc ctgtaatccc agctactctg gaggctgaga ggaaggatgc 81660
cttgagccca ggagttcaga atcagcctgg gcaaaattgc gagagaaaag aaaaaagaaa 81720
aaaataatgt cacaggtgtc ctgactctaa acctggacat tagcccaggt ctcactctca 81780
ccaagccctc taaagaactc attctatcag ataagtgatc agatgaatta ttctacctcc 81840
atactatgaa atcctatgtc accattgaaa ttaatgtggt gtataatctc caaaggcaat 81900
gaaaaaaaaa gaacaaatta atgtagtgct tctacacaca ctgtatcaga atatcttacg 81960
tgaaaaaagt caaagaacaa agcataagtg taattttttt tttttggcca aattttaaaa 82020
agagggaggg aaatatatgt atgtgtatac aaaggcacca gcaaagtcct gcaagttctg 82080
tgcctaactc ttattgtggt cacctttgga aaaggaaagg aagaagacag gaggaggcca 82140
ggggcagttg cttacgcctg taatcccagc actttgggag gccaaggtaa gtggatctct 82200
tgagcccagg agttcgagac cagcctgggc aacatggcaa aacccggtgt ctacaaaaaa 82260
tataaaaatt agccaagcat ggtggtgtgt gcctgtagtc ctagctactc aggaggctga 82320
agtgggagaa tcacttgagc ctgggaggtc taggctgcag tgagccgtga tcacgccatt 82380
gcactccagc ctgggcaaca gagtgaaacc ctgtctccaa aaaggaaaag agaaggtgag 82440
gacacttaca ttttcacatt ttatttgata tatttatatg tggcttgaat ctcttacatt 82500
catgcattac atgtgcaagt ttgaaaataa agtgcaggtg gattatttta aaatttggag 82560
gctgggcccg gtggctcaca cctgtaattc cagcactttg agaggccaag gcaggaggat 82620
cacctgaggt cagaggtttg agatcagcct ggtcaacatg gcgaaacccc gtctctacta 82680
aaaatacaaa aattagctgg gtgtggtggc gcgtgcctgt aatcccagct actcaggagg 82740
ctgaggcagg agaatcactt gaacccagga agcagaggtt gcagtgaact gagacggtgc 82800
cactgcattc cagcctgggc aacaagagtg aaactccatc tcaaaaaaaa aaaaaaattt 82860
ggaaagcaca caaaacaaaa agaacaacat aagtctctct cactgtcaca ctgctcagtg 82920
gaagcactgt taaaaggctg gtgcatgtgt ttccagcacg cactaggagc actgaggaac 82980
actgcttccc ctgcttgccc ccaggaaggg ggcctggcca atgccctgga ctagacatct 83040
attctgctgt ccagcatcac ccatgccact gccctgcccc accctgagcc actcctggag 83100
acacctccca gtgcagggag tctcccagaa gctttgggcc agcagaatgc tcagctccca 83160
agccaaaatg tccttctctt tgttaactac aaaataaaca tctccaggcc ccctgggcca 83220
cttgcagtac agatgtttat gcctttggaa agagacaaaa agagaaagac tcttgcaatt 83280
tctccctgag acaatgggtg ccaagttggt aattaaccct cagcaaccag ggcgtctgat 83340
cttccaccag ccagtctgca gcaggttgtg ggagtgattg attgggcctg tgctagaact 83400
tggtgattgg tgggccttcc aggccttgga atgctctccg cacaggaatg ctctccgcac 83460
aggacgctgg ctgcctcttc aaaactctaa atgaggtact aggaacccac ccctaagaag 83520
gcccccacac tgctgcatcc cattccagat gaagggctgt gagcagccct agcattcatc 83580
aaaccactcg ggggagcccc agggcctgca cgcagagctg ggaggagcaa ggctgctgag 83640
gggcaggcac tcggtcatct tgacattgca ttcactaaac accctcggac caggctcccc 83700
gctcaactct acatacggtg ccttatttcc tttgactctc ccagcaaccc catgaggtag 83760
gtacagttct attccagttt ttatagatga ggaaattgag tcttggagaa ataaagcctg 83820
tgctgccatc acttaatcct gggtggataa catctcttct tcagacaggt gttcctagac 83880
caaggtcatc ctgctggtaa gtgggggtaa agatggactg aacccttttt acaactttga 83940
agccacacct gcccatcccc acatattcat attggaaaac tctttccaga gggttatcat 84000
cttcaggctt ctacaaacta tgccaagtca gaggagccga cctgtggggg ctccacgcaa 84060
agattacagt caggtcttcc cttggatgta gccagagaca gctgagagct gtcccctgga 84120
ccagaattcc atcatgagag gctgggggat tgccttcttt ccagtggggg agccgaggcc 84180
cagagagcag aattcgtgtc caaggcccca ccatgacttt gtttttcgtt gtggtttgag 84240
atggagtctc gctcttgttg cccaggctgg agtgcaatgg cacgatctca gctcactgca 84300
acctccacct cctgggttca ggtgattctc ctgcctcagc ctcccgaata gctgggatta 84360
caggcatgtg ccaccacgcc cagctaattt ttgtattttt agtagaaatg gtgtttcacc 84420
atgttggcca ggctggtctc gaactcctgg cctcaagtga tccacctgcc tcggcctccc 84480
aaagtgctgg gattacaggt gtgagccacc acatccagcc cccaccatga ctttgcctct 84540
gtggccaatg tcatgtccat ggctgcacgg agcttcctga aaacacggag gctggtggca 84600
aggacccgcc ttggaaaatg gggagaaagc caatccccct agatacatcc cctgagccct 84660
tgggctggga gaagggcatt gtgtagcctc taagggagac tacaaagtaa gaagggattg 84720
cttccatctt gtcattccac catctgtgtc acaaacaggc aggtcagggg agcaaacatg 84780
gcagagggac atggcctagg agtcctgtac ttcattttcc ctcacatttc attgtctgtt 84840
acaggtcaca tggtctcacc tggatgcaaa ggccactggg aaatgtagtc ttccagtggg 84900
ccaggagttg tgtacaatga aattagcgaa tatatagcct gtctctgcca cactattcaa 84960
aaactcgtag tcatgtcagg gcccagaatg ccttgagatt gttgctcagc acatgagagc 85020

```
atgaggctgg agaagtgggc tggcccagtg tgagaaacac gggtaaaaca cggggtacca  85080
atttgcaatc tagccccatg tggtccaggt tcctcacgtg cagccagcca tggcagtaga  85140
gggacaaaat gatgccggag caagagacag agtcccccag atgaatgtca agggaaaccc  85200
aatagccctg aagacatcaa ggggaggcca cgccagccaa gattcctggc tcactttgca  85260
gaaaagagga tgtaagaggg cactggggaa ggaaaaggga gaacagcgga gaggcgccga  85320
catggggcac ggggaattct agggaaactg ggcctggagg gctggaaaag tctctgccac  85380
cagcagggca gcttcatgga tgtgcagcct ccacagtcac acagagccca tcctcacaaa  85440
ggccccacat ttggccctag ctgtcactgt cttgaaattc ttaatcattt tccaagaagg  85500
ggccccatat ttttattttg cactgggcct cacaaattac aaagtcagtc ctgagtccag  85560
aagggatcag tcttggttcc agatggcccc acctccaggg catggctgtg gctgatggtt  85620
atttgccagc ctagtgggag accaagacca caggaaatgg gtctggaaga tgatcggcag  85680
tagtggtcag ctcaagagtg ttgatttttt gttttgtttt tgttttttga gacggagtct  85740
cagtctgttg cccaggctgg ctcactgctc agctcgctgc aacctccgcc tcctgggttc  85800
aagcgattct cctgcctcag cctcccaagt agctgggatt acatgcagct gccaccaagc  85860
tgggctaatt tttgtatttt tagtagagac agggtttctc catgttggcc agagctggtc  85920
tcgaactcct gaccacaagt gatccacctg ccttggcctc ctaaagtgct gggattacag  85980
gcatgagcca cggtgcccag ccaagtgttt tttttttttt tttttttttt tagagacagg  86040
atctcacttc gttgcccagg ctggtctcga actcctgggc tcaagtgatc cttcctcctt  86100
ggcctcccaa agtgctggga tttcaggcat gagccactgc acccagccag cccaggagtg  86160
ttttgctcct taatgttctc aggtgtaaac attcaggaag caaaaacaaa acaaaaccaa  86220
aggccaggag cggtggctga tgcctgtaat cccagctctt tgggaggttg aggcgggtgg  86280
atcttgaggt caggagttcg agaccagcct gaccaacatg gtgaaaccct atctctacta  86340
aaaatacaaa aattagccag gtgtggtggc gcacgcctgt aatcccagct actcaggagg  86400
ctgaggcagg agaattgcat gaacccagga gacggaggtt gcagtgagcc gagatcacgt  86460
cactgcactc cagcctgggc aacagagcga gactctgtct aaaaaataaa aaacaaaaac  86520
aaaaataaat aaataaacaa acattcagga agcacaggtt tcagactctc cttgctaagg  86580
agcaagactg gtcagaaaca ggtgcttact ggtgagagat tttcacaaa cagagaacga  86640
tgaactctgc acgtgacgtg atgttgagga tggcagatgg gtggatgaag tccgtgccca  86700
tataggaaaa tggggacatc agattaaagc aagagggagg ctaacctcag gggactctac  86760
ttatatatat gtagaaacac ttaaggagac ctggactttt ttttaaagat aaggtctctt  86820
agccccataa tagtggagga cttcaacacc ccactgacag cattagacag atcatcaagg  86880
cagaaaacta ccaaagaatt tctggactta aactcagcac ttgaccaatt ggacctatta  86940
gacatctatg gaaaactcca cccatcagcc acagaatata cattcttctc atccacacat  87000
ggaacatatt ccaagatcaa ccacatgctc agccatagag caagtctcaa tacattcaaa  87060
aaaatcaaaa tcataccagc catactcttg gaccacagta gaatgaagac ggaaaatact  87120
aagaagattt cggctgggtg tggtggctca ctcctgtaat cctagcactt cgggaggcca  87180
aggcaggtgg atcacttgag gtcaggagtt cgagaccagc ctgcccaaca tggtgaaacc  87240
ctgtctcaac taaaaataca aaaaaaaaaa aaattagcta agcatggtgg caggtgcctg  87300
taatcccagc tactcgggag gctgaggcag gagaatcact tgaacctggg agatggaggt  87360
tgcagtgagc cgagatcatg ccactgcact ccagcctggg tgacagaccg agactccgtc  87420
```

tcaaaaaaaa aaaaaaaaaa aaaaaattaa gaagatctct caaaaccata caattacatg 87480
aaaattaaat gacttgctcc tgaatgattt tgggggtaaa caacaaaata aaggcacaaa 87540
atcaaaaaaa ttctttgaaa gaaatgaaaa cagagataca aaataccaaa atctctggga 87600
tgcagcaaaa gcagtgttaa gaggaaagct gatggtgctc aatgcctacc tcaagaagtt 87660
agacctcaga ttaaccatct aatatcgcac atagaggaac tagaaaaaca agaacaagct 87720
aacccagaag atagcagaag aaaagaaata actaaaatca gagtagaact taatgaaatt 87780
gagacacaaa aattcataca aagaatcagc aaaaccaaaa gttgattatt tgaaaggata 87840
aacaggatca gtaaaccgct agctagatta acaaagaaag agagatcaaa taagcaaaat 87900
cagaaataac aaatgtgtca cttgtaataa gggaccccac aatacaaaag atcctcagag 87960
actattatga acacctctgc acacataaac tagaaaatct agaggcaata gataaattcc 88020
tggaaacaca ccatctccca agagtgaatc aggaagaaac tgaaagactg aacaaatcaa 88080
tatcatgttc agaaattgaa tcagcactgg ccaggcgtgg tggctcatgc ctgtgatccc 88140
agcactttgg ggggccaagg tgggcagatc atgaggtcag gagatcgaga ccatcctggc 88200
taacatgatg aaaccccgtc tgtactaaaa atacaaaaaa ttagccaggc gtggtggcag 88260
gcgcctgtag tcccaactac ttgggaggct gaggcaggag aatggcgtga acccgggagg 88320
cagagcttgc agtgagctga gattgcgcca ctgcactcca gcctgggtga cagagtgaga 88380
ctccatctca aaaaaaaaaa aaaaaaaaaa aaaagatatt gaattggtac taaaaaactt 88440
accagccaaa aaatgctttg gaccagttat atttacagcc acattccacc agatgtacaa 88500
ggaagagctg ctaccaattc tactgaaact attccaaaaa atcaggtagg aggaactctt 88560
ctctaactca ttctatgaag ccagcatcac cctgacctca aaacctggca aagacacagt 88620
gaaaaaagaa agcttcaggc caatatccct gatgaacata gacacaacaa tcctcaacaa 88680
aatactagca aactgaattc aacagcacat caaaaagttg gccgggtggt ggctcatgct 88740
gtaatcccag cactttggga ggctgaggtg gatagatcac tagaggccat aagttcgaga 88800
ccagcctgac caacatggcg aaaccccatc tctactaaaa atacaaaaaa attagccagg 88860
tatggtggtg catgtctata atcccagctc ctcgggaggc tgaggcagga gaatcacttg 88920
aacctggagg tggaggttgc agtgagccga gattgtgtca ctgcactcta gcctgaataa 88980
cagagcgaga ctctacctca aaaaaaaaaa aaagattaat tcactatgat caagtaggtt 89040
tcattcctgt gatgcaagat tggttcaaca tgcatgaatc aataaatgtg attcaccaca 89100
taaacagaat tacaaacaaa aaccatcatc ccaatagatg cagaaaatgc tttcaataaa 89160
ctccaacatc ctttcgtgat aaaaaccctc aagaaactag gcatcgaagg aatgtacctc 89220
aaaataataa gagccatcta tgacaaaccc acagccaaca tcatactgaa taggcaaaca 89280
ctgaagcatt ccccccttgga acaagaaaag caatgccggc cgggcacagt ggctcacacc 89340
tataatccca gcactctggg aggctgaggc aagtggatga actgaggtca ggagttcaag 89400
accagcctgg ccaacatggt gaaaccccgt ttccactaaa aatacagaaa attagctggg 89460
cgtggtggca gatgcctgta atctcagcta ctcgggaggc aggagaattg cttgaaccct 89520
ggaggtggag gctgcagtga accgagattg tgccactgca ttccagcctg ggcaacaaga 89580
gcaaaactcc gtcacacaaa aaaaaagaaa aaaagaaaaa aaagcaattc cattattggg 89640
tatatatcca aaaggaaaca aagtattata ccaaaatgac ataggcactt gtgtgtgcat 89700
tgcggcacta ttcacaatag caaagacaag gaatcaacgt aggtgcccat caatggtgga 89760
ttagataaag aaatcatagt acatatacat tgtggaatac tacataatca taaaaaagaa 89820
ttaaatcatg tactttgcag caatacagat ccagctggag gccattcaca agtacataaa 89880
accataaaca ttgggtactg atatggtttg gctctgtgtc ctcacacaaa tctcatctcg 89940
aatcgtaatc cctgcttgcc aaggagggac ctgtaatccc cacgtgttga gggagggaag 90000
gattaccggg gcaattcccc accgccccgc cgttctcgtg atagtgagtg aatgtcgcga 90060
gatttgatgg ttttaaaagt ggaatttttt cctgctctag ctctcacgct ctcctgccat 90120
ctcttgaagg aggtgtctgc ttctcctttt gccttccgcc atgcttgtaa gtttcctgag 90180
gcctccccag caaataatgc gaaactgtga gtcaattaag cctctttcct ttataaatta 90240
cccagtttca ggtatttctt tcttgttttg tttttttgag atggagtttc actctcatcg 90300
cccaggctgg agtgcagtgg cgcgaactcg gctcactgca atatccgcct cccgggttca 90360
aacgattctc ttacctcagt ctcccgaata gctgggatta caggggccac caccacgccc 90420
agctaatttt tgtattttta gtagagacag ggtttcatca tgttggccag gttggtctgg 90480
aactcctgac ctcaagtgat ccacccacct cagcctcccg aagtgctggg attacaggca 90540
tgagccacca cgcccggcct caggcatttc tttataacag tgtgagaaca gactaataca 90600
ggtactcagg gacataaaga tggcaacagt agacactggg gactactaag gggggaaggg 90660
agagaagggg tcaagggttg aaaaaactaa ctcttgggaa ctatgctcac cacctggctg 90720
atgggatcat tcatatccca aacctcagca tcacgcaata cacccacgta acaaacctgc 90780
gtatgtacgc cctacatcta aaataaaagt tgaaaaaaaa aacgaggtct tgctatgttg 90840
cccaggctgg agtgcagggc ccattcacag attgaatcat agcgcactgc agcctcaaac 90900
cgctgggctc aagggacaaa ccgctgggct caagggatct tcccacctca gcctcccgag 90960
tagctgggat tacaggcgcg cattgctgcg cccagctgag gaccttacat tttaaaaaga 91020
acagtccaga tgtaagagat ttacaaaagc aggatatcaa ttaactagtc caaaatggaa 91080
acggctgttg actatggtgt ggggggcctt cttgaagtca aagaggaatc tggacacacc 91140
tggcaaactg atgggaccag tcctttgttg tattggctgg aacggttgaa ggagagaagg 91200
agcctggcac aatgatctca atctggttac aaagcatgat tccagagaag aaggttgatt 91260
agtaacagcg ccttgctatc atttattgat ctcttactgt gctccaggca ttggactaca 91320
cacatgcatt tgtcatcctt tgccatgtaa caaactatcc aaaaatttac cagcttaaaa 91380
caaggaactg gaggccaagg caggcagatc atgaggtcag aagttcgaga ccagcctggc 91440
caacacagtg gaaccccatc tctactaaaa atacaaaaat tagctgggtg tggtggcggg 91500
tgcctgtaat cccagctact tcggaggctg aggcaggaga atcacttgaa cccgggaggc 91560
agaggttgca gtgagccaag atcgtgccac tgcactccag cctgggctac aagagtgaaa 91620
ctccatctca aaaaaaaaac aaaaaaaaaa acccaaaaca aggaactatg attatcctga 91680
gtttctgtgg gtcagggatt caagagcagt ttaggccagg catggtggct cacacctgta 91740
atcccagcac tttgggatca agaggccagg agtttggcca ggcatggtag ctcaggcctc 91800
taatcccagc actttgggag gcccaggcag gcggatcaca aagtcagggg ttctagacca 91860
gcctggccaa tatggtgaaa ccccgtccct actaaaaata caaaaattag ccgggcatgg 91920
tggtgcgtgc ctgtggtccc agctgctcag gaggctgagg cagaggagtc gcttgaacct 91980
gggaggtgga ggttgctgtg agccgaggtt gtgccattgc actccagcct gggcaacgga 92040
gcgagactcc atctcaaaaa aataaaaata aaaataaagg ccaggagttc aagactggcc 92100
agggcaacag agcaagaccc tatctctaca aaaaattcaa aaaatagccc gatgtggtag 92160
tgtgtacttg tagtcctccg gaggctgaga cgggagattc cttgagccca ggagttcaaa 92220
ggtacagtga gccacgattg tgccactgca ctccagcctg ggtgacagag caagagcctg 92280
tcacaaaaaa aaaaaaaagt agttcagaaa tcatactgtc attttcacaa catccaattg 92340
gtacagaagc cagccctatt cagtatggga ggtgaccgta ccagggcatg aagccaggag 92400
gtggggctca ttggccacac tctcatcttg gaggctgccg cccaccacgt gttacttcat 92460
gatcctgttc aataatcaca acaggctagt aataattttc cccctactca aaagagggaa 92520
ttttgctcaa gaccaaacaa ctaagaagtg gcaggccttg gatttgaacc ccactgtcct 92580
tggctatgtt ggagctctat ggtatgcaga ggcaatacaa gcaaggactg atagaagtgt 92640
cccccgaacc ccattcaacg ctggactcca ggcggcaaga cattgtgttt ctctcctcct 92700
gccgggtccc taggggggact tgcatcttct ctcagactct cacacaggtc aaggggagct 92760
taggccctgg gagggcgccc gttagcagcg gggagaggaa agagctgcct ctctcctgtc 92820
actccccatt ttgccccaag atgagggctg ccattcagaa tgggtcaggt tccaggacag 92880
tgactgggtc aaatttgctg gaaggcaggg tcactatcag aagacctatc ccctcaccac 92940
acacacacca tatgtgtgca cacatgcaca cacaggtaca agcacacaag tacccatgca 93000
cacatcaccc acatgcacgc ccaccataac atgcacacac atgcacacac atccatacac 93060
atgcacactc gcctcctagt cgtctgcttc tgagtgacca gatggctctt tttttttttt 93120
tttccacaaa tacttattga gcacctgcta ggtgactggt attctgctgg atgcaaagga 93180
cacagggcat ggaacagaga gacatggtgt ctgctcgtgt ggagcctgtg gtcatgcacc 93240
tgctggacag ctgcctttcc gggggtcact tctgctcctc acatctgctg ggactcattg 93300
acttcttcca catggtgttt gggcacaggc atggggaggt ccccctagac ctcgagccta 93360
agcctcgaac tctggcccac tttacaaaag cccaaattaa ggaattgatc atccacttag 93420
taatagttta gaacctttag agtatgttac aacctgcaga agttacagaa acccagcctc 93480
tctcaactct tttagtcaca gtgagatgga gctttcagaa aatcaagaga ccaagatcag 93540
gccaggcgcg gtagctcaca cctgtagtcc cagcactttg ggaatccgag gtggaaggat 93600
cacttgagcc caggagtttg agaccagcct gggcaatata gtgagacccc atctttcaaa 93660
aaaaaattag cctaatgtgg tggcacatgc ctgtaatccc agctattcag gaagctgagg 93720
caggaagatc gctggagtcc aagagtttga ggctgcagtg agccatgatc agaccaccgc 93780
actccaggct gggtgacaga gtgaggccct gtctcaaaaa caaaacaaaa gagaccaaaa 93840
tcagtcaaat gcttctaact gttctctccc tccgtgccta gggctgtact ttcagacacc 93900
actcattgtc cttcctacct tcccaggcaa ttcaggactc ggaagtgaca tcactcatct 93960
ggtctcaggg gcagcccaga agtatctgac tgtagacaca actaggctcc gtgggcatat 94020
ctgggtggca atttcagagg gcagagggga caccttcatt gcctctcctc gcacagaaat 94080
ggtgggctct ctctggccca gcgtggtggt tcatgcctgt aataccagcg ttttgggagg 94140
ctgagatggg aggattgctt gagcccagga ggtcgaggct gcagtgagct atgatcacac 94200
caccacactc cagcctgagc agcagagcgg gacctcgtct ctaagaatag aaagaaagaa 94260
agagaaacgg tgtcctccgc acagccggtc agaactgtgt gactcacttg aggcaggacc 94320
gagagtgaca tccagttgca cctttctcac ctactttggg acctttgggg gtgagttccc 94380
ctttgtcctc tcgtggaaac agcacacagc aagcaaccac aaaaccagag cggaaggagg 94440
gacttcccac cggcatccgg ccccagtgcc atgttttatc atctggaacg gttgtgaagc 94500

```
tttgtgtgac ttgctcagga tcagcagtca ccatggtcta atcccaagag ggactcgtca  94560

cccagagacc tcaaaaggcc ccaggcctac tgtggttttt tctgagaggc tcccagaacc  94620

aagtggcacg ttggtttcct gtgcgtctgt gtctttgtgc ctgtatctcg ctgggggact  94680

tcacaggaag caggatttgg gcattcctga agctcccagc tggacaccac tcctgagcgc  94740

cacatcccat gatcacttca accacaggcc tttgactttg ccacatggca aggcacccag  94800

cagaagatga ggatgacggg tgatgctaga tggatgtgta cctggtggat ggcccacgca  94860

cgaagactca agaccctcag gactggccat ataatctgca aggtccagta tgaaataaga  94920

ataagcagcc cacacaactg ggcatagtgg ttcatgcctg taatcccagc actttgggag  94980

gctgaggagg gtggatcact tgaggccagg aattcgagac cagcctggcc aacatggcga  95040

aaacccatct ctactaaaaa tacaaaaatt agttgggcat ggtggcacac acctgtaatc  95100

ccagctactc ggaggctgag gcacaagaat tgcttgaacc tgggaggcgg aggttgcagt  95160

gagctgagat aacgccactg cactccagtg taggcaacag agtgagaccc tgtctc      95216


<210> SEQ ID NO 2
<211> LENGTH: 2719
<212> TYPE: RNA
<213> ORGANISM: homo sapien

<400> SEQUENCE: 2

gcacugacgg cccauggcgc cgccagccgc ccgccucgcc cugcucuccg ccgcggcgcu     60

cacgcuggcg gcccggcccg cgccuagccc cggccucggc cccggacccg aguguuucac    120

agccaauggu gcggauuaua ggggaacaca gaacuggaca gcacuacaag gcgggaagcc    180

augucuguuu uggaacgaga cuuuccagca uccauacaac acucugaaau accccaacgg    240

ggagggggc cugggugagc acaacuauug cagaaaucca gauggagacg ugagccccug    300

gugcuaugug gcagagcacg aggauggugu cuacuggaag uacugugaga uaccugcuug    360

ccagaugccu ggaaaccuug gcugcuacaa ggaucaugga aacccaccuc cucuaacugg    420

caccaguaaa acguccaaca aacucaccau acaaacuugc aucaguuuuu gucggaguca    480

gagguucaag uuugcuggga uggagucagg cuaugcuugc uucuguggaa acaauccuga    540

uuacuggaag uacggggagg cagccaguac cgaaugcaac agcgucugcu ucggggauca    600

cacccaaccc ugugguggcg auggcaggau cauccucuuu gauacucucg ugggcgccug    660

cggugggaac uacucagcca ugucuucugu ggucuauucc ccugacuucc ccgacaccua    720

ugccacgggg agggucugcu acuggaccau ccggguuccg ggggccuccc acauccacuu    780

cagcuucccc cuauuugaca ucagggacuc ggcggacaug guggagcuuc uggauggcua    840

cacccaccgu guccuagccc gcuuccacgg gaggagccgc ccaccucugu ccuucaacgu    900

cucucuggac uucgucaucu uguauuucuu cucugaucgc aucaaucagg cccagggauu    960

ugcuguuuua uaccaagccg ucaaggaaga acugccacag gagaggcccg cugucaacca   1020

gacgguggcc gaggugauca cggagcaggc caaccucagu gucagcgcug cccgguccuc   1080

caaaguccuc uaugucauca ccaccagccc cagccaccca ccucagacug ucccagguag   1140

caauuccugg gcgccaccca ugggggcugg aagccacaga guugaaggau ggacagucua   1200

uggucuggca acucuccuca uccucacagu cacagccauu guagcaaaga uacuucugca   1260

cgucacauuc aaaucccauc guguuccugc uucaggggac cuuagggauu gucaucaacc   1320

agggacuucg ggggaaaucu ggagcauuuu uuacaagccu uccacuucaa uuuccaucuu   1380

uaagaagaaa cucaaggguc agagucaaca agaugaccgc aauccccuug caauucagga   1440
```

cucggaagug acaucacuca ucuggucuca ggggcagccc agaaguaucu gacuguagac 1500
acaacuaggc uccgugggca uaucugggug gcaauuucag agggcagagg ggacaccuuc 1560
auugccucuc cucgcacaga aaugguggge ucucucuggc ccagcguggu gguucaugcc 1620
uguaauacca gcguuuuggg aggcugagau gggaggauug cuugagccca ggaggucgag 1680
gcugcaguga gcuaugauca caccaccaca cuccagccug agcagcagag cgggaccucg 1740
ucucuaagaa uagaaagaaa gaaagagaaa cggugucuc cgcacagccg gucagaacug 1800
ugugacucac uugaggcagg accgagagug acauccaguu gcaccuuucu caccuacuuu 1860
gggaccuuug ggggugaguu ccccuuuguc cucucgugga aacagcacac agcaagcaac 1920
cacaaaacca gagcggaagg agggacuucc caccggcauc cggccccagu gccauguuuu 1980
aucaucugga acgguuguga agcuuugugu gacuugcuca ggaucagcag ucaccauggu 2040
cuaaucccaa gagggacucg ucacccagag accucaaaag gccccaggcc uacuguggu 2100 uuuucugaga ggcucccaga accaaguggc acguugguuu ccugugcguc ugugucuuug 2160
ugccuguauc ucgcuggggg acuucacagg aagcaggauu ugggcauucc ugaagcuccc 2220
agcuggacac cacuccugag cgccacaucc caugaucacu ucaaccacag gccuuugacu 2280
uugccacaug gcaaggcacc cagcagaaga ugaggaugac gggugaugcu agauggaugu 2340
guaccuggug gauggcccac gcacgaagac ucaagacccu caggacuggc cauauaaucu 2400
gcaaggucca guaugaaaua agaauaagca gcccacacaa cugggcauag ugguucaugc 2460
cuguaauccc agcacuuugg gaggcugagg agggguggauc acuugaggcc aggaauucga 2520
gaccagccug gccaacaugg cgaaaaccca ucucuacuaa aaauacaaaa auuaguuggg 2580
cauggugcga cacaccugua aucccagcua cucggaggcu gaggcacaag aauugcuuga 2640
accugggagg cggagguugc agugagcuga gauaacgcca cugcacucca guguaggcaa 2700
cagagugaga cccugucuc 2719

<210> SEQ ID NO 3
<211> LENGTH: 6181
<212> TYPE: RNA
<213> ORGANISM: homo sapien

<400> SEQUENCE: 3
acucgggccc cgcguccugc ucccauggcc gcccccggcu ccccgcgcug cccccuuuac 60
cccgggccgc gccccggggc cccgcacuga cggcccaugg cgccgccagc cgcccgccuc 120
gcccugcucu ccgccgcggc gcucacgcug gcggcccggc ccgcgccuag ccccggccuc 180
ggccccggac ccgaguguuu cacagccaau ggugcggauu auaggggaac acagaacugg 240
acagcacuac aaggcgggaa gccaugucug uuuuggaacg agacuuucca gcauccauac 300
aacacucuga aauaccccaa cggggagggg ggccugggug agcacaacua uugcagaaau 360
ccagauggag acgugagccc cuggugcuau guggcagagc acgaggaugg ugucuacugg 420
aaguacugug agauaccugc uugccagaug ccuggaaacc uuggcugcua caaggaucau 480
ggaaacccac cuccucuaac uggcaccagu aaaacgucca acaaacucac cauacaaacu 540
ugcaucaguu uuugucggag ucagagguuc aaguuugcug ggauggaguc aggcuaugcu 600
ugcuucugug gaaacaaucc ugauuacugg aaguacgggg aggcagccag uaccgaaugc 660
aacagcgucu gcuucgggga ucacacccaa cccugugugg gcgauggcag gaucauccuc 720
uuugauacuc ucgugggcgc cugcgguggg aacuacucag ccaugucuuc uguggucuau 780

```
uccccugacu uccccgacac cuaugccacg gggagggucu gcuacuggac cauccggguu    840
ccgggggccu cccacaucca cuucagcuuc ccccuauuug acaucaggga cucggcggac    900
augguggagc uucuggaugg cuacacccac cguguccuag cccgcuucca cgggaggagc    960
cgcccaccuc uguccuucaa cgucucucug gacuucguca ucuuguauuu cuucucugau   1020
cgcaucaauc aggcccaggg auuugcuguu uuauaccaag ccgucaagga agaacugcca   1080
caggagaggc ccgcugucaa ccagacggug gccgagguga ucacggagca ggccaaccuc   1140
agugucagcg cugcccgguc cuccaaaguc cucuauguca ucaccaccag ccccagccac   1200
ccaccucaga cugucccagg auggacaguc uauggucugg caacucuccu cauccucaca   1260
gucacagcca uuguagcaaa gauacuucug cacgucacau ucaaauccca ucguguuccu   1320
gcuucagggg accuuaggga uugucaucaa ccagggacuu cgggggaaau cuggagcauu   1380
uuuuacaagc cuuccacuuc aauuuccauc uuuaagaaga aacucaaggg ucagagucaa   1440
caagaugacc gcaaucccu ugugagugac uaaaaacccc acugugccua ggacuugagg   1500
ucccucuuug agcucaaggc ugccgugguc aaccucuccu gugguucuuc ucugacagac   1560
ucuuccccuc cucucccucu gccucggccu cuucggggaa acccuccucc uacagacuag   1620
gaagaggcac ccugcugcca gggcaggcag agccuggauu ccuccugcuu caucgauugc   1680
acuuaggaga gagacucaaa gcccuggggc ccggcccucu cugcaucucu cucugaucua   1740
gcuagcagug ggggugucag gacagugagg cugagaugac agaggugguc auggcuggca   1800
cagggcucag guacauucua gauggcuguc agguggugg uagcuuuagu uacauugaau   1860
uuuucuugcu ucucuauuuu uguccacaca caaaucaguu ucuccugauc uuuaugucuu   1920
ggaacagggc cagacaggga gaacucucag guacucuugg gaguuggucc cauacaagug   1980
cggacuccug gacauuagcg agguguaaag agggcagugu cugugcugcc ccggcagcuu   2040
ugcucuccag augcuggacu agggugggcc uccuucagcc ugggaggguc ugagaauaag   2100
aucuagugac cccauuuau aucaaaccug auaccuuaca caugggcuuc uuucuagauu   2160
cuucuuucca uagcucaugg agcugcaggg aaagcuuuaa gagcuuuggu cauauaaaac   2220
auccauucag cugggcgcga uggcucaugc cuguaauccc agcacugugg gaggcugagg   2280
cgggcagauc accugagguc aggaguucga gaccagccug gccaacaugg ugaaaccccg   2340
ucucuacuaa aaauauaaaa auuagucagg cgugguggca ggcgccugua aucccagcua   2400
cucagaaggc ugagacagaa gaacagcuug aacccaggag gcugagauug cagugagccg   2460
agaucgcacc acugcacucc agccugggug acaagaguga gacucugucu caaaaaaaca   2520
aaacacaaau aaacaaaaaa aauccauuca uuuacucaug caauaaauuc uccugcaagc   2580
uuuuaugggc acucaguaag uacucaggau uggcuuuauc agccuugcca cugagcagcu   2640
caugguccua uggaaccuga gccaggccuc agucucucca ugauuggcuc agcuaacucu   2700
caguucagag uggagaguau caaucuugug uuuuugcccu uaggcagcac uauaugagac   2760
augggccug ugguccuucc uucuggugug ccccguguua aaagauaaaa aacaccccaa   2820
gggccgggcg cgguggcuca ugccuguaau cccagcacuu ugggaggcug aggcgggugg   2880
aucacgaggu caggugaucg aaaccauccu ggcuaagaug gugaaacccc gucucuacua   2940
aaaauacaaa aaauuagcug ggugugugg ugggcgccug uagucccagc ugcucgggag   3000
gcugaggcag gagaauggcg ugaacccggg aggcggagcu ugcagugagc agagaucacg   3060
ccacugcacu ccagccuggg ugacagugca agacucuguc ucaaaaaaaa aaaaaacacu   3120
ccaagggcca uccgugcucu cugccccucc uguggggacc aagugggguu aggaauggcu   3180
```

```
caguggggaa ggagagcacu cuugucccca gucccuugcc acccuguccc uuagauaggg   3240
aggugggcug cagagauugg ugccagaaga ggguggguuu gggaauugga gcuccuccaa   3300
ggagcuccuc cuaagauuga gugcugcagc uguaguggcu gcugguuggg agaguaagug   3360
ccaucacuaa uuuaaaaguc cuugccaucu ggaaucaggc uuugucaaca gcagcugaga   3420
aaagcagccu gugccucugc uggccaggcc uaggcccucg ucagagcgug ccucuccaca   3480
aggcacuugg gccuggguga uuguugcgcc ucuggcuuug gcguuuccuc uuugcagcac   3540
uuugccuacc ucccccaagc ccugagccac ugccugcugg ggcuccuacu gagguucugg   3600
aaacaccucu gcaccugccg ccccugggag gaaagagggc cacacaggaa gugucugcag   3660
ggagaggugg cacucggcag ccugaguuca ggagaggugc uuggagcuuc aggcagaggg   3720
gccuucagag gagggaaacg gagcaaugug ucacaggcag gcaggggcag gacugccacc   3780
ccaggccccg ugggaggccu gcugagggca cagagcugcu cggugcagcc uucaugcuuu   3840
gaucuggaaa gagcagcugu ccgcaggccu cugucuccaa gaggccuguc acacaggagg   3900
accgcuggaa acauaccaac acgugcaguc uccccuccaa gcuauucaug cuguuugugg   3960
aaucucucuc aaacauaagu gucaggugug ugucguccca acggguccug ugcugugaau   4020
agauccaugu gcagcacaaa gggaaugugg cacguggccc caggaagagu ucacccggcc   4080
agggggcagu uguucaguug ccuggggcug acacugacca cuggccucug ggguguccug   4140
cagcccaaau gcccaccuug cccuccucac aucucaguca ggggaggcca ugcccaagcc   4200
aaugugcugu cacagccugc agcgggggca gcacuuccuc ggagggccug ggaggugcug   4260
gggaugcccc agcgcuucuc uuccugccuc gcccuggcau ggcccagcgc cucuaggauc   4320
aacuuacgau ccguggagca gccccgggaa acccaaaucu ggcucaggac agcguacggg   4380
caggagggcu guaaaucauc ccaggcuaag ccuccguggg cacuggcucc ugccgcagcc   4440
uggcuaugga cucaguuaga accagguaga aagucagcga caccccacag aaggccacug   4500
cggcuaggua aacaccugag aaagaaacug cuccagaaga gaugacgugg gcuuccagga   4560
gcauggagga gguggcacuu gaacuuuuag gaaacuccuu agaugagaua aagugggggu   4620
uggagguggc gaaaagaggg uaacccuggg aaagucaguc agaacccaug gcagaagacu   4680
gcaggagagg caggggaggg gcuucgggga ccacugugga cagagcucug aaagcacccu   4740
ggccaaagcc ccuccugagg ugacagagcg ugggaggagg cugcacuggg ccugcgugcc   4800
auccucaccc cuguuccccg cuggcgccag gcccugccuu cuugguaccu gugccaacag   4860
gagagcccuc accagccgau cuugucacuc uccgugguga cagugucuug gccagcugug   4920
gccccuaguu ucuagcagcg uuucucagug uccuuggccc uucugagaag gcaggcggga   4980
ggcacacggu gcccuguucu uccccguuug uccaguugcu ugcaaagcag agaaugagua   5040
ggagugaacc cgagugacuu cacccgcccu gucccccacg ucaggacagg cuugaggccu   5100
cucugggcgu gagcgaggaa accaggcugc ucuaacuucu gaagaguggg cucuggcuca   5160
agacuccaau cggccagaag cccacagaga ucaaagcacu agcaaguuca gcuguccugg   5220
cccucgggua gaacccacgg gcgugccugg gugcggcucc acccacaugc cccacuguca   5280
gcccaggcag gagccuuccu ggccgggcuc aggaucugcc ugcagcccag ccaggccauc   5340
acccagcccc gaugcauccu ggcacugcac gcuuacucuu cacaagcacu uauacgcgga   5400
uggccuccga gacccugccu cccuggucug cugaggucag gccaggucuc ccacggagcc   5460
gggcagcucc acaccccacc accuggcacc guuagguuuc agaucucccg ugugguguuu   5520
```

gaugucggcu uuuguuccua ccuugggagu uuggauuguu uccucuggug ucuuuguuua 5580
ccuuccucac uguucuaccu ccuggccagg ucucagcuua gcuucccugg ugugggggugu 5640 uuuucaagcc uuccagccac agcugucucc ccucaggcug gacggcuccg gggugacagg 5700
gcuucacccu cugccugcag accccuggug ggcacaucuc acaggcuucc gucuugcuga 5760
guuggguacg gaggcagaag uggggugugg aggaaaguca gagggaaauc ugcuucagaa 5820 aggaagggguc uuuagacaca aagacuggag gcccuucccc gcccgcacgg gagcugccau 5880
cgugggucuc augcacguca agaccuuccc acauccaaac ucagcuucca gcagggauuu 5940
ugacuuugga ugacaaggcu uuauuuguaa auaugcucuu aauaugcaac uuugagaaua 6000
aaauagaaac aucauguauu uuaaaauaua agaugaagug ugacgcacug uauacaauuu 6060
aauauauauu uuuaggguuu uguuauuuaa gaaaauggaa uguaauggua cuuuuacaaa 6120
cgagaaaaaa uguuauuuuu acuuucugga aaaaauaaau auucucauug uuguagaaag 6180
a 6181

<210> SEQ ID NO 4
<211> LENGTH: 1422
<212> TYPE: RNA
<213> ORGANISM: homo sapien

<400> SEQUENCE: 4
auggcgccgc cagccgcccg ccucgcccug cucuccgccg cggcgcucac gcuggcggcc 60
cggcccgcgc cuagccccgg ccucggcccc gaguguuuca cagccaaugg ugcggauuau 120
aggggaacac agaacuggac agcacuacaa ggcgggaagc caugucuguu uuggaacgag 180
acuuuccagc auccauacaa cacucugaaa uaccccaacg gggagggggg ccugggugag 240
cacaacuauu gcagaaaucc agauggagac gugagccccu ggugcuaugu ggcagagcac 300
gaggauggug ucuacuggaa guacugugag auaccugcuu gccagaugcc uggaaaccuu 360
ggcugcuaca aggaucaugg aaacccaccu ccucuaacug gcaccaguaa aacguccaac 420
aaacucacca uacaaacuug caucaguuuu ugucggaguc agagguucaa guuugcuggg 480
auggagucag gcuaugcuug cuucugugga aacaauccug auuacuggaa guacggggag 540
gcagccagua ccgaaugcaa cagcgucugc uucggggauc acacccaacc cugugguggc 600
gauggcagga ucauccucuu ugauacucuc gugggcgccu gcggugggaa cuacucagcc 660
augucuucug uggucuauuc cccugacuuc cccgacaccu augccacggg gagggucugc 720
uacuggacca uccggguucc gggggccucc cacauccacu ucagcuuccc ccuauuugac 780
aucagggacu cggcggacau gguggagcuu cuggauggcu acacccaccg uguccuagcc 840
cgcuuccacg ggaggagccg cccaccucug uccuucaacg ucucucugga cuucgucauc 900
uuguauuucu ucucugaucg caucaaucag gcccagggau uugcuguuuu auaccaagcc 960
gucaaggaag aacugccaca ggagaggccc gcugucaacc agacggugge cgaggugauc 1020 acggagcagg ccaaccucag ugucagcgcu gcccggucc ccaaagucuu cuaugucauc 1080
accaccagcc ccagccaccc accucagacu gucccaggua gcaauuccug ggcgccaccc 1140
augggggcug gaagccacag aguugaagga uggacagucu auggucuggc aacucuccuc 1200
auccucacag ucacagccau uguagcaaag auacuucugc acgucacauu caaaucccau 1260
cguguuccug cuucagggga ccuuagggau ugucaucaac cagggacuuc gggggaaauc 1320
uggagcauuu uuuacaagcc uuccacuuca auuuccaucu uuaagaagaa acucaagggu 1380
cagagucaac aagaugaccg caaucccuu gugagugacu aa 1422

<210> SEQ ID NO 5
<211> LENGTH: 2802
<212> TYPE: RNA
<213> ORGANISM: homo sapien

<400> SEQUENCE: 5
acucgggccc cgcguccugc ucccauggcc gcccccggcu ccccgcgcug cccccuuuac 60
cccgggccgc gccccggggc cccgcacuga cggcccaugg cgccgccagc cgcccgccuc 120
gcccugcucu ccgccgcggc gcucacgcug gcggcccggc ccgcgccuag ccccggccuc 180
ggccccggac ccgaguguuu cacagccaau ggugcggauu auaggggaac acagaacugg 240
acagcacuac aaggcgggaa gccaugucug uuuuggaacg agacuuucca gcauccauac 300
aacacucuga aauaccccaa cggggagggg ggccugggug agcacaacua uugcagaaau 360
ccagauggag acgugagccc cuggugcuau guggcagagc acgaggaugg ugucuacugg 420
aaguacugug agauaccugc uugccagaug ccuggaaacc uuggcugcua caaggaucau 480
ggaaacccac cuccucuaac uggcaccagu aaaacgucca acaaacucac cauacaaacu 540
ugcaucaguu uuugucggag ucagagguuc aaguuugcug ggauggaguc aggcuaugcu 600
ugcuucugug gaaacaaucc ugauuacugg aaguacgggg aggcagccag uaccgaaugc 660
aacagcgucu gcuucgggga ucacacccaa cccuguggug gcgauggcag gaucauccuc 720
uuugauacuc ucgugggcgc cugcggguggg aacuacucag ccaugucuuc uguggucuau 780
uccccugacu uccccgacac cuaugccacg gggagggucu gcuacuggac cauccggguu 840
ccgggggccu cccacaucca cuucagcuuc ccccuauuug acaucaggga cucggcggac 900
augguggagc uucuggaugg cuacacccac cguguccuag cccgcuucca cgggaggagc 960
cgcccaccuc uguccuucaa cgucucucug gacuucguca ucuuguauuu cuucucugau 1020
cgcaucaauc aggcccaggg auuugcuguu uuauaccaag ccgucaagga agaacugcca 1080
caggagaggc ccgcugucaa ccagacggug gccgagguga ucacggagca ggccaaccuc 1140
agugucagcg cugcccgguc cuccaaaguc cucuauguca ucaccaccag ccccagccac 1200
ccaccucaga cugucccagg uagcaauucc ugggcgccac ccaugggggc uggaagccac 1260
agaguugaag gauggacagu cuauggucug gcaacucucc ucauccucac agucacagcc 1320
auuguagcaa agauacuucu gcacgucaca uucaaauccc aucguguucc ugcuucaggg 1380
gaccuuaggg auugucauca accagggacu ucgggggaaa ucuggagcau uuuuuacaag 1440
ccuuccacuu caauuuccau cuuuaagaag aaacucaagg gucagaguca acaagaugac 1500
cgcaaucccc uugcaauuca ggacucggaa gugacaucac ucaucugguc ucaggggcag 1560
cccagaagua ucugacugua gacacaacua ggcuccgugg gcauaucugg guggcaauuu 1620
cagagggcag aggggacacc uucauugccu cuccucgcac agaaauggug ggcucucucu 1680
ggcccagcgu ggugguucau gccuguaaua ccagcguuuu gggaggcuga gaugggagga 1740
uugcuugagc ccaggagguc gaggcugcag ugagcuauga ucacaccacc acacuccagc 1800
cugagcagca gagcgggacc ucgucucuaa gaauagaaag aaagaaagag aaacgguguc 1860
cuccgcacag ccggucagaa cugugugacu cacuugaggc aggaccgaga gugacaucca 1920
guugcaccuu ucucaccuac uuugggaccu uuggggguga guuccccuuu guccucucgu 1980
ggaaacagca cacagcaagc aaccacaaaa ccagagcgga aggagggacu ucccaccggc 2040
auccggcccc agugccaugu uuuaucaucu ggaacgguug ugaagcuuug ugugacuugc 2100
ucaggaucag cagucaccau ggucuaaucc caagagggac ucgucaccca gagaccucaa 2160
aaggccccag gccuacugug guuuuuucug agaggcuccc agaaccaagu ggcacguugg 2220
uuuccugugc gucugugucu uugugccugu aucucgcugg gggacuucac aggaagcagg 2280
auuugggcau uccugaagcu cccagcugga caccacuccu gagcgccaca ucccaugauc 2340
acuucaacca caggccuuug acuuugccac auggcaaggc acccagcaga agaugaggau 2400
gacgggugau gcuagaugga uguguaccug guggauggcc cacgcacgaa gacucaagac 2460
ccucaggacu ggccauauaa ucugcaaggu ccaguaugaa auaagaauaa gcagcccaca 2520
caacugggca uagugguuca ugccuguaau cccagcacuu ugggaggcug aggagggugg 2580
aucacuugag gccaggaauu cgagaccagc cuggccaaca uggcgaaaac ccaucucuac 2640
uaaaaauaca aaaauuaguu gggcauggug gcacacaccu guaaucccag cuacucggag 2700
gcugaggcac aagaauugcu ugaaccuggg aggcggaggu ugcagugagc ugagauaacg 2760
ccacugcacu ccaguguagg caacagagug agacccuguc uc 2802

<210> SEQ ID NO 6
<211> LENGTH: 3087
<212> TYPE: RNA
<213> ORGANISM: homo sapien

<400> SEQUENCE: 6
cggacgcgug ggcgcgcugc ccccuuuacc ccgggccgcg ccccggggcc ccgcacugac 60
ggcccauggc gccgcccgcc gcccgccucg cccugcucuc cgccgcggcg cucacgcugg 120
cggcccggcc cgcgccuagc cccggccucg gccccggacc cgaguguuuc acagccaaug 180
gugcggauua uaggggaaca cagaacugga cagcacuaca aggcgggaag ccaugucugu 240
uuuggaacga gacuuuccag cauccauaca acacucugaa auaccccaac ggggaggggg 300
gccuggguga gcacaacuau ugcagaaauc cagauggaga cgugagcccc uggugcuaug 360
uggcagagca cgaggauggu gucuacugga aguacuguga gauaccugcu ugccagaugc 420
cuggaaaccu uggcugcuac aaggaucaug gaaacccacc uccucuaacu ggcaccagua 480
aaacguccaa caaacucacc auacaaacuu gcaucaguuu uugucggagu cagagguuca 540
aguuugcugg gauggaguca ggcuaugcuu gcuucugugg aaacaauccu gauuacugga 600
aguacgggga ggcagccagu accgaaugca acagcgucug cuucggggau cacacccaac 660 ccugugguggg cgauggcagg aucauccucu uugauacucu cgugggcgcc ugcggguggga 720 acuacucagc caugucuucu guggucuauu ccccugacuu ccccgacacc uaugccacgg 780
ggagggucug cuacuggacc auccggguuc cgggggccuc ccacauccac uucagcuucc 840
cccuauuuga caucagggac ucggcggaca ugguggagcu ucuggauggc uacacccacc 900
guguccuagc ccgcuuccac gggaggagcc gcccaccucu guccuucaac gucucucugg 960
acuucgucau cuuguauuuc uucucugauc gcaucaauca ggcccaggga uuugcuguuu 1020
uauaccaagc cgucaaggaa gaacugccac aggagaggcc cgcugucaac cagacggugg 1080
ccgaggugau cacggagcag gccaaccuca gugucagcgc ugcccggucc uccaaagucc 1140
ucuaugucau caccaccagc cccagccacc caccucagac ugucccagga uggacagucu 1200
auggucuggc aacucuccuc auccucacag ucacagccau uguagcaaag auacuucugc 1260
acgucacauu caaaucccau cguguuccug cuucagggga ccuuagggau ugucaucaac 1320
cagggacuuc gggggaaauc uggagcauuu uuuacaagcc uuccacuuca auuuccaucu 1380
uuaagaagaa acucaagggu cagagucaac aagaugaccg caauccccuu gugagugacu 1440

```
aaaaacccca cugugccuag gacuugaggu cccucuuuga gcucaaggcu gccgugguca   1500
accucuccug ugguucuucu cugacagacu cuuccccucc ucucccucug ccucggccuc   1560
uucggggaaa cccuccuccu acagacuagg aagaggcacc cugcugccag ggcaggcaga   1620
gccuggauuc cuccugcuuc aucgauugca cuuaggagag agacucaaag cccuggggcc   1680
cggcccucuc ugcaucucuc ucugaucuag cuagcagugg ggugucagg acagugaggc   1740
ugagaugaca gaggugguca uggcuggcac agggcucagg uacauucuag auggcuguca   1800
gguggugggu agcuuuaguu acauugaauu uuucuugcuu cucuauuuuu guccacacac   1860
aaaucaguuu cuccugaucu uuaugucuug gaacagggcc agacagggag aacucucagg   1920
uacucuuggg aguuggucce auacaagugc ggacuccugg acauuagcga gguguaaaga   1980
gggcaguguc ugugcugccc cggcagcuuu gcucuccaga ugcuggacua gggugggccu   2040
ccuucagccu gggagggucu gagaauaaga ucuagugacc cccauuuaua ucaaaccuga   2100
uaccuuacac augggcuucu uucuagauuc uucuuuccau agcucaugga gcugcaggga   2160
aagcuuuaag agcuuugguc auauaaaaca uccauucagc ugggcgcgau ggcucaugcc   2220
uguaauccca gcacuguggg aggcugaggc gggcagauca ccugagguca ggaguucgag   2280
accagccugg ccaacauggu gaaaccccgu cucuacuaaa aauauaaaaa uuagucaggc   2340
gugguggcag gcgccuguaa ucccagcuac ucagaaggcu gagacagaag aacagcuuga   2400
acccaggagg cugagauugc agugagccga gaucgcacca cugcacucca gccuggguga   2460
caagagugag acucugucuc aaaaaaacaa aacacaaaua aacaaaaaaa auccauucau   2520
uuacucaugc aauaaauucu ccugcaagcu uuuaugggca cucaguaagu acucaggauu   2580
ggcuuuauca gccuugccac ugagcagcuc augguccuau ggaaccugag ccaggccuca   2640
gucucuccau gauuggcuca gcuaacucuc aguucagagu ggagaguauc aaucuugugu   2700
uuuugcccuu aggcagcacu auaugagaca uggggccugu gguccuuccu ucugguguce   2760
cccguguuaa aagauaaaaa acaccccaag ggccgggcgc gguggcucau gccuguaauc   2820
ccagcacuuu gggaggcuga ggcgggugga ucacgagguc aggugaucga aaccauccug   2880
gcuaagacgg ugaaaccccg ucucuacuaa aaauacaaaa aauuagcugg guguggugguu  2940
gggcgccugu agucccagcu gcucgggagg cugaggcagg agaauggcgu gaacccggga   3000
ggcggagcuu gcagugagca gagaucacgc cacugcacuc cagccugggu gacagugcaa   3060
gacucugucu caaaaaaaaa aaaaaaa                                       3087
```

<210> SEQ ID NO 7
<211> LENGTH: 6138
<212> TYPE: RNA
<213> ORGANISM: homo sapien

<400> SEQUENCE: 7

```
cgcgcugccc ccuuuacccc gggccgcgcc ccggggcccc gcacugacgg cccauggcgc     60
cgccagccgc ccgccucgcc cugcucuccg ccgcggcgcu cacgcuggcg gcccggcccg    120
cgccuagccc cggccucggc cccggacccg aguguuucac agccaauggu gcggauuaua    180
ggggaacaca gaacuggaca gcacuacaag gcgggaagcc augucuguuu uggaacgaga    240
cuuuccagca uccauacaac acucugaaau accccaacgg ggagggggc cugggugagc     300
acaacuauug cagaaaucca gauggagacg ugagccccug gugcuaugug gcagagcacg    360
aggauggugu cuacuggaag uacugugaga uaccugcuug ccagaugccu ggaaaccuug    420
```

```
gcugcuacaa ggaucaugga aacccaccuc cucuaacugg caccaguaaa acguccaaca    480
aacucaccau acaaacuugc aucaguuuuu gucggaguca gagguucaag uuugcuggga    540
uggagucagg cuaugcuugc uucuguggaa acaauccuga uuacuggaag uacggggagg    600
cagccaguac cgaaugcaac agcgucugcu ucggggauca cacccaaccc uguggugcg     660
auggcaggau cauccucuuu gauacucucg ugggcgccug cggugggaac uacucagcca    720
ugucuucugu ggucuauucc ccugacuucc ccgacaccua ugccacgggg agggucugcu    780
acuggaccau ccggguuccg gggccuccc acauccacuu cagcuucccc cuauuugaca     840
ucagggacuc ggcggacaug guggagcuuc uggauggcua cacccaccgu guccuagccc    900
gcuuccacgg gaggagccgc ccaccucugu ccuucaacgu cucucuggac uucgucaucu    960
uguauuucuu cucugaucgc aucaaucagg cccagggauu ugcuguuuua uaccaagccg   1020
ucaaggaaga acugccacag gagaggcccg cugucaacca gacgguggcc gaggugauca   1080
cggagcaggc caaccucagu gucagcgcug cccgguccuc caaaguccuc uaugucauca   1140
ccaccagccc cagccaccca ccucagacug ucccaggaug gacagucuau ggucuggcaa   1200
cucuccucau ccucacaguc acagccauug uagcaaagau acuucugcac gucacauuca   1260
aauccca ucg uguuccugcu ucaggggacc uuagggauug ucaucaacca gggacuucgg   1320
gggaaaucug gagcauuuuu uacaagccuu ccacuucaau uuccaucuuu aagaagaaac   1380
ucaaggguca gagucaacaa gaugaccgca aucccuugu gagugacuaa aaaccccacu    1440
gugccuagga cuugaggucc cucuuugagc ucaaggcugc cgugguaaac cucuccugug   1500
guucuucucu gacagacucu uccccuccuc ucccucugcc ucggccucuu cggggaaacc   1560
cuccuccuac agacuaggaa gaggcacccu gcugccaggg caggcagagc cuggauuccu   1620
ccugcuucau cgauugcacu uaggagagag acucaaagcc cuggggcccg gcccucucug   1680
caucucucuc ugaucuagcu agcagugggg gugucaggac agugaggcug agaugacaga   1740
gguggucaug gcuggcacag ggcucaggua cauucuagau ggcugucagg ugguggguag   1800
cuuuaguuac auugaauuuu ucuugcuucu cuauuuuugu ccacacacaa aucaguuucu   1860
ccugaucuuu augucuugga acagggccag acagggagaa cucucaggua cucuugggag   1920
uugguc ccau acaagugcgg acuccuggac auuagcgagg uguaaagagg gcagugucug   1980
ugcugccccg gcagcuuugc ucuccagaug cuggacuagg gugggccucc uucagccugg   2040
gagggucuga gaauaagauc uagugacccc cauuuauauc aaaccugaua ccuuacacau   2100
gggcuucuuu cuagauucuu cuuuccauag cucauggagc ugcagggaaa gcuuuaagag   2160
cuuugguc au auaaaacauc cauucagcug ggcgcgaugg cucaugccug uaaucccagc   2220
acugugggag gcugaggcgg gcagaucacc ugaggucagg aguucgagac cagccuggcc   2280
aacauggu ga aaccccgucu cuacuaaaaa uauaaaaauu agucaggcgu gguggcaggc   2340
gccuguaauc ccagcuacuc agaaggcuga gacagaagaa cagcuugaac ccaggaggcu   2400
gagauugcag ugagccgaga ucgcaccacu gcacuccagc cugggugaca agagugagac   2460
ucugucucaa aaaaacaaaa cacaaauaaa caaaaaaaau ccauucauuu acucaugcaa   2520
uaaauucucc ugcaagcuuu uaugggcacu caguaaguac ucaggauugg cuuuaucagc   2580
cuugccacug agcagcucau gguccuaugg aaccugagcc aggccucagu cucuccauga   2640
uuggcucagc uaacucucag uucagagugg agaguaucaa ucuuguguuu uugcccuuag   2700
gcagcacuau augagacaug gggccugugg uccuuccuuc ugguguccc cguguuaaaa    2760
gauaaaaaac accccaaggg ccgggcgcgg uggcucaugc cuguaauccc agcacuuugg   2820
```

```
gaggcugagg cgggugggauc acgaggucag gugaucgaaa ccauccuggc uaagauggug   2880
aaaccccguc ucuacuaaaa auacaaaaaa uuagcugggu gugguggugg gcgccuguag   2940
ucccagcugc ucgggaggcu gaggcaggag aauggcguga acccgggagg cggagcuugc   3000
agugagcaga gaucacgcca cugcacucca gccugggugga cagugcaaga cucugucuca   3060
aaaaaaaaaa aaacacucca agggccaucc gugcucucug ccccuccugu ggggaccaag   3120
uggggguuagg aauggcucag uggggaagga gagcacucuu guccccaguc ccuugccacc   3180
cugucccuua gauagggagg ugggcugcag agauuggugc cagaagaggg uggguuuggg   3240
aauuggagcu ccuccaagga gcuccuccua agauugagug cugcagcugu aguggcugcu   3300
gguugggaga guaagugcca ucacuaauuu aaaaguccuu gccaucugga aucaggcuuu   3360
gucaacagca gcugagaaaa gcagccugug ccucugcugg ccaggccuag gcccucguca   3420
gagcgugccu cuccacaagg cacuugggcc ugggugauug uugcgccucu ggcuuuggcg   3480
uuuccucuuu gcagcacuuu gccuaccucc cccaagcccu gagccacugc cugcuggggc   3540
uccuacugag guucuggaaa caccucugca ccugccgccc cugggaggaa agagggccac   3600
acaggaagug ucugcaggga gaggguggcac ucggcagccu gaguucagga gaggugcuug   3660
gagcuucagg cagaggggcc uucagaggag ggaaacggag caauguguca caggcaggca   3720
ggggcaggac ugccacccca ggccccgugg gaggccugcu gagggcacag agcugcucgg   3780
ugcagccuuc augcuuugau cuggaaagag cagcuguccg caggccucug ucuccaagag   3840
gccugucaca caggaggacc gcuggaaaca uaccaacacg ugcagucucc ccuccaagcu   3900
auucaugcug uuuguggaau cucucucaaa cauaaguguc aggugugugu cgucccaacg   3960
gguccugugc ugugaauaga uccaugugca gcacaaaggg aauguggcac guggccccag   4020
gaagaguuca cccggccagg gggcaguugu ucaguugccu ggggcugaca cugaccacug   4080
gccucugggg uguccugcag cccaaaugcc caccuugccc uccucacauc ucagucaggg   4140
gaggccaugc ccaagccaau gugcugucac agccugcagc gggggcagca cuuccucgga   4200
gggccuggga ggugcugggg augccccagc gcuucucuuc cugccucgcc cuggcauggc   4260
ccagcgccuc uaggaucaac uuacgauccg uggagcagcc ccgggaaacc caaaucuggc   4320
ucaggacagc guacgggcag gagggcugua aaucauccca ggcuaagccu ccgugggcac   4380
uggcuccugc cgcagccugg cuauggacuc aguuagaacc agguagaaag ucagcgacac   4440
cccacagaag gccacugcgg cuagguaaac accugagaaa gaaacugcuc cagaagagau   4500
gacgugggcu uccaggagca uggaggaggu ggcacuugaa cuuuuaggaa acuccuuaga   4560
ugagauaaag ugggggguugg agguggcgaa aagaggguaa cccugggaaa gucagucaga   4620
acccauggca gaagacugca ggagaggcag gggaggggcu ucggggacca cuguggacag   4680
agcucugaaa gcacccuggc caaagccccu ccugagguga cagagcgugg gaggaggcug   4740
cacugggccu gcgugccauc cucaccccug uuccccgcug gcgccaggcc cugccuucuu   4800
gguaccugug ccaacaggag agcccucacc agccgaucuu gucacucucc guggugacag   4860
ugucuuggcc agcuguggcc ccuaguuucu agcagcguuu cucagugucc uuggcccuuc   4920
ugagaaggca ggcgggaggc acacggugcc cuguucuucc ccguuugucc aguugcuugc   4980
aaagcagaga augaguagga gugaacccga gugacuucac ccgcccuguc ccccacguca   5040
ggacaggcuu gaggccucuc ugggcgugag cgaggaaacc aggcugcucu aacuucugaa   5100
gagugggcuc uggcucaaga cuccaaucgg ccagaagccc acagagauca aagcacuagc   5160
```

aaguucagcu guccuggccc ucggguagaa cccacgggcg ugccugggug cggcuccacc 5220
cacaugcccc acugucagcc caggcaggag ccuuccuggc cgggcucagg aucugccugc 5280
agcccagcca ggccaucacc cagccccgau gcauccuggc acugcacgcu uacucuucac 5340
aagcacuuau acgcggaugg ccuccgagac ccugccuccc uggucugcug aggucaggcc 5400
aggucuccca cggagccggg cagcuccaca ccccaccacc uggcaccguu agguuucaga 5460
ucucccgugu gguguuugau gucggcuuuu guuccuaccu ugggaguuug gauuguuucc 5520
ucuggugucu uuguuuaccu uccucacugu ucuaccuccu ggccaggucu cagcuuagcu 5580
ucccuggugu ggggugucuu ucaagccuuc cagccacagc ugucuccccu caggcuggac 5640
ggcuccgggg ugacagggcu ucacccucug ccugcagacc ccuggugggc acaucucaca 5700
ggcuuccguc uugcugaguu ggguacggag gcagaagugg ggugugggagg aaagucagag 5760 ggaaaucugc uucagaaagg aagggucuuu agacacaaag acuggaggcc cuuccccgcc 5820
cgcacgggag cugccaucgu gggucucaug cacgucaaga ccuucccaca uccaaacuca 5880
gcuuccagca gggauuuuga cuuuggauga caaggcuuua uuuguaaaua ugcucuuaau 5940
augcaacuuu gagaauaaaa uagaaacauc auguauuuua aaauauaaga ugaaguguga 6000
cgcacuguau acaauuuaau auauauuuuu aggguuuugu uauuuaagaa aauggaaugu 6060
aaugguacuu uuacaaacga gaaaaaaugu uauuuuuacu uucuggaaaa aauaaauauu 6120
cucauuguug uagaaaga 6138

<210> SEQ ID NO 8
<211> LENGTH: 2719
<212> TYPE: DNA
<213> ORGANISM: homo sapien

<400> SEQUENCE: 8
gcactgacgg cccatggcgc cgccagccgc ccgcctcgcc ctgctctccg ccgcggcgct 60
cacgctggcg gcccggcccg cgcctagccc cggcctcggc cccggacccg agtgtttcac 120
agccaatggt gcggattata ggggaacaca gaactggaca gcactacaag gcgggaagcc 180
atgtctgttt tggaacgaga ctttccagca tccatacaac actctgaaat accccaacgg 240
ggaggggggc ctgggtgagc acaactattg cagaaatcca gatggagacg tgagcccctg 300
gtgctatgtg gcagagcacg aggatggtgt ctactggaag tactgtgaga tacctgcttg 360
ccagatgcct ggaaaccttg gctgctacaa ggatcatgga aacccacctc ctctaactgg 420
caccagtaaa acgtccaaca aactcaccat acaaacttgc atcagttttt gtcggagtca 480
gaggttcaag tttgctggga tggagtcagg ctatgcttgc ttctgtggaa acaatcctga 540
ttactggaag tacggggagg cagccagtac cgaatgcaac agcgtctgct tcggggatca 600
cacccaaccc tgtggtggcg atggcaggat catcctcttt gatactctcg tgggcgcctg 660
cggtgggaac tactcagcca tgtcttctgt ggtctattcc cctgacttcc ccgacaccta 720
tgccacgggg agggtctgct actggaccat ccgggttccg ggggcctccc acatccactt 780
cagcttcccc ctatttgaca tcagggactc ggcggacatg gtggagcttc tggatggcta 840
cacccaccgt gtcctagccc gcttccacgg gaggagccgc ccacctctgt ccttcaacgt 900
ctctctggac ttcgtcatct tgtatttctt ctctgatcgc atcaatcagg cccagggatt 960
tgctgtttta taccaagccg tcaaggaaga actgccacag gagaggcccg ctgtcaacca 1020
gacggtggcc gaggtgatca cggagcaggc caacctcagt gtcagcgctg cccggtcctc 1080
caaagtcctc tatgtcatca ccaccagccc cagccaccca cctcagactg tcccaggtag 1140

```
caattcctgg gcgccaccca tgggggctgg aagccacaga gttgaaggat ggacagtcta   1200
tggtctggca actctcctca tcctcacagt cacagccatt gtagcaaaga tacttctgca   1260
cgtcacattc aaatcccatc gtgttcctgc ttcaggggac cttagggatt gtcatcaacc   1320
agggacttcg gggaaatct ggagcatttt ttacaagcct tccacttcaa tttccatctt    1380
taagaagaaa ctcaagggtc agagtcaaca agatgaccgc aatccccttg caattcagga   1440
ctcggaagtg acatcactca tctggtctca ggggcagccc agaagtatct gactgtagac   1500
acaactaggc tccgtgggca tatctgggtg gcaatttcag agggcagagg ggacaccttc   1560
attgcctctc ctcgcacaga aatggtgggc tctctctggc ccagcgtggt ggttcatgcc   1620
tgtaatacca gcgttttggg aggctgagat gggaggattg cttgagccca ggaggtcgag   1680
gctgcagtga gctatgatca caccaccaca ctccagcctg agcagcagag cgggacctcg   1740
tctctaagaa tagaaagaaa gaaagagaaa cggtgtcctc cgcacagccg gtcagaactg   1800
tgtgactcac ttgaggcagg accgagagtg acatccagtt gcacctttct cacctacttt   1860
gggacctttg ggggtgagtt ccccttgtc ctctcgtgga aacagcacac agcaagcaac    1920
cacaaaacca gagcggaagg agggacttcc caccggcatc cggccccagt gccatgtttt   1980
atcatctgga acggttgtga agctttgtgt gacttgctca ggatcagcag tcaccatggt   2040
ctaatcccaa gagggactcg tcacccagag acctcaaaag gccccaggcc tactgtggtt   2100
ttttctgaga ggctcccaga accaagtggc acgttggttt cctgtgcgtc tgtgtctttg   2160
tgcctgtatc tcgctggggg acttcacagg aagcaggatt tgggcattcc tgaagctccc   2220
agctggacac cactcctgag cgccacatcc catgatcact tcaaccacag gcctttgact   2280
ttgccacatg gcaaggcacc cagcagaaga tgaggatgac gggtgatgct agatggatgt   2340
gtacctggtg gatggcccac gcacgaagac tcaagaccct caggactggc catataatct   2400
gcaaggtcca gtatgaaata agaataagca gcccacacaa ctgggcatag tggttcatgc   2460
ctgtaatccc agcactttgg gaggctgagg agggtggatc acttgaggcc aggaattcga   2520
gaccagcctg gccaacatgg cgaaaaccca tctctactaa aaatacaaaa attagttggg   2580
catggtggca cacacctgta atcccagcta ctcggaggct gaggcacaag aattgcttga   2640
acctgggagg cggaggttgc agtgagctga gataacgcca ctgcactcca gtgtaggcaa   2700
cagagtgaga ccctgtctc                                                2719
```

<210> SEQ ID NO 9
<211> LENGTH: 6181
<212> TYPE: DNA
<213> ORGANISM: homo sapien

<400> SEQUENCE: 9

```
actcgggccc cgcgtcctgc tcccatggcc gcccccggct ccccgcgctg ccccctttac     60
cccgggccgc gccccggggc cccgcactga cggcccatgg cgccgccagc cgcccgcctc    120
gccctgctct ccgccgcggc gctcacgctg gcggcccggc ccgcgcctag ccccggcctc    180
ggccccggac ccgagtgttt cacagccaat ggtgcggatt ataggggaac acagaactgg    240
acagcactac aaggcgggaa gccatgtctg ttttggaacg agactttcca gcatccatac    300
aacactctga aataccccaa cggggagggg ggcctgggtg agcacaacta ttgcagaaat    360
ccagatggag acgtgagccc ctggtgctat gtggcagagc acgaggatgg tgtctactgg    420
aagtactgtg agatacctgc ttgccagatg cctggaaacc ttggctgcta caaggatcat    480
```

```
ggaaacccac ctcctctaac tggcaccagt aaaacgtcca acaaactcac catacaaact    540
tgcatcagtt tttgtcggag tcagaggttc aagtttgctg ggatggagtc aggctatgct    600
tgcttctgtg gaaacaatcc tgattactgg aagtacgggg aggcagccag taccgaatgc    660
aacagcgtct gcttcgggga tcacacccaa ccctgtggtg gcgatggcag gatcatcctc    720
tttgatactc tcgtgggcgc ctgcggtggg aactactcag ccatgtcttc tgtggtctat    780
tcccctgact tccccgacac ctatgccacg gggagggtct gctactggac catccgggtt    840
ccgggggcct cccacatcca cttcagcttc cccctatttg acatcaggga ctcggcggac    900
atggtggagc ttctggatgg ctacacccac cgtgtcctag cccgcttcca cgggaggagc    960
cgcccacctc tgtccttcaa cgtctctctg gacttcgtca tcttgtattt cttctctgat   1020
cgcatcaatc aggcccaggg atttgctgtt ttataccaag ccgtcaagga agaactgcca   1080
caggagaggc ccgctgtcaa ccagacggtg gccgaggtga tcacggagca ggccaacctc   1140
agtgtcagcg ctgcccggtc ctccaaagtc ctctatgtca tcaccaccag ccccagccac   1200
ccacctcaga ctgtcccagg atggacagtc tatggtctgg caactctcct catcctcaca   1260
gtcacagcca ttgtagcaaa gatacttctg cacgtcacat tcaaatccca tcgtgttcct   1320
gcttcagggg accttaggga ttgtcatcaa ccagggactt cgggggaaat ctggagcatt   1380
ttttacaagc cttccacttc aatttccatc tttaagaaga aactcaaggg tcagagtcaa   1440
caagatgacc gcaatcccct tgtgagtgac taaaaacccc actgtgccta ggacttgagg   1500
tccctctttg agctcaaggc tgccgtggtc aacctctcct gtggttcttc tctgacagac   1560
tcttcccctc ctctccctct gcctcggcct cttcggggaa accctcctcc tacagactag   1620
gaagaggcac cctgctgcca gggcaggcag agcctggatt cctcctgctt catcgattgc   1680
acttaggaga gagactcaaa gccctggggc ccggccctct ctgcatctct ctctgatcta   1740
gctagcagtg gggggtgtcag gacagtgagg ctgagatgac agaggtggtc atggctggca   1800
cagggctcag gtacattcta gatggctgtc aggtggtggg tagctttagt tacattgaat   1860
ttttcttgct tctctatttt tgtccacaca caaatcagtt tctcctgatc tttatgtctt   1920
ggaacagggc cagacaggga gaactctcag gtactcttgg gagttggtcc catacaagtg   1980
cggactcctg gacattagcg aggtgtaaag agggcagtgt ctgtgctgcc ccggcagctt   2040
tgctctccag atgctggact agggtgggcc tccttcagcc tgggagggtc tgagaataag   2100
atctagtgac ccccatttat atcaaacctg ataccttaca catgggcttc tttctagatt   2160
cttctttcca tagctcatgg agctgcaggg aaagctttaa gagctttggt catataaaac   2220
atccattcag ctgggcgcga tggctcatgc ctgtaatccc agcactgtgg gaggctgagg   2280
cgggcagatc acctgaggtc aggagttcga gaccagcctg gccaacatgg tgaaaccccg   2340
tctctactaa aaatataaaa attagtcagg cgtggtggca ggcgcctgta atcccagcta   2400
ctcagaaggc tgagacagaa gaacagcttg aacccaggag gctgagattg cagtgagccg   2460
agatcgcacc actgcactcc agcctgggtg acaagagtga gactctgtct caaaaaaaca   2520
aaacacaaat aaacaaaaaa aatccattca tttactcatg caataaattc tcctgcaagc   2580
ttttatgggc actcagtaag tactcaggat tggctttatc agccttgcca ctgagcagct   2640
catggtccta tggaacctga gccaggcctc agtctctcca tgattggctc agctaactct   2700
cagttcagag tggagagtat caatcttgtg tttttgccct taggcagcac tatatgagac   2760
atggggcctg tggtccttcc ttctggtgtc ccccgtgtta aaagataaaa aacaccccaa   2820
gggccgggcg cggtggctca tgcctgtaat cccagcactt tgggaggctg aggcgggtgg   2880
```

```
atcacgaggt caggtgatcg aaaccatcct ggctaagatg gtgaaacccc gtctctacta   2940
aaaatacaaa aaattagctg ggtgtggtgg tgggcgcctg tagtcccagc tgctcgggag   3000
gctgaggcag gagaatggcg tgaacccggg aggcggagct tgcagtgagc agagatcacg   3060
ccactgcact ccagcctggg tgacagtgca agactctgtc tcaaaaaaaa aaaaaacact   3120
ccaagggcca tccgtgctct ctgcccctcc tgtggggacc aagtggggtt aggaatggct   3180
cagtggggaa ggagagcact cttgtcccca gtcccttgcc accctgtccc ttagataggg   3240
aggtgggctg cagagattgg tgccagaaga gggtgggttt gggaattgga gctcctccaa   3300
ggagctcctc ctaagattga gtgctgcagc tgtagtggct gctggttggg agagtaagtg   3360
ccatcactaa tttaaaagtc cttgccatct ggaatcaggc tttgtcaaca gcagctgaga   3420
aaagcagcct gtgcctctgc tggccaggcc taggccctcg tcagagcgtg cctctccaca   3480
aggcacttgg gcctgggtga ttgttgcgcc tctggctttg gcgtttcctc tttgcagcac   3540
tttgcctacc tcccccaagc cctgagccac tgcctgctgg ggctcctact gaggttctgg   3600
aaacacctct gcacctgccg cccctgggag gaaagagggc cacacaggaa gtgtctgcag   3660
ggagaggtgg cactcggcag cctgagttca ggagaggtgc ttggagcttc aggcagaggg   3720
gccttcagag gagggaaacg gagcaatgtg tcacaggcag gcaggggcag gactgccacc   3780
ccaggccccg tgggaggcct gctgagggca cagagctgct cggtgcagcc ttcatgcttt   3840
gatctggaaa gagcagctgt ccgcaggcct ctgtctccaa gaggcctgtc acacaggagg   3900
accgctggaa acataccaac acgtgcagtc tcccctccaa gctattcatg ctgtttgtgg   3960
aatctctctc aaacataagt gtcaggtgtg tgtcgtccca acgggtcctg tgctgtgaat   4020
agatccatgt gcagcacaaa gggaatgtgg cacgtggccc caggaagagt tcacccggcc   4080
agggggcagt tgttcagttg cctggggctg acactgacca ctggcctctg gggtgtcctg   4140
cagcccaaat gcccaccttg ccctcctcac atctcagtca ggggaggcca tgcccaagcc   4200
aatgtgctgt cacagcctgc agcgggggca gcacttcctc ggagggcctg ggaggtgctg   4260
gggatgcccc agcgcttctc ttcctgcctc gccctggcat ggcccagcgc ctctaggatc   4320
aacttacgat ccgtggagca gccccgggaa acccaaatct ggctcaggac agcgtacggg   4380
caggagggct gtaaatcatc ccaggctaag cctccgtggg cactggctcc tgccgcagcc   4440
tggctatgga ctcagttaga accaggtaga aagtcagcga cacccccacag aaggccactg   4500
cggctaggta aacacctgag aaagaaactg ctccagaaga gatgacgtgg gcttccagga   4560
gcatggagga ggtggcactt gaacttttag gaaactcctt agatgagata aagtgggggt   4620
tggaggtggc gaaaagaggg taaccctggg aaagtcagtc agaacccatg gcagaagact   4680
gcaggagagg caggggaggg gcttcgggga ccactgtgga cagagctctg aaagcaccct   4740
ggccaaagcc cctcctgagg tgacagagcg tgggaggagg ctgcactggg cctgcgtgcc   4800
atcctcaccc ctgttccccg ctggcgccag gccctgcctt cttggtacct gtgccaacag   4860
gagagccctc accagccgat cttgtcactc tccgtggtga cagtgtcttg gccagctgtg   4920
gcccctagtt tctagcagcg tttctcagtg tccttggccc ttctgagaag gcaggcggga   4980
ggcacacggt gccctgttct tccccgtttg tccagttgct tgcaaagcag agaatgagta   5040
ggagtgaacc cgagtgactt cacccgccct gtcccccacg tcaggacagg cttgaggcct   5100
ctctgggcgt gagcgaggaa accaggctgc tctaacttct gaagagtggg ctctggctca   5160
agactccaat cggccagaag cccacagaga tcaaagcact agcaagttca gctgtcctgg   5220
```

ccctcgggta gaacccacgg gcgtgcctgg gtgcggctcc acccacatgc cccactgtca 5280
gcccaggcag gagccttcct ggccgggctc aggatctgcc tgcagcccag ccaggccatc 5340
acccagcccc gatgcatcct ggcactgcac gcttactctt cacaagcact tatacgcgga 5400
tggcctccga gaccctgcct ccctggtctg ctgaggtcag gccaggtctc ccacggagcc 5460
gggcagctcc acaccccacc acctggcacc gttaggtttc agatctcccg tgtggtgttt 5520
gatgtcggct tttgttccta ccttgggagt ttggattgtt tcctctggtg tctttgttta 5580
ccttcctcac tgttctacct cctggccagg tctcagctta gcttccctgg tgtggggtgt 5640
ttttcaagcc ttccagccac agctgtctcc cctcaggctg gacggctccg gggtgacagg 5700
gcttcaccct ctgcctgcag acccctggtg ggcacatctc acaggcttcc gtcttgctga 5760
gttgggtacg gaggcagaag tggggtgtgg aggaaagtca gagggaaatc tgcttcagaa 5820
aggaagggtc tttagacaca aagactggag gcccttcccc gcccgcacgg gagctgccat 5880
cgtgggtctc atgcacgtca agaccttccc acatccaaac tcagcttcca gcagggattt 5940
tgactttgga tgacaaggct ttatttgtaa atatgctctt aatatgcaac tttgagaata 6000
aaatagaaac atcatgtatt ttaaaatata agatgaagtg tgacgcactg tatacaattt 6060
aatatatatt tttagggttt tgttatttaa gaaaatggaa tgtaatggta cttttacaaa 6120
cgagaaaaaa tgttattttt actttctgga aaaaataaat attctcattg ttgtagaaag 6180
a 6181

<210> SEQ ID NO 10
<211> LENGTH: 1422
<212> TYPE: DNA
<213> ORGANISM: homo sapien

<400> SEQUENCE: 10
atggcgccgc cagccgcccg cctcgccctg ctctccgccg cggcgctcac gctggcggcc 60
cggcccgcgc ctagccccgg cctcggcccc gagtgtttca cagccaatgg tgcggattat 120
aggggaacac agaactggac agcactacaa ggcgggaagc catgtctgtt ttggaacgag 180
actttccagc atccatacaa cactctgaaa taccccaacg gggagggggg cctgggtgag 240
cacaactatt gcagaaatcc agatggagac gtgagcccct ggtgctatgt ggcagagcac 300
gaggatggtg tctactggaa gtactgtgag atacctgctt gccagatgcc tggaaacctt 360
ggctgctaca aggatcatgg aaacccacct cctctaactg gcaccagtaa aacgtccaac 420
aaactcacca tacaaacttg catcagtttt tgtcggagtc agaggttcaa gtttgctggg 480
atggagtcag gctatgcttg cttctgtgga aacaatcctg attactggaa gtacggggag 540
gcagccagta ccgaatgcaa cagcgtctgc ttcggggatc acacccaacc ctgtggtggc 600
gatggcagga tcatcctctt tgatactctc gtgggcgcct gcggtgggaa ctactcagcc 660
atgtcttctg tggtctattc ccctgacttc cccgacacct atgccacggg gagggtctgc 720
tactggacca tccgggttcc gggggcctcc cacatccact tcagcttccc cctatttgac 780
atcagggact cggcggacat ggtggagctt ctggatggct acacccaccg tgtcctagcc 840
cgcttccacg ggaggagccg cccacctctg tccttcaacg tctctctgga cttcgtcatc 900
ttgtatttct tctctgatcg catcaatcag gcccagggat ttgctgtttt ataccaagcc 960
gtcaaggaag aactgccaca ggagaggccc gctgtcaacc agacggtggc cgaggtgatc 1020
acggagcagg ccaacctcag tgtcagcgct gcccggtcct ccaaagtcct ctatgtcatc 1080
accaccagcc ccagccaccc acctcagact gtcccaggta gcaattcctg ggcgccaccc 1140

```
atgggggctg gaagccacag agttgaagga tggacagtct atggtctggc aactctcctc   1200
atcctcacag tcacagccat tgtagcaaag atacttctgc acgtcacatt caaatcccat   1260
cgtgttcctg cttcagggga ccttagggat tgtcatcaac cagggacttc gggggaaatc   1320
tggagcattt tttacaagcc ttccacttca atttccatct ttaagaagaa actcaagggt   1380
cagagtcaac aagatgaccg caatcccctt gtgagtgact aa                      1422
```

<210> SEQ ID NO 11
<211> LENGTH: 2802
<212> TYPE: DNA
<213> ORGANISM: homo sapien

<400> SEQUENCE: 11

```
actcgggccc cgcgtcctgc tcccatggcc gcccccggct ccccgcgctg cccccttac      60
cccgggccgc gccccggggc cccgcactga cggcccatgg cgccgccagc cgcccgcctc    120
gccctgctct ccgccgcggc gctcacgctg gcggcccggc ccgcgcctag ccccggcctc    180
ggccccggac ccgagtgttt cacagccaat ggtgcggatt ataggggaac acagaactgg    240
acagcactac aaggcgggaa gccatgtctg ttttggaacg agactttcca gcatccatac    300
aacactctga aatacccaa cggggagggg ggcctgggtg agcacaacta ttgcagaaat    360
ccagatggag acgtgagccc ctggtgctat gtggcagagc acgaggatgg tgtctactgg    420
aagtactgtg agatacctgc ttgccagatg cctggaaacc ttggctgcta caaggatcat    480
ggaaacccac ctcctctaac tggcaccagt aaaacgtcca acaaactcac catacaaact    540
tgcatcagtt tttgtcggag tcagaggttc aagtttgctg ggatggagtc aggctatgct    600
tgcttctgtg gaaacaatcc tgattactgg aagtacgggg aggcagccag taccgaatgc    660
aacagcgtct gcttcgggga tcacacccaa ccctgtggtg gcgatggcag gatcatcctc    720
tttgatactc tcgtgggcgc ctgcggtggg aactactcag ccatgtcttc tgtggtctat    780
tcccctgact tccccgacac ctatgccacg gggagggtct gctactggac catccgggtt    840
ccgggggcct cccacatcca cttcagcttc cccctatttg acatcaggga ctcggcggac    900
atggtggagc ttctggatgg ctacacccac cgtgtcctag cccgcttcca cgggaggagc    960
cgcccacctc tgtccttcaa cgtctctctg gacttcgtca tcttgtattt cttctctgat   1020
cgcatcaatc aggcccaggg atttgctgtt ttataccaag ccgtcaagga agaactgcca   1080
caggagaggc ccgctgtcaa ccagacggtg gccgaggtga tcacggagca ggccaacctc   1140
agtgtcagcg ctgcccggtc ctccaaagtc ctctatgtca tcaccaccag ccccagccac   1200
ccacctcaga ctgtcccagg tagcaattcc tgggcgccac ccatgggggc tggaagccac   1260
agagttgaag gatggacagt ctatggtctg gcaactctcc tcatcctcac agtcacagcc   1320
attgtagcaa agatacttct gcacgtcaca ttcaaatccc atcgtgttcc tgcttcaggg   1380
gaccttaggg attgtcatca accagggact tcgggggaaa tctggagcat tttttacaag   1440
ccttccactt caatttccat ctttaagaag aaactcaagg gtcagagtca acaagatgac   1500
cgcaatcccc ttgcaattca ggactcggaa gtgacatcac tcatctggtc tcaggggcag   1560
cccagaagta tctgactgta gacacaacta ggctccgtgg gcatatctgg gtggcaattt   1620
cagagggcag aggggacacc ttcattgcct ctcctcgcac agaaatggtg ggctctctct   1680
ggcccagcgt ggtggttcat gcctgtaata ccagcgtttt gggaggctga gatgggagga   1740
ttgcttgagc ccaggaggtc gaggctgcag tgagctatga tcacaccacc acactccagc   1800
```

```
ctgagcagca gagcgggacc tcgtctctaa gaatagaaag aaagaaagag aaacggtgtc   1860
ctccgcacag ccggtcagaa ctgtgtgact cacttgaggc aggaccgaga gtgacatcca   1920
gttgcacctt tctcacctac tttgggacct ttgggggtga gttcccttt gtcctctcgt   1980
ggaaacagca cacagcaagc aaccacaaaa ccagagcgga aggagggact tcccaccggc   2040
atccggcccc agtgccatgt tttatcatct ggaacggttg tgaagctttg tgtgacttgc   2100
tcaggatcag cagtcaccat ggtctaatcc caagagggac tcgtcaccca gagacctcaa   2160
aaggccccag gcctactgtg gtttttctg agaggctccc agaaccaagt ggcacgttgg   2220
tttcctgtgc gtctgtgtct ttgtgcctgt atctcgctgg gggacttcac aggaagcagg   2280
atttgggcat tcctgaagct cccagctgga caccactcct gagcgccaca tcccatgatc   2340
acttcaacca caggcctttg actttgccac atggcaaggc acccagcaga agatgaggat   2400
gacgggtgat gctagatgga tgtgtacctg gtggatggcc cacgcacgaa gactcaagac   2460
cctcaggact ggccatataa tctgcaaggt ccagtatgaa ataagaataa gcagcccaca   2520
caactgggca tagtggttca tgcctgtaat cccagcactt tgggaggctg aggagggtgg   2580
atcacttgag gccaggaatt cgagaccagc ctggccaaca tggcgaaaac ccatctctac   2640
taaaaataca aaaattagtt gggcatggtg gcacacacct gtaatcccag ctactcggag   2700
gctgaggcac aagaattgct tgaacctggg aggcggaggt tgcagtgagc tgagataacg   2760
ccactgcact ccagtgtagg caacagagtg agaccctgtc tc                      2802
```

<210> SEQ ID NO 12
<211> LENGTH: 3087
<212> TYPE: DNA
<213> ORGANISM: homo sapien

<400> SEQUENCE: 12

```
cggacgcgtg ggcgcgctgc cccctttacc ccgggccgcg ccccggggcc ccgcactgac     60
ggcccatggc gccgcccgcc gcccgcctcg ccctgctctc cgccgcggcg ctcacgctgg    120
cggcccggcc cgcgcctagc cccggcctcg gccccggacc cgagtgtttc acagccaatg    180
gtgcggatta taggggaaca cagaactgga cagcactaca aggcgggaag ccatgtctgt    240
tttggaacga gactttccag catccataca acactctgaa ataccccaac ggggaggggg    300
gcctgggtga gcacaactat tgcagaaatc cagatggaga cgtgagcccc tggtgctatg    360
tggcagagca cgaggatggt gtctactgga agtactgtga gatacctgct tgccagatgc    420
ctggaaacct tggctgctac aaggatcatg gaaacccacc tcctctaact ggcaccagta    480
aaacgtccaa caaactcacc atacaaactt gcatcagttt ttgtcggagt cagaggttca    540
agtttgctgg gatggagtca ggctatgctt gcttctgtgg aaacaatcct gattactgga    600
agtacgggga ggcagccagt accgaatgca acagcgtctg cttcggggat cacacccaac    660
cctgtggtgg cgatggcagg atcatcctct ttgatactct cgtgggcgcc tgcggtggga    720
actactcagc catgtcttct gtggtctatt cccctgactt ccccgacacc tatgccacgg    780
ggagggtctg ctactggacc atccgggttc cgggggcctc ccacatccac ttcagcttcc    840
ccctatttga catcagggac tcggcggaca tggtggagct tctggatggc tacacccacc    900
gtgtcctagc ccgcttccac gggaggagcc gcccacctct gtccttcaac gtctctctgg    960
acttcgtcat cttgtatttc ttctctgatc gcatcaatca ggcccaggga tttgctgttt   1020
tataccaagc cgtcaaggaa gaactgccac aggagaggcc cgctgtcaac cagacggtgg   1080
ccgaggtgat cacggagcag gccaacctca gtgtcagcgc tgcccggtcc tccaaagtcc   1140
```

```
tctatgtcat caccaccagc cccagccacc cacctcagac tgtcccagga tggacagtct   1200
atggtctggc aactctcctc atcctcacag tcacagccat tgtagcaaag atacttctgc   1260
acgtcacatt caaatcccat cgtgttcctg cttcagggga ccttagggat tgtcatcaac   1320
cagggacttc gggggaaatc tggagcattt tttacaagcc ttccacttca atttccatct   1380
ttaagaagaa actcaagggt cagagtcaac aagatgaccg caatcccctt gtgagtgact   1440
aaaaaacccca ctgtgcctag gacttgaggt ccctctttga gctcaaggct gccgtggtca   1500
acctctcctg tggttcttct ctgacagact cttcccctcc tctccctctg cctcggcctc   1560
ttcggggaaa ccctcctcct acagactagg aagaggcacc ctgctgccag ggcaggcaga   1620
gcctggattc ctcctgcttc atcgattgca cttaggagag agactcaaag ccctggggcc   1680
cggccctctc tgcatctctc tctgatctag ctagcagtgg gggtgtcagg acagtgaggc   1740
tgagatgaca gaggtggtca tggctggcac agggctcagg tacattctag atggctgtca   1800
ggtggtgggt agctttagtt acattgaatt tttcttgctt ctctattttt gtccacacac   1860
aaatcagttt ctcctgatct ttatgtcttg gaacagggcc agacagggag aactctcagg   1920
tactcttggg agttggtccc atacaagtgc ggactcctgg acattagcga ggtgtaaaga   1980
gggcagtgtc tgtgctgccc cggcagcttt gctctccaga tgctggacta gggtgggcct   2040
ccttcagcct gggagggtct gagaataaga tctagtgacc cccatttata tcaaacctga   2100
taccttacac atgggcttct ttctagattc ttctttccat agctcatgga gctgcaggga   2160
aagctttaag agctttggtc atataaaaca tccattcagc tgggcgcgat ggctcatgcc   2220
tgtaatccca gcactgtggg aggctgaggc gggcagatca cctgaggtca ggagttcgag   2280
accagcctgg ccaacatggt gaaaccccgt ctctactaaa aatataaaaa ttagtcaggc   2340
gtggtggcag gcgcctgtaa tcccagctac tcagaaggct gagacagaag aacagcttga   2400
acccaggagg ctgagattgc agtgagccga gatcgcacca ctgcactcca gcctgggtga   2460
caagagtgag actctgtctc aaaaaaacaa aacacaaata aacaaaaaaa atccattcat   2520
ttactcatgc aataaattct cctgcaagct tttatgggca ctcagtaagt actcaggatt   2580
ggctttatca gccttgccac tgagcagctc atggtcctat ggaacctgag ccaggcctca   2640
gtctctccat gattggctca gctaactctc agttcagagt ggagagtatc aatcttgtgt   2700
ttttgccctt aggcagcact atatgagaca tggggcctgt ggtccttcct tctggtgtcc   2760
cccgtgttaa aagataaaaa acaccccaag ggccgggcgc ggtggctcat gcctgtaatc   2820
ccagcacttt gggaggctga ggcgggtgga tcacgaggtc aggtgatcga aaccatcctg   2880
gctaagacgg tgaaaccccg tctctactaa aaatacaaaa aattagctgg gtgtggtggt   2940
gggcgcctgt agtcccagct gctcgggagg ctgaggcagg agaatggcgt gaacccggga   3000
ggcggagctt gcagtgagca gagatcacgc cactgcactc cagcctgggt gacagtgcaa   3060
gactctgtct caaaaaaaaa aaaaaaa                                        3087
```

<210> SEQ ID NO 13
<211> LENGTH: 6138
<212> TYPE: DNA
<213> ORGANISM: homo sapien

<400> SEQUENCE: 13

```
cgcgctgccc cctttacccc gggccgcgcc ccggggcccc gcactgacgg cccatggcgc     60
cgccagccgc ccgcctcgcc ctgctctccg ccgcggcgct cacgctggcg gcccggcccg    120
```

```
cgcctagccc cggcctcggc cccggacccg agtgtttcac agccaatggt gcggattata    180
ggggaacaca gaactggaca gcactacaag gcgggaagcc atgtctgttt tggaacgaga    240
ctttccagca tccatacaac actctgaaat accccaacgg ggaggggggc ctgggtgagc    300
acaactattg cagaaatcca gatggagacg tgagcccctg gtgctatgtg gcagagcacg    360
aggatggtgt ctactggaag tactgtgaga tacctgcttg ccagatgcct ggaaaccttg    420
gctgctacaa ggatcatgga aacccacctc ctctaactgg caccagtaaa acgtccaaca    480
aactcaccat acaaacttgc atcagttttt gtcggagtca gaggttcaag tttgctggga    540
tggagtcagg ctatgcttgc ttctgtggaa acaatcctga ttactggaag tacggggagg    600
cagccagtac cgaatgcaac agcgtctgct tcggggatca cacccaaccc tgtggtggcg    660
atggcaggat catcctcttt gatactctcg tgggcgcctg cggtgggaac tactcagcca    720
tgtcttctgt ggtctattcc cctgacttcc ccgacaccta tgccacgggg agggtctgct    780
actggaccat ccgggttccg gggcctccc acatccactt cagcttcccc ctatttgaca    840
tcagggactc ggcggacatg gtggagcttc tggatggcta cacccaccgt gtcctagccc    900
gcttccacgg gaggagccgc ccacctctgt ccttcaacgt ctctctggac ttcgtcatct    960
tgtatttctt ctctgatcgc atcaatcagg cccagggatt tgctgtttta taccaagccg   1020
tcaaggaaga actgccacag gagaggcccg ctgtcaacca gacggtggcc gaggtgatca   1080
cggagcaggc caacctcagt gtcagcgctg cccggtcctc caaagtcctc tatgtcatca   1140
ccaccagccc cagccaccca cctcagactg tcccaggatg gacagtctat ggtctggcaa   1200
ctctcctcat cctcacagtc acagccattg tagcaaagat acttctgcac gtcacattca   1260
aatcccatcg tgttcctgct tcaggggacc ttagggattg tcatcaacca gggacttcgg   1320
gggaaatctg gagcattttt tacaagcctt ccacttcaat ttccatcttt aagaagaaac   1380
tcaagggtca gagtcaacaa gatgaccgca atccccttgt gagtgactaa aaaccccact   1440
gtgcctagga cttgaggtcc ctctttgagc tcaaggctgc cgtggtcaac ctctcctgtg   1500
gttcttctct gacagactct tcccctcctc tccctctgcc tcggcctctt cggggaaacc   1560
ctcctcctac agactaggaa gaggcaccct gctgccaggg caggcagagc ctggattcct   1620
cctgcttcat cgattgcact taggagagag actcaaagcc ctggggcccg gccctctctg   1680
catctctctc tgatctagct agcagtgggg gtgtcaggac agtgaggctg agatgacaga   1740
ggtggtcatg gctggcacag ggctcaggta cattctagat ggctgtcagg tggtgggtag   1800
ctttagttac attgaatttt tcttgcttct ctatttttgt ccacacacaa atcagtttct   1860
cctgatcttt atgtcttgga acagggccag acagggagaa ctctcaggta ctcttgggag   1920
ttggtcccat acaagtgcgg actcctggac attagcgagg tgtaaagagg gcagtgtctg   1980
tgctgccccg gcagctttgc tctccagatg ctggactagg gtgggcctcc ttcagcctgg   2040
gagggtctga gaataagatc tagtgacccc catttatatc aaacctgata ccttacacat   2100
gggcttcttt ctagattctt ctttccatag ctcatggagc tgcagggaaa gctttaagag   2160
ctttggtcat ataaaacatc cattcagctg ggcgcgatgg ctcatgcctg taatcccagc   2220
actgtgggag gctgaggcgg gcagatcacc tgaggtcagg agttcgagac cagcctggcc   2280
aacatggtga aaccccgtct ctactaaaaa tataaaaatt agtcaggcgt ggtggcaggc   2340
gcctgtaatc ccagctactc agaaggctga gacagaagaa cagcttgaac ccaggaggct   2400
gagattgcag tgagccgaga tcgcaccact gcactccagc ctgggtgaca agagtgagac   2460
tctgtctcaa aaaaacaaaa cacaaataaa caaaaaaaat ccattcattt actcatgcaa   2520
```

```
taaattctcc tgcaagcttt tatgggcact cagtaagtac tcaggattgg ctttatcagc   2580
cttgccactg agcagctcat ggtcctatgg aacctgagcc aggcctcagt ctctccatga   2640
ttggctcagc taactctcag ttcagagtgg agagtatcaa tcttgtgttt ttgcccttag   2700
gcagcactat atgagacatg gggcctgtgg tccttccttc tggtgtcccc cgtgttaaaa   2760
gataaaaaac accccaaggg ccgggcgcgg tggctcatgc ctgtaatccc agcactttgg   2820
gaggctgagg cgggtggatc acgaggtcag gtgatcgaaa ccatcctggc taagatggtg   2880
aaaccccgtc tctactaaaa atacaaaaaa ttagctgggt gtggtggtgg gcgcctgtag   2940
tcccagctgc tcgggaggct gaggcaggag aatggcgtga acccgggagg cggagcttgc   3000
agtgagcaga gatcacgcca ctgcactcca gcctgggtga cagtgcaaga ctctgtctca   3060
aaaaaaaaaa aaacactcca agggccatcc gtgctctctg cccctcctgt ggggaccaag   3120
tggggttagg aatggctcag tggggaagga gagcactctt gtccccagtc ccttgccacc   3180
ctgtccctta gatagggagg tgggctgcag agattggtgc cagaagaggg tgggtttggg   3240
aattggagct cctccaagga gctcctccta agattgagtg ctgcagctgt agtggctgct   3300
ggttgggaga gtaagtgcca tcactaattt aaaagtcctt gccatctgga atcaggcttt   3360
gtcaacagca gctgagaaaa gcagcctgtg cctctgctgg ccaggcctag gccctcgtca   3420
gagcgtgcct ctccacaagg cacttgggcc tgggtgattg ttgcgcctct ggctttggcg   3480
tttcctcttt gcagcacttt gcctacctcc cccaagccct gagccactgc ctgctggggc   3540
tcctactgag gttctggaaa cacctctgca cctgccgccc ctgggaggaa agagggccac   3600
acaggaagtg tctgcaggga gaggtggcac tcggcagcct gagttcagga gaggtgcttg   3660
gagcttcagg cagaggggcc ttcagaggag ggaaacggag caatgtgtca caggcaggca   3720
ggggcaggac tgccacccca ggccccgtgg gaggcctgct gagggcacag agctgctcgg   3780
tgcagccttc atgctttgat ctggaaagag cagctgtccg caggcctctg tctccaagag   3840
gcctgtcaca caggaggacc gctggaaaca taccaacacg tgcagtctcc cctccaagct   3900
attcatgctg tttgtggaat ctctctcaaa cataagtgtc aggtgtgtgt cgtcccaacg   3960
ggtcctgtgc tgtgaataga tccatgtgca gcacaaaggg aatgtggcac gtggccccag   4020
gaagagttca cccggccagg gggcagttgt tcagttgcct ggggctgaca ctgaccactg   4080
gcctctgggg tgtcctgcag cccaaatgcc caccttgccc tcctcacatc tcagtcaggg   4140
gaggccatgc ccaagccaat gtgctgtcac agcctgcagc gggggcagca cttcctcgga   4200
gggcctggga ggtgctgggg atgccccagc gcttctcttc ctgcctcgcc ctggcatggc   4260
ccagcgcctc taggatcaac ttacgatccg tggagcagcc ccgggaaacc caaatctggc   4320
tcaggacagc gtacgggcag gagggctgta aatcatccca ggctaagcct ccgtgggcac   4380
tggctcctgc cgcagcctgg ctatggactc agttagaacc aggtagaaag tcagcgacac   4440
cccacagaag gccactgcgg ctaggtaaac acctgagaaa gaaactgctc cagaagagat   4500
gacgtgggct tccaggagca tggaggaggt ggcacttgaa cttttaggaa actccttaga   4560
tgagataaag tgggggttgg aggtggcgaa aagagggtaa ccctgggaaa gtcagtcaga   4620
acccatggca gaagactgca ggagaggcag gggaggggct tcggggacca ctgtggacag   4680
agctctgaaa gcaccctggc caaagcccct cctgaggtga cagagcgtgg gaggaggctg   4740
cactgggcct gcgtgccatc ctcacccctg ttccccgctg gcgccaggcc ctgccttctt   4800
ggtacctgtg ccaacaggag agccctcacc agccgatctt gtcactctcc gtggtgacag   4860
```

```
tgtcttggcc agctgtggcc cctagtttct agcagcgttt ctcagtgtcc ttggcccttc   4920

tgagaaggca ggcgggaggc acacggtgcc ctgttcttcc ccgtttgtcc agttgcttgc   4980

aaagcagaga atgagtagga gtgaacccga gtgacttcac ccgccctgtc ccccacgtca   5040

ggacaggctt gaggcctctc tgggcgtgag cgaggaaacc aggctgctct aacttctgaa   5100

gagtgggctc tggctcaaga ctccaatcgg ccagaagccc acagagatca aagcactagc   5160

aagttcagct gtcctggccc tcgggtagaa cccacgggcg tgcctgggtg cggctccacc   5220

cacatgcccc actgtcagcc caggcaggag ccttcctggc cgggctcagg atctgcctgc   5280

agcccagcca ggccatcacc cagccccgat gcatcctggc actgcacgct tactcttcac   5340

aagcacttat acgcggatgg cctccgagac cctgcctccc tggtctgctg aggtcaggcc   5400

aggtctccca cggagccggg cagctccaca ccccaccacc tggcaccgtt aggtttcaga   5460

tctcccgtgt ggtgtttgat gtcggctttt gttcctacct tgggagtttg gattgtttcc   5520

tctggtgtct ttgtttacct tcctcactgt tctacctcct ggccaggtct cagcttagct   5580

tccctggtgt ggggtgtttt tcaagccttc cagccacagc tgtctcccct caggctggac   5640

ggctccgggg tgacagggct tcaccctctg cctgcagacc cctggtgggc acatctcaca   5700

ggcttccgtc ttgctgagtt gggtacggag gcagaagtgg ggtgtggagg aaagtcagag   5760

ggaaatctgc ttcagaaagg aagggtcttt agacacaaag actggaggcc cttccccgcc   5820

cgcacgggag ctgccatcgt gggtctcatg cacgtcaaga ccttcccaca tccaaactca   5880

gcttccagca gggattttga ctttggatga caaggcttta tttgtaaata tgctcttaat   5940

atgcaacttt gagaataaaa tagaaacatc atgtatttta aaatataaga tgaagtgtga   6000

cgcactgtat acaatttaat atatattttt agggttttgt tatttaagaa aatggaatgt   6060

aatggtactt ttacaaacga gaaaaaatgt tatttttact ttctggaaaa aataaatatt   6120

ctcattgttg tagaaaga                                                 6138
```

<210> SEQ ID NO 14
<211> LENGTH: 492
<212> TYPE: PRT
<213> ORGANISM: homo sapien

<400> SEQUENCE: 14

```
Met Ala Pro Pro Ala Ala Arg Leu Ala Leu Leu Ser Ala Ala Ala Leu
1               5                   10                  15

Thr Leu Ala Ala Arg Pro Ala Pro Ser Pro Gly Leu Gly Pro Gly Pro
            20                  25                  30

Glu Cys Phe Thr Ala Asn Gly Ala Asp Tyr Arg Gly Thr Gln Asn Trp
        35                  40                  45

Thr Ala Leu Gln Gly Gly Lys Pro Cys Leu Phe Trp Asn Glu Thr Phe
    50                  55                  60

Gln His Pro Tyr Asn Thr Leu Lys Tyr Pro Asn Gly Glu Gly Gly Leu
65                  70                  75                  80

Gly Glu His Asn Tyr Cys Arg Asn Pro Asp Gly Asp Val Ser Pro Trp
                85                  90                  95

Cys Tyr Val Ala Glu His Glu Asp Gly Val Tyr Trp Lys Tyr Cys Glu
            100                 105                 110

Ile Pro Ala Cys Gln Met Pro Gly Asn Leu Gly Cys Tyr Lys Asp His
        115                 120                 125

Gly Asn Pro Pro Pro Leu Thr Gly Thr Ser Lys Thr Ser Asn Lys Leu
    130                 135                 140
```

```
Thr Ile Gln Thr Cys Ile Ser Phe Cys Arg Ser Gln Arg Phe Lys Phe
145                 150                 155                 160

Ala Gly Met Glu Ser Gly Tyr Ala Cys Phe Cys Gly Asn Asn Pro Asp
                165                 170                 175

Tyr Trp Lys Tyr Gly Glu Ala Ala Ser Thr Glu Cys Asn Ser Val Cys
            180                 185                 190

Phe Gly Asp His Thr Gln Pro Cys Gly Gly Asp Gly Arg Ile Ile Leu
        195                 200                 205

Phe Asp Thr Leu Val Gly Ala Cys Gly Gly Asn Tyr Ser Ala Met Ser
    210                 215                 220

Ser Val Val Tyr Ser Pro Asp Phe Pro Asp Thr Tyr Ala Thr Gly Arg
225                 230                 235                 240

Val Cys Tyr Trp Thr Ile Arg Val Pro Gly Ala Ser His Ile His Phe
                245                 250                 255

Ser Phe Pro Leu Phe Asp Ile Arg Asp Ser Ala Asp Met Val Glu Leu
            260                 265                 270

Leu Asp Gly Tyr Thr His Arg Val Leu Ala Arg Phe His Gly Arg Ser
        275                 280                 285

Arg Pro Pro Leu Ser Phe Asn Val Ser Leu Asp Phe Val Ile Leu Tyr
    290                 295                 300

Phe Phe Ser Asp Arg Ile Asn Gln Ala Gln Gly Phe Ala Val Leu Tyr
305                 310                 315                 320

Gln Ala Val Lys Glu Glu Leu Pro Gln Glu Arg Pro Ala Val Asn Gln
                325                 330                 335

Thr Val Ala Glu Val Ile Thr Glu Gln Ala Asn Leu Ser Val Ser Ala
            340                 345                 350

Ala Arg Ser Ser Lys Val Leu Tyr Val Ile Thr Thr Ser Pro Ser His
        355                 360                 365

Pro Pro Gln Thr Val Pro Gly Ser Asn Ser Trp Ala Pro Pro Met Gly
    370                 375                 380

Ala Gly Ser His Arg Val Glu Gly Trp Thr Val Tyr Gly Leu Ala Thr
385                 390                 395                 400

Leu Leu Ile Leu Thr Val Thr Ala Ile Val Ala Lys Ile Leu Leu His
                405                 410                 415

Val Thr Phe Lys Ser His Arg Val Pro Ala Ser Gly Asp Leu Arg Asp
            420                 425                 430

Cys His Gln Pro Gly Thr Ser Gly Glu Ile Trp Ser Ile Phe Tyr Lys
        435                 440                 445

Pro Ser Thr Ser Ile Ser Ile Phe Lys Lys Lys Leu Lys Gly Gln Ser
    450                 455                 460

Gln Gln Asp Asp Arg Asn Pro Leu Ala Ile Gln Asp Ser Glu Val Thr
465                 470                 475                 480

Ser Leu Ile Trp Ser Gln Gly Gln Pro Arg Ser Ile
                485                 490


<210> SEQ ID NO 15
<211> LENGTH: 458
<212> TYPE: PRT
<213> ORGANISM: homo sapien

<400> SEQUENCE: 15

Met Ala Pro Pro Ala Ala Arg Leu Ala Leu Leu Ser Ala Ala Ala Leu
1               5                   10                  15

Thr Leu Ala Ala Arg Pro Ala Pro Ser Pro Gly Leu Gly Pro Gly Pro
            20                  25                  30
```

```
Glu Cys Phe Thr Ala Asn Gly Ala Asp Tyr Arg Gly Thr Gln Asn Trp
        35                  40                  45

Thr Ala Leu Gln Gly Gly Lys Pro Cys Leu Phe Trp Asn Glu Thr Phe
    50                  55                  60

Gln His Pro Tyr Asn Thr Leu Lys Tyr Pro Asn Gly Glu Gly Gly Leu
65                  70                  75                  80

Gly Glu His Asn Tyr Cys Arg Asn Pro Asp Gly Asp Val Ser Pro Trp
                85                  90                  95

Cys Tyr Val Ala Glu His Glu Asp Gly Val Tyr Trp Lys Tyr Cys Glu
            100                 105                 110

Ile Pro Ala Cys Gln Met Pro Gly Asn Leu Gly Cys Tyr Lys Asp His
        115                 120                 125

Gly Asn Pro Pro Pro Leu Thr Gly Thr Ser Lys Thr Ser Asn Lys Leu
    130                 135                 140

Thr Ile Gln Thr Cys Ile Ser Phe Cys Arg Ser Gln Arg Phe Lys Phe
145                 150                 155                 160

Ala Gly Met Glu Ser Gly Tyr Ala Cys Phe Cys Gly Asn Asn Pro Asp
                165                 170                 175

Tyr Trp Lys Tyr Gly Glu Ala Ala Ser Thr Glu Cys Asn Ser Val Cys
            180                 185                 190

Phe Gly Asp His Thr Gln Pro Cys Gly Gly Asp Gly Arg Ile Ile Leu
        195                 200                 205

Phe Asp Thr Leu Val Gly Ala Cys Gly Gly Asn Tyr Ser Ala Met Ser
    210                 215                 220

Ser Val Val Tyr Ser Pro Asp Phe Pro Asp Thr Tyr Ala Thr Gly Arg
225                 230                 235                 240

Val Cys Tyr Trp Thr Ile Arg Val Pro Gly Ala Ser His Ile His Phe
                245                 250                 255

Ser Phe Pro Leu Phe Asp Ile Arg Asp Ser Ala Asp Met Val Glu Leu
            260                 265                 270

Leu Asp Gly Tyr Thr His Arg Val Leu Ala Arg Phe His Gly Arg Ser
        275                 280                 285

Arg Pro Pro Leu Ser Phe Asn Val Ser Leu Asp Phe Val Ile Leu Tyr
    290                 295                 300

Phe Phe Ser Asp Arg Ile Asn Gln Ala Gln Gly Phe Ala Val Leu Tyr
305                 310                 315                 320

Gln Ala Val Lys Glu Glu Leu Pro Gln Glu Arg Pro Ala Val Asn Gln
                325                 330                 335

Thr Val Ala Glu Val Ile Thr Glu Gln Ala Asn Leu Ser Val Ser Ala
            340                 345                 350

Ala Arg Ser Ser Lys Val Leu Tyr Val Ile Thr Thr Ser Pro Ser His
        355                 360                 365

Pro Pro Gln Thr Val Pro Gly Trp Thr Val Tyr Gly Leu Ala Thr Leu
    370                 375                 380

Leu Ile Leu Thr Val Thr Ala Ile Val Ala Lys Ile Leu Leu His Val
385                 390                 395                 400

Thr Phe Lys Ser His Arg Val Pro Ala Ser Gly Asp Leu Arg Asp Cys
                405                 410                 415

His Gln Pro Gly Thr Ser Gly Glu Ile Trp Ser Ile Phe Tyr Lys Pro
            420                 425                 430

Ser Thr Ser Ile Ser Ile Phe Lys Lys Lys Leu Lys Gly Gln Ser Gln
        435                 440                 445
```

Gln Asp Asp Arg Asn Pro Leu Val Ser Asp
450 455

<210> SEQ ID NO 16
<211> LENGTH: 473
<212> TYPE: PRT
<213> ORGANISM: homo sapien

<400> SEQUENCE: 16

Met Ala Pro Pro Ala Ala Arg Leu Ala Leu Leu Ser Ala Ala Ala Leu
1 5 10 15

Thr Leu Ala Ala Arg Pro Ala Pro Ser Pro Gly Leu Gly Pro Glu Cys
20 25 30

Phe Thr Ala Asn Gly Ala Asp Tyr Arg Gly Thr Gln Asn Trp Thr Ala
35 40 45

Leu Gln Gly Gly Lys Pro Cys Leu Phe Trp Asn Glu Thr Phe Gln His
50 55 60

Pro Tyr Asn Thr Leu Lys Tyr Pro Asn Gly Glu Gly Gly Leu Gly Glu
65 70 75 80

His Asn Tyr Cys Arg Asn Pro Asp Gly Asp Val Ser Pro Trp Cys Tyr
85 90 95

Val Ala Glu His Glu Asp Gly Val Tyr Trp Lys Tyr Cys Glu Ile Pro
100 105 110

Ala Cys Gln Met Pro Gly Asn Leu Gly Cys Tyr Lys Asp His Gly Asn
115 120 125

Pro Pro Pro Leu Thr Gly Thr Ser Lys Thr Ser Asn Lys Leu Thr Ile
130 135 140

Gln Thr Cys Ile Ser Phe Cys Arg Ser Gln Arg Phe Lys Phe Ala Gly
145 150 155 160

Met Glu Ser Gly Tyr Ala Cys Phe Cys Gly Asn Asn Pro Asp Tyr Trp
165 170 175

Lys Tyr Gly Glu Ala Ala Ser Thr Glu Cys Asn Ser Val Cys Phe Gly
180 185 190

Asp His Thr Gln Pro Cys Gly Gly Asp Gly Arg Ile Ile Leu Phe Asp
195 200 205

Thr Leu Val Gly Ala Cys Gly Gly Asn Tyr Ser Ala Met Ser Ser Val
210 215 220

Val Tyr Ser Pro Asp Phe Pro Asp Thr Tyr Ala Thr Gly Arg Val Cys
225 230 235 240

Tyr Trp Thr Ile Arg Val Pro Gly Ala Ser His Ile His Phe Ser Phe
245 250 255

Pro Leu Phe Asp Ile Arg Asp Ser Ala Asp Met Val Glu Leu Leu Asp
260 265 270

Gly Tyr Thr His Arg Val Leu Ala Arg Phe His Gly Arg Ser Arg Pro
275 280 285

Pro Leu Ser Phe Asn Val Ser Leu Asp Phe Val Ile Leu Tyr Phe Phe
290 295 300

Ser Asp Arg Ile Asn Gln Ala Gln Gly Phe Ala Val Leu Tyr Gln Ala
305 310 315 320

Val Lys Glu Glu Leu Pro Gln Glu Arg Pro Ala Val Asn Gln Thr Val
325 330 335

Ala Glu Val Ile Thr Glu Gln Ala Asn Leu Ser Val Ser Ala Ala Arg
340 345 350

Ser Ser Lys Val Leu Tyr Val Ile Thr Thr Ser Pro Ser His Pro Pro
355 360 365

```
Gln Thr Val Pro Gly Ser Asn Ser Trp Ala Pro Pro Met Gly Ala Gly
    370                 375                 380

Ser His Arg Val Glu Gly Trp Thr Val Tyr Gly Leu Ala Thr Leu Leu
385                 390                 395                 400

Ile Leu Thr Val Thr Ala Ile Val Ala Lys Ile Leu Leu His Val Thr
                405                 410                 415

Phe Lys Ser His Arg Val Pro Ala Ser Gly Asp Leu Arg Asp Cys His
            420                 425                 430

Gln Pro Gly Thr Ser Gly Glu Ile Trp Ser Ile Phe Tyr Lys Pro Ser
        435                 440                 445

Thr Ser Ile Ser Ile Phe Lys Lys Lys Leu Lys Gly Gln Ser Gln Gln
    450                 455                 460

Asp Asp Arg Asn Pro Leu Val Ser Asp
465                 470


<210> SEQ ID NO 17
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 17

cactctgaaa taccccaacg                                                20


<210> SEQ ID NO 18
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 18

tgattactgg aagtacgggg                                                20


<210> SEQ ID NO 19
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 19

tccccgacac ctatgccacg                                                20


<210> SEQ ID NO 20
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 20

aactggacag cactacaagg                                                20


<210> SEQ ID NO 21
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 21
```

ggaagcgggc taggacacgg 20

<210> SEQ ID NO 22
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 22
tctgaaatac cccaacgggg 20

<210> SEQ ID NO 23
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 23
cttccccgac acctatgcca 20

<210> SEQ ID NO 24
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 24
gtctcgttcc aaaacagaca 20

<210> SEQ ID NO 25
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 25
gaagcgggct aggacacggt 20

<210> SEQ ID NO 26
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 26
tcctgattac tggaagtacg 20

<210> SEQ ID NO 27
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 27
aacactctga aataccccaa 20

<210> SEQ ID NO 28
<211> LENGTH: 20
<212> TYPE: DNA

<213> ORGANISM: artificial sequence
<220> FEATURE:
<223> OTHER INFORMATION: Synthetic sequence; gRNA Recognition Sequence

<400> SEQUENCE: 28
ccgacaccta tgccacgggg 20

<210> SEQ ID NO 29
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 29
actggaccat ccgggttccg 20

<210> SEQ ID NO 30
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 30
gccaatggtg cggattatag 20

<210> SEQ ID NO 31
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 31
gtataaaaca gcaaatccct 20

<210> SEQ ID NO 32
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 32
actggacagc actacaaggc 20

<210> SEQ ID NO 33
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 33
cgtgagcccc tggtgctatg 20

<210> SEQ ID NO 34
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 34
gggcatactc actatcaaag 20

```
<210> SEQ ID NO 35
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 35

ttactggtgc cagttagagg                                                20


<210> SEQ ID NO 36
<211> LENGTH: 20
<212> TYPE: DNA
<213> ORGANISM: artificial sequence
<220> FEATURE:
<223> OTHER INFORMATION: Synthetic sequence; gRNA Recognition Sequence

<400> SEQUENCE: 36

gtgctatgtg gcagagcacg                                                20
```

METHODS OF TREATING DECREASED BONE MINERAL DENSITY WITH KRINGLE CONTAINING TRANSMEMBRANE PROTEIN 1 (KREMEN1) INHIBITORS

REFERENCE TO SEQUENCE LISTING

This application includes a Sequence Listing filed electronically as a text file named 18923808101SEQ, created on Jun. 29, 2022, with a size of 196 kilobytes. The Sequence Listing is incorporated herein by reference.

FIELD

The present disclosure relates generally to the treatment of subjects having decreased bone mineral density or at risk of developing decreased bone mineral density with Kringle Containing Transmembrane Protein 1 (KREMEN1) inhibitors, and methods of identifying subjects having an increased risk of developing decreased bone mineral density.

BACKGROUND

Degenerative conditions of the bone can make individuals susceptible to bone fractures, bone pain, and other complications. Two significant degenerative conditions of the bone are osteopenia and osteoporosis. Decreased bone mineral density (osteopenia) is a condition of the bone that is a precursor to osteoporosis and is characterized by a reduction in bone mass due to the loss of bone at a rate greater than new bone growth. Osteopenia manifests in bone having a mineral density lower than normal peak bone mineral density, but not as low as found in osteoporosis. Osteopenia can arise from a decrease in muscle activity, which may occur as the result of a bone fracture, bed rest, fracture immobilization, joint reconstruction, arthritis, and the like. Osteoporosis is a progressive disease characterized by a gradual bone weakening due to demineralization of the bone. Osteoporosis manifests in bones that are thin and brittle making them more susceptible to breaking. Hormone deficiencies related to menopause in women, and hormone deficiencies due to aging in both sexes contribute to degenerative conditions of the bone. In addition, insufficient dietary uptake of minerals essential to bone growth and maintenance are significant causes of bone loss.

The effects of osteopenia can be slowed, stopped, and even reversed by reproducing some of the effects of muscle use on the bone. This typically involves some application or simulation of the effects of mechanical stress on the bone. Compounds for the treatment of osteopenia or osteoporosis include pharmaceutical preparations that induce bone growth or retard bone demineralization, or mineral complexes that supplement the diet in an effort to replenish lost bone minerals. Low levels of estrogen in women, and low levels of androgen in men are the primary hormonal deficiencies that cause osteoporosis in the respective sexes. Other hormones such as the thyroid hormones, progesterone, and testosterone contribute to bone health. As such, the aforementioned hormonal compounds have been developed synthetically, or extracted from non-mammalian sources, and compounded into therapies for treating osteoporosis. Mineral supplement preparations containing iodine, zinc, manganese, boron, strontium, vitamin D3, calcium, magnesium, vitamin K, phosphorous, and copper have also been used to supplement insufficient dietary uptake of such minerals. However, long-term hormonal therapies have undesirable side effects such as increased cancer risk. Moreover, therapies using many synthetic or non-mammalian hormones have additional undesirable side effects, such as an increased risk of cardiovascular disorders, neurological disorders, or the exacerbation of pre-existing conditions.

Kringle Containing Transmembrane Protein 1 (KREMEN1) is a cell surface molecule that regulates WNT signaling by binding to DKK and LRP5/6, thereby promoting uptake of this complex through clathrin-mediated endocytosis (Mao et al., Nature, 2002, 417, 664-667).

SUMMARY

The present disclosure provides methods of treating a subject having decreased bone mineral density or at risk of developing decreased bone mineral density, the methods comprising administering a KREMEN1 inhibitor to the subject.

The present disclosure also provides methods of treating a subject having osteopenia or at risk of developing osteopenia, the methods comprising administering a KREMEN1 inhibitor to the subject.

The present disclosure also provides methods of treating a subject having Type I osteoporosis or at risk of developing Type I osteoporosis, the methods comprising administering a KREMEN1 inhibitor to the subject.

The present disclosure also provides methods of treating a subject having Type II osteoporosis or at risk of developing Type II osteoporosis, the methods comprising administering a KREMEN1 to the subject.

The present disclosure also provides methods of treating a subject having secondary osteoporosis or at risk of developing secondary osteoporosis, the methods comprising administering a KREMEN1 inhibitor to the subject.

The present disclosure also provides methods of treating a subject with a therapeutic agent that treats or prevents decreased bone mineral density, wherein the subject has decreased bone mineral density or is at risk of developing decreased bone mineral density, the methods comprising the steps of: determining whether the subject has a KREMEN1 variant nucleic acid molecule encoding a KREMEN1 predicted loss-of-function polypeptide by: obtaining or having obtained a biological sample from the subject; and performing or having performed a sequence analysis on the biological sample to determine if the subject has a genotype comprising the KREMEN1 variant nucleic acid molecule encoding a KREMEN1 predicted loss-of-function polypeptide; and: i) administering or continuing to administer the therapeutic agent that treats or prevents decreased bone mineral density in a standard dosage amount to a subject that is KREMEN1 reference, and/or administering a KREMEN1 inhibitor to the subject; ii) administering or continuing to administer the therapeutic agent that treats or prevents decreased bone mineral density in an amount that is the same as or less than a standard dosage amount to a subject that is heterozygous for the KREMEN1 variant nucleic acid molecule, and/or administering a KREMEN1 inhibitor to the subject; or iii) administering or continuing to administer the therapeutic agent that treats or prevents decreased bone mineral density in an amount that is the same as or less than a standard dosage amount to a subject that is homozygous for the KREMEN1 variant nucleic acid molecule; wherein the presence of a genotype having the KREMEN1 variant nucleic acid molecule encoding the KREMEN1 predicted loss-of-function polypeptide indicates the subject has a decreased risk of developing decreased bone mineral density.

The present disclosure also provides methods of identifying a subject having an increased risk of developing decreased bone mineral density, the methods comprising: determining or having determined the presence or absence of a KREMEN1 variant nucleic acid molecule encoding a KREMEN1 predicted loss-of-function polypeptide in a biological sample obtained from the subject; when the subject is KREMEN1 reference, then the subject has an increased risk of developing decreased bone mineral density; and when the subject is heterozygous or homozygous for the KREMEN1 variant nucleic acid molecule encoding the KREMEN1 predicted loss-of-function polypeptide, then the subject has a decreased risk of developing decreased bone mineral density.

The present disclosure also provides therapeutic agents that treat or prevent decreased bone mineral density for use in the treatment or prevention of decreased bone mineral density in a subject having: a KREMEN1 variant genomic nucleic acid molecule encoding a KREMEN1 predicted loss-of-function polypeptide; a KREMEN1 variant mRNA molecule encoding a KREMEN1 predicted loss-of-function polypeptide; or a KREMEN1 variant cDNA molecule encoding a KREMEN1 predicted loss-of-function polypeptide.

The present disclosure also provides KREMEN1 inhibitors for use in the treatment or prevention of decreased bone mineral density in a subject that: a) is reference for a KREMEN1 genomic nucleic acid molecule, a KREMEN1 mRNA molecule, or a KREMEN1 cDNA molecule; or b) is heterozygous for: i) a KREMEN1 variant genomic nucleic acid molecule encoding a KREMEN1 predicted loss-of-function polypeptide; ii) a KREMEN1 variant mRNA molecule encoding a KREMEN1 predicted loss-of-function polypeptide; or iii) a KREMEN1 variant cDNA molecule encoding a KREMEN1 predicted loss-of-function polypeptide.

BRIEF DESCRIPTION OF THE DRAWINGS

The accompanying figures, which are incorporated in and constitute a part of this specification, illustrate several features of the present disclosure.

FIG. 1 shows an association of rare predicted loss-of-function (pLoF) and predicted deleterious missense variants in KREMEN1 with higher estimated bone mineral density (eBMD). Estimates of association for the burden of KREMEN1 pLoF or predicted deleterious missense variants with AAF <1%, as derived in United Kingdom Biobank (UKB). Missense variants were predicted to be deleterious by five out five in silico algorithms (see Genotype Data for description of in silico algorithms used to characterize variant deleteriousness). Genotype counts indicates the number of individuals in each of three genotype categories: RR indicates individuals carrying no rare pLoF or predicted deleterious missense variants in KREMEN1; RA indicates individuals carrying a rare pLoF or predicted deleterious missense variant in a single KREMEN1 allele; AA indicates individuals carrying rare pLoF or predicted deleterious missense variants in both KREMEN1 alleles. AAF indicates the alternative allele frequency of variants included in this analysis. g/cm$^2$, grams per centimeter squared; SD, standard deviation; CI, confidence interval.

FIG. 2 shows an association of rare pLoF variants in KREMEN1 with higher eBMD. Estimates of association pertain to the burden of KREMEN1 pLoF variants with AAF <1% and were derived in UKB. Genotype counts indicates the number of individuals in each of three genotype categories: RR indicates individuals carrying no rare pLoF variants in KREMEN1; RA indicates individuals carrying at least one rare pLoF in a single KREMEN1 allele; AA indicates individuals carrying any rare pLoF variants in both KREMEN1 alleles. AAF, alternative allele frequency of variants included in this analysis. g/cm$^2$, grams per centimeter squared; SD, standard deviation; CI, confidence interval.

FIG. 3 shows KREMEN1 pLoF or predicted deleterious missense variants identified by whole-exome sequencing (WES) and included in the gene burden association analysis. The genomic coordinates column indicates the chromosome, physical genomic position in base pairs, reference allele, and alternative allele for each variant, according to build 38 of the Human Genome sequence by the Human Genome Reference Consortium. Coding DNA and protein changes are provided according to the Human Genome Variation Society nomenclature, and refer to the KREMEN1 transcripts shown in the "Transcript(s)" column. Transcripts were sourced from the Ensembl database (Howe et al., Nuc. Acids Res., 2020, 49(D1), D884-D891). AAF, alternative allele frequency of variants included in this analysis; pLoF, predicted loss-of-function.

DESCRIPTION

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or Alternately phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human. In some embodiments, the human is a patient under the care of a physician.

It has been observed in accordance with the present disclosure that KREMEN1 variant nucleic acid molecules encoding a KREMEN1 predicted loss-of-function polypeptide (whether these variations are homozygous or heterozygous in a particular subject) associate with a decreased risk of developing decreased bone mineral density. It is believed that KREMEN1 variant nucleic acid molecules encoding a KREMEN1 predicted loss-of-function polypeptide have not been associated with decreased bone mineral density in genome-wide or exome-wide association studies. Therefore, subjects that are KREMEN1 reference or heterozygous for KREMEN1 variant nucleic acid molecules encoding KREMEN1 predicted loss-of-function polypeptides may be treated with a KREMEN1 inhibitor such that decreased bone mineral density is inhibited, the symptoms thereof are reduced, and/or development of symptoms is repressed. It is also believed that such subjects having decreased bone mineral density may further be treated with therapeutic agents that treat or prevent decreased bone mineral density.

For purposes of the present disclosure, any particular subject, such as a human, can be categorized as having one of three KREMEN1 genotypes: i) KREMEN1 reference; ii) heterozygous for a KREMEN1 variant nucleic acid molecule encoding a KREMEN1 predicted loss-of-function polypeptide; or iii) homozygous for a KREMEN1 variant nucleic acid molecules encoding a KREMEN1 predicted loss-of-function polypeptide. A subject is KREMEN1 reference when the subject does not have a copy of a KREMEN1 variant nucleic acid molecules encoding a KREMEN1 predicted loss-of-function polypeptide. A subject is heterozygous for a KREMEN1 variant nucleic acid molecules encoding a KREMEN1 predicted loss-of-function polypeptide when the subject has a single copy of a KREMEN1 variant nucleic acid molecule encoding a KREMEN1 predicted loss-of-function polypeptide. A KREMEN1 variant nucleic acid molecule encoding a KREMEN1 predicted loss-of-function polypeptide is any nucleic acid molecule (such as, a genomic nucleic acid molecule, an mRNA molecule, or a cDNA molecule) encoding a variant KREMEN1 polypeptide having a partial loss-of-function, a complete loss-of-function, a predicted partial loss-of-function, or a predicted complete loss-of-function. A subject who has a KREMEN1 polypeptide having a partial loss-of-function (or predicted partial loss-of-function) is hypomorphic for KREMEN1. A subject is homozygous for a KREMEN1 variant nucleic acid molecule encoding a KREMEN1 predicted loss-of-function polypeptide when the subject has two copies (same or different) of a KREMEN1 variant nucleic acid molecules encoding a KREMEN1 predicted loss-of-function polypeptide.

For subjects that are genotyped or determined to be KREMEN1 reference, such subjects have an increased risk of developing decreased bone mineral density, such as osteopenia, Type I osteoporosis, Type II osteoporosis, and/or secondary osteoporosis. For subjects that are genotyped or determined to be either KREMEN1 reference or heterozygous for a KREMEN1 variant nucleic acid molecules encoding a KREMEN1 predicted loss-of-function polypeptide, such subjects or subjects can be treated with a KREMEN1 inhibitor.

In any of the embodiments described herein, the KREMEN1 variant nucleic acid molecules encoding a KREMEN1 predicted loss-of-function polypeptide can be any nucleic acid molecule (such as, for example, genomic nucleic acid molecule, mRNA molecule, or cDNA molecule) encoding a KREMEN1 variant polypeptide having a partial loss-of-function, a complete loss-of-function, a predicted partial loss-of-function, or a predicted complete loss-of-function. In some embodiments, the KREMEN1 variant nucleic acid molecules encoding a KREMEN1 predicted loss-of-function polypeptide is associated with a reduced in vitro response to KREMEN1 ligands compared with reference KREMEN1. In some embodiments, the KREMEN1 variant nucleic acid molecules encoding a KREMEN1 predicted loss-of-function polypeptide is a KREMEN1 variant that results or is predicted to result in a premature truncation of a KREMEN1 polypeptide compared to the human reference genome sequence. In some embodiments, the KREMEN1 variant nucleic acid molecules encoding a KREMEN1 predicted loss-of-function polypeptide is a variant that is predicted to be damaging by in vitro prediction algorithms such as Polyphen, SIFT, or similar algorithms. In some embodiments, the KREMEN1 variant nucleic acid molecules encoding a KREMEN1 predicted loss-of-function polypeptide is a variant that causes or is predicted to cause a nonsynonymous amino-acid substitution in KREMEN1 and whose allele frequency is less than 1/100 alleles in the population from which the subject is selected. In some embodiments, the KREMEN1 variant nucleic acid molecules encoding a KREMEN1 predicted loss-of-function polypeptide is any rare variant (allele frequency <0.1%; or 1 in 1,000 alleles), or any splice-site, stop-gain, start-loss, stop-loss, frameshift, or in-frame indel, or other frameshift KREMEN1 variant.

In any of the embodiments described herein, the KREMEN1 predicted loss-of-function polypeptide can be any KREMEN1 polypeptide having a partial loss-of-function, a complete loss-of-function, a predicted partial loss-of-function, or a predicted complete loss-of-function.

In any of the embodiments described herein, the KREMEN1 variant nucleic acid molecules encoding a KREMEN1 predicted loss-of-function polypeptide can include variations at positions of chromosome 22 using the nucleotide sequence of the KREMEN1 reference genomic nucleic acid molecule (SEQ ID NO:1; ENSG00000183762.13; ENST00000327813.9; chr22:29073118-29168333 in the GRCh38/hg38 human genome assembly; alternately, chr22:29073035-29168333 or chr22:29073077-29168333) as a reference sequence.

Numerous genetic variants in KREMEN1 exist which cause subsequent changes in the KREMEN1 polypeptide sequence including, but not limited to the variants listed in FIG. 3, Table 2, or otherwise listed herein.

Any one or more (i.e., any combination) of the KREMEN1 variant nucleic acid molecules encoding a KREMEN1 predicted loss-of-function polypeptide can be used within any of the methods described herein to determine whether a subject has an increased risk of developing decreased bone mineral density. The combinations of particular variants can form a mask used for statistical analysis of the particular correlation of KREMEN1 and increased risk of developing decreased bone mineral density.

In any of the embodiments described herein, the decreased bone mineral density is osteopenia, Type I osteoporosis, Type II osteoporosis, and/or secondary osteoporosis. In some embodiments, the decreased bone mineral density is osteopenia. In some embodiments, the decreased bone mineral density is Type I osteoporosis. In some embodiments, the decreased bone mineral density is Type II osteoporosis. In some embodiments, the decreased bone mineral density is secondary osteoporosis.

Symptoms of a decreased bone mineral density include, but are not limited to, increased bone fragility (manifesting as bone fracture as a result of a mild to moderate trauma), reduced bone density, localized bone pain and weakness in an area of a broken bone, loss of height or change in posture, such as stooping over, high levels of serum calcium or alkaline phosphatase on a blood test, vitamin D deficiency, and joint or muscle aches, or any combination thereof.

The present disclosure provides methods of treating a subject having decreased bone mineral density or at risk of developing decreased bone mineral density, the methods comprising administering a KREMEN1 inhibitor to the subject.

The present disclosure also provides methods of treating a subject having osteopenia or at risk of developing osteopenia, the methods comprising administering a KREMEN1 inhibitor to the subject.

The present disclosure also provides methods of treating a subject having Type I osteoporosis or at risk of developing Type I osteoporosis, the methods comprising administering a KREMEN1 inhibitor to the subject.

The present disclosure also provides methods of treating a subject having Type II osteoporosis or at risk of developing Type II osteoporosis, the methods comprising administering a KREMEN1 to the subject.

The present disclosure also provides methods of treating a subject having secondary osteoporosis or at risk of developing secondary osteoporosis, the methods comprising administering a KREMEN1 inhibitor to the subject.

In some embodiments, the KREMEN1 inhibitor comprises an inhibitory nucleic acid molecule. Examples of inhibitory nucleic acid molecules include, but are not limited to, antisense nucleic acid molecules, small interfering RNAs (siRNAs), and short hairpin RNAs (shRNAs). Such inhibitory nucleic acid molecules can be designed to target any region of a KREMEN1 nucleic acid molecule. In some embodiments, the antisense RNA, siRNA, or shRNA hybridizes to a sequence within a KREMEN1 genomic nucleic acid molecule or mRNA molecule and decreases expression of the KREMEN1 polypeptide in a cell in the subject. In some embodiments, the KREMEN1 inhibitor comprises an antisense molecule that hybridizes to a KREMEN1 genomic nucleic acid molecule or mRNA molecule and decreases expression of the KREMEN1 polypeptide in a cell in the subject. In some embodiments, the KREMEN1 inhibitor comprises an siRNA that hybridizes to a KREMEN1 genomic nucleic acid molecule or mRNA molecule and decreases expression of the KREMEN1 polypeptide in a cell in the subject. In some embodiments, the KREMEN1 inhibitor comprises an shRNA that hybridizes to a KREMEN1 genomic nucleic acid molecule or mRNA molecule and decreases expression of the KREMEN1 polypeptide in a cell in the subject.

The inhibitory nucleic acid molecules can comprise RNA, DNA, or both RNA and DNA. The inhibitory nucleic acid molecules can also be linked or fused to a heterologous nucleic acid sequence, such as in a vector, or a heterologous label. For example, the inhibitory nucleic acid molecules can be within a vector or as an exogenous donor sequence comprising the inhibitory nucleic acid molecule and a heterologous nucleic acid sequence. The inhibitory nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The inhibitory nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The inhibitory nucleic acid molecules can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $—O[(CH_2)_nO]_mCH_3$, $—O(CH_2)_nOCH_3$, $—O(CH_2)_nNH_2$, $—O(CH_2)_nCH_3$, $—O(CH_2)_n—ONH_2$, and $—O(CH_2)_nON[(CH_2)_nCH_3)]_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

In some embodiments, the antisense nucleic acid molecules are gapmers, whereby the first one to seven nucleotides at the 5' and 3' ends each have 2'-methoxyethyl (2'-MOE) modifications. In some embodiments, the first five nucleotides at the 5' and 3' ends each have 2'-MOE modifications. In some embodiments, the first one to seven nucleotides at the 5' and 3' ends are RNA nucleotides. In some embodiments, the first five nucleotides at the 5' and 3' ends are RNA nucleotides. In some embodiments, each of the backbone linkages between the nucleotides is a phosphorothioate linkage.

In some embodiments, the siRNA molecules have termini modifications. In some embodiments, the 5' end of the antisense strand is phosphorylated. In some embodiments, 5'-phosphate analogs that cannot be hydrolyzed, such as 5'-(E)-vinyl-phosphonate are used.

In some embodiments, the siRNA molecules have backbone modifications. In some embodiments, the modified phosphodiester groups that link consecutive ribose nucleosides have been shown to enhance the stability and in vivo bioavailability of siRNAs The non-ester groups (—OH, =O) of the phosphodiester linkage can be replaced with sulfur, boron, or acetate to give phosphorothioate, boranophosphate, and phosphonoacetate linkages. In addition, substituting the phosphodiester group with a phosphotriester can facilitate cellular uptake of siRNAs and retention on serum components by eliminating their negative charge. In some embodiments, the siRNA molecules have sugar modifications. In some embodiments, the sugars are deprotonated (reaction catalyzed by exo- and endonucleases) whereby the 2'-hydroxyl can act as a nucleophile and attack the adjacent phosphorous in the phosphodiester bond. Such alternatives include 2'-O-methyl, 2'-O-methoxyethyl, and 2'-fluoro modifications.

In some embodiments, the siRNA molecules have base modifications. In some embodiments, the bases can be substituted with modified bases such as pseudouridine, 5'-methylcytidine, N6-methyladenosine, inosine, and N7-methylguanosine.

In some embodiments, the siRNA molecules are conjugated to lipids. Lipids can be conjugated to the 5' or 3' termini of siRNA to improve their in vivo bioavailability by allowing them to associate with serum lipoproteins. Representative lipids include, but are not limited to, cholesterol and vitamin E, and fatty acids, such as palmitate and tocopherol.

In some embodiments, a representative siRNA has the following formula:

Sense: mN*mN*/i2FN/mN/i2FN/mN/i2FN/mN/i2FN/mN/i2FN/mN/i2FN/mN/i2FN/mN/i2FN/*mN*/32FN/

Antisense: /52FN/*/i2FN/*mN/i2FN/mN/i2FN/mN/i2FN/mN/i2FN/mN/i2FN/mN/i2FN/mN/i2FN/mN/i2FN/mN*N*N wherein: "N" is the base; "2F" is a 2'-F modification; "m" is a 2'-O-methyl modification, "I" is an internal base; and "*" is a phosphorothioate backbone linkage.

The present disclosure also provides vectors comprising any one or more of the inhibitory nucleic acid molecules. In some embodiments, the vectors comprise any one or more of the inhibitory nucleic acid molecules and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

The present disclosure also provides compositions comprising any one or more of the inhibitory nucleic acid molecules. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

Exemplary KREMEN1 inhibitors include, but are not limited to, KREMEN2 (Sumia et al., Cell Death Discovery, 2019, 5, 91) and its ligand Dickkopf-1 (DKK-1), a secreted glycoprotein, as well as R-Spondin1.

In some embodiments, the KREMEN1 inhibitor comprises a nuclease agent that induces one or more nicks or double-strand breaks at a recognition sequence(s) or a DNA-binding protein that binds to a recognition sequence within a KREMEN1 genomic nucleic acid molecule. The recognition sequence can be located within a coding region of the KREMEN1 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the KREMEN1 gene. For example, the recognition sequence can be located about 10, about 20, about 30, about 40, about 50, about 100, about 200, about 300, about 400, about 500, or about 1,000 nucleotides from the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair, about 15-18 bp for each ZFN, about 36 bp for a TALE protein or TALEN, and about 20 bp for a CRISPR/Cas guide RNA.

In some embodiments, CRISPR/Cas systems can be used to modify a KREMEN1 genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of KREMEN1 nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in a KREMEN1 genomic nucleic acid molecule or it can be a nickase that creates a single-strand break in a KREMEN1 genomic nucleic acid molecule. Additional examples of Cas proteins include, but are not limited to, Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of KREMEN1 genomic nucleic acid molecules can be generated by contacting a cell with a Cas protein and one or more gRNAs that hybridize to one or more gRNA recognition sequences within a target genomic locus in the KREMEN1 genomic nucleic acid molecule. For example, a gRNA recognition sequence can be located within a region of SEQ ID NO:1. The gRNA recognition sequence can include or be proximate to the start codon of a KREMEN1 genomic nucleic acid molecule or the stop codon of a KREMEN1 genomic nucleic acid molecule. For example, the gRNA recognition sequence can be located from about 10, from about 20, from about 30, from about 40, from about 50, from about 100, from about 200, from about 300, from about 400, from about 500, or from about 1,000 nucleotides of the start codon or the stop codon.

The gRNA recognition sequences within a target genomic locus in a KREMEN1 genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within a KREMEN1 genomic nucleic acid molecule. An exemplary gRNA is a gRNA effective to direct a Cas enzyme to bind to or cleave a KREMEN1 genomic nucleic acid molecule, wherein the gRNA comprises a DNA-targeting segment that hybridizes to a gRNA recognition sequence within the KREMEN1 genomic nucleic acid molecule. Exemplary gRNAs comprise a DNA-targeting segment that hybridizes to a gRNA recognition sequence present within a KREMEN1 genomic nucleic acid molecule that includes or is proximate to the start codon or the stop codon. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the start codon or located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the human KREMEN1 reference gene are set forth in Table 1 as SEQ ID NOs:17-36.

TABLE 1

Guide RNA Recognition Sequences Near KREMEN1

| Strand | gRNA Recognition Sequence | SEQ ID NO: |
|---|---|---|
| + | CACTCTGAAATACCCCAACG | 17 |
| + | TGATTACTGGAAGTACGGGG | 18 |
| + | TCCCCGACACCTATGCCACG | 19 |
| + | AACTGGACAGCACTACAAGG | 20 |
| - | GGAAGCGGGCTAGGACACGG | 21 |
| + | TCTGAAATACCCCAACGGGG | 22 |
| + | CTTCCCCGACACCTATGCCA | 23 |
| - | GTCTCGTTCCAAAACAGACA | 24 |
| - | GAAGCGGGCTAGGACACGGT | 25 |
| + | TCCTGATTACTGGAAGTACG | 26 |
| + | AACACTCTGAAATACCCCAA | 27 |
| + | CCGACACCTATGCCACGGGG | 28 |
| + | ACTGGACCATCCGGGTTCCG | 29 |
| + | GCCAATGGTGCGGATTATAG | 30 |
| - | GTATAAAACAGCAAATCCCT | 31 |
| + | ACTGGACAGCACTACAAGGC | 32 |
| + | CGTGAGCCCCTGGTGCTATG | 33 |
| - | GGGCATACTCACTATCAAAG | 34 |

TABLE 1-continued

Guide RNA Recognition Sequences Near KREMEN1

| Strand | gRNA Recognition Sequence | SEQ ID NO: |
|---|---|---|
| - | TTACTGGTGCCAGTTAGAGG | 35 |
| + | GTGCTATGTGGCAGAGCACG | 36 |

The Cas protein and the gRNA form a complex, and the Cas protein cleaves the target KREMEN1 genomic nucleic acid molecule. The Cas protein can cleave the nucleic acid molecule at a site within or outside of the nucleic acid sequence present in the target KREMEN1 genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the KREMEN1 genomic nucleic acid molecule to which a DNA-targeting segment of a gRNA will bind.

Such methods can result, for example, in a KREMEN1 genomic nucleic acid molecule in which a region of SEQ ID NO:1 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the KREMEN1 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the methods of treatment further comprise detecting the presence or absence of a KREMEN1 variant nucleic acid molecule encoding a KREMEN1 predicted loss-of-function polypeptide in a biological sample from the subject. As used throughout the present disclosure, a "KREMEN1 variant nucleic acid molecule encoding a KREMEN1 predicted loss-of-function polypeptide" is any KREMEN1 nucleic acid molecule (such as, for example, genomic nucleic acid molecule, mRNA molecule, or cDNA molecule) encoding a KREMEN1 polypeptide having a partial loss-of-function, a complete loss-of-function, a predicted partial loss-of-function, or a predicted complete loss-of-function.

The present disclosure also provides methods of treating a subject with a therapeutic agent that treats or prevents decreased bone mineral density, wherein the subject has decreased bone mineral density or is at risk of developing decreased bone mineral density. In some embodiments, the subject has decreased bone mineral density. In some embodiments, the subject is at risk of developing decreased bone mineral density. In some embodiments, the methods comprise determining whether the subject has a KREMEN1 variant nucleic acid molecule encoding a KREMEN1 predicted loss-of-function polypeptide by obtaining or having obtained a biological sample from the subject, and performing or having performed a sequence analysis on the biological sample to determine if the subject has a genotype comprising the KREMEN1 variant nucleic acid molecule encoding a KREMEN1 predicted loss-of-function polypeptide. In some embodiments, the methods further comprise administering or continuing to administer the therapeutic agent that treats or prevents decreased bone mineral density in a standard dosage amount to a subject that is KREMEN1 reference, and/or administering a KREMEN1 inhibitor to the subject. In some embodiments, the methods further comprise administering or continuing to administer the therapeutic agent that treats or prevents decreased bone mineral density in an amount that is the same as or less than a standard dosage amount to a subject that is heterozygous for the KREMEN1 variant nucleic acid molecule, and/or administering a KREMEN1 inhibitor to the subject. In some embodiments, the methods further comprise administering or continuing to administer the therapeutic agent that treats or prevents decreased bone mineral density in an amount that is the same as or less than a standard dosage amount to a subject that is homozygous for the KREMEN1 variant nucleic acid molecule. The presence of a genotype having the KREMEN1 variant nucleic acid molecule encoding the KREMEN1 predicted loss-of-function polypeptide indicates the subject has a decreased risk of developing decreased bone mineral density. In some embodiments, the subject is KREMEN1 reference. In some embodiments, the subject is heterozygous for a KREMEN1 variant nucleic acid molecule encoding a KREMEN1 predicted loss-of-function polypeptide.

For subjects that are genotyped or determined to be either KREMEN1 reference or heterozygous for a KREMEN1 variant nucleic acid molecule encoding a KREMEN1 predicted loss-of-function polypeptide, such subjects can be treated with a KREMEN1 inhibitor, as described herein.

Detecting the presence or absence of a KREMEN1 variant nucleic acid molecule encoding a KREMEN1 predicted loss-of-function polypeptide in a biological sample from a subject and/or determining whether a subject has a KREMEN1 variant nucleic acid molecule encoding a KREMEN1 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when the subject is KREMEN1 reference, the subject is administered a therapeutic agent that treats or prevents decreased bone mineral density in a standard dosage amount. In some embodiments, when the subject is heterozygous for a KREMEN1 variant nucleic acid molecule encoding a KREMEN1 predicted loss-of-function polypeptide, the subject is administered a therapeutic agent that treats or prevents decreased bone mineral density in a dosage amount that is the same as or less than a standard dosage amount.

In some embodiments, the treatment methods further comprise detecting the presence or absence of a KREMEN1 predicted loss-of-function polypeptide in a biological sample from the subject. In some embodiments, when the subject does not have a KREMEN1 predicted loss-of-function polypeptide, the subject is administered a therapeutic agent that treats or prevents decreased bone mineral density in a standard dosage amount. In some embodiments, when the subject has a KREMEN1 predicted loss-of-function polypeptide, the subject is administered a therapeutic agent that treats or prevents decreased bone mineral density in a dosage amount that is the same as or less than a standard dosage amount.

The present disclosure also provides methods of treating a subject with a therapeutic agent that treats or prevents decreased bone mineral density, wherein the subject has decreased bone mineral density or is at risk of developing decreased bone mineral density. In some embodiments, the subject has decreased bone mineral density. In some embodiments, the subject is at risk of developing decreased bone mineral density. In some embodiments, the method comprises determining whether the subject has a KREMEN1 predicted loss-of-function polypeptide by obtaining or having obtained a biological sample from the subject, and performing or having performed an assay on the biological sample to determine if the subject has a KREMEN1 predicted loss-of-function polypeptide. When the subject does not have a KREMEN1 predicted loss-of-function polypeptide, the therapeutic agent that treats or prevents decreased bone mineral density is administered or continued to be administered to the subject in a standard dosage amount, and/or a KREMEN1 inhibitor is administered to the subject. When the subject has a KREMEN1 predicted loss-of-function polypeptide, the therapeutic agent that treats or prevents decreased bone mineral density is administered or continued to be administered to the subject in an amount that is the same as or less than a standard dosage amount, and/or a KREMEN1 inhibitor is administered to the subject. The presence of a KREMEN1 predicted loss-of-function polypeptide indicates the subject has a decreased risk of developing decreased bone mineral density. In some embodiments, the subject has a KREMEN1 predicted loss-of-function polypeptide. In some embodiments, the subject does not have a KREMEN1 predicted loss-of-function polypeptide.

Detecting the presence or absence of a KREMEN1 predicted loss-of-function polypeptide in a biological sample from a subject and/or determining whether a subject has a KREMEN1 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

Examples of therapeutic agents that treat or prevent decreased bone mineral density include, but are not limited to: calcium and vitamin D supplementation (vitamin D2, vitamin D3, and cholecalciferol), bisphosphonate medications, such as FOSAMAX®, (alendronate), BONIVA® (ibandronate), RECLAST® (zoledronate), ACTONEL® (risedronate), MIACALCIN®, FORTICAL®, and CALCIMAR® (calcitonin), FORTEO® (teriparatide), PROLIA® (denosumab), hormone replacement therapy with estrogen and progesterone as well as EVISTA® (raloxifene). In some embodiments, the therapeutic agent that treats or prevents decreased bone mineral density is vitamin D2, vitamin D3, cholecalciferol, alendronate, ibandronate, zoledronate, risedronate, calcitonin, teriparatide, denosumab, EVENITY® (romosozumab), or raloxifene. In some embodiments, the therapeutic agent that treats or prevents decreased bone mineral density is vitamin D2. In some embodiments, the therapeutic agent that treats or prevents decreased bone mineral density is vitamin D3. In some embodiments, the therapeutic agent that treats or prevents decreased bone mineral density is cholecalciferol. In some embodiments, the therapeutic agent that treats or prevents decreased bone mineral density is alendronate. In some embodiments, the therapeutic agent that treats or prevents decreased bone mineral density is ibandronate. In some embodiments, the therapeutic agent that treats or prevents decreased bone mineral density is zoledronate. In some embodiments, the therapeutic agent that treats or prevents decreased bone mineral density is risedronate. In some embodiments, the therapeutic agent that treats or prevents decreased bone mineral density is calcitonin. In some embodiments, the therapeutic agent that treats or prevents decreased bone mineral density is teriparatide. In some embodiments, the therapeutic agent that treats or prevents decreased bone mineral density is denosumab. In some embodiments, the therapeutic agent that treats or prevents decreased bone mineral density is raloxifene.

In some embodiments, the dose of the therapeutic agents that treat or prevent decreased bone mineral density can be decreased by about 10%, by about 20%, by about 30%, by about 40%, by about 50%, by about 60%, by about 70%, by about 80%, or by about 90% for subjects that are heterozygous for a KREMEN1 variant nucleic acid molecule encoding a KREMEN1 predicted loss-of-function polypeptide (i.e., a less than the standard dosage amount) compared to subjects that are KREMEN1 reference (who may receive a standard dosage amount). In some embodiments, the dose of the therapeutic agents that treat or prevent decreased bone mineral density can be decreased by about 10%, by about 20%, by about 30%, by about 40%, or by about 50%. In addition, the subjects that are heterozygous for a KREMEN1 variant nucleic acid molecule encoding a KREMEN1 predicted loss-of-function polypeptide can be administered less frequently compared to subjects that are KREMEN1 reference.

In some embodiments, the dose of the therapeutic agents that treat or prevent decreased bone mineral density can be decreased by about 10%, by about 20%, by about 30%, by about 40%, by about 50%, for subjects that are homozygous for a KREMEN1 variant nucleic acid molecule encoding a KREMEN1 predicted loss-of-function polypeptide compared to subjects that are heterozygous for a KREMEN1 variant nucleic acid molecule encoding a KREMEN1 predicted loss-of-function polypeptide. In some embodiments, the dose of the therapeutic agents that treat or prevent decreased bone mineral density can be decreased by about 10%, by about 20%, by about 30%, by about 40%, or by about 50%. In addition, the dose of therapeutic agents that treat or prevent decreased bone mineral density in subjects that are homozygous for a KREMEN1 variant nucleic acid molecule encoding a KREMEN1 predicted loss-of-function polypeptide can be administered less frequently compared to subjects that are heterozygous for a KREMEN1 variant nucleic acid molecule encoding a KREMEN1 predicted loss-of-function polypeptide.

Administration of the therapeutic agents that treat or prevent decreased bone mineral density and/or KREMEN1 inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or prevent decreased bone mineral density and/or KREMEN1 inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in decreased bone mineral density, a decrease/reduction in the severity of decreased bone mineral density (such as, for example, a reduction or inhibition of development of decreased bone mineral density), a decrease/reduction in symptoms and decreased bone mineral density-related effects, delaying the onset of symptoms and decreased bone mineral density-related effects, reducing the severity of symptoms of decreased bone mineral density-related effects, reducing the number of symptoms and decreased bone mineral density-related effects, reducing the latency of symptoms and decreased bone mineral density-related effects, an amelioration of symptoms and decreased bone mineral density-related effects, reducing secondary symptoms, reducing secondary infections, preventing relapse to decreased bone mineral density, decreasing the number or frequency of relapse episodes, increasing latency between symptomatic episodes, increasing time to sustained progression, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of decreased bone mineral density development/progression (such as, for example, a complete or partial avoidance/inhibition or a delay), and an increased survival time of the affected host animal, following administration of a therapeutic protocol. Treatment of decreased bone mineral density encompasses the treatment of a subject already diagnosed as having any form of decreased bone mineral density at any clinical stage or manifestation, the delay of the onset or evolution or aggravation or deterioration of the symptoms or signs of decreased bone mineral density, and/or preventing and/or reducing the severity of decreased bone mineral density.

The present disclosure also provides methods of identifying a subject having an increased risk of developing decreased bone mineral density. In some embodiments, the method comprises determining or having determined in a biological sample obtained from the subject the presence or absence of a KREMEN1 variant nucleic acid molecule (such as a genomic nucleic acid molecule, mRNA molecule, and/or cDNA molecule) encoding a KREMEN1 predicted loss-of-function polypeptide encoding a KREMEN1 polypeptide. When the subject lacks a KREMEN1 variant nucleic acid molecule encoding a KREMEN1 predicted loss-of-function polypeptide (i.e., the subject is genotypically categorized as a KREMEN1 reference), then the subject has an increased risk of developing decreased bone mineral density. When the subject has a KREMEN1 variant nucleic acid molecule encoding a KREMEN1 predicted loss-of-function polypeptide (i.e., the subject is heterozygous or homozygous for a KREMEN1 variant nucleic acid molecule encoding a KREMEN1 predicted loss-of-function polypeptide), then the subject has a decreased risk of developing decreased bone mineral density.

Having a single copy of a KREMEN1 variant nucleic acid molecule encoding a KREMEN1 predicted loss-of-function polypeptide is more protective of a subject from developing decreased bone mineral density than having no copies of a KREMEN1 variant nucleic acid molecule encoding a KREMEN1 predicted loss-of-function polypeptide. Without intending to be limited to any particular theory or mechanism of action, it is believed that a single copy of a KREMEN1 variant nucleic acid molecule encoding a KREMEN1 predicted loss-of-function polypeptide (i.e., heterozygous for a KREMEN1 variant nucleic acid molecule encoding a KREMEN1 predicted loss-of-function polypeptide) is protective of a subject from developing decreased bone mineral density, and it is also believed that having two copies of a KREMEN1 variant nucleic acid molecule encoding a KREMEN1 predicted loss-of-function polypeptide (i.e., homozygous for a KREMEN1 variant nucleic acid molecule encoding a KREMEN1 predicted loss-of-function polypeptide) may be more protective of a subject from developing decreased bone mineral density, relative to a subject with a single copy. Thus, in some embodiments, a single copy of a KREMEN1 variant nucleic acid molecule encoding a KREMEN1 predicted loss-of-function polypeptide may not be completely protective, but instead, may be partially or incompletely protective of a subject from developing decreased bone mineral density. While not desiring to be bound by any particular theory, there may be additional factors or molecules involved in the development of decreased bone mineral density that are still present in a subject having a single copy of a KREMEN1 variant nucleic acid molecule encoding a KREMEN1 predicted loss-of-function polypeptide, thus resulting in less than complete protection from the development of decreased bone mineral density.

Determining whether a subject has a KREMEN1 variant nucleic acid molecule encoding a KREMEN1 predicted loss-of-function polypeptide in a biological sample from a subject and/or determining whether a subject has a KREMEN1 variant nucleic acid molecule encoding a KREMEN1 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when a subject is identified as having an increased risk of developing decreased bone mineral density, the subject is treated with a therapeutic agent that treats or prevents decreased bone mineral density, and/or a KREMEN1 inhibitor, as described herein. For example, when the subject is KREMEN1 reference, and therefore has an increased risk of developing decreased bone mineral density, the subject is administered a KREMEN1 inhibitor. In some embodiments, such a subject is also administered a therapeutic agent that treats or prevents decreased bone mineral density. In some embodiments, when the subject is heterozygous for a KREMEN1 variant nucleic acid molecule encoding a KREMEN1 predicted loss-of-function polypeptide, the subject is administered the therapeutic agent that treats or prevents decreased bone mineral density in a dosage amount that is the same as or less than a standard dosage amount, and is also administered a KREMEN1 inhibitor. In some embodiments, such a subject is also administered a therapeutic agent that treats or prevents decreased bone mineral density. In some embodiments, when the subject is homozygous for a KREMEN1 variant nucleic acid molecule encoding a KREMEN1 predicted loss-of-function polypeptide, the subject is administered the therapeutic agent that treats or prevents decreased bone mineral density in a dosage amount that is the same as or less than a standard dosage amount. In some embodiments, the subject is KREMEN1 reference. In some embodiments, the subject is heterozygous for a KREMEN1 variant nucleic acid molecule encoding a KREMEN1 predicted loss-of-function polypeptide. In some embodiments, the subject is homozygous for a KREMEN1 variant nucleic acid molecule encoding a KREMEN1 predicted loss-of-function polypeptide.

In some embodiments, any of the methods described herein can further comprise determining the subject's aggregate burden of having a KREMEN1 variant nucleic acid molecule encoding a KREMEN1 predicted loss-of-function polypeptide, and/or a KREMEN1 predicted loss-of-function variant polypeptide associated with a decreased risk of developing decreased bone mineral density. The gene burden is the aggregate of all variants in the KREMEN1 gene, which can be carried out in an association analysis with bone mineral density. In some embodiments, the subject is homozygous for one or more KREMEN1 variant nucleic acid molecules encoding a KREMEN1 predicted loss-of-function polypeptide associated with a decreased risk of developing decreased bone mineral density. In some embodiments, the subject is heterozygous for one or more KREMEN1 variant nucleic acid molecules encoding a KREMEN1 predicted loss-of-function polypeptide associated with a decreased risk of developing decreased bone mineral density. The result of the association analysis suggests that KREMEN1 variant nucleic acid molecules encoding a KREMEN1 predicted loss-of-function polypeptide are associated with decreased risk of developing decreased bone mineral density. When the subject has a lower aggregate burden, the subject is at a higher risk of developing decreased bone mineral density and the subject is administered or continued to be administered the therapeutic agent that treats or prevents decreased bone mineral density in a standard dosage amount. When the subject has a greater aggregate burden, the subject is at a lower risk of developing decreased bone mineral density and the subject is administered or continued to be administered the therapeutic agent that treats or prevents decreased bone mineral density in an amount that is the same as or less than the standard dosage amount. The greater the aggregate burden, the lower the risk of developing decreased bone mineral density.

The KREMEN1 variant nucleic acid molecule encoding a KREMEN1 predicted loss-of-function polypeptide, and/or a KREMEN1 predicted loss-of-function variant polypeptide used for determining the subject's aggregate burden include, but are not limited to the variants listed in FIG. 3, Table 2, or otherwise listed herein.

In some embodiments, the subject's aggregate burden of having any one or more KREMEN1 variant nucleic acid molecules encoding a KREMEN1 predicted loss-of-function polypeptide represents a weighted sum of a plurality of any of the KREMEN1 variant nucleic acid molecules encoding a KREMEN1 predicted loss-of-function polypeptide. In some embodiments, the aggregate burden is calculated using at least about 2, at least about 3, at least about 4, at least about 5, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, at least about 1,000, at least about 10,000, at least about 100,000, or at least about or more than 1,000,000 genetic variants present in or around (up to 10 Mb) the KREMEN1 gene where the genetic burden is the number of alleles multiplied by the association estimate with decreased bone mineral density or related outcome for each allele (e.g., a weighted polygenic burden score). This can include any genetic variants, regardless of their genomic annotation, in proximity to the KREMEN1 gene (up to 10 Mb around the gene) that show a non-zero association with bone mineral density-related traits in a genetic association analysis. In some embodiments, when the subject has an aggregate burden above a desired threshold score, the subject has a decreased risk of developing decreased bone mineral density. In some embodiments, when the subject has an aggregate burden below a desired threshold score, the subject has an increased risk of developing decreased bone mineral density.

In some embodiments, the aggregate burden may be divided into quintiles, e.g., top quintile, intermediate quintile, and bottom quintile, wherein the top quintile of aggregate burden corresponds to the lowest risk group and the bottom quintile of aggregate burden corresponds to the highest risk group. In some embodiments, a subject having a greater aggregate burden comprises the highest weighted aggregate burdens, including, but not limited to the top 10%, top 20%, top 30%, top 40%, or top 50% of aggregate burdens from a subject population. In some embodiments, the genetic variants comprise the genetic variants having association with decreased bone mineral density in the top 10%, top 20%, top 30%, top 40%, or top 50% of p-value range for the association. In some embodiments, each of the identified genetic variants comprise the genetic variants having association with decreased bone mineral density with p-value of no more than about $10^{-2}$, about $10^{-3}$, about $10^{-4}$, about $10^{-5}$, about $10^{-6}$, about $10^{-7}$, about $10^{-8}$, about $10^{-9}$, about $10^{-10}$, about $10^{-11}$, about $10^{-12}$, about $10^{-13}$, about $10^{-14}$, about or $10^{-15}$. In some embodiments, the identified genetic variants comprise the genetic variants having association with decreased bone mineral density with p-value of less than $5\times10^{-8}$. In some embodiments, the identified genetic variants comprise genetic variants having association with decreased bone mineral density in high-risk subjects as compared to the rest of the reference population with odds ratio (OR) about 1.5 or greater, about 1.75 or greater, about 2.0 or greater, or about 2.25 or greater for the top 20% of the distribution; or about 1.5 or greater, about 1.75 or greater, about 2.0 or greater, about 2.25 or greater, about 2.5 or greater, or about 2.75 or greater. In some embodiments, the odds ratio (OR) may range from about 1.0 to about 1.5, from about 1.5 to about 2.0, from about 2.0 to about 2.5, from about 2.5 to about 3.0, from about 3.0 to about 3.5, from about 3.5 to about 4.0, from about 4.0 to about 4.5, from about 4.5 to about 5.0, from about 5.0 to about 5.5, from about 5.5 to about 6.0, from about 6.0 to about 6.5, from about 6.5 to about 7.0, or greater than 7.0. In some embodiments, high-risk subjects comprise subjects having aggregate burdens in the bottom decile, quintile, or tertile in a reference population. The threshold of the aggregate burden is determined on the basis of the nature of the intended practical application and the risk difference that would be considered meaningful for that practical application.

In some embodiments, when a subject is identified as having an increased risk of developing decreased bone mineral density, the subject is treated with a therapeutic agent that treats or prevents decreased bone mineral density, and/or a KREMEN1 inhibitor, as described herein. For example, when the subject is KREMEN1 reference, and therefore has an increased risk of developing decreased bone mineral density, the subject is administered a KREMEN1 inhibitor. In some embodiments, such a subject is administered a therapeutic agent that treats or prevents decreased bone mineral density. In some embodiments, when the subject is heterozygous for a KREMEN1 variant nucleic acid molecule encoding a KREMEN1 predicted loss-of-function polypeptide, the subject is administered the therapeutic agent that treats or prevents decreased bone mineral density in a dosage amount that is the same as or less than a standard dosage amount, and is also administered a KREMEN1 inhibitor. In some embodiments, the subject is KREMEN1 reference. In some embodiments, the subject is heterozygous for a KREMEN1 variant nucleic acid molecule encoding a KREMEN1 predicted loss-of-function polypeptide. Furthermore, when the subject has a lower aggregate burden for having a KREMEN1 variant nucleic acid molecule encoding a KREMEN1 predicted loss-of-function polypeptide, and therefore has an increased risk of developing decreased bone mineral density, the subject is administered a therapeutic agent that treats or prevents decreased bone mineral density. In some embodiments, when the subject has a lower aggregate burden for having a KREMEN1 variant nucleic acid molecule encoding a KREMEN1 predicted loss-of-function polypeptide, the subject is administered the therapeutic agent that treats or prevents decreased bone mineral density in a dosage amount that is the same as or greater than the standard dosage amount administered to a subject who has a greater aggregate burden for having a KREMEN1 variant nucleic acid molecule encoding a KREMEN1 predicted loss-of-function polypeptide.

The present disclosure also provides methods of detecting the presence or absence of a KREMEN1 variant nucleic acid molecule (i.e., a genomic nucleic acid molecule, an mRNA molecule, or a cDNA molecule produced from an mRNA molecule) encoding a KREMEN1 predicted loss-of-function polypeptide in a biological sample from a subject. It is understood that gene sequences within a population and mRNA molecules encoded by such genes can vary due to polymorphisms such as single-nucleotide polymorphisms. The sequences provided herein for the KREMEN1 variant genomic nucleic acid molecule, KREMEN1 variant mRNA molecule, and KREMEN1 variant cDNA molecule are only exemplary sequences. Other sequences for the KREMEN1 variant genomic nucleic acid molecule, variant mRNA molecule, and variant cDNA molecule are also possible.

The biological sample can be derived from any cell, tissue, or biological fluid from the subject. The biological sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any KREMEN1 variant nucleic acid molecule encoding a KREMEN1 predicted loss-of-function polypeptide, preliminary processing designed to isolate or enrich the biological sample for the genomic DNA can be employed. A variety of techniques may be used for this purpose. When detecting the level of any KREMEN1 variant mRNA molecule, different techniques can be used enrich the biological sample with mRNA molecules. Various methods to detect the presence or level of an mRNA molecule or the presence of a particular variant genomic DNA locus can be used.

In some embodiments, detecting a KREMEN1 variant nucleic acid molecule encoding a KREMEN1 predicted loss-of-function polypeptide in a subject comprises performing a sequence analysis on a biological sample obtained from the subject to determine whether a KREMEN1 genomic nucleic acid molecule in the biological sample, and/or a KREMEN1 mRNA molecule in the biological sample, and/or a KREMEN1 cDNA molecule produced from an mRNA molecule in the biological sample, comprises one or more variations that cause a loss-of-function (partial or complete) or are predicted to cause a loss-of-function (partial or complete).

In some embodiments, the methods of detecting the presence or absence of a KREMEN1 variant nucleic acid molecule encoding a KREMEN1 predicted loss-of-function polypeptide (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence.

In some embodiments, the biological sample comprises a cell or cell lysate. Such methods can further comprise, for example, obtaining a biological sample from the subject comprising a KREMEN1 genomic nucleic acid molecule or mRNA molecule, and if mRNA, optionally reverse transcribing the mRNA into cDNA. Such assays can comprise, for example determining the identity of these positions of the particular KREMEN1 nucleic acid molecule. In some embodiments, the method is an in vitro method.

In some embodiments, the determining step, detecting step, or sequence analysis comprises sequencing at least a portion of the nucleotide sequence of the KREMEN1 genomic nucleic acid molecule, the KREMEN1 mRNA molecule, or the KREMEN1 cDNA molecule in the biological sample, wherein the sequenced portion comprises one or more variations that cause a loss-of-function (partial or complete) or are predicted to cause a loss-of-function (partial or complete).

In some embodiments, the assay comprises sequencing the entire nucleic acid molecule. In some embodiments, only a KREMEN1 genomic nucleic acid molecule is analyzed. In some embodiments, only a KREMEN1 mRNA is analyzed. In some embodiments, only a KREMEN1 cDNA obtained from KREMEN1 mRNA is analyzed.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay comprises contacting the biological sample with a primer or probe, such as an alteration-specific primer or alteration-specific probe, that specifically hybridizes to a KREMEN1 variant genomic sequence, variant mRNA sequence, or variant cDNA sequence and not the corresponding KREMEN1 reference sequence under stringent conditions, and determining whether hybridization has occurred.

In some embodiments, the determining step, detecting step, or sequence analysis comprises: a) amplifying at least a portion of the nucleic acid molecule that encodes the KREMEN1 polypeptide; b) labeling the amplified nucleic acid molecule with a detectable label; c) contacting the labeled nucleic acid molecule with a support comprising an alteration-specific probe; and d) detecting the detectable label.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a KREMEN1 variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to KREMEN1 variant nucleic acid molecules (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to KREMEN1 variant genomic nucleic acid molecules, KREMEN1 variant mRNA molecules, and/or KREMEN1 variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the KREMEN1 variant genomic nucleic acid molecules, KREMEN1 variant mRNA molecules, and/or KREMEN1 variant cDNA molecules disclosed herein. The primers described herein can be used to amplify KREMEN1 variant genomic nucleic acid molecules, KREMEN1 variant mRNA molecules, or KREMEN1 variant cDNA molecules, or a fragment thereof.

In the context of the disclosure "specifically hybridizes" means that the probe or primer (such as, for example, the alteration-specific probe or alteration-specific primer) does not hybridize to a nucleic acid sequence encoding a KREMEN1 reference genomic nucleic acid molecule, a KREMEN1 reference mRNA molecule, and/or a KREMEN1 reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The nucleotide sequence of a KREMEN1 reference genomic nucleic acid molecule is set forth in SEQ ID NO:1 (ENSG00000183762.13; ENST00000327813.9; chr22:29073118-29168333 in the GRCh38/hg38 human genome assembly; alternately, chr22:29073035-29168333 or chr22:29073077-29168333).

The nucleotide sequence of a KREMEN1 reference mRNA molecule is set forth in SEQ ID NO:2. The nucleotide sequence of another KREMEN1 reference mRNA molecule is set forth in SEQ ID NO:3. The nucleotide sequence of another KREMEN1 reference mRNA molecule is set forth in SEQ ID NO:4. The nucleotide sequence of another KREMEN1 reference mRNA molecule is set forth in SEQ ID NO:5. The nucleotide sequence of another KREMEN1 reference mRNA molecule is set forth in SEQ ID NO:6. The nucleotide sequence of another KREMEN1 reference mRNA molecule is set forth in SEQ ID NO:7.

The nucleotide sequence of a KREMEN1 reference cDNA molecule is set forth in SEQ ID NO:8. The nucleotide sequence of another KREMEN1 reference cDNA molecule is set forth in SEQ ID NO:9. The nucleotide sequence of another KREMEN1 reference cDNA molecule is set forth in SEQ ID NO:10. The nucleotide sequence of another KREMEN1 reference cDNA molecule is set forth in SEQ ID NO:11. The nucleotide sequence of another KREMEN1 reference cDNA molecule is set forth in SEQ ID NO:12. The nucleotide sequence of another KREMEN1 reference cDNA molecule is set forth in SEQ ID NO:13.

The amino acid sequence of a KREMEN1 reference polypeptide is set forth in SEQ ID NO:14, and is 492 amino acids in length. The nucleotide sequence of another KREMEN1 reference polypeptide is set forth in SEQ ID NO:15, and is 458 amino acids in length. The nucleotide sequence of another KREMEN1 reference polypeptide is set forth in SEQ ID NO:16, and is 473 amino acids in length.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The isolated nucleic acid molecules, or the complement thereof, can also be present within a host cell. In some embodiments, the host cell can comprise the vector that comprises any of the nucleic acid molecules described herein, or the complement thereof. In some embodiments, the nucleic acid molecule is operably linked to a promoter active in the host cell. In some embodiments, the promoter is an exogenous promoter. In some embodiments, the promoter is an inducible promoter. In some embodiments, the host cell is a bacterial cell, a yeast cell, an insect cell, or a mammalian cell. In some embodiments, the host cell is a bacterial cell. In some embodiments, the host cell is a yeast cell. In some embodiments, the host cell is an insect cell. In some embodiments, the host cell is a mammalian cell.

The disclosed nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $—O[(CH_2)_nO]_mCH_3$, $—O(CH_2)_nOCH_3$, $—O(CH_2)_nNH_2$, $—O(CH_2)_nCH_3$, $—O(CH_2)_n—ONH_2$, and $—O(CH_2)_nON[(CH_2)_nCH_3)]_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

Desired regulatory sequences for mammalian host cell expression can include, for example, viral elements that direct high levels of polypeptide expression in mammalian cells, such as promoters and/or enhancers derived from retroviral LTRs, cytomegalovirus (CMV) (such as, for example, CMV promoter/enhancer), Simian Virus 40 (SV40) (such as, for example, SV40 promoter/enhancer), adenovirus, (such as, for example, the adenovirus major late promoter (AdMLP)), polyoma and strong mammalian promoters such as native immunoglobulin and actin promoters. Methods of expressing polypeptides in bacterial cells or fungal cells (such as, for example, yeast cells) are also well known. A promoter can be, for example, a constitutively active promoter, a conditional promoter, an inducible promoter, a temporally restricted promoter (such as, for example, a developmentally regulated promoter), or a spatially restricted promoter (such as, for example, a cell-specific or tissue-specific promoter).

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat or prevent decreased bone mineral density for use in the treatment or prevention of decreased bone mineral density in a subject having: a KREMEN1 variant genomic nucleic acid molecule encoding a KREMEN1 predicted loss-of-function polypeptide; a KREMEN1 variant mRNA molecule encoding a KREMEN1 predicted loss-of-function polypeptide; or a KREMEN1 variant cDNA molecule encoding a KREMEN1 predicted loss-of-function polypeptide. Any of the therapeutic agents that treat or prevent decreased bone mineral density described herein can be used in these methods. The subject can have or have a risk of developing decreased bone mineral density, osteopenia, Type I osteoporosis, Type II osteoporosis, or secondary osteoporosis.

The present disclosure also provides uses of therapeutic agents that treat or prevent decreased bone mineral density for use in the preparation of a medicament for treating or preventing decreased bone mineral density in a subject having: a KREMEN1 variant genomic nucleic acid molecule encoding a KREMEN1 predicted loss-of-function polypeptide; a KREMEN1 variant mRNA molecule encoding a KREMEN1 predicted loss-of-function polypeptide; or a KREMEN1 variant cDNA molecule encoding a KREMEN1 predicted loss-of-function polypeptide. Any of the therapeutic agents that treat or prevent decreased bone mineral density described herein can be used in these methods. The subject can have or have a risk of developing decreased bone mineral density, osteopenia, Type I osteoporosis, Type II osteoporosis, or secondary osteoporosis.

The present disclosure also provides KREMEN1 inhibitors for use in the treatment or prevention of decreased bone mineral density in a subject that: a) is reference for a KREMEN1 genomic nucleic acid molecule, a KREMEN1 mRNA molecule, or a KREMEN1 cDNA molecule; or b) is heterozygous for: i) a KREMEN1 variant genomic nucleic acid molecule encoding a KREMEN1 predicted loss-of-function polypeptide; ii) a KREMEN1 variant mRNA molecule encoding a KREMEN1 predicted loss-of-function polypeptide; or iii) a KREMEN1 variant cDNA molecule encoding a KREMEN1 predicted loss-of-function polypeptide. Any of the KREMEN1 inhibitors described herein can be used in these methods. The subject can have or have a risk of developing decreased bone mineral density, osteopenia, Type I osteoporosis, Type II osteoporosis, or secondary osteoporosis.

The present disclosure also provides uses of KREMEN1 inhibitors in the preparation of a medicament for treating or preventing decreased bone mineral density in a subject that: a) is reference for a KREMEN1 genomic nucleic acid molecule, a KREMEN1 mRNA molecule, or a KREMEN1 cDNA molecule; or b) is heterozygous for: i) a KREMEN1 variant genomic nucleic acid molecule encoding a KREMEN1 predicted loss-of-function polypeptide; ii) a KREMEN1 variant mRNA molecule encoding a KREMEN1 predicted loss-of-function polypeptide; or iii) a KREMEN1 variant cDNA molecule encoding a KREMEN1 predicted loss-of-function polypeptide. Any of the KREMEN1 inhibitors described herein can be used in these methods. The subject can have or have a risk of developing decreased bone mineral density, osteopenia, Type I osteoporosis, Type II osteoporosis, or secondary osteoporosis.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: General Methodology

Cohort Description

The United Kingdom (UK) Biobank (UKB) is a population-based cohort of individuals aged between 40 to 69 years at baseline and recruited via 22 testing centers in the UK between 2006-2010 (Bycroft et al., Nature, 2018, 562, 203-209). Genetic and phenotypic data from close to 420,000 European-ancestry participants in UKB was used. This study was approved by relevant ethics committees and participants provided informed consent for participation in UKB.

Phenotype Definition

Data pertaining to quantitative ultrasound of the heel were extracted from UKB. eBMD trait values (in g/cm$^2$) were derived using a combination of speed of sound (SOS) and bone ultrasound attenuation (BUA; eBMD=0.002592×(BUA+SOS)−3.687). Sex-specific quality control measures were implemented for SOS (subjects were excluded if SOS ≤1,450 or ≥1,700 m/s for men, ≤1,455 or ≥1,700 m/s for women), BUA (exclude if BUA ≤27 or ≥138 dB/MHz for men, ≤22 or ≥138 dB/MHz for women), and eBMD (exclude if 0.18 or 1.06 g/cm$^2$ for men, ≤0.12 or ≥1.025 g/cm$^2$ for women). Phenotypic values for eBMD were first transformed using rank-based inverse normal transformation, applied within each ancestry group and separately in men and women, and adjusted for fine-mapped common (MAF>=0.01) genetic variants associated with eBMD.

Genotype Data

High coverage whole exome sequencing was performed as previously described (Dewey et al., Science, 2016, 354, 6319:aaf6814; and Van Hout et al., Nature, 2020, 586, 749-756) and as summarized below. A modified version of the xGen design available from Integrated DNA Technologies (IDT) was used for target sequence capture of the exome. A unique 10 bp barcode (IDT) was added to each DNA fragment during library preparation to facilitate multiplexed exome capture and sequencing. Equal amounts of sample were pooled prior to exome capture. Sequencing was performed using 75 bp paired-end reads on Illumina NovaSeq instruments. Sequencing had a coverage depth (i.e., number of sequence-reads covering each nucleotide in the target areas of the genome) sufficient to provide greater than 20× coverage over 90% of targeted bases in 99% of IDT samples. Data processing steps included sample de-multiplexing using Illumina software, alignment to the GRCh38 Human Genome reference sequence including generation of binary alignment and mapping files (BAM), processing of BAM files (e.g., marking of duplicate reads and other read mapping evaluations). Variant calling was performed using the GLNexus system (Lin et al., bioRxiv, 2018, 343970). Variant mapping and annotation were based on the GRCh38 Human Genome reference sequence and Ensembl v85 gene definitions using the snpEff software. The snpEff predictions that involve protein-coding transcripts with an annotated start and stop were then combined into a single functional impact prediction by selecting the most deleterious functional effect class for each gene. The hierarchy (from most to least deleterious) for these annotations was frameshift, stop-gain, stop-loss, splice acceptor, splice donor, stop-lost, in-frame indel, missense, other annotations. Predicted LoF genetic variants included: a) insertions or deletions resulting in a frameshift, b) insertions, deletions or single nucleotide variants resulting in the introduction of a premature stop codon or in the loss of the transcription start site or stop site, and c) variants in donor or acceptor splice sites. Missense variants were classified for likely functional impact according to the number of in silico prediction algorithms that predicted deleteriousness using SIFT (Vaser et al., Nature Protocols, 2016, 11, 1-9), Polyphen2_HDIV and Polyphen2_HVAR (Adzhubei et al., Nat. Methods, 2010, 7, 248-249), LRT (Chun et al., Genome Res., 2009, 19, 1553-1561) and MutationTaster (Schwarz et al., Nat. Methods, 2010, 7, 575-576). For each gene, the alternative allele frequency (AAF) and functional annotation of each variant determined inclusion into 7 gene burden exposures: 1) pLoF variants with AAF <1%; 2) pLoF or missense variants predicted deleterious by 5/5 algorithms with AAF <1%; 3) pLoF or missense variants predicted deleterious by 5/5 algorithms with AAF <0.1%; 4) pLoF or missense variants predicted deleterious by at least ⅕ algorithms with AAF <1%; 5) pLoF or missense variants predicted deleterious by at least ⅕ algorithms with AAF <0.1%; 6) pLoF or any missense with AAF <1%; 7) pLoF or any missense variants with AAF <0.1%. The results described elsewhere in this document as pertaining to "pLoF or predicted deleterious missense variants" refer to analysis performed using the aggregate burden of pLoF variants or missense variants predicted to by deleterious by 5/5 algorithms.

Association Analysis of Gene Burden of Rare pLoF and Missense Variation in KREMEN1

Association between the burden of rare pLoF or missense variants in a given gene and eBMD was examined by fitting a linear regression model adjusted for a polygenic score that approximates a genomic kinship matrix, using REGENIE v1.0 (Mbatchou et al., Nature Genetics, 2021). Analyses were adjusted for age, age$^2$, sex, age-by-sex and age$^2$-by-sex interaction terms, experimental batch-related covariates, ten common variant-derived principal components, and twenty rare variant-derived principal components. Association analyses were performed using single variants, and using gene burden tests. In gene burden tests, all individuals are labelled as heterozygotes if they carry one or more qualifying rare variant (as described above based on frequency and functional annotation) and as homozygotes if they carry any qualifying variant in the homozygous state. This "composite genotype" is then used to test for association.

Example 2: Loss-of-Function of KREMEN1 is Associated with Higher Estimated Bone Mineral Density Whole exome sequencing of 419,737 European-ancestry individuals in the UK Biobank (UKB) was performed to identify protein-coding variants in each gene in the genome. The association of each sequenced gene and genetic variant with estimated bone mineral density (eBMD, measured using ultrasound of the heel) was examined. eBMD is a commonly used biomarker of bone density and strength, and is highly correlated with bone mineral density as measured using dual-energy X-ray absorptiometry (DXA) technology. Lower levels of bone density are strongly associated with a higher risk of osteoporotic fractures.

The exome-wide analysis in UKB found that the burden of rare (alternative allele frequency [AAF]<1%) predicted loss-of-function (pLoF) or predicted deleterious missense variants (with predicted deleteriousness for missense variants based on agreement between five in silico prediction algorithms) in the KREMEN1 gene was associated with 0.13 standard deviation units (or 0.015 g/cm$^2$ units) higher eBMD (P-value=$2.1\times10^{-7}$, meeting a Bonferroni-corrected, exome-wide statistical significance threshold of P<$3.6\times10^{-7}$ (correction for 20,000 genes and seven variant aggregation models at an alpha of 0.05)) (see, FIG. 1).

A nominally significant association was observed between the aggregate burden of KREMEN1 pLoF variants only (excluding missense variants) and higher eBMD (see, FIG. 2). The effect estimate for the burden of pLoF variants (0.18 SD or 0.022 g/cm$^2$ higher eBMD per KREMEN1 allele copy, as shown in FIG. 2) was similar to the effect of the burden of pLoF or predicted deleterious missense variants (0.13 SD or 0.015 g/$cm^2$ higher eBMD per KREMEN1 allele copy, as shown in FIG. 1). This suggests that most of the missense variants included in the analysis result in KREMEN1 loss-of-function, and that the association with higher eBMD can be attributed to KREMEN1 loss-of-function.

FIG. 3 shows all pLoF and predicted deleterious missense variants included in the KREMEN1 gene burden analyses of eBMD.

Example 3: Converging Evidence from Exome Sequencing and Common Variants Implicates KREMEN1 for Osteoporosis UKB Cohort From within the UKB, a total of 291,932 participants (278,807 of European ancestry and 13,125 of African, East-Asian, or South Asian ancestry) with available whole-exome sequencing and eBMD data were included in the analyses.

Whole Exome Sequencing in UKB

Sample preparation and sequencing of the UKB samples were performed and briefly summarized below. A modified version of the xGen exome design available from Integrated DNA Technologies was used for target DNA capture. Sequencing was performed using 75 bp paired-end reads on Illumina NovaSeq instruments. Sequencing had a coverage depth sufficient to provide greater than 20× coverage over 90% of targeted bases in 99% of samples. Variant calling and annotation were based on the GRCh38 Human Genome reference sequence and Ensembl v85 gene definitions using the snpEff software. Variants were annotated according to the most deleterious functional effect in this order (of descending deleteriousness): frameshift, stop-gain, stop-loss, splice acceptor, splice donor, in-frame indel, missense, other annotations. Predicted LOF variants included: a) insertions or deletions resulting in a frameshift, b) insertions, deletions or single nucleotide variants resulting in the introduction of a premature stop codon or in the loss of the transcription start site or stop site, and c) variants in donor or acceptor splice sites. Missense variants were classified for predicted functional impact using a number of in silico prediction algorithms that predicted deleteriousness (SIFT, PolyPhen2 (HDIV), PolyPhen2 (HVAR), LRT, and MutationTaster). For each gene, the alternative allele frequency (AAF) and functional annotation of each variant determined inclusion into seven gene burden exposures as previously described (Akbari et al., 2021, Science 373, eabf8683): 1) pLOF variants with AAF <1%; 2) pLOF or missense variants predicted deleterious by 5/5 algorithms with AAF <1%; 3) pLOF or missense variants predicted deleterious by 5/5 algorithms with AAF <0.1%; 4) pLOF or missense variants predicted deleterious by at least ⅕ algorithms with AAF <1%; 5) pLOF or missense variants predicted deleterious by at least ⅕ algorithms with AAF <0.1%; 6) pLOF or any missense with AAF <1%; 7) pLOF or any missense variants with AAF <0.1%. SNP array genotyping and imputation was performed in the UKB as previously described.

Phenotype Definition in UKB eBMD of the heel was derived from quantitative ultrasound SOS and broadband ultrasound attenuation using a previously described model (Morris et al., Nat. Genet., 2018, 51, 258-66). An in-depth data curation pipeline yielded high quality eBMD data while maximizing the number of participants compared to using direct bone-densitometry of the heel reported in UKB as reported in a previous study. eBMD is used as a surrogate of bone mineral density (BMD) because of eBMD's high correlation with dual-energy X-ray absorptiometry (DXA)-derived BMD (Pearson's correlation r=0.69) and eBMD's strong association with risk of osteoporotic fracture. Before analysis, rank-inverse normal transformation of the eBMD phenotype, by sex and within each ancestry, was performed.

Exome-Wide Association Analyses in UKB

The association of genetic variants or their gene burden with eBMD by fitting mixed-effects regression models using REGENIE v1.0.6.8 was estimated. REGENIE accounts for relatedness, polygenicity, and population structure by approximating the genomic kinship matrix using predictions of individual trait values that are based on genotypes from across the genome. Then, the association of genetic variants or their burden is estimated conditional upon that polygenic predictor along with other covariates. Covariates in association models included age, $age^2$, sex, age-by-sex interaction term, $age^2$-by-sex interaction term, experimental batch-related covariates, ten common-variant derived principal components, and twenty rare-variant derived principal components. To ensure that rare coding variant or gene-burden associations were statistically independent of eBMD-associated common genetic variants, exome association analyses for sentinel common variants (MAF ≥1%) identified by fine-mapping genome-wide associations of common alleles with eBMD were further adjusted as previously described (Akbari et al., 2021, Science 373, eabf8683). Meta-analysis between subgroup results were performed using fixed-effect inverse-variance weighted models. The exome-wide level of statistical significance for the gene burden analysis was defined as $p<3.6\times10^{-7}$, a Bonferroni correction at the type I error rate of 0.05 which assumes 20,000 genes and accounts for the seven variant selection models used per gene (Akbari et al., 2021, Science 373, eabf8683). In a secondary analysis, the association with eBMD of individual nonsynonymous and/or pLOF variants (minor allele frequency <1% and minor allele count ≥25) identified by exome sequencing was estimated. The threshold of $p<5\times10^{-8}$, which is a Bonferroni correction based on one million effective number of independent tests at the type I error rate of 0.05, was used to identify exome-wide significant single variants as described (Akbari et al., 2021, Science 373, eabf8683).

For all secondary analyses involving false discovery rate (FDR)-corrected results, FDR-adjusted p-values were obtained by first preselecting for each gene and each gene-burden exposures with the strongest associations (lowest p value) and then correcting for multiple testing using the Benjamini-Hochberg approach across all genes in this subset. Hence, the reported FDR threshold of 1% (corresponding to an unadjusted p-value threshold of $1.49\times10^{-5}$) is applied to 18,866 genes, after selection of the best gene-burden exposure per gene. This translates to an FDR threshold of 2.05%, if the FDR correction had been applied to the overall analysis, and not a preselected subset.

Fine-Mapping of GWAS Common Variants eBMD-associated common variants were identified by performing a genome-wide association study based on imputed genetic variants. Imputation was based on the HRC reference panel supplemented with UK10K. Genome-wide association analyses were performed in the UKB by fitting mixed-effects linear regression models using REGENIE v1.0.6.8. Within each ancestry, fine-mapping was performed using the FINEMAP software at genomic regions harboring genetic variants associated with eBMD at the genome-wide significance threshold of $p<5\times10^{-8}$. Linkage disequilibrium was estimated using genetic data from the exact set of individuals included in each ancestry-specific genome-wide association analyses.

Test of Association with Fracture and Osteoporosis

The association with fracture and osteoporosis in UK Biobank was tested for genes that met the exome-wide level of statistical significance in the gene burden analysis of eBMD. Fracture cases were defined as individuals with a history of electronic health record-coded or self-reported fracture (not including, where possible, fractures of the skull, facial bones, hands, or toes), and individuals with a history of any type of fracture were excluded from the control group. Osteoporosis cases were defined as individuals with a history of electronic health record-coded or self-reported osteoporosis. Individuals with a self-reported history of osteopaenia were further excluded from the control group.

Test of Enrichment for Positive Control Genes for Osteoporosis

To evaluate the ability of WES to detect effector genes for osteoporosis, a set of positive control genes for this disease was identified. Fifty-six protein coding genes which are either known drug targets for osteoporosis or whose perturbation causes a Mendelian form of osteoporosis or bone mass disease, resulting in changes to bone density, bone mineralization or bone mass, were included as positive control genes (Morris et al., Nat. Genet., 2018, 51, 258-66). A Fisher's test was used to estimate the enrichment for positive control genes among the exome-wide significant genes in the gene burden analysis.

Effector Index for eBMD Effector Genes

The development of Effector index (Ei) was recently described (Forgetta et al., Hum. Genet., 2022, (world wide web "doi.org/10.1007/s00439-022-02434-z"). A goal of the Ei is to generate a probability of causality for each protein coding gene at a genome-wide association study (GWAS) locus, assigning a score from zero to one. GWAS loci were defined by 500 kb around the lead GWAS SNP following linkage disequilibrium (LD) clumping (Forgetta et al., Hum. Genet., 2022, world wide web at "doi.org/10.1007/s00439-022-02434-z"). Protein coding genes with at least 50% of their gene body located in a GWAS locus were included, and overlapping GWAS loci were merged. In short, to generate Ei scores for eBMD, positive control genes for 12 diseases and traits (type 2 diabetes, low-density lipoprotein cholesterol level, adult height, calcium level, hypothyroidism, triglyceride level, eBMD, glucose level, red blood cell count systolic blood pressure, diastolic blood pressure, and direct bilirubin level) were selected. GWAS followed by fine-mapping was performed for each disease, and genomic annotations at GWAS loci were used as features to predict positive control genes. This was achieved by first training a gradient boosted trees algorithm (XGBoost) to generate the probability of causality for genes in GWAS loci for 11 diseases and traits (excluding eBMD), and then applying this trained algorithm to derive Ei scores from eBMD GWAS data. Generalized linear models implemented in R were used to assess the association of the Ei score with the odds of being an exome-wide significant gene. A further, complementary gene prioritization method called Polygenic Priority Score (PoPS) was used to identify effector genes for eBMD from GWAS data (Weeks et al., medRxiv, 2020, world wide web at "doi:10.1101/2020.09.08.20190561."

Test of Enrichment for Ei Prioritized Genes within Loci Identified Using Exome-Wide Gene-Burden Results for Osteoporosis 2×2 contingency tables were generated comparing genes prioritized by Ei to genes identified from the exome-wide analyses per locus. The data were then aggregated across these loci and tested for enrichment using a stratified Fisher's exact test approach. Estimation of the odds ratio and its confidence interval were then based on the conditional Maximum Likelihood Estimate and estimation of the exact confidence bounds using the tail approach for discrete distributions, respectively.

Two-Sample Mendelian Randomization

Two-sample Mendelian randomization (MR) analyses were performed to identify circulating proteins that influence eBMD. Two-sample MR uses genetic variants strongly and specifically associated with circulating protein levels (pQTLs) as instrumental variables to estimate the causal relationship between a given protein and an outcome (in this case eBMD). This approach is less affected by confounding and reverse causality than observational epidemiology biomarker studies. The MR framework is based on three main assumptions: First, the SNPs are robustly associated with the exposure. Second, the SNPs are not associated with factors that confound the relationship between the exposure and the outcome. Third, the SNPs have no effect on the outcome that is independent of the exposure (i.e. a lack of horizontal pleiotropy). Of these, the most challenging to assess is the third assumption since the biological mechanistic effect of SNPs on outcomes like eBMD is most often not known. However, in the case of circulating proteins, SNPs that are associated with the protein level and close to the gene that encodes the protein are more likely to have an effect via the protein level by influencing the transcription or translation of the gene into the protein. Such SNPs are called cis-SNPs and may help to reduce potential bias from horizontal pleiotropy.

To select genetic instruments for circulating proteins, summary-level data were used from two proteomic GWAS studies that both measured serum protein levels on the SOMAlogic platform. For the primary analysis, the INTERVAL study was used as a source of pQTL data, which included the measurement of 1,478 serum proteins in 3,301 individuals. In a replication analysis, the AGES study was used, which included measurement of 4,137 serum proteins in 3,200 individuals. Proteins were selected for inclusion in the analysis if the proteins had cis-acting associated SNPs ("cis-SNPs"), because such instruments may be less likely to be affected by horizontal pleiotropy (Swerdlow et al., Int. J. Epidemiol. 2016, 45, 1600-16). The cis-SNPs from INTERVAL were independent, genome-wide significant SNPs ($P<1.5\times10^{-11}$, the multiple-testing corrected genome-wide significance threshold previously adopted in INTERVAL) within 1 Mb of the transcription start site (TSS) of the gene encoding the protein. To select these cis-SNPs, PLINK and the 1000 Genomes Project European population reference panel (1KG EUR) were used to clump and select independent SNPs ($R^2<0.001$, distance 1000 kb) for each protein. The cis-SNPs from AGES were the sentinel cis-SNPs (genome-wide significant SNPs of $P<5\times10^{-8}$ and with the lowest P value for each protein) within 300 kb of the corresponding protein-coding gene (Milsson et al., Science, 2018, 1327, 1-12). The association of each cis-SNP with eBMD (i.e., the outcome in the MR analysis) was taken from a recent eBMD GWAS, including 426,824 white British individuals (Surakka et al., Nat. Commun., 2020, 11, 4093). Palindromic cis-SNPs with minor allele frequency (MAF)

>0.42 (as recommended by the TwoSampleMR R package) were removed prior to MR to prevent allele-mismatches. For cis-SNPs that were not present in the eBMD GWAS, SNPs with LD $R^2$>0.8 and with MAF <0.42 were selected as proxies. For the alignment of SNP proxies, MAF >0.3 was used as a threshold for removal of palindromic SNPs.

After matching of the cis-SNPs of proteins with eBMD GWAS and the removal of palindromic SNPs, 550 SOMAmer reagents (517 proteins) from INTERVAL (including 515 matching cis-SNPs and 59 LD-proxy cis-SNPs) and 749 circulating proteins from AGES (including 706 unique matching cis-SNPs, 41 LD-proxy cis-SNPs, and 2 cis-SNPs each for two proteins) were included in the MR analyses. Independent cis-pQTL data were selected from INTERVAL data ($p<1.5\times10^{-11}$).

MR analyses were performed using the TwoSampleMR package in R, using the Wald ratio ($\beta_{eBMD}/\beta_{protein}$) to estimate the effect of each circulating protein on eBMD. For any proteins with multiple independent cis-SNPs, the inverse variance weighted (IVW) method was used to meta-analyze their combined effects[64]. A Bonferroni correction was used to control for the number proteins tested in INTERVAL and AGES independently.

Results

Whole-exome sequencing was performed in nearly 300,000 people from the UK Biobank cohort (UKB and, for each gene in the genome, estimated associations with eBMD for the burden of rare nonsynonymous and/or pLOF variants. In the larger European ancestry subset of UKB (N=278,807), KREMEN1 was identified (p<3.6×10). This association did not arise from common genetic variants since these WES analyses were designed to be independent of eBMD-associated fine-mapped common alleles. An exome-wide multi-ancestry meta-analysis identified two additional genes (WNT5B and KREMEN1) at exome-wide significance (FIGS. 4 and 5), providing an exome-wide significant gene. Table 2 shows all variants in the KREMEN1 gene burden test that were observed in only one ancestry.

TABLE 2

| Ancestry | Genetic exposure, variant type; allele frequency cut-off in % | CPRA | RSID | AAF, fraction of 1 | Beta (95% CI) per allele in SD units of eBMD | Beta (95% CI) per allele in g/cm2 units of eBMD | p | Protein effect |
|---|---|---|---|---|---|---|---|---|
| EUR | pLOF plus deleterious missense (5/5); AAF < 0.1% | 22: 29121465: G:A | rs200023748 | 0.0002026 | 0.25 (0.081, 0.41) | 0.03 (0.0099, 0.05) | 3.39E−03 | p.Arg154Gln: p.Arg152Gln: p.Arg154Gln |
| EUR | pLOF plus deleterious missense (5/5); AAF < 0.1% | 22: 29125344: G:A | rs745457999 | 0.0001184 | 0.11 (−0.11, 0.32) | 0.013 (−0.013, 0.039) | 3.22E−01 | p.Glu187Lys: p.Glu185Lys: p.Glu187Lys |
| EUR | pLOF plus deleterious missense (5/5); AAF < 0.1% | 22: 29125417: G:T | rs369977022 | 9.15E−05 | 0.23 (−0.016, 0.47) | 0.028 (−0.0019, 0.057) | 6.64E−02 | |
| EUR | pLOF plus deleterious missense (5/5); AAF < 0.1% | 22: 29138713: G:A | rs201316832 | 8.61E−05 | −0.05 (−0.3, 0.2) | −0.0061 (−0.037, 0.025) | 6.97E−01 | p.Ala352Thr: p.Ala350Thr: p.Ala352Thr |
| EUR | pLOF plus deleterious missense (5/5); AAF < 0.1% | 22: 29125368: G:T | rs778844831 | 7.89E−05 | 0.059 (−0.2, 0.32) | 0.0071 (−0.025, 0.039) | 6.63E−01 | p.Asp195Tyr: p.Asp193Tyr: p.Asp195Tyr |
| EUR | pLOF plus deleterious missense (5/5); AAF < 0.1% | 22: 29125365: G:A | rs774154713 | 6.81E−05 | 0.38 (0.1, 0.67) | 0.047 (0.012, 0.081) | 8.00E−03 | p.Gly194Arg: p.Gly192Arg: p.Gly194Arg |
| EUR | pLOF plus deleterious missense (5/5); AAF < 0.1% | 22: 29138812: GC:G | rs780654165 | 6.10E−05 | 0.11 (−0.19, 0.41) | 0.014 (−0.023, 0.05) | 4.59E−01 | p.Ala383fs: p.Ala385fs |
| EUR | pLOF plus deleterious missense (5/5); AAF < 0.1% | 22: 29138753: GC:G | rs751192135 | 5.92E−05 | 0.14 (−0.17, 0.44) | 0.017 (−0.02, 0.054) | 3.72E−01 | p.Ser367fs: p.Ser365fs: p.Ser367fs |
| EUR | pLOF plus deleterious missense (5/5); AAF < 0.1% | 22: 29121464: C:T | rs377056181 | 4.66E−05 | 0.052 (−0.29, 0.39) | 0.0063 (−0.035, 0.048) | 7.66E−01 | p.Arg154Trp: p.Arg152Trp: p.Arg154Trp |

TABLE 2-continued

| Ancestry | Genetic exposure, variant type; allele frequency cut-off in % | CPRA | RSID | AAF, fraction of 1 | Beta (95% CI) per allele in SD units of eBMD | Beta (95% CI) per allele in g/cm2 units of eBMD | p | Protein effect |
|---|---|---|---|---|---|---|---|---|
| EUR | pLOF plus deleterious missense (5/5); AAF < 0.1% | 22: 29137540: C:T | rs971202099 | 2.51E−05 | 0.27 (−0.2, 0.74) | 0.033 (−0.024, 0.089) | 2.57E−01 | p.Thr277Ile: p.Thr275Ile: p.Thr277Ile |
| EUR | pLOF plus deleterious missense (5/5); AAF < 0.1% | 22: 29121372: G:T | rs768929560 | 2.51E−05 | 0.096 (−0.37, 0.56) | 0.012 (−0.045, 0.068) | 6.88E−01 | p.Gly123Val: p.Gly121Val: p.Gly123Val |
| EUR | pLOF plus deleterious missense (5/5); AAF < 0.1% | 22: 29125372: A:T | rs372602179 | 2.51E−05 | −0.058 (−0.52, 0.41) | −0.007 (−0.064, 0.05) | 8.08E−01 | p.His196Leu: p.His194Leu: p.His196Leu |
| EUR | pLOF plus deleterious missense (5/5); AAF < 0.1% | 22: 29125270: G:A | | 2.15E−05 | 0.05 (−0.45, 0.55) | 0.0061 (−0.055, 0.067) | 8.46E−01 | p.Gly162Glu: p.Gly160Glu: p.Gly162Glu |
| EUR | pLOF plus deleterious missense (5/5); AAF < 0.1% | 22: 29121359: C:A | rs1316057401 | 1.97E−05 | −0.31 (−0.83, 0.22) | −0.037 (−0.1, 0.027) | 2.53E−01 | p.Pro119Thr: p.Pro117Thr: p.Pro119Thr |
| EUR | pLOF plus deleterious missense (5/5); AAF < 0.1% | 22: 29098884: C:T | | 1.97E−05 | −0.094 (−0.62, 0.43) | −0.011 (−0.075, 0.052) | 7.27E−01 | p.Pro95Ser: p.Pro93Ser: p.Pro95Ser |
| EUR | pLOF plus deleterious missense (5/5); AAF < 0.1% | 22: 29137657: T:C | rs752867471 | 1.79E−05 | 0.89 (0.33, 1.4) | 0.11 (0.04, 0.17) | 1.67E−03 | p.Phe316Ser: p.Phe314Ser: p.Phe316Ser |
| EUR | pLOF plus deleterious missense (5/5); AAF < 0.1% | 22: 29138740: G:C | rs1374143255 | 1.79E−05 | 0.0068 (−0.55, 0.56) | 0.00083 (−0.066, 0.068) | 9.81E−01 | p.Val361Leu: p.Val359Leu: p.Val361Leu |
| EUR | pLOF plus deleterious missense (5/5); AAF < 0.1% | 22: 29125297: G:T | rs766694351 | 1.61E−05 | −0.16 (−0.74, 0.43) | −0.019 (−0.09, 0.052) | 5.97E−01 | p.Cys171Phe: p.Cys169Phe: p.Cys171Phe |
| EUR | pLOF plus deleterious missense (5/5); AAF < 0.1% | 22: 29125392: G:A | rs775655154 | 1.61E−05 | −0.032 (−0.61, 0.55) | −0.0039 (−0.074, 0.067) | 9.15E−01 | p.Asp203Asn: p.Asp201Asn: p.Asp203Asn |
| EUR | pLOF plus deleterious missense (5/5); AAF < 0.1% | 22: 29140311: C:T | | 1.43E−05 | −0.35 (−0.97, 0.26) | −0.043 (−0.12, 0.032) | 2.60E−01 | p.Leu385Phe: p.Leu400Phe: p.Leu402Phe |
| EUR | pLOF plus deleterious missense (5/5); AAF < 0.1% | 22: 29140294: A:G | rs765361896 | 1.43E−05 | 0.17 (−0.45, 0.79) | 0.021 (−0.054, 0.096) | 5.90E−01 | p.Tyr379Cys: p.Tyr394Cys: p.Tyr396Cys |
| EUR | pLOF plus deleterious missense (5/5); AAF < 0.1% | 22: 29140308: C:G | rs763307050 | 1.26E−05 | 0.61 (−0.049, 1.3) | 0.074 (−0.0059, 0.15) | 6.96E−02 | p.Leu384Val: p.Leu399Val: p.Leu401Val |
| EUR | pLOF plus deleterious missense (5/5); AAF < 0.1% | 22: 29167043: G:A | rs1350020628 | 1.26E−05 | 0.28 (−0.38, 0.94) | 0.034 (−0.046, 0.11) | 4.07E−01 | |

TABLE 2-continued

| Ancestry | Genetic exposure, variant type; allele frequency cut-off in % | CPRA | RSID | AAF, fraction of 1 | Beta (95% CI) per allele in SD units of eBMD | Beta (95% CI) per allele in g/cm2 units of eBMD | p | Protein effect |
|---|---|---|---|---|---|---|---|---|
| EUR | pLOF plus deleterious missense (5/5); AAF < 0.1% | 22: 29142018: T:G | rs1196930418 | 1.26E−05 | 0.12 (−0.54, 0.78) | 0.014 (−0.066, 0.094) | 7.28E−01 | p.Ile428Ser: p.Ile443Ser: p.Ile445Ser |
| EUR | pLOF plus deleterious missense (5/5); AAF < 0.1% | 22: 29098926: A:G | | 1.08E−05 | −0.18 (−0.9, 0.53) | −0.022 (−0.11, 0.064) | 6.11E−01 | p.Lys109Glu: p.Lys107Glu: p.Lys109Glu |
| EUR | pLOF plus deleterious missense (5/5); AAF < 0.1% | 22: 29098885: C:T | | 8.97E−06 | −0.41 (−1.2, 0.37) | −0.049 (−0.14, 0.045) | 3.07E−01 | p.Pro95Leu: p.Pro93Leu: p.Pro95Leu |
| EUR | pLOF plus deleterious missense (5/5); AAF < 0.1% | 22: 29098940: A:G | rs746388017 | 8.97E−06 | −0.28 (−1.1, 0.5) | −0.034 (−0.13, 0.061) | 4.85E−01 | p.Ile113Met: p.Ile111Met: p.Ile113Met |
| EUR | pLOF plus deleterious missense (5/5); AAF < 0.1% | 22: 29137539: ACC:A | | 7.17E−06 | 0.97 (0.098, 1.8) | 0.12 (0.012, 0.22) | 2.92E−02 | p.His278fs: p.His276fs: p.His278fs |
| EUR | pLOF plus deleterious missense (5/5); AAF < 0.1% | 22: 29098878: G:A | rs1237728918 | 7.17E−06 | 0.71 (−0.17, 1.6) | 0.086 (−0.02, 0.19) | 1.12E−01 | p.Val93Met: p.Val91Met: p.Val93Met |
| EUR | pLOF plus deleterious missense (5/5); AAF < 0.1% | 22: 29137404: T:C | rs754510885 | 7.17E−06 | 0.54 (−0.33, 1.4) | 0.066 (−0.04, 0.17) | 2.25E−01 | p.Phe232Leu: p.Phe230Leu: p.Phe232Leu |
| EUR | pLOF plus deleterious missense (5/5); AAF < 0.1% | 22: 29094276: G:A | rs776500404 | 7.17E−06 | −0.25 (−1.1, 0.62) | −0.03 (−0.14, 0.076) | 5.74E−01 | p.Gly39Asp: p.Gly37Asp: p.Gly39Asp |
| EUR | pLOF plus deleterious missense (5/5); AAF < 0.1% | 22: 29121416: A:G | rs377416427 | 5.38E−06 | 0.73 (−0.28, 1.7) | 0.088 (−0.034, 0.21) | 1.58E−01 | p.Ser138Gly: p.Ser136Gly: p.Ser138Gly |
| EUR | pLOF plus deleterious missense (5/5); AAF < 0.1% | 22: 29137671: C:T | | 5.38E−06 | 0.59 (−0.42, 1.6) | 0.072 (−0.051, 0.19) | 2.51E−01 | p.Gln321*: p.Gln319*: p.Gln321* |
| EUR | pLOF plus deleterious missense (5/5); AAF < 0.1% | 22: 29094342: A:G | | 5.38E−06 | −0.57 (−1.6, 0.44) | −0.069 (−0.19, 0.053) | 2.69E−01 | p.Asn61Ser: p.Asn59Ser: p.Asn61Ser |
| EUR | pLOF plus deleterious missense (5/5); AAF < 0.1% | 22: 29094396: G:T | rs777119022 | 5.38E−06 | 0.5 (−0.51, 1.5) | 0.061 (−0.062, 0.18) | 3.32E−01 | p.Gly79Val: p.Gly77Val: p.Gly79Val |
| EUR | pLOF plus deleterious missense (5/5); AAF < 0.1% | 22: 29094282: A:G | rs774706235 | 5.38E−06 | −0.47 (−1.5, 0.54) | −0.057 (−0.18, 0.066) | 3.64E−01 | p.Asp41Gly: p.Asp39Gly: p.Asp41Gly |
| EUR | pLOF plus deleterious missense (5/5); AAF < 0.1% | 22: 29138723: C:T | | 5.38E−06 | 0.37 (−0.64, 1.4) | 0.045 (−0.078, 0.17) | 4.75E−01 | p.Ser355Phe: p.Ser353Phe: p.Ser355Phe |

TABLE 2-continued

| Ancestry | Genetic exposure, variant type; allele frequency cut-off in % | CPRA | RSID | AAF, fraction of 1 | Beta (95% CI) per allele in SD units of eBMD | Beta (95% CI) per allele in g/cm2 units of eBMD | p | Protein effect |
|---|---|---|---|---|---|---|---|---|
| EUR | pLOF plus deleterious missense (5/5); AAF < 0.1% | 22: 29137557: C:T | rs764867793 | 3.59E−06 | 1.2 (−0.032, 2.4) | 0.15 (−0.0038, 0.3) | 5.62E−02 | p.Arg283Cys: p.Arg281Cys: p.Arg283Cys |
| EUR | pLOF plus deleterious missense (5/5); AAF < 0.1% | 22: 29138716: G:T | rs769585716 | 3.59E−06 | 0.87 (−0.37, 2.1) | 0.11 (−0.045, 0.25) | 1.69E−01 | p.Ala353Ser: p.Ala351Ser: p.Ala353Ser |
| EUR | pLOF plus deleterious missense (5/5); AAF < 0.1% | 22: 29137654: G:A | | 3.59E−06 | 0.77 (−0.47, 2) | 0.093 (−0.056, 0.24) | 2.22E−01 | p.Gly315Glu: p.Gly313Glu: p.Gly315Glu |
| EUR | pLOF plus deleterious missense (5/5); AAF < 0.1% | 22: 29094270: C:A | | 3.59E−06 | −0.69 (−1.9, 0.55) | −0.083 (−0.23, 0.067) | 2.76E−01 | p.Ala37Asp: p.Ala35Asp: p.Ala37Asp |
| EUR | pLOF plus deleterious missense (5/5); AAF < 0.1% | 22: 29094267: C:T | rs1399637574 | 3.59E−06 | 0.65 (−0.58, 1.9) | 0.079 (−0.071, 0.23) | 3.00E−01 | p.Thr36Ile: p.Thr34Ile: p.Thr36Ile |
| EUR | pLOF plus deleterious missense (5/5); AAF < 0.1% | 22: 29138806: ATGGGGGCT: A | rs1211200038 | 3.59E−06 | −0.65 (−1.9, 0.59) | −0.078 (−0.23, 0.071) | 3.05E−01 | p.Met381fs: p.Met383fs |
| EUR | pLOF plus deleterious missense (5/5); AAF < 0.1% | 22:291 38818: A:AT | | 3.59E−06 | −0.65 (−1.9, 0.59) | −0.078 (−0.23, 0.071) | 3.05E−01 | p.Ser385fs: p.Ser387fs |
| EUR | pLOF plus deleterious missense (5/5); AAF < 0.1% | 22: 29138623: G:A | rs750903841 | 3.59E−06 | −0.46 (−1.7, 0.78) | −0.056 (−0.21, 0.094) | 4.68E−01 | |
| EUR | pLOF plus deleterious missense (5/5); AAF < 0.1% | 22: 29137559: CT:C | | 3.59E−06 | −0.45 (−1.7, 0.79) | −0.054 (−0.2, 0.096) | 4.79E−01 | p.Phe284fs: p.Phe282fs: p.Phe284fs |
| EUR | pLOF plus deleterious missense (5/5); AAF < 0.1% | 22: 29121450: G:A | rs1250219980 | 3.59E−06 | 0.39 (−0.85, 1.6) | 0.047 (−0.1, 0.2) | 5.37E−01 | p.Cys149Tyr: p.Cys147Tyr: p.Cys149Tyr |
| AFR | pLOF plus deleterious missense (5/5); AAF < 0.1% | 22: 29137398: C:T | rs1484654267 | 0.0001957 | −0.31 (−1.6, 1) | −0.037 (−0.2, 0.12) | 6.49E−01 | p.Pro230Ser: p.Pro228Ser: p.Pro230Ser |
| EUR | pLOF plus deleterious missense (5/5); AAF < 0.1% | 22: 29137600: C:T | | 3.59E−06 | −0.26 (−1.5, 0.97) | −0.032 (−0.18, 0.12) | 6.78E−01 | p.Ser297Phe: p.Ser295Phe: p.Ser297Phe |
| EUR | pLOF plus deleterious missense (5/5); AAF < 0.1% | 22: 29121444: A:T | | 3.59E−06 | −0.24 (−1.5, 1) | −0.029 (−0.18, 0.12) | 7.05E−01 | p.Gln147Leu: p.Gln145Leu: p.Gln147Leu |
| EUR | pLOF plus deleterious missense (5/5); AAF < 0.1% | 22: 29098869: G:C | rs1326783697 | 3.59E−06 | 0.23 (−1, 1.5) | 0.028 (−0.12, 0.18) | 7.11E−01 | p.Asp90His: p.Asp88His: p.Asp90His |

TABLE 2-continued

| Ancestry | Genetic exposure, variant type; allele frequency cut-off in % | CPRA | RSID | AAF, fraction of 1 | Beta (95% CI) per allele in SD units of eBMD | Beta (95% CI) per allele in g/cm2 units of eBMD | p | Protein effect |
|---|---|---|---|---|---|---|---|---|
| EUR | pLOF plus deleterious missense (5/5); AAF < 0.1% | 22: 29141987: C:T | | 3.59E−06 | 0.21 (−1, 1.4) | 0.025 (−0.12, 0.17) | 7.44E−01 | p.Gln418*: p.Gln433*: p.Gln435* |
| EUR | pLOF plus deleterious missense (5/5); AAF < 0.1% | 22: 29073134: G: GCGCCGCC | | 3.59E−06 | −0.081 (−1.3, 1.2) | −0.0098 (−0.16, 0.14) | 8.98E−01 | p.Arg7fs: p.Arg7fs: p.Arg7fs |
| EUR | pLOF plus deleterious missense (5/5); AAF < 0.1% | 22: 29138687: C:T | rs558712379 | 3.59E−06 | −0.062 (−1.3, 1.2) | −0.0075 (−0.16, 0.14) | 9.22E−01 | p.Thr343Met: p.Thr341Met: p.Thr343Met |
| EUR | pLOF plus deleterious missense (5/5); AAF < 0.1% | 22:291 42019: T:G | | 3.59E−06 | −0.046 (−1.3, 1.2) | −0.0056 (−0.16, 0.14) | 9.42 E−01 | p.Ile428Met: p.Ile443Met: p.Ile445Met |
| EUR | pLOF plus deleterious missense (5/5); AAF < 0.1% | 22: 29167083: CA:C | | 3.59E−06 | 0.021 (−1.2, 1.3) | 0.0025 (−0.15, 0.15) | 9.74E−01 | p.Gln486fs |
| EUR | pLOF plus deleterious missense (5/5); AAF < 0.1% | 22: 29125296: TC | | 3.59E−06 | −0.014 (−1.2, 1.2) | −0.0018 (−0.15, 0.15) | 9.82E−01 | p.Cys171Arg: p.Cys169Arg: p.Cys171Arg |
| EUR | pLOF plus deleterious missense (5/5); AAF < 0.1% | 22: 29138738: A:G | rs766331382 | 1.79E−06 | 2.4 (0.62, 4.1) | 0.29 (0.075, 0.5) | 7.99E−03 | p.Tyr360Cys: p.Tyr358Cys: p.Tyr360Cys |
| AFR | pLOF plus deleterious missense (5/5); AAF < 0.1% | 22: 29138764: C:G | | 9.79E−05 | 2.2 (0.37, 4.1) | 0.27 (0.045, 0.5) | 1.91E−02 | p.Pro369Ala: p.Pro367Ala: p.Pro369Ala |
| EUR | pLOF plus deleterious missense (5/5); AAF < 0.1% | 22: 29140318: TCA:T | | 1.79E−06 | 2 (0.21, 3.7) | 0.24 (0.025, 0.45) | 2.83E−02 | p.Thr388fs: p.Thr403fs: p.Thr405fs |
| AFR | pLOF plus deleterious missense (5/5); AAF < 0.1% | 22: 29094420: G:A | | 9.79E−05 | 1.9 (0.015, 3.8) | 0.23 (0.0019, 0.46) | 4.81E−02 | p.Arg87Lys: p.Arg85Lys: p.Arg87Lys |
| EUR | pLOF plus deleterious missense (5/5); AAF < 0.1% | 22: 29121428: A:C | rs370491326 | 1.79E−06 | −1.6 (−3.4, 0.098) | −0.2 (−0.41, 0.012) | 6.43E−02 | p.Asn142His: p.Asn140His: p.Asn142His |
| EUR | pLOF plus deleterious missense (5/5); AAF < 0.1% | 22: 29121443: C:T | | 1.79E−06 | 1.6 (−0.19, 3.3) | 0.19 (−0.023, 0.4) | 8.03E−02 | p.Gln147*: p.Gln145*: p.Gln147* |
| EUR | pLOF plus deleterious missense (5/5); AAF < 0.1% | 22: 29073228: G:T | | 1.79E−06 | 1.6 (−0.2, 3.3) | 0.19 (−0.024, 0.4) | 8.18E−02 | |
| EUR | pLOF plus deleterious missense (5/5); AAF < 0.1% | 22: 29137521: G:A | rs1282517348 | 1.79E−06 | −1.5 (−3.2, 0.26) | −0.18 (−0.39, 0.031) | 9.48E−02 | p.Glu271Lys: p.Glu269Lys: p.Glu271Lys |

TABLE 2-continued

| Ancestry | Genetic exposure, variant type; allele frequency cut-off in % | CPRA | RSID | AAF, fraction of 1 | Beta (95% CI) per allele in SD units of eBMD | Beta (95% CI) per allele in g/cm2 units of eBMD | p | Protein effect |
|---|---|---|---|---|---|---|---|---|
| EUR | pLOF plus deleterious missense (5/5); AAF < 0.1% | 22: 29094391: G:C | | 1.79E−06 | 1.4 (−0.3, 3.2) | 0.18 (−0.036, 0.39) | 1.04E−01 | p.Glu77Asp: p.Glu75Asp: p.Glu77Asp |
| EUR | pLOF plus deleterious missense (5/5); AAF < 0.1% | 22: 29125383: TC | | 1.79E−06 | 1.4 (−0.3, 3.2) | 0.18 (−0.036, 0.39) | 1.04E−01 | p.Cys200Arg: p.Cys198Arg: p.Cys200Arg |
| EUR | pLOF plus deleterious missense (5/5); AAF < 0.1% | 22: 29140285: G:A | | 1.79E−06 | 1.2 (−0.54, 3) | 0.15 (−0.065, 0.36) | 1.75E−01 | p.Trp376*: p.Trp391*: p.Trp393* |
| EUR | pLOF plus deleterious missense (5/5); AAF < 0.1% | 22: 29121372: G:A | | 1.79E−06 | 1.2 (−0.54, 3) | 0.15 (−0.066, 0.36) | 1.76E−01 | p.Gly123Asp: p.Gly121Asp: p.Gly123Asp |
| EUR | pLOF plus deleterious missense (5/5); AAF < 0.1% | 22: 29125288: C:T | rs568747143 | 1.79E−06 | 1.2 (−0.56, 2.9) | 0.14 (−0.067, 0.36) | 1.82E−01 | p.Ala168Val: p.Ala166Val: p.Ala168Val |
| EUR | pLOF plus deleterious missense (5/5); AAF < 0.1% | 22: 29121371: G:C | | 1.79E−06 | 1.2 (−0.56, 2.9) | 0.14 (−0.068, 0.36) | 1.84E−01 | p.Gly123Arg: p.Gly121Arg: p.Gly123Arg |
| EUR | pLOF plus deleterious missense (5/5); AAF < 0.1% | 22: 29137351: G:A | | 1.79E−06 | 1.1 (−0.61, 2.9) | 0.14 (−0.073, 0.35) | 2.00E−01 | p.Gly214Asp: p.Gly212Asp: p.Gly214Asp |
| EUR | pLOF plus deleterious missense (5/5); AAF < 0.1% | 22: 29138770: C:T | | 1.79E−06 | 1.1 (−0.62, 2.9) | 0.14 (−0.075, 0.35) | 2.07E−01 | p.Gln371*: p.Gln369*: p.Gln371* |
| EUR | pLOF plus deleterious missense (5/5); AAF < 0.1% | 22: 29142029: C:G | rs140385700 | 1.79E−06 | −1.1 (−2.8, 0.69) | −0.13 (−0.34, 0.083) | 2.34E−01 | p.Pro432Ala: p.Pro447Ala: p.Pro449Ala |
| EUR | pLOF plus deleterious missense (5/5); AAF < 0.1% | 22: 29094354: A:G | rs1329701509 | 1.79E−06 | −1.1 (−2.8, 0.69) | −0.13 (−0.34, 0.084) | 2.36E−01 | p.Gln65Arg: p.Gln63Arg: p.Gln65Arg |
| EUR | pLOF plus deleterious missense (5/5); AAF < 0.1% | 22: 29121477: TC:T | | 1.79E−06 | 1.1 (−0.69, 2.8) | 0.13 (−0.084, 0.34) | 2.37E−01 | p.Phe158fs: p.Phe156fs: p.Phe158fs |
| EUR | pLOF plus deleterious missense (5/5); AAF < 0.1% | 22: 29073133: G:T | | 1.79E−06 | 0.99 (−0.76, 2.7) | 0.12 (−0.092, 0.33) | 2.68E−01 | p.Met1?: p.Met1?: p.Met1? |
| EUR | pLOF plus deleterious missense (5/5); AAF < 0.1% | 22: 29098866: C:A | rs763361689 | 1.79E−06 | 0.88 (−0.86, 2.6) | 0.11 (−0.1, 0.32) | 3.21E−01 | p.Pro89Thr: p.Pro87Thr: p.Pro89Thr |
| EUR | pLOF plus deleterious missense (5/5); AAF < 0.1% | 22: 29137492: T:G | rs759044199 | 1.79E−06 | 0.88 (−0.86, 2.6) | 0.11 (−0.1, 0.32) | 3.21E−01 | p.Phe261Cys: p.Phe259Cys: p.Phe261Cys |

TABLE 2-continued

| Ancestry | Genetic exposure, variant type; allele frequency cut-off in % | CPRA | RSID | AAF, fraction of 1 | Beta (95% CI) per allele in SD units of eBMD | Beta (95% CI) per allele in g/cm2 units of eBMD | p | Protein effect |
|---|---|---|---|---|---|---|---|---|
| EUR | pLOF plus deleterious missense (5/5); AAF < 0.1% | 22: 29098925: G:A | | 1.79E−06 | 0.87 (−0.88, 2.6) | 0.11 (−0.11, 0.32) | 3.28E−01 | p.Trp108*: p.Trp106*: p.Trp108* |
| EUR | pLOF plus deleterious missense (5/5); AAF < 0.1% | 22: 29121405: T:A | | 1.79E−06 | 0.85 (−0.9, 2.6) | 0.1 (−0.11, 0.32) | 3.40E−01 | p.Leu134Gln: p.Leu132Gln: p.Leu134Gln |
| EUR | pLOF plus deleterious missense (5/5); AAF < 0.1% | 22: 29094257: G:A | | 1.79E−06 | −0.82 (−2.6, 0.93) | −0.099 (−0.31, 0.11) | 3.58E−01 | |
| EUR | pLOF plus deleterious missense (5/5); AAF < 0.1% | 22: 29140320: A:C | | 1.79E−06 | −0.8 (−2.5, 0.95) | −0.096 (−0.31, 0.12) | 3.72E−01 | p.Thr388Pro: p.Thr403Pro: p.Thr405Pro |
| EUR | pLOF plus deleterious missense (5/5); AAF < 0.1% | 22: 29137340: A:G | | 1.79E−06 | 0.79 (−0.96, 2.5) | 0.096 (−0.12, 0.31) | 3.76E−01 | |
| EUR | pLOF plus deleterious missense (5/5); AAF < 0.1% | 22: 29094363: A:G | | 1.79E−06 | −0.77 (−2.5, 0.98) | −0.093 (−0.31, 0.12) | 3.89E−01 | p.Tyr68Cys: p.Tyr66Cys: p.Tyr68Cys |
| AFR | pLOF plus deleterious missense (5/5); AAF < 0.1% | 22:1 2937483: T:TC | | 9.79E−05 | −0.81 (−2.7, 1.1) | −0.098 (−0.33, 0.13) | 3.98E−01 | p.Leu260fs: p.Leu258fs: p.Leu260fs |
| EUR | pLOF plus deleterious missense (5/5); AAF < 0.1% | 22: 29138834: G:A | | 1.79E−06 | −0.74 (−2.5, 1) | −0.09 (−0.3, 0.12) | 4.05E−01 | |
| EAS | pLOF plus deleterious missense (5/5); AAF < 0.1% | 22: 29098903: A:G | | 0.0003592 | 0.69 (−1.1, 2.5) | 0.084 (−0.13, 0.3) | 4.46E−01 | p.Glu101Gly: p.Glu99Gly: p.Glu101Gly |
| EUR | pLOF plus deleterious missense (5/5); AAF < 0.1% | 22:291 25389: G:A | | 1.79E−06 | 0.59 (−1.2, 2.3) | 0.071 (−0.14, 0.28) | 5.10E−01 | p.Gly202Ser: p.Gly200Ser: p.Gly202Ser |
| EUR | pLOF plus deleterious missense (5/5); AAF < 0.1% | 22: 29137447: T:TCC | rs752591633 | 1.79E−06 | −0.58 (−2.3, 1.2) | −0.07 (−0.28, 0.14) | 5.17E−01 | p.Arg247fs: p.Arg245fs: p.Arg247fs |
| EAS | pLOF plus deleterious missense (5/5); AAF < 0.1% | 22: 29138691: GCAGGCCAAC CT:G | rs777458364 | 0.0003592 | 0.59 (−1.2, 2.4) | 0.071 (−0.15, 0.29) | 5.20E−01 | p.Ala346fs: p.Ala344fs: p.Ala346fs |
| EUR | pLOF plus deleterious missense (5/5); AAF < 0.1% | 22: 29167104: T:A | | 1.79E−06 | 0.53 (−1.2, 2.3) | 0.065 (−0.15, 0.28) | 5.49E−01 | p.Ter493Argext*2 |
| EUR | pLOF plus deleterious missense (5/5); AAF < 0.1% | 22: 29121359: C:T | | 1.79E−06 | −0.53 (−2.3, 1.2) | −0.064 (−0.28, 0.15) | 5.54E−01 | p.Pro119Ser: p.Pro117Ser: p.Pro119Ser |

TABLE 2-continued

| Ancestry | Genetic exposure, variant type; allele frequency cut-off in % | CPRA | RSID | AAF, fraction of 1 | Beta (95% CI) per allele in SD units of eBMD | Beta (95% CI) per allele in g/cm2 units of eBMD | p | Protein effect |
|---|---|---|---|---|---|---|---|---|
| EUR | pLOF plus deleterious missense (5/5); AAF < 0.1% | 22: 29138753: G:T | | 1.79E−06 | −0.5 (−2.2, 1.3) | −0.06 (−0.27, 0.15) | 5.78E−01 | p.Ser365Ile: p.Ser363Ile: p.Ser365Ile |
| EUR | pLOF plus deleterious missense (5/5); AAF < 0.1% | 22: 29094348: CTT:C | | 1.79E−06 | −0.49 (−2.2, 1.3) | −0.059 (−0.27, 0.15) | 5.83E−01 | p.Phe64fs: p.Phe62fs: p.Phe64fs |
| EUR | pLOF plus deleterious missense (5/5); AAF < 0.1% | 22: 29137417: A:G | rs777755270 | 1.79E−06 | −0.48 (−2.2, 1.3) | −0.058 (−0.27, 0.15) | 5.93E−01 | p.Tyr236Cys: p.Tyr234Cys: p.Tyr236Cys |
| EUR | pLOF plus deleterious missense (5/5); AAF < 0.1% | 22: 29125325: C:G | | 1.79E−06 | 0.46 (−1−3, 2.2) | 0.056 (−0.16, 0.27) | 6.03E−01 | p.Tyr180*: p.Tyr178*: p.Tyr180* |
| EUR | pLOF plus deleterious missense (5/5); AAF < 0.1% | 22: 29137495: A:C | | 1.79E−06 | 0.42 (−1−3, 2.2) | 0.051 (−0.16, 0.26) | 6.38E−01 | p.Asp262Ala: p.Asp260Ala: p.Asp262Ala |
| EUR | pLOF plus deleterious missense (5/5); AAF < 0.1% | 22: 29142029: C:A | rs140385700 | 1.79E−06 | −0.42 (−2.2, 1.3) | −0.051 (−0.26, 0.16) | 6.40E−01 | p.Pro432Thr: p.Pro447Thr: p.Pro449Thr |
| EUR | pLOF plus deleterious missense (5/5); AAF < 0.1% | 22: 29094328: AT:A | | 1.79E−06 | 0.39 (−1.4, 2.1) | 0.047 (−0.17, 0.26) | 6.65E−01 | p.Cys57fs: p.Cys55fs: p.Cys57fs |
| EUR | pLOF plus deleterious missense (5/5); AAF < 0.1% | 22: 29098922: C:A | | 1.79E−06 | −0.36 (−2.1, 1.4) | −0.044 (−0.26, 0.17) | 6.82E−01 | p.Tyr107*: p.Tyr105*: p.Tyr107* |
| EUR | pLOF plus deleterious missense (5/5); AAF < 0.1% | 22: 29140284: T:C | | 1.79E−06 | 0.36 (−1.4, 2.1) | 0.044 (−0.17, 0.26) | 6.84E−01 | p.Trp376Arg: p.Trp391Arg: p.Trp393Arg |
| EUR | pLOF plus deleterious missense (5/5); AAF < 0.1% | 22: 98893: 290TC | | 1.79E−06 | 0.36 (−1.4, 2.1) | 0.043 (−0.17, 0.26) | 6.89E−01 | p.Tyr98His: p.Tyr96His: p.Tyr98His |
| EUR | pLOF plus deleterious missense (5/5); AAF < 0.1% | 22: 29121482: G:C | | 1.79E−06 | −0.36 (−2.1, 1.4) | −0.043 (−0.25, 0.17) | 6.90E−01 | |
| EUR | pLOF plus deleterious missense (5/5); AAF < 0.1% | 22: 29098911: G:C | | 1.79E−06 | 0.34 (−1−4, 2.1) | 0.041 (−0.17, 0.25) | 7.07E−01 | p.Asp104His: p.Asp102His: p.Asp104His |
| EUR | pLOF plus deleterious missense (5/5); AAF < 0.1% | 22: 29094324: A:T | | 1.79E−06 | −0.33 (−2.1, 1.4) | −0.039 (−0.25, 0.17) | 7.15E−01 | p.Lys55Met: p.Lys53Met: p.Lys55Met |
| EAS | pLOF plus deleterious missense (5/5); AAF < 0.1% | 22: 29121358: G:T | rs780469996 | 0.0003592 | 0.32 (−1.5, 2.1) | 0.039 (−0.18, 0.26) | 7.24E−01 | p.Met118Ile: p.Met116Ile: p.Met118Ile |

TABLE 2-continued

| Ancestry | Genetic exposure, variant type; allele frequency cut-off in % | CPRA | RSID | AAF, fraction of 1 | Beta (95% CI) per allele in SD units of eBMD | Beta (95% CI) per allele in g/cm2 units of eBMD | p | Protein effect |
|---|---|---|---|---|---|---|---|---|
| SAS | pLOF plus deleterious missense (5/5); AAF < 0.1% | 22: 29098861: G:T | | 7.55E−05 | −0.32 (−2.2, 1.5) | −0.038 (−0.26, 0.19) | 7.38E−01 | |
| EUR | pLOF plus deleterious missense (5/5); AAF < 0.1% | 22: 29098866: C:G | | 1.79E−06 | −0.28 (−2, 1.5) | −0.034 (−0.25, 0.18) | 7.55E−01 | p.Pro89Ala: p.Pro87Ala: p.Pro89Ala |
| EUR | pLOF plus deleterious missense (5/5); AAF < 0.1% | 22: 29094282: A:T | | 1.79E−06 | 0.26 (−1.5, 2) | 0.032 (−0.18, 0.24) | 7.70E−01 | p.Asp41Val: p.Asp39Val: p.Asp41Val |
| EUR | pLOF plus deleterious missense (5/5); AAF < 0.1% | 22: 29094296: CAG:C | | 1.79E−06 | −0.25 (−2, 1.5) | −0.031 (−0.24, 0.18) | 7.76E−01 | p.Asn47fs: p.Asn45fs: p.Asn47fs |
| EUR | pLOF plus deleterious missense (5/5); AAF < 0.1% | 22: 29142017: A:AT | | 1.79E−06 | 0.24 (−1.5, 2) | 0.03 (−0.18, 0.24) | 7.84E−01 | p.Tyr430fs: p.Tyr445fs: p.Tyr447fs |
| EUR | pLOF plus deleterious missense (5/5); AAF < 0.1% | 22: 29138755: C:G | rs758662506 | 1.79E−06 | −0.24 (−2, 1.5) | −0.029 (−0.24, 0.18) | 7.90E−01 | p.Pro366Ala: p.Pro364Ala: p.Pro366Ala |
| EUR | pLOF plus deleterious missense (5/5); AAF < 0.1% | 22: 29125269: G:A | | 1.79E−06 | 0.23 (−1.5, 2) | 0.028 (−0.18, 0.24) | 7.96E−01 | p.Gly162Arg: p.Gly160Arg: p.Gly162Arg |
| AFR | pLOF plus deleterious missense (5/5); AAF < 0.1% | 22: 29098935: G:GA | | 9.79E−05 | 0.22 (−1.7, 2.1) | 0.027 (−0.2, 0.25) | 8.15E−01 | p.Ile113fs: p.Ile111fs: p.Ile113fs |
| EUR | pLOF plus deleterious missense (5/5); AAF < 0.1% | 22: 29142057: A:T | | 1.79E−06 | 0.19 (−1.6, 1.9) | 0.023 (−0.19, 0.24) | 8.28E−01 | p.Lys441Met: p.Lys456Met: p.Lys458Met |
| EAS | pLOF plus deleterious missense (5/5); AAF < 0.1% | 22: 29138796: G:A | rs1270896219 | 0.0003592 | 0.2 (−1.6, 2) | 0.024 (−0.19, 0.24) | 8.29E−01 | p.Trp377*: p.Trp379* |
| EUR | pLOF plus deleterious missense (5/5); AAF < 0.1% | 22: 29137674: G:C | | 1.79E−06 | −0.19 (−1.9, 1.6) | −0.022 (−0.23, 0.19) | 8.36E−01 | p.Ala322Pro: p.Ala320Pro: p.Ala322Pro |
| EUR | pLOF plus deleterious missense (5/5); AAF < 0.1% | 22: 29094256: A:G | | 1.79E−06 | −0.17 (−1.9, 1.6) | −0.021 (−0.23, 0.19) | 8.49E−01 | |
| EUR | pLOF plus deleterious missense (5/5); AAF < 0.1% | 22: 29137353: G:C | | 1.79E−06 | 0.15 (−1.6, 1.9) | 0.018 (−0.19, 0.23) | 8.70E−01 | p.Ala215Pro: p.Ala213Pro: p.Ala215Pro |
| EUR | pLOF plus deleterious missense (5/5); AAF < 0.1% | 22: 29140318: T:A | | 1.79E−06 | 0.13 (−1.6, 1.9) | 0.015 (−0.2, 0.23) | 8.87E−01 | p.Leu387His: p.Leu402His: p.Leu404His |

TABLE 2-continued

| Ancestry | Genetic exposure, variant type; allele frequency cut-off in % | CPRA | RSID | AAF, fraction of 1 | Beta (95% CI) per allele in SD units of eBMD | Beta (95% CI) per allele in g/cm2 units of eBMD | p | Protein effect |
|---|---|---|---|---|---|---|---|---|
| EUR | pLOF plus deleterious missense (5/5); AAF < 0.1% | 22: 29138765: C:T | | 1.79E−06 | 0.12 (−1.6, 1.9) | 0.015 (−0.2, 0.23) | 8.93E−01 | p.Pro369Leu: p.Pro367Leu: p.Pro369Leu |
| EUR | pLOF plus deleterious missense (5/5); AAF < 0.1% | 22: 29098939: T:C | rs1348515584 | 1.79E−06 | 0.1 (−1.6, 1.8) | 0.012 (−0.2, 0.22) | 9.09E−01 | p.Ile113Thr: p.Ile111Thr: p.Ile113Thr |
| EUR | pLOF plus deleterious missense (5/5); AAF < 0.1% | 22: 29137575: C:T | rs757200121 | 1.79E−06 | 0.083 (−1.7, 1.8) | 0.01 (−0.2, 0.22) | 9.25E−01 | p.Arg289Cys: p.Arg287Cys: p.Arg289Cys |
| EUR | pLOF plus deleterious missense (5/5); AAF < 0.1% | 22: 29142101: G:A | | 1.79E−06 | 0.081 (−1.7, 1.8) | 0.0098 (−0.2, 0.22) | 9.28E−01 | |
| EUR | pLOF plus deleterious missense (5/5); AAF < 0.1% | 22: 29094281: G:C | rs1255710108 | 1.79E−06 | 0.075 (−1.7, 1.8) | 0.0091 (−0.2, 0.22) | 9.33E−01 | p.Asp41His: p.Asp39His: p.Asp41His |
| SAS | pLOF plus deleterious missense (5/5); AAF < 0.1% | 22: 29137518: G:A | rs1208119541 | 7.55E−05 | −0.063 (−1.9, 1.8) | −0.0076 (−0.23, 0.22) | 9.47E−01 | p.Val270Met: p.Val268Met: p.Val270Met |
| EAS | pLOF plus deleterious missense (5/5); AAF < 0.1% | 22: 29138740: G:A | | 0.0003592 | −0.055 (−1.8, 1.7) | −0.0067 (−0.22, 0.21) | 9.52E−01 | p.Val361Ile: p.Val359Ile: p.Val361Ile |
| EUR | pLOF plus deleterious missense (5/5); AAF < 0.1% | 22: 2912531: G:A | rs1395949514 | 1.79E−06 | 0.044 (−1.7, 1.8) | 0.0054 (−0.21, 0.22) | 9.60E−01 | p.Trp178*: p.Trp176*: p.Trp178* |
| EUR | pLOF plus deleterious missense (5/5); AAF < 0.1% | 22: 29137644: C:A | | 1.79E−06 | −0.03 (−1.8, 1.7) | −0.0037 (−0.22, 0.21) | 9.73E−01 | p.Gln312Lys: p.Gln310Lys: p.Gln312Lys |
| EUR | pLOF plus deleterious missense (5/5); AAF < 0.1% | 22: 29094257: G:T | rs1171737622 | 1.79E−06 | −0.023 (−1.8, 1.7) | −0.0028 (−0.21, 0.21) | 9.79E−01 | |
| EUR | pLOF plus deleterious missense (5/5); AAF < 0.1% | 22: 29094333: T:G | | 1.79E−06 | −0.015 (−1.8, 1.7) | −0.0019 (−0.21, 0.21) | 9.86E−01 | p.Leu58Arg: p.Leu56Arg: p.Leu58Arg |

Abbreviations: pLOF, predicted loss of function; CPRA, chromosome position reference alternative; RR, reference homozygote genotype; RA, reference-alternative genotype; AA, alternative homozygote genotype; SD, standard deviation; CI, confidence interval; p, P-value; AAF alternative allele frequency; AAC, alternate allele count.

A distinct GWAS effector gene prioritization method, the gene-level Polygenic Priority Score (PoPS), yielded similar results to the Ei.

KREMEN1 as a gene associated with eBMD at exome-wide significance and their evidence from common variant GWAS, predicted by PoPS. "Positive control" indicates whether a gene is among a subset of 56 expert-curated genes implicated in bone mineral density by Mendelian genetics or pharmacological validation. eBMD PoP scores were calculated for all genes in the genome, whereas the PoPS rank was only derived for genes in GWAS loci (a total of 857 eBMD GWAS loci are included).

Table 3 shows that KREMEN1 was discovered exclusively in multi-ancestry meta-analysis of eBMD (Genetic exposure, variant type; frequency cutoff in %=pLOF plus deleterious missense (5/5); AAF <1%). Abbreviations: European, EUR; African, AFR; South asians, SAS; East asians, EAS; predicted loss of function, pLOF; alternative allele frequency, AAF; confidence interval, CI; standard deviation, SD; estimated bone mineral density, eBMD; P-value, p; reference-reference genotype, RR; reference-alternative genotype, RA; alternative-alternative genotype, AA; grams per square centimeter, g/cm$^2$; ratio of true heterogeneity to total observed variation, I2.

Mendelian Randomization of Circulating Protein Abundances with eBMD

Large-scale proteomics data were leveraged to provide further evidence implicating KREMEN1 in bone mineral density. Two-sample Mendelian randomization (MR; Davey Smith et al., Int. J. Epidemiol., 2003, 32, 1-22) to identify circulating proteins genetically-associated with eBMD. First, cis-SNPs associated with 863 circulating protein levels from two proteomic GWAS were identified, the INTERVAL study and the AGES study. Both studies measured circulating proteins using the SomaScan platform, and included 3,301 and 3,200 European ancestry individuals, respectively. MR analyses revealed that genetically-predicted concentrations of KREMEN1 from INTERVAL ($P<9.2\times10^{-5}$, corresponding to a Bonferroni correction for KREMEN1 tested in INTERVAL) and KREMEN1 from AGES ($P<6.5\times10^{-5}$, corresponding to a Bonferroni correction for KREMEN1 tested in AGES) were associated with eBMD. In addition, KREMEN1 as a protein was significantly associated with eBMD from INTERVAL (MR pval$<9.2\times10^{-5}$) and AGES (MR pval$<6.45\times10^{-5}$). Beta: effect estimate for eBMD in SD units, per SD unit increase in protein level.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

TABLE 3

| Ancestry | AAF, fraction of 1 | Beta (95% Cl) per allele in SD units of eBMD | Beta (95% Cl) per allele in g/cm$^2$ units of eBMD | P |
|---|---|---|---|---|
| EUR | 0.0016 | 0.1382(0.0802,0.1961) | 0.0168(0.0097,0.0238) | 2.96E−06 |
| AFR | 0.0019 | 0.5045(0.0727,0.9363) | 0.0612(0.0088,0.1136) | 2.20E−02 |
| EAS | 0.0029 | 0.2963(−0.3345,0.9271) | 0.0359(−0.0406,0.1125) | 3.57E−01 |
| SAS | 0.0020 | 0.316(−0.0411,0.6731) | 0.0383(−0.005,0.0816) | 8.29E−02 |

| Ancestry | Genotype counts, RR\|RA\|AA genotypes | p-value for heterogeneity in effect estimates between ancestries | Multi-ancestry beta (95% Cl) per allele in SD units of eBMD | Multi-ancestry P | I$^2$ |
|---|---|---|---|---|---|
| EUR | 277,895\| 912\|0 | 2.86E−01 | 0.1502(0.0937,0.2066) | 1.87485E−07 | 20.76% |
| AFR | 5,090\|19\|0 | | | | |
| EAS | 1,384\|8\|0 | | | | |
| SAS | 6,597\|27\|0 | | | | |

What is claimed is:

1. A method of treating a subject with a therapeutic agent that treats or prevents decreased bone mineral density, wherein the subject has decreased bone mineral density or is at risk of developing decreased bone mineral density, the method comprising the steps of:

determining whether the subject has a Kringle Containing Transmembrane Protein 1 (KREMEN1) variant nucleic acid molecule encoding a KREMEN1 predicted loss-of-function polypeptide by:

obtaining or having obtained a biological sample from the subject; and performing or having performed a sequence analysis on the biological sample to determine if the subject has a genotype comprising the KREMEN1 variant nucleic acid molecule; and administering or continuing to administer the therapeutic agent that treats or prevents decreased bone mineral density in a standard dosage amount to a subject that is KREMEN1 reference, and/or administering a KREMEN1 inhibitor to the subject;

administering or continuing to administer the therapeutic agent that treats or prevents decreased bone mineral density in an amount that is the same as or less than a standard dosage amount to a subject that is heterozygous for the KREMEN1 variant nucleic acid molecule, and/or administering a KREMEN1 inhibitor to the subject; or administering or continuing to administer the therapeutic agent that treats or prevents decreased bone mineral density in an amount that is the same as or less than a standard dosage amount to a subject that is homozygous for the KREMEN1 variant nucleic acid molecule;

wherein the KREMEN1 inhibitor comprises an antisense nucleic acid molecule, a small interfering RNA (siRNA), or a short hairpin RNA (shRNA) that hybridizes to a KREMEN1 nucleic acid molecule;

wherein the presence of a genotype having the KREMEN1 variant nucleic acid molecule encoding the KREMEN1 predicted loss-of-function polypeptide indicates the subject has a decreased risk of developing decreased bone mineral density;

wherein the KREMEN1 inhibitor decreases expression of KREMEN1 polypeptide in a cell in the subject; and wherein the therapeutic agent is chosen from alendronate, ibandronate, zoledronate, risedronate, calcitonin, teriparatide, denosumab, estrogen and progesterone, raloxifene, or any combination thereof.

2. The method according to claim 1, wherein the subject is KREMEN1 reference, and the subject is administered or continued to be administered the therapeutic agent that treats or prevents decreased bone mineral density in a standard dosage amount, and is administered a KREMEN1 inhibitor.

3. The method according to claim 1, wherein the subject is heterozygous for a KREMEN1 variant nucleic acid molecule, and the subject is administered or continued to be administered the therapeutic agent that treats or prevents decreased bone mineral density in an amount that is the same as or less than a standard dosage amount, and is administered a KREMEN1 inhibitor.

4. The method according to claim 1, wherein the KREMEN1 variant nucleic acid molecule is a splice-site variant, a stop-gain variant, a start-loss variant, a stop-loss variant, a frameshift variant, or an in-frame indel variant, or a variant that encodes a truncated KREMEN1 predicted loss-of-function polypeptide.

5. The method according to claim 1, wherein the KREMEN1 predicted loss-of-function variant nucleic acid molecule is: genomic variant 22:29121465:G:A, 22:29125344:G:A, 22:29125417:G:T, 22:29138713:G:A, 22:29125368:G:T, 22:29125365:G:A, 22:29138812:GC:G, 22:29138753:GC:G, 22:29121464:C:T, 22:29137540:C:T, 22:29121372:G:T, 22:29125372:A:T, 22:29125270:G:A, 22:29121359:C:A, 22:29098884:C:T, 22:29137657:T:C, 22:29138740:G:C, 22:29125297:G:T, 22:29125392:G:A, 22:29140311:C: T, 22:29140294:A:G, 22:29140308:C:G, 22:29167043:G:A, 22:29142018:T: , 22:29098926: A:G, 22:29098885:C:T, 22:29098940:A:G, 22:29137539:ACC: A, 22:29098878:G:A, 22:29137404: T:C, 22:29094276:G: A, 22:29121416:A:G, 22:29137671: C:T, 22:29094342:A: G, 22:29094396:G:T, 22:29094282:A:G, 22:29138723:C:T, 22:29137557:C:T, 22:29138716:G:T, 22:29137654:G:A, 22:29094270:C:A, 22:29094267:C:T, 22:29138806: ATGGGGGCT:A, 22:29138818:A:AT, 22:29138623:G:A, 22:29137559:CT:C, 22:29121450:G:A, 22:29137398:C:T, 22:29137600:C:T, 22:29121444:A:T, 22:29098869:G:C, 22:29141987:C:T, 22:29073134:G:GCGCCGCC, 22:29138687:C:T, 22:29142019:T:G, 22:29167083:CA:C, 22:29125296:TC, 22:29138738:A:G, 22:29138764:C:G, 22:29140318:TCA: T, 22:29094420:G:A, 22:29121428:A: C, 22:29121443:C: , 22:29073228:G:T, 22:29137521:G:A, 22:29094391:G:C, 22:29125383:TC, 22:29140285:G:A, 22:29121372: G:A, 22:29125288:C:T, 22:29121371:G:C, 22:29137351:G:A, 22:29138770:C:T, 22:29142029:C:G, 22:29094354:A:G, 22:29121477:TC:T, 22:29073133:G:T, 22:29098866:C:A, 22:29137492:T:G, 22:29098925:G:A, 22:29121405:T:A, 22:29094257:G:A, 22:29140320:A:C, 22:29137340:A:G, 22:29094363:A:G, 22:12937483:T:TC, 22:29138834:G:A, 22:29098903:A:G, 22:29125389:G:A, 22:29137447:T:TCC, 22:29138691:GCAGGCCAAC, CT:G22: 29167104:T:A, 22:29121359:C:T, 22:29138753: G:T, 22:29094348:CTT:C, 22:29137417:A:G, 22:29125325: C:G, 22:29137495: A:C, 22:29142029:G:A, 22:29094328:AT:A, 22:29098922:C:A, 22:29140284:T:C, 22:98893:290TC, 22:29121482:G: , 22:29098911:G:C, 22:29094324:A:T, 22:29121358:G:T, 22:29098861:G:T, 22:29098866:C:G, 22:29094282:A:T, 22:29094296:CAG: C, 22:29142017:A:AT, 22:29138755:C:G, 22:29125269:G: A, 22:29098935:G:GA, 22:29142057:A:T, 22:29138796: G:A, 22:29137674:G:C,22:29094256:A:G, 22:29137353:G: C, 22:29140318:T:A, 22:29138765:C:T, 22:29098939:T:C, 22:29137575:C:T, 22:29142101:G:A, 22:29094281:G:C, 22:29137518:G:A, 22:29138740:G:A, 22:2912531:G:A, 22:29137644:C:A, 22:29094257:G:T, 22:29094333:T:G, 22:29137557:C:T, 22:29073216:GC:G, 22:29094283:T:G, 22:29140320:A:G, 22:29125344:G:T, 22:29125365:G:A, 22:29137644:C:A, 22:29094396:G:T, 22:29098872:G:A, 22:29137405:TC:T, 22:29073155:GC:G, 22:29137575:C:T, 22:29142018:T:G, 22:29094298:G:C, 22:29125319:G:A, 22:29140320:A: C, 22:29121374:T:C, 22:29138623:G:A, 22:29121482:G:C, 22:29137353:G:A, 22:29140353:CA:C, 22:29121438:C:T, 22:29138834:G:A, 22:29125366:G:T, 22:29137600:C:T, 22:29138738:A:G, 22:29098925:G:A, 22:29137447:T:TCC, 22:29142017:A:AT, 22:29094255: TA: , 22:29094328:AT:A, 22:29121477:TC:T, 22:29140297:GTCTGGCA:G, 22:29094403: G:T, 22:29138783:G:A, 22:29138753:GC:G, 22:29125269:G:A, 22:29094387:G:C, 22:29137495:A:C, 22:29140285:G:A, 22:29142101:G: , 22:29094273: A:G, 22:29125282:G:A, 22:29094267:C:T, 22:29137674:G:C, 22:29125329:G: , 22:29137417: A:G, 22:29125392:G:A, 22:29137657:T:C, 22:29140312:T:C, 22:29098866:C: G, 22:29125325:C:G, 22:29138723:C:T, 22:29140353:C:T, 22:29137341:G:A, 22:29073204: GC: G, 22:29125288:C: T, 22:29125297:G:T, 22:29137492:T:G, 22:29167105:G:C, 22:29073228:G: T, 22:29094320:G: A, 22:29137579:C:T, 22:29094321:G:A, 22:29137340:A:G, 22:29137521:G:A, 22:29073213:T: TCGG000, 22:29137654:G:A, 22:29138746: A:G, 22:29137340:A:C, 22:29094324:A:T, 22:29137647:G:A, 22:29137360:G:T, 22:29094390:A:G, 22:29167083:CAG: C, 22:29138812:GC:G, 22:29094363: A:G, 22:29140318:T: A, 22:29098926:A:G, 22:29125372:A:T, 22:29140318: TCA:T, 22:29094354:A:G, 22:29141946:C:T, 22:29094256:A:G, 22:29094391:G:C, 22:29125384:G:C, 22:29138687:C:T, 22:29138737:T:G, 22:29121450:G:A, 22:29167083:CA:C, 22:29073212:CT:C, 22:29121416:A: G, 22:29098873:G:T, 22:29094257:G:A, 22:29098911:G:C, 22:29142057:A:T, 22:29094270:C:A, 22:29094344:G:A, 22:29121372:G:A, 22:29142110: T:G, 22:29137559:CT: C, 22:29098953:A:C, 22:29137407:C:T, 22:29094395:G:A, 22:29121359:C:T, 22:29098893:T:C, 22:29142029:C:A, 22:29121379:C:G, 22:29121359:C A, 22:29094342:A:G, 22:29138806:ATGGGGGCT: A, 22:29137558:G: A, 22:29098878:G:A, 22:29094276:G:A, 22:29125415: TAGTG: T, 22:29137654:G:T, 22:29137650:C:T, 22:29137539: ACC:A, 22:29140311:C:T, 22:29121371:G: C, 22:29125368:G:T, 22:29138740:G:C, 22:29073228:G:A, 22:29121465:G:A, 22:29098885:C:T, 22:29121464:C:T, 22:29142029: C:G, 22:29098908:G:A, 22:29142005:GA: G, 22:29138713:G:A, 22:29138818:A:AT, 22:29138756:C: G, 22:29167104:T:A, 22:29094282:A:T, 22:29121443:C:T, 22:29138759:G:T, 22:29138765:C:T, 22:29140308:C:G, 22:29094257:G:T, 22:29137524:C:T, 22:29094387:G:T, 22:29125342:C:T, 22:29138717:C:T, 22:29098926:A:T, 22:29121405:T:A, 22:29098934:T:G, 22:29125267:C:T, 22:29137351:G:A, 22:29137353:G:C, 22:29098924:G:C, 22:29140329:G:A, 22:29098866:C:A, 22:29094296:CAG: C, 22:29137359:G:A, 22:29142019:T:G, 22:29125417:G: , 22:29121423:C:T, 22:29098869:G:C, 22:29121444:A:T, 22:29137633: A: T, 22:29094282: A:G, 22:29138716:G:T, 22:29140294:A:G, 22:29094269:GC:G, 22:29125389:G: A, 22:29137540:C:T, 22:29094389:G:C, 22:29098940:A:G, 22:29098939:T:C, 22:29121428: A: C, 22:29137350:G:T, 22:29138770:C:T, 22:29073134:G:GCGCCGCC, 22:29140284:T:C, 22:29137404:T: C, 22:29137552:T:C, 22:29094362:T:C, 22:29125385:T:G, 22:29094333:T: G, 22:29121443:C:A, 22:29137498:T:C, 22:29073133:G:T, 22:29098922:C:A, 22:29137530:G:T, 22:29125270:G:A, 22:29125282:G:T, 22:29138676:CG:C, 22:29121383:G:A, 22:29125344:G:A, 22:29094281:G:C, 22:29138677:G:A, 22:29073186:CG:C, 22:29141987:C:T, 22:29098920:T: C, 22:29137671:C:T, 22:29167043:G A, 22:29098884:C:T, 22:29121372:G:T, 22:29125396:G: A, 22:29094291:G:C, 22:29098870:A:G, 22:29138755:C:G, 22:29094348:CTT:C, 22:29094390:A:AG, 22:29125383:T:C, 22:29138753:G:T, 22:29125296:T:C, 22:29142029:C:T, 22:29142077:C:T, or 22:29137668:T:C, or an mRNA molecule produced therefrom, or a cDNA molecule produced from the mRNA molecule.

6. The method according to claim 1, wherein the KREMEN1 variant nucleic acid molecule encodes a truncated KREMEN1 predicted loss-of-function polypeptide.

7. The method according to claim 1, wherein the decreased bone mineral density is an osteopenia.

8. The method according to claim 1, wherein the decreased bone mineral density is Type I osteoporosis.

9. The method according to claim 1, wherein the decreased bone mineral density is Type II osteoporosis.

10. The method according to claim 1, wherein the decreased bone mineral density is secondary osteoporosis.

* * * * *